United States Patent
Tempest et al.

(10) Patent No.: US 11,642,413 B2
(45) Date of Patent: *May 9, 2023

(54) COMPOUNDS FOR DEGRADING TAU PROTEIN AGGREGATES AND USES THEREOF

(71) Applicant: Aprinoia Therapeutics Limited, Wanchai (CN)

(72) Inventors: Paul Tempest, Taipei (TW); Ming-Kuei Jang, Taipei (TW); Yih-Shyan Lin, Kaohsiung (TW)

(73) Assignee: APRINOIA THERAPEUTICS LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/687,570

(22) Filed: Mar. 4, 2022

(65) Prior Publication Data

US 2022/0267316 A1 Aug. 25, 2022

Related U.S. Application Data

(63) Continuation of application No. PCT/US2020/060459, filed on Nov. 13, 2020.

(60) Provisional application No. 62/935,017, filed on Nov. 13, 2019.

(51) Int. Cl.

| | | |
|---|---|---|
| *C07D 417/14* | (2006.01) | |
| *C07D 471/04* | (2006.01) | |
| *A61K 47/55* | (2017.01) | |
| *A61P 25/28* | (2006.01) | |
| *A61K 31/427* | (2006.01) | |
| *A61K 31/437* | (2006.01) | |
| *A61K 31/4439* | (2006.01) | |
| *A61K 31/454* | (2006.01) | |
| *A61K 31/506* | (2006.01) | |
| *C07D 413/14* | (2006.01) | |
| *A61K 47/54* | (2017.01) | |
| *A61K 31/444* | (2006.01) | |

(52) U.S. Cl.
CPC ............ *A61K 47/55* (2017.08); *A61K 31/427* (2013.01); *A61K 31/437* (2013.01); *A61K 31/444* (2013.01); *A61K 31/4439* (2013.01); *A61K 31/454* (2013.01); *A61K 31/506* (2013.01); *A61K 47/54* (2017.08); *A61K 47/545* (2017.08); *A61P 25/28* (2018.01); *C07D 413/14* (2013.01); *C07D 417/14* (2013.01); *C07D 471/04* (2013.01)

(58) Field of Classification Search
CPC .......................... C07D 417/14; C07D 471/04
See application file for complete search history.

(56) References Cited

U.S. PATENT DOCUMENTS

| | | |
|---|---|---|
| 3,833,863 A | 9/1974 | Webster et al. |
| 5,130,228 A | 7/1992 | Wade et al. |
| 5,264,329 A | 11/1993 | Wade et al. |
| 7,060,697 B2 | 6/2006 | Marsilje et al. |
| 7,910,579 B2 | 3/2011 | Kudo et al. |
| 9,750,816 B2 | 9/2017 | Bradner et al. |
| 9,770,512 B2 | 9/2017 | Bradner et al. |
| 9,808,542 B2 | 11/2017 | Walji et al. |
| 9,821,068 B2 | 11/2017 | Bradner et al. |
| 10,125,114 B2 | 11/2018 | Bradner et al. |
| 10,308,871 B2 | 6/2019 | Yano |
| 10,464,925 B2 | 11/2019 | Bradner et al. |
| 10,604,516 B2 | 3/2020 | Higuchi et al. |
| 10,669,253 B2 | 6/2020 | Bradner et al. |
| 10,730,870 B2 | 8/2020 | Crew et al. |
| 10,772,962 B2 | 9/2020 | Qian et al. |
| 10,849,980 B2 | 12/2020 | Bradner et al. |
| 2006/0018825 A1 | 1/2006 | Kudo et al. |
| 2009/0028787 A1 | 1/2009 | Gravenfors et al. |
| 2009/0257949 A1 | 10/2009 | Hefti et al. |
| 2010/0239496 A1 | 9/2010 | Gangadharmath et al. |
| 2011/0130305 A1 | 6/2011 | Patton et al. |
| 2012/0214994 A1 | 8/2012 | Chi et al. |
| 2014/0147428 A1 | 5/2014 | Shchepinov |
| 2015/0197498 A1 | 7/2015 | Song et al. |
| 2017/0189566 A1 | 7/2017 | Tu et al. |
| 2017/0233655 A1 | 8/2017 | Saito |
| 2017/0362507 A1 | 12/2017 | Okabe |
| 2018/0125821 A1 | 5/2018 | Crew et al. |

(Continued)

FOREIGN PATENT DOCUMENTS

| | | |
|---|---|---|
| AU | 2017204357 A1 | 8/2017 |
| CN | 1791592 A | 6/2006 |
| CN | 1867552 A | 11/2006 |

(Continued)

OTHER PUBLICATIONS

International Report on Patentability dated May 17, 2022 issued in International Application No. PCT/US2020/060459 by the International Bureau of WIPO, 5 pages.

(Continued)

*Primary Examiner* — Samira J Jean-Louis

(74) *Attorney, Agent, or Firm* — Foley & Lardner LLP

(57) ABSTRACT

Disclosed herein are novel compounds for degrading Tau protein aggregates, pharmaceutical acceptable salts, enantiomers, non-enantiomers, tautomers, racemates, solvates, metabolic precursors, or prodrugs thereof. Also disclosed herein are uses of the compounds, pharmaceutical acceptable salts, enantiomers, non-enantiomers, tautomers, racemates, solvates, metabolic precursors, or prodrugs thereof in manufacture a medicament for treating a tauopathy, as well as method for aiding in the treatment of a tauopathy or treating a tauopathy in a subject.

30 Claims, 1 Drawing Sheet

(56) References Cited

U.S. PATENT DOCUMENTS

2020/0085793 A1  3/2020  Crew et al.

FOREIGN PATENT DOCUMENTS

| CN | 102639135 A | 8/2012 |
|---|---|---|
| CN | 107207459 A | 9/2017 |
| EP | 1 655 287 A1 | 5/2006 |
| EP | 2 397 139 A1 | 12/2011 |
| JP | S4874796 A | 10/1973 |
| JP | S5553333 A | 4/1980 |
| JP | 61-275836 A | 12/1986 |
| JP | H03-144569 A | 6/1991 |
| JP | 2007-106755 A | 4/2007 |
| JP | 2009-519239 A | 5/2009 |
| JP | 2011-512354 A | 4/2011 |
| JP | 2011-516866 A | 5/2011 |
| JP | 2012-102106 A | 5/2012 |
| TW | 201722957 A | 7/2017 |
| TW | 201722958 A | 7/2017 |
| WO | WO-2005/016888 A1 | 2/2005 |
| WO | WO-2007/034282 A2 | 3/2007 |
| WO | WO-2008/078424 A1 | 7/2008 |
| WO | WO-2010/011964 A2 | 1/2010 |
| WO | WO-2010/024769 A1 | 3/2010 |
| WO | WO-2010/087315 A1 | 8/2010 |
| WO | WO-2011/045415 A2 | 4/2011 |
| WO | WO-2011/065980 A2 | 6/2011 |
| WO | WO-2011/119565 A1 | 9/2011 |
| WO | WO-2015/188368 A1 | 12/2015 |
| WO | WO-2016/105518 A1 | 6/2016 |
| WO | WO-2016/149668 A1 | 9/2016 |
| WO | WO-2017/007612 A1 | 1/2017 |
| WO | WO-2017/030814 A1 | 2/2017 |
| WO | WO-2018/011073 A1 | 1/2018 |
| WO | WO-2018/017370 A1 | 1/2018 |
| WO | WO-2018/102067 A2 | 6/2018 |
| WO | WO-2018/119448 A1 | 6/2018 |
| WO | WO-2019/014429 A1 | 1/2019 |
| WO | WO-2019/214681 A1 | 11/2019 |
| WO | WO-2020/006264 A1 | 1/2020 |
| WO | WO-2020/041331 A1 | 2/2020 |
| WO | WO-2021/011913 A1 | 1/2021 |

OTHER PUBLICATIONS

Non-Final Office Action on U.S. Appl. No. 17/477,411 dated Jun. 14, 2022.
Yang, Yanping, et al., "Radiolabeled bioactive benzoheterocycles for imaging Beta-amyloid plaques in Alzheimer's disease," European Journal of Medicinal Chemistry, vol. 87, 2014, pp. 703-721.
Non-Final Office Action on U.S. Appl. No. 17/320,882 dated Sep. 14, 2022.
Non-Final Office Action on U.S. Appl. No. 17/477,479 dated Aug. 19, 2022.
Examination Report No. 2 for Standard patent application dated Sep. 27, 2021 issued in AU Patent Application No. 2019265346, 11 pages.
Feng, Xun, et al., "Aerobic Oxidation of Alcohols and the Synthesis of Benzoxazoles Catalyzed by a Cuprocupric Coordination Polymer ($Cu^+$-CP) Assisted by TEMPO," Inorganic Chemistry, 2015, vol. 54, Issue No. 5, pp. 2088-2090. (Author's copy).
International Search Report and Written Opinion of the International Searching Authority dated Feb. 9, 2022 issued in International Application No. PCT/IB2021/054167, 13 pages.
Perry, Robert, J., et al.,"Palladium-Catalyzed Syntheses of 2-Arylbenzothiazoles," Organometallics, 1994, vol. 13, pp. 3346-3350.
Rao, R Nishanth, et al., "Efficient access to imidazo[1,2-a]pyridines/pyrazines/pyrimidines via catalyst free annulation reaction under microwave irradiation in green solvent," ACS Combinatorial Science, 2018, vol. 20, Issue No. 3, pp. 164-171 (Accepted Manuscript).
Santra, Sourav Kumar, et al., "Peroxide Free Pd(II)-Catalyzed ortho-Aroylation and ortho-Halogenation of Directing Arenes," J. Org. Chem., 2016, vol. 81, Issue No. 14, pp. 6066-6074. (Accepted manuscript).
Xie, Yuan-Yuan, et al., "Organic reactions in ionic liquids: cyclocondensation of α-bromoketones with 2-aminopyridine", J. Chem. Research (S), 2003, pp. 614-615. (Short Paper).
Aakeroy, C.B. et al., Directed Supramolecular Assembly of Cu(II)-based "paddlewheels" into Infinite 1-D Chains Using Structurally Bifunctional Ligands, The Royal Society of Chemistry, Dalton Trans. 2006, pp. 1627-1635.
Allowance Decision from the Intellectual Property Office dated Dec. 9, 2021 issued in TW Application No. 109139798, with English translation, 4 pages.
Arriagada et al., Neurofibrillary Tangles but not Senile Plaques Parallel Duration and Severity of Alzheimer's Diseases, Neurology, 1992, vol. 42, pp. 631-639.
Ballatore, et al., "Tau-mediated Neurodegeneration in Alzheimer's Disease and related Disorders," Nature Reviews/Neuroscience, Sep. 2007, vol. 8, pp. 663-672.
Braak, Heiko, et al., "Staging of Alzheimer disease-associated neurofibrillary pathology using paraffin sections and immunocytochemistry," Acta Neuropathol (2006), vol. 112, pp. 389-404.
Braak, Heiko, et al., "Staging of Alzheimer's Disease-Related Neurofibrillary Changes," Neurobiology of Aging, vol. 16, No. 3, (1995), pp. 271-284.
Braymer, Joseph J., et al., "Recent Development of Bifunctional Small Molecules to Study Metal-Amyloid-B Species in Alzheimer's Disease," International Journal of Alzheimer's Disease, vol. 2011, Article ID 623051, (2011), doi: 10.4061/2011/623051, 9 pages.
Cary, Brian P., et al., "Targeting Metal-Aβ Aggregates with Bifunctional Radioligand [11 C]L2-b and a Flourine-18 Analogue [18 F]FL2-b," ACS Medicinal Chemistry Letters, vol. 6, Nov. 9, 2014, pp. 112-116.
DeVos, Sarah L., et al., "Synaptic Tau Seeding Precedes Tau Pathology in Human Alzheimer's Disease Brain," Frontiers in Neuroscience, Apr. 2018, vol. 12, Article 267, 15 pages.
Ehrenberg, Benjamin, et al., "Surface potential on purple membranes and its sidedness studied by a resonance Raman dye probe", Biophysical Journal, 1984, vol. 45, pp. 663-670.
Etaiw et al., "Photophysics of benzazole derived push-pull butadienes: A highly sensitive fluorescence probes", Journal of Photochemistry and Photobiology, A: Chemistry, 2006, vol. 177, No. 2-3, pp. 238-247.
Final Office Action on U.S. Appl. No. 16/798,226 dated Feb. 16, 2021.
Final Office Action on U.S. Appl. No. 16/798,226 dated Sep. 7, 2021.
Final Office Action on U.S. Appl. No. 17/320,882 dated Dec. 20, 2021.
International Preliminary Report on Patentability dated Sep. 18, 2020 issued in International Application No. PCT/CN2019/086201, 72 pages.
International Search Report dated Aug. 12, 2019 issued in International Application No. PCT/CN2019/0826201, 7 pages.
International Search Report dated Feb. 9, 2021 issued in International Application No. PCT/US2020/060459, 3 pages.
International Search Report dated Jan. 29, 2021 issued in International Application No. PCT/IB2020/057415, 10 pages.
International Search Report for PCT/JP2012/083286, dated Mar. 5, 2013, 3 pgs.
Kfoury, Najla, et al., "Trans-cellular Propagation of Tau Aggregation by Fibrillar Species," The Journal of Biological Chemistry, vol. 287, No. 23, (2012), pp. 19440-19451.
Klunk, William E., et al., Uncharged thioflavin-T derivatives bind to amyloid-beta protein with high affinity and readily enter the brain, Life Sciences, vol. 69, (2001), pp. 1471-1484.
Kung, H.F. et al. (Dec. 19, 2001). "Novel stilbenes as probes for amyloid plaques," J Am Chem Soc 123(50):12740-12741.

(56) References Cited

OTHER PUBLICATIONS

La Clair, James J., "Selective Detection of the Carbohydrate-Bound State of Concanavalin A at the Single Molecule Level", Journal of the American Chemical Society, 1997, vol. 119, No. 33, pp. 7676-7684.

Maruyama, et al., "Imaging of Tau Pathology in a Tauopathy Mouse Model and in Alzheimer Patients Compared to Normal Controls", Neuron Article, vol. 79, Sep. 18, 2013, pp. 1094-1108.

Matsumura, K. et al. (2011). "Phenyldiazenyl benzothiazole derivatives as probes for in vivo imaging of neurofibrillary tangles in Alzheimer's disease brains," MedChemComm 2:596-600.

Nakazono, Manabu, et al., "Novel styrylbenzene derivatives for detecting amyloid deposits," Clinica Chimica Acta, vol. 436, May 9, 2014, pp. 27-34.

Non-Final Office Action on U.S. Appl. No. 16/798,226 dated Oct. 26, 2020.

Non-Final Office Action on U.S. Appl. No. 17/320,882 dated Oct. 7, 2021.

Non-Final Office Action on U.S. Appl. No. 17/320,913 dated Sep. 21, 2021.

Notice of Allowance on U.S. Appl. No. 14/346,914 dated Nov. 1, 2019.

Notice of grant for patent dated Jul. 30, 2019 issued in Australian Application No. 2017204357, 1 page.

Ono, Maiko, et al., "Distinct binding of PET ligands PBB3 and AV-1451 to tau fibril strains in neurodegenerative tauopathies," Brain, (2017), 140(3), pp. 764-780, doi:10.1093/brain/aww339.

Rudikoff, Stuart, et al., "Single amino acid substitution altering antigen-binding specificity," Proc. Natl. Acad. Sci. USA, vol. 79, (1982), pp. 1979-1983.

Sanders, David W., et al., "Distinct Tau Prion Strains Propagate in Cells and Mice and Define Different Tauopathies," Neuron, vol. 82, (2014), pp. 1271-1288.

SantaCruz, K., et al., "Tau Suppression in a Neurodegenerative Mouse Model Improves Memory Function," Science, (2005), 309(5733), pp. 476-481.

Silva, Catarina, et al., "Targeted degradation of aberrant tau in frontotemporal dementia patient-derived neuronal cell models," eLife, 2019, 8e45457, 31 pages.

Song, Lixin, et al., "Analysis of tau post-translational modifications in rTg4510 mice, a model of tau pathology," Molecular Neurodegeneration, (2015), 10:14, 11 pages.

Takuwa, Hiroyuki, et al., "Hemodynamic changes during neural deactivation in awake mice: A measurement by laser-Doppler flowmetry in crossed cerebellar diaschisis," Brain Research, (2013), vol. 1537, pp. 350-355, doi: 10.1016/j.brainres.2013.09.023.

Tomita, Yutaka, et al., "Long-term in vivo investigation of mouse cerebral microcirculation by fluorescence confocal microscopy in the area of focal ischemia," Journal of Cerebral Blood Flow & Metabolism, (2005), vol. 25, pp. 858-867, doi: 10.1038/sj.jcbfm.9600077.

U.S. Notice of Allowance on U.S. Appl. No. 17/320,913 dated Nov. 29, 2021.

U.S. Office Action on U.S. Appl. No. 16/798,226 dated Oct. 26, 2020.

Wang et al., "A near infrared dye laser pumped by nitrogen laser light", Zhongguo Jiguang, 1989, vol. 16, No. 8, pp. 492-495.

Wilen, Samuel H., et al., "Strategies in Optical Resolutions," Tetrahedron Report No. 38, Tetrahedron, vol. 33, Pergamon Press, (1977), pp. 2725-2736.

Written Opinion of the International Searching Authority dated Aug. 12, 2019 issued in International Application No. PCT/CN2019/086201, 4 pages.

Written Opinion of the International Searching Authority dated Feb. 9, 2021 issued in International Application No. PCT/US2020/060459, 4 pages.

Xu et al. "Tau protein, aβprotein and Alzheimer's disease A protein and its role", Journal of Practice on Clinical Medicines, 2008, vol. 12, No. 3, pp. 118-120, Chinese language.

Yoshiyama, et al., Synapse Loss and Microglial Activation Precede Tangles in a P301S Tauopathy Mouse Model, Neuron, Feb. 1, 2007, vol. 53, pp. 337-351.

Zhuang, Z.P. et al., Radioiodinated Styrylbenzenes and Thioflavins as Probes for Amyloid Aggregates, J. Med. Chem. 2001, vol. 44, pp. 1905-1914.

Final Office Action on U.S. Appl. No. 17/477,411 dated Sep. 30, 2022.

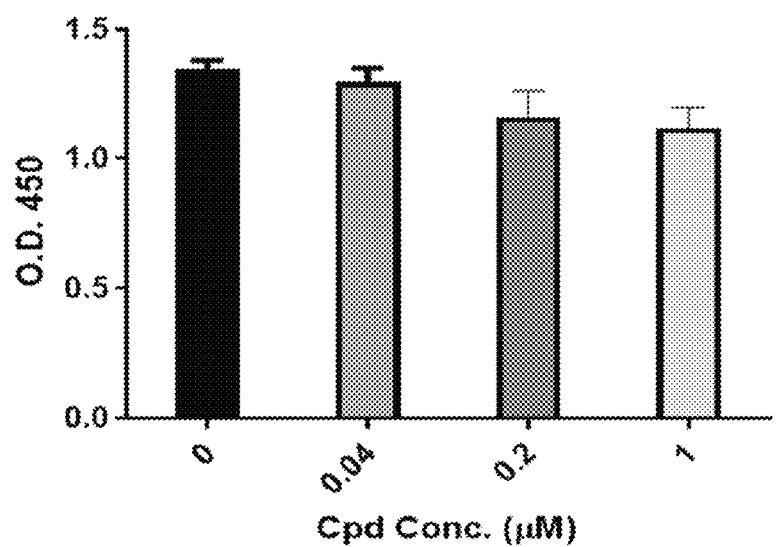

COMPOUNDS FOR DEGRADING TAU PROTEIN AGGREGATES AND USES THEREOF

CROSS-REFERENCE TO RELATED APPLICATIONS

This application is a continuation of International Application No. PCT/US2020/060459 filed Nov. 13, 2020, which is based upon and claims priority to U.S. Provisional Application No. 62/935,017, filed Nov. 13, 2019, the contents of which are incorporated herein by reference in their entireties.

BACKGROUND

Neurodegenerative diseases affect an estimated 50 million Americans each year, exacting an incalculable personal toll and an annual economic cost of hundreds of billions of dollars in medical expenses and lost productivity. Tauopathies are a class of neurodegenerative diseases associated with pathological aggregation of Tau protein (microtubule-associated protein tau, MAPT) in the human brain, and include Alzheimer's disease (AD), amyotrophic lateral sclerosis (ALS), Huntington's disease (HD), Parkinson's disease (PD), Pick's Disease (PiD), and Progressive Supranuclear Palsy (PSP). In tauopathy, aggregation of Tau spreads through the brain in a prion-like manner, such as seen in AD brain (H. Braak et al., Neurobiol Aging (1995), 16(3):271-78; H. Braak et al., Acta Neuropathol (2006) 112(4):389-404), where Tau pathology manifests in a consistent spatiotemporal pattern. Tau propagation seeds, consisting mainly of short fibrils, have been found to be significantly enriched in the synaptic fractions of brain regions lacking extensive cellular Tau pathology, indicating that Tau seeds are able to spread through the human brain along synaptically-connected neuronal networks.

Despite many therapeutic approaches aimed at removing aggregated Tau species that have been or are currently being investigated, at present there are no effective treatments for halting, preventing, or reversing the progression of such neurodegenerative diseases. Therefore, there is a need for new agents capable of slowing the progression of these neurodegenerative diseases and/or preventing them from developing. Further, there is a need for agents that distinguish between pathological forms of tau and tau in its normal, functional configuration, such that its normal intracellular function is not disrupted.

SUMMARY

The present disclosure relates to novel bispecific conjugate compounds that bind to Tau aggregates, and recruit a ubiquitin E3 ligase to mark the aggregates for proteomic degradation and clearance. These compounds bind specifically to Tau aggregates, and discriminate between Tau aggregates and monomeric (normal) Tau. These results suggest the suitability of compounds for use in the clinic, where they have the potential for promoting the clearance of pathogenic Tau with minimal effects on normal/physiological Tau species in the brains of human tauopathy patients.

The present disclosure provides compositions and methods for the treatment of a group of disorders and abnormalities associated with Tau aggregates. Methods of the invention include the administration of a bispecific conjugate described herein or a pharmaceutical composition to a subject comprising a therapeutically effective amount of a compound of the invention effective to treat, alleviate or prevent a disorder or abnormality associated with Tau aggregates. In certain embodiments, a therapeutically effective amount of a compound described herein is effective for halting, preventing, or reversing the progression of neurodegenerative diseases.

In some embodiments, pharmaceutical compositions of compounds for the treatment of Tau-associated neurodegenerative diseases are provided. Provided compositions comprise an effective amount of a compound as described herein, and a pharmaceutically acceptable excipient.

One aspect of the disclosure is a compound of any one of the Formula (I)-(VI):

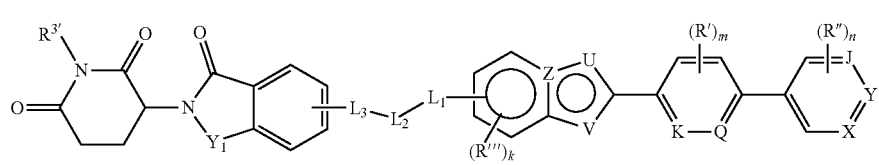

I

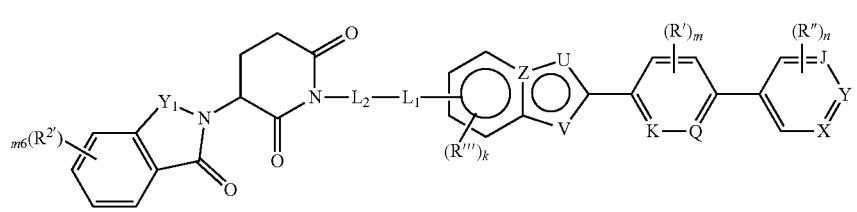

II

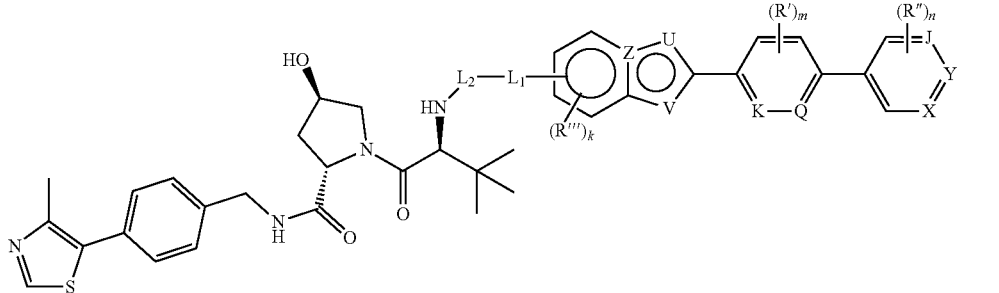

III

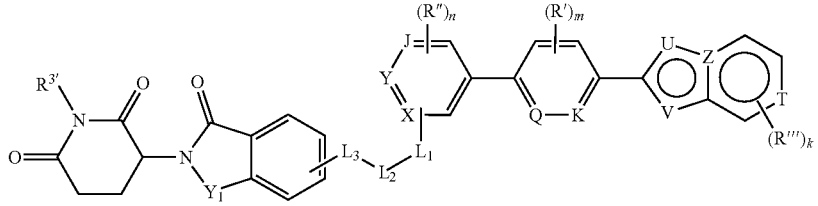

IV

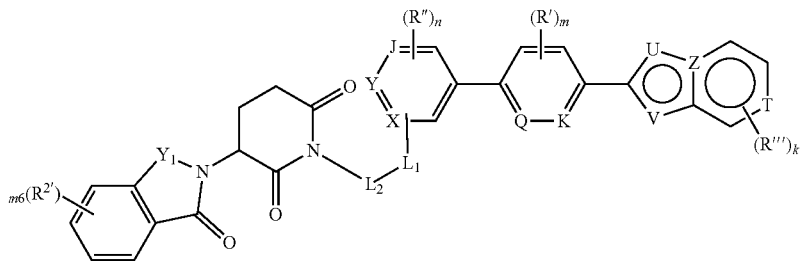

V

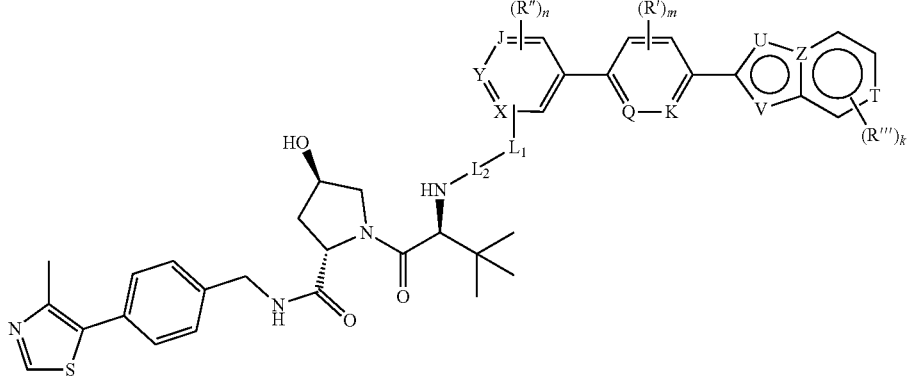

VI or pharmaceutically acceptable salts, solvates, hydrates, polymorphs, co-crystals, tautomers, stereoisomers, isotopically labeled derivatives, or prodrugs thereof, wherein $L_1$, $L_2$, $L_3$, X, Y, J, Q, K, T, U, V, Z, $Y_1$, R', R", R''', $R^{2'}$, $R^{3'}$, n, m, k and m6 are as defined herein.

Another aspect of the disclosure is a composition comprising a compound of the disclosure, and a pharmaceutically acceptable excipient.

Another aspect of the disclosure is a method for aiding in the treatment of a tauopathy in a subject, the method comprising administering an effective amount of a compound of the disclosure, or the composition the disclosure, wherein the compound or the composition treats the subject or aids in the treatment of the subject.

Another aspect of the disclosure is the use of a compound of the disclosure in the treatment of a tauopathy or a tau-associated disease or disorder.

Another aspect of the disclosure is the use of a compound of the disclosure for the manufacture of a medicament for the treatment of a tauopathy or a tau-associated disease or disorder.

Another aspect of the disclosure is the use of a compound of the disclosure in the diagnosis of a tauopathy or a tau-associated disease or disorder.

Another aspect of the disclosure is a kit, comprising a compound of the disclosure, or the composition of the disclosure, and printed instructions for the use thereof.

Another aspect of the disclosure is a method for synthesizing the compounds of the disclosure.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWING

The FIGURE shows the degradation of Tau aggregates measured by APNmAb005 ELISA assay. Upon treatment of 1 μM compound 162842, Optical Density (O.D.) 450 value decreases 20% compared to vehicle, reflecting the reduction of Tau aggregates.

DETAILED DESCRIPTION OF THE DISCLOSURE

The present disclosure provides compounds that specifically bind to aggregated forms of Tau protein, and also bind to a ubiquitin E3 ligase. E3 ligases are intracellular enzymes that transfer activated ubiquitin to a specific site of a targeted protein.

Ubiquitin is a highly conserved small protein (8 kDa, 76 amino acids), which is ubiquitously expressed intracellularly. After expression, ubiquitin is activated by an ubiquitin-activating enzyme ("E1"), then transferred to a ubiquitin-conjugating enzyme ("E2"). An E3 ligase transfers the ubiquitin from the E2 enzyme to a target substrate. There are estimated to be more than 600 different E3 ligases, which recognize a variety of different protein substrates. Once ubiquitinated, the substrate is transferred to a proteasome, which degrades the protein into oligopeptides, eventually degrading these to single amino acids. The ubiquitin-proteasome system serves to regulate the concentration of some proteins, and to degrade and recycle damaged or misfolded proteins.

The present disclosure provides compositions and methods for the treatment of a group of disorders and abnormalities associated with Tau aggregates. Methods of the invention include the administration of a compound described herein or a pharmaceutical composition to a subject comprising a therapeutically effective amount of a compound of the invention effective to treat, alleviate or prevent a disorder or abnormality associated with Tau aggregates. In certain embodiments, a therapeutically effective amount of a compound described herein is effective for halting, preventing, or reversing the progression of neurodegenerative diseases.

One aspect of the disclosure is a compound of any one of the Formula (I)-(VI):

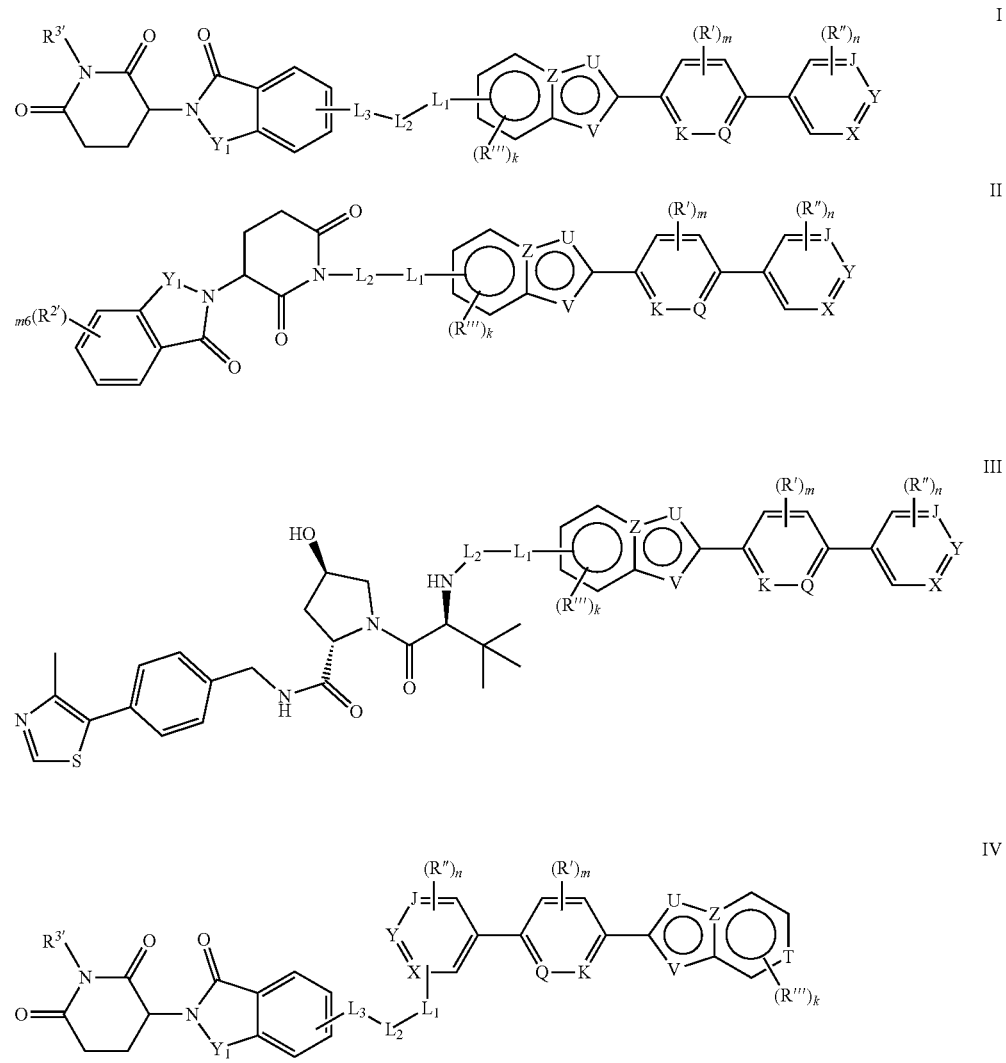

-continued

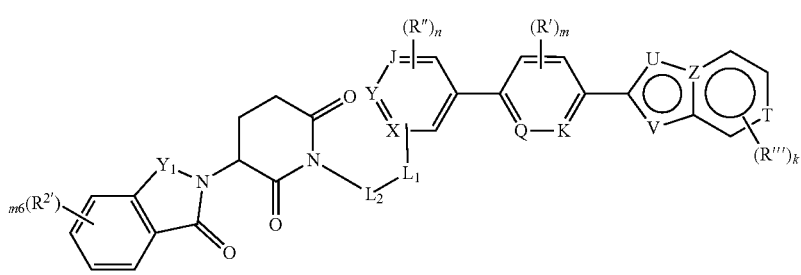

V

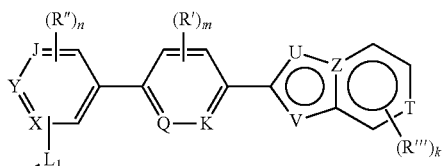

VI wherein, in Formula I, $R^{3'}$ is H or $C_{1-6}$ alkyl; $Y_1$ is $CH_2$ or

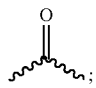;

$L_1$ is a bond, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N, where Z and U are not heteroatoms at the same time; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;
in Formula II, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

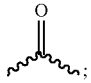;

$L_1$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N, where Z and U are not heteroatoms at the same time; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo; in Formula III, $L_1$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N, where Z and U are not heteroatoms at the same time; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula IV, $R^{3'}$ is H or $C_{1-6}$ alkyl; $Y_1$ is $CH_2$ or

$L_1$ is a bond, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N or NH; T is CH or N; where up to two of U, Z, V and T contain heteroatoms; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino, and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula V, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

$L_1$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N or NH; T is CH or N; where up to two of U, Z, V and T contain heteroatoms; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula VI, $L_1$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; V is N; T is CH or N; where up to two of U, Z, V and T contain heteroatoms; K is CH or N; Q is CH or N; where K and Q are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R" is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; J is $CR^6$ or N; X is $CR^6$ or N; Y is $CR^6$ or N; where at least one of J, X and Y is N, but J and Y are not N at the same time, X and Y are not N at the same time; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo.

In certain embodiments, the compound is of the structure of Formula I.

In certain embodiments, the compound is of the structure of Formula II.

In certain embodiments, the compound is of the structure of Formula III.

In certain embodiments, the compound is of the structure of Formula IV.

In certain embodiments, the compound is of the structure of Formula V.

In certain embodiments, the compound is of the structure of Formula VI.

In certain embodiments, the moiety

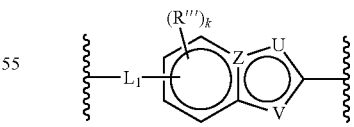

in Formula (I), (II) and (III) is

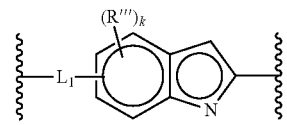

-continued
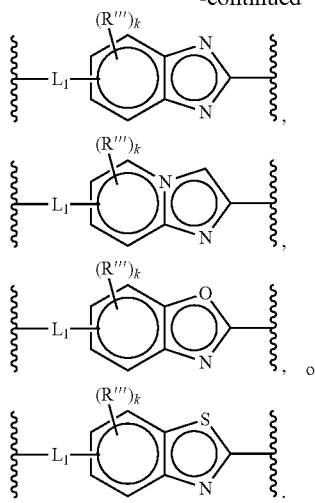
In certain embodiments, the moiety
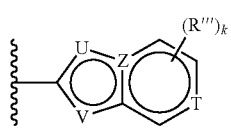
in Formula (IV), (V) and (VI) is
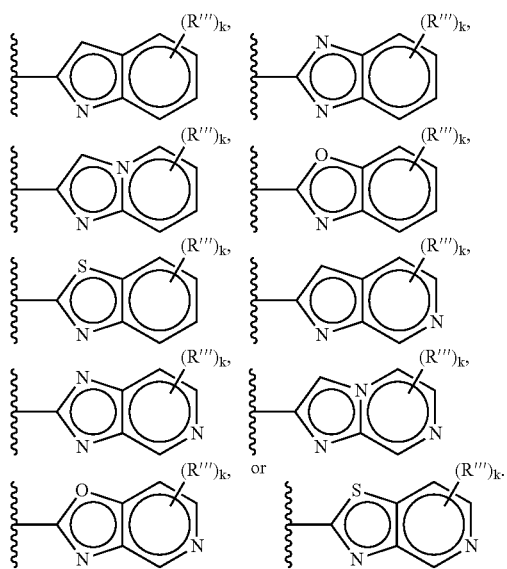
In certain embodiments, the moiety
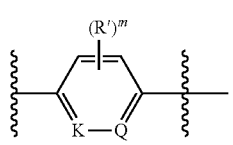
in Formulae (I)-(VI) is
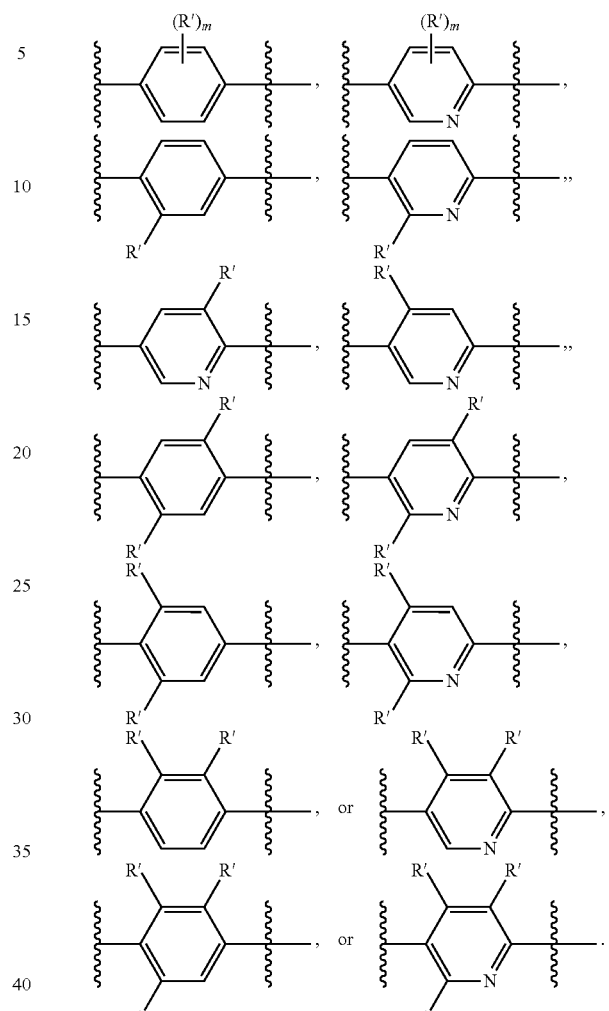
In certain embodiments, the moiety
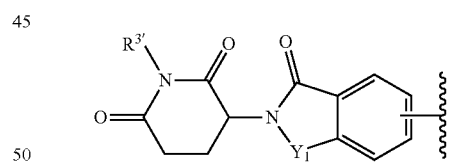
in Formula (I) and (IV) is
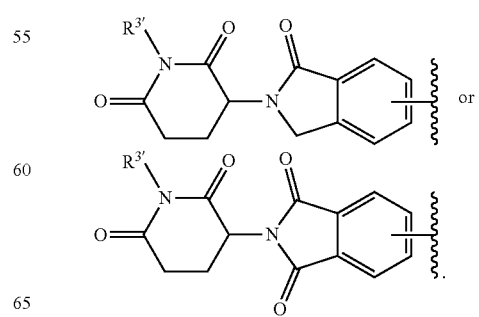

In certain embodiments, the moiety

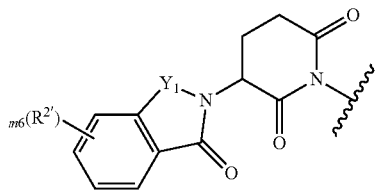

in Formula (II) and (V) is

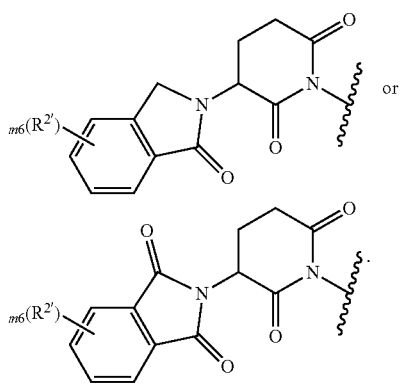

In one embodiment of the disclosure, L1 is a bond.

In one embodiment of the disclosure, L1 is —NH—, —O—, or —S—.

In one embodiment of the disclosure, L3 is a bond.

In one embodiment of the disclosure, L3 is —NH—, —O—, or —S—.

In one embodiment of the disclosure, L2 is a substituted or unsubstituted $C_{1-30}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is an unsubstituted $C_{1-30}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is a substituted or unsubstituted $C_{1-24}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is an unsubstituted $C_{1-24}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is a substituted or unsubstituted $C_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, L2 is an unsubstituted $C_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted $C_{1-6}$ alkyl or a nitrogen protecting group.

In certain embodiments, at least one chain atom of the hydrocarbon chain of L2 is independently replaced with —O—.

In certain embodiments, the chain of L2 comprises up to 50 consecutive covalently bonded atoms in length, excluding hydrogen atoms and substituents.

In certain embodiments, L2 comprises up to, for example 46, 45, 40, 35, 32, 30, 25, 23, 20, 15, 14, 12, 11, 10, 9, 8, 7, 6, 5, 3 consecutive covalently bonded atoms in length, excluding hydrogen atoms and substituents.

In certain embodiments, any of the atoms in L2 can be substituted. In certain embodiments, none of the atoms in the linker L2 are substituted. In certain embodiments, none of the carbon atoms in the linker are substituted.

In certain embodiments, L2 is a linker that contains an asymmetric carbon/stereocenter, i.e., an sp3 hybridized carbon atom bearing 4 different groups attached thereto. In certain embodiments, the compound comprising such an L2 group is enantiomerically enriched or substantially enantiomerically enriched. In certain embodiments, the compound comprising such an L2 group is enantiomerically pure. In certain embodiments, the compound comprising such an L2 group is racemic.

In certain embodiments, L2 comprises substituted or unsubstituted carbocyclylene, substituted or unsubstituted heterocyclylene, substituted or unsubstituted arylene, substituted or unsubstituted heteroarylene, or substituted or unsubstituted heteroalkylene, or combinations thereof. In certain embodiments, L2 is substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, L2 is a linker selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof.

Reference to L2 being a combination of at least two instances of the divalent moieties described herein refers to a linker consisting of at least one instance of a first divalent moiety and at least one instance of a second divalent moiety, wherein the first and second divalent moieties are the same or different and are within the scope of the divalent moieties described herein, and the instances of the first and second divalent moieties are consecutive covalently attached to each other. For example, when L2 is a combination of alkylene and heteroalkylene linkers, -alkylene-heteroalkylene-, -alkylene-(heteroalkylene)$_2$-, and -heteroalkylene-alkylene-heteroalkylene- are all within the scope of L2, wherein each instance of alkylene in any one of the linkers may be the same or different, and each instance of heteroalkylene in any one of the linkers may be the same or different.

In certain embodiments, L2 comprises at least one instance of substituted or unsubstituted alkylene, e.g., substituted or unsubstituted $C_{1-6}$ alkylene, substituted or unsubstituted $C_{1-2}$ alkylene, substituted or unsubstituted $C_{1-3}$ alkylene, substituted or unsubstituted $C_{3-4}$ alkylene, substituted or unsubstituted $C_{4-5}$ alkylene, substituted or unsubstituted $C_{5-6}$alkylene, substituted or unsubstituted $C_{3-6}$ alkylene, or substituted or unsubstituted $C_{4-6}$alkylene. Exemplary alkylene groups include unsubstituted alkylene groups such as methylene (—$CH_2$—), ethylene (—$(CH_2)_2$—), n-propylene (—$(CH_2)_3$—), n-butylene (—$(CH_2)_4$—), n-pentylene (—$(CH_2)_5$—), and n-hexylene (—$(CH_2)_6$—).

In certain embodiments, L2 comprises at least one instance of substituted or unsubstituted alkenylene, e.g., substituted or unsubstituted $C_{2-6}$ alkenylene, substituted or unsubstituted $C_{1-3}$ alkenylene, substituted or unsubstituted $C_{3-4}$ alkenylene, substituted or unsubstituted $C_{4-5}$ alkenylene or substituted or unsubstituted $C_{5-6}$ alkenylene.

In certain embodiments, L2 comprises at least one instance of substituted or unsubstituted alkynylene, e.g., substituted or unsubstituted $C_{2-6}$ alkynylene, substituted or unsubstituted $C_{2-3}$ alkynylene, substituted or unsubstituted $C_{3-4}$ alkynylene, substituted or unsubstituted $C_{4-5}$ alkynylene or substituted or unsubstituted $C_{5-6}$ alkynylene.

In certain embodiments, L2 comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$alkylene or substituted or unsubstituted hetero$C_{5-6}$alkylene. Exemplary heteroalkylene groups include unsubstituted heteroalkylene groups, such as —$(CH_2)_2$—$O(CH_2)_2$—, —$OCH_2$—, —$CH_2O$—, —$O(CH_2)_2$—, —$(CH_2)_2O$—, —$O(CH_2)_3$—, —$(CH_2)_3O$—, —$O(CH_2)_4$—, —$(CH_2)_4O$—, —$O(CH_2)_5$—, —$(CH_2)_5O$—, —$O(CH_2)_6$—, and —$O(CH_2)_6O$—, and amide groups (e.g., —NH—C(=O)— and —C(=O)NH—).

In certain embodiments, L2 comprises at least one instance of substituted or unsubstituted heteroalkenylene, e.g., substituted or unsubstituted hetero$C_{2-6}$alkenylene, substituted or unsubstituted hetero$C_{1-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, L2 comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$ alkynylene, substituted or unsubstituted hetero$C_{4-5}$alkynylene, or substituted or unsubstituted hetero$C_{5-6}$alkynylene.

In certain embodiments, L2 comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, L2 comprises at least one instance of substituted or unsubstituted heterocyclylene, e.g., substituted or unsubstituted 3-6 membered heterocyclylene, substituted or unsubstituted 3-4 membered heterocyclylene, substituted or unsubstituted 4-5 membered heterocyclylene, or substituted or unsubstituted 5-6 membered heterocyclylene. In certain embodiments, at least one chain atom of the hydrocarbon chain of L2 is independently replaced with a 5-8 membered heterocyclyl group with 1-4 ring heteroatoms selected from the group consisting of nitrogen, oxygen, and sulfur. In certain embodiments, at least one chain atom of the hydrocarbon chain of L2 is independently replaced with a 6-membered heterocyclyl group with 1-3 ring heteroatoms selected from the group consisting of nitrogen and oxygen. In certain embodiments, at least one chain atom of the hydrocarbon chain of L2 is independently replaced with piperidine, piperazine or morpholine.

In certain embodiments, L2 comprises at least one instance of substituted or unsubstituted arylene, e.g., substituted or unsubstituted phenylene. In certain embodiments, at least one chain atom of the hydrocarbon chain of L2 is independently replaced with an optionally substituted phenyl group.

In certain embodiments, L2 comprises at least one instance of substituted or unsubstituted heteroarylene, e.g., substituted or unsubstituted 5- to 6-membered heteroarylene.

In certain embodiments, L2 is an unsubstituted hydrocarbon chain, optionally wherein one or more chain atoms of the hydrocarbon chain are independently replaced with —$NR^{a1}$— and each instance of $R^{a1}$ is independently hydrogen, substituted or unsubstituted $C_{1-6}$ alkyl or a nitrogen protecting group, or optionally two instances of $R^{a1}$ are taken together with their intervening atoms to form a substituted or unsubstituted heterocyclic or substituted or unsubstituted heteroaryl ring. In certain embodiments, at least one instance of $R^{a1}$ is hydrogen. In certain embodiments, at least one instance of $R^{a1}$ is substituted or unsubstituted $C_{1-6}$ alkyl (e.g., substituted or unsubstituted methyl or ethyl). In certain embodiments, at least one instance of $R^{a1}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl or p-toluenesulfonamide (Ts)).

In certain embodiments, L2 is an optionally substituted $C_{1-45}$ hydrocarbon chain, optionally wherein one or more chain atoms of the hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group. In certain embodiments, L2 is an unsubstituted $C_{1-45}$ hydrocarbon chain, optionally wherein one or more chain atoms of the hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group. In certain embodiments, L2 is an optionally substituted $C_{1-24}$ hydrocarbon chain, optionally wherein one or more chain atoms of the hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group. In certain embodiments, L2 is an unsubstituted $C_{1-24}$ hydrocarbon chain, optionally wherein one or more chain atoms of the hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group. In certain embodiments, L2 is an optionally substituted $C_{1-20}$ hydrocarbon chain, optionally wherein one or more chain atoms of the hydrocarbon chain are independently replaced with —C(=O)—, —O—, —$NR^{a1}$—, —S— or a cyclic moiety, wherein $R^{a1}$ is independently hydrogen, substituted or unsubstituted $C_{1-6}$ alkyl, or a nitrogen protecting group. In certain embodiments, L2 is an unsubstituted $C_{1-20}$ hydrocarbon chain, optionally wherein one or more chain atoms of the hydrocarbon chain are independently replaced with —C(=O)—, —O—, —NR$^{a1}$—, —S— or a cyclic moiety, wherein R$^{a1}$ is independently hydrogen, substituted or unsubstituted C$_{1-6}$ alkyl or a nitrogen protecting group. In certain embodiments, L2 is an optionally substituted C$_{1-30}$ hydrocarbon chain, wherein one or more chain atoms of the hydrocarbon chain are independently replaced with —O— or —NR$^{a1}$—. In certain embodiments, L2 is an unsubstituted C$_{1-30}$ hydrocarbon chain, wherein one or more chain atoms of the hydrocarbon chain are independently replaced with —O— or —NR$^{a1}$—. In certain embodiments, L2 is an unsubstituted C$_{1-30}$ hydrocarbon chain, wherein at least one chain atom of the hydrocarbon chain is independently replaced with —O—. In certain embodiments, L2 is an unsubstituted C$_{1-26}$ hydrocarbon chain, wherein one or more chain atoms of the hydrocarbon chain are independently replaced with —C(=O)—, —O— or —NR$^{a1}$—. In certain embodiments, L2 is an unsubstituted C$_{1-20}$ hydrocarbon chain, wherein one or more chain atoms of the hydrocarbon chain are independently replaced with —O—. In certain embodiments, L2 is an unsubstituted C$_{5-26}$ hydrocarbon chain, wherein one or more chain atoms of the hydrocarbon chain are independently replaced with —C(=O)—, —O— or —NR$^{a1}$—. In certain embodiments, L2 is an unsubstituted C$_{5-26}$ hydrocarbon chain, wherein one or more chain atoms of the hydrocarbon chain are independently replaced with —O—. In certain embodiments, L2 is an unsubstituted C$_{5-20}$ hydrocarbon chain, wherein one or more chain atoms of the hydrocarbon chain are independently replaced with —C(=O)—, —O— or —NR$^{a1}$—. In certain embodiments, L2 is an unsubstituted C$_{5-20}$ hydrocarbon chain, wherein one or more chain atoms of the hydrocarbon chain are independently replaced with —O—, or —NR$^{a1}$—. In certain embodiments, L2 is an unsubstituted C$_{5-15}$ hydrocarbon chain, wherein one or more chain atoms of the hydrocarbon chain are independently replaced with —C(=O)—, —O— or —NR$^{a1}$—. In certain embodiments, L2 is an unsubstituted C$_{15-20}$ hydrocarbon chain, wherein one or more chain atoms of the hydrocarbon chain are independently replaced with —C(=O)—, —O— or —NR$^{a1}$—. In certain embodiments, L2 is an unsubstituted C$_{20-25}$ hydrocarbon chain, wherein one or more chain atoms of the hydrocarbon chain are independently replaced with —C(=O)—, —O— or —NR$^{a1}$—. In certain embodiments, L2 is a substituted or unsubstituted C$_{1-45}$ hydrocarbon chain. In certain embodiments, L2 is a substituted or unsubstituted C$_{5-40}$ hydrocarbon chain. In certain embodiments, one or more chain atoms of the hydrocarbon chain of L2 are independently replaced with —C(=O)—, —O—, —S—, —NR$^{a1}$—, —N= or =N—. In certain embodiments, one or more chain atoms of the hydrocarbon chain of L2 are independently replaced with —C(=O)—, —O— or —NR$^{a1}$—, wherein R$^{a1}$ is independently hydrogen, substituted or unsubstituted C$_{1-6}$ alkyl or a nitrogen protecting group. In certain embodiments, L2 is an unsubstituted C$_{1-26}$ hydrocarbon chain, wherein at least one chain atom of the hydrocarbon chain is independently replaced with —O—. The cyclic moiety herein refers to a cycloalkylene or a heterocycloalkylene, such as

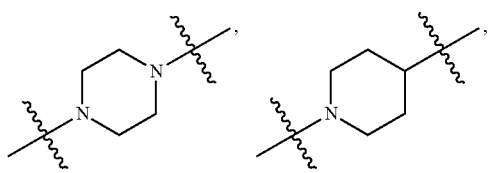

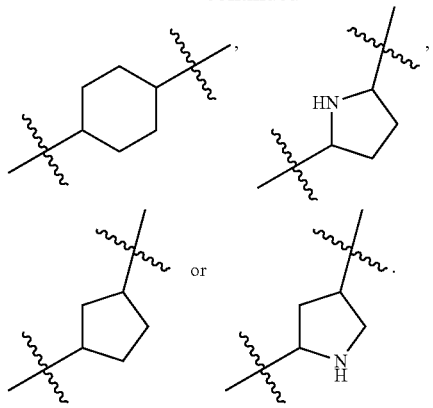

In certain embodiments, L2 is an all-carbon, substituted or unsubstituted C$_{1-45}$ hydrocarbon chain. In certain embodiments, L2 is an all-carbon, substituted or unsubstituted C$_{1-30}$ hydrocarbon chain. In certain embodiments, L2 is an all-carbon, substituted or unsubstituted C$_{1-26}$ hydrocarbon chain. In certain embodiments, L2 is an all-carbon, substituted or unsubstituted C$_{1-24}$ hydrocarbon chain. In certain embodiments, L2 is an all-carbon, substituted or unsubstituted C$_{1-20}$ hydrocarbon chain. In certain embodiments, L2 is an all-carbon, substituted or unsubstituted C$_{1-20}$ hydrocarbon chain.

In certain embodiments, L2 is

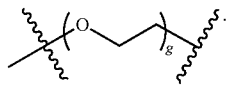

In certain embodiments, L2 includes the moiety, wherein g is 1, 2, 3, 4, 5, or 6. In certain embodiments, g is 1. In certain embodiments, g is 2. In certain embodiments, g is 3. In certain embodiments, g is 4. In certain embodiments, g is 5. In certain embodiments, g is 6.

In certain embodiments, L2 includes the moiety —NHC(=O)—.

In certain embodiments, L2 includes the moiety —NH—.

Examples of L2 of the disclosure include, but are not limited to:

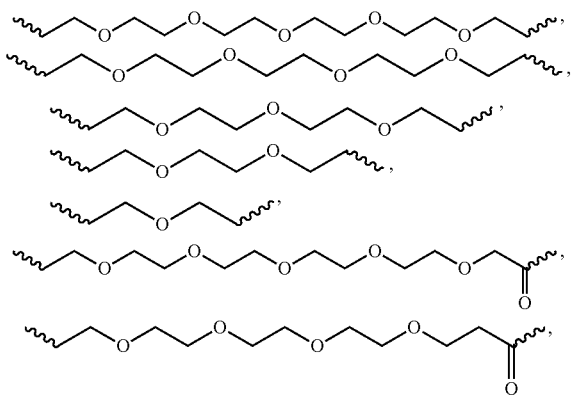

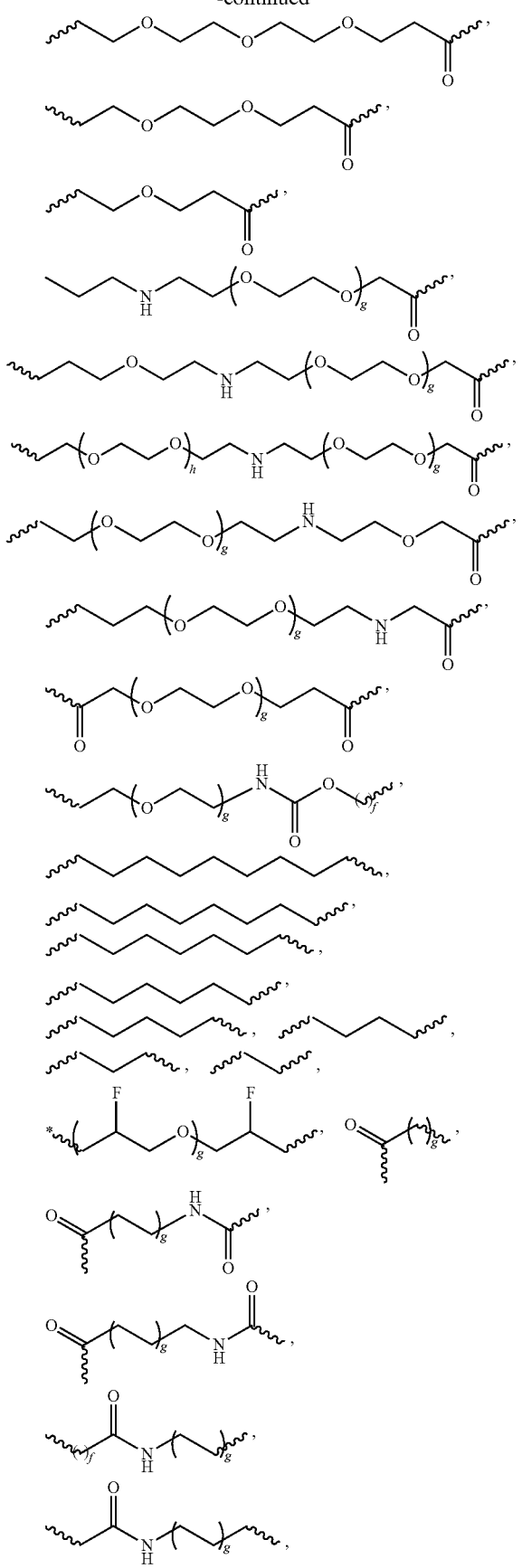
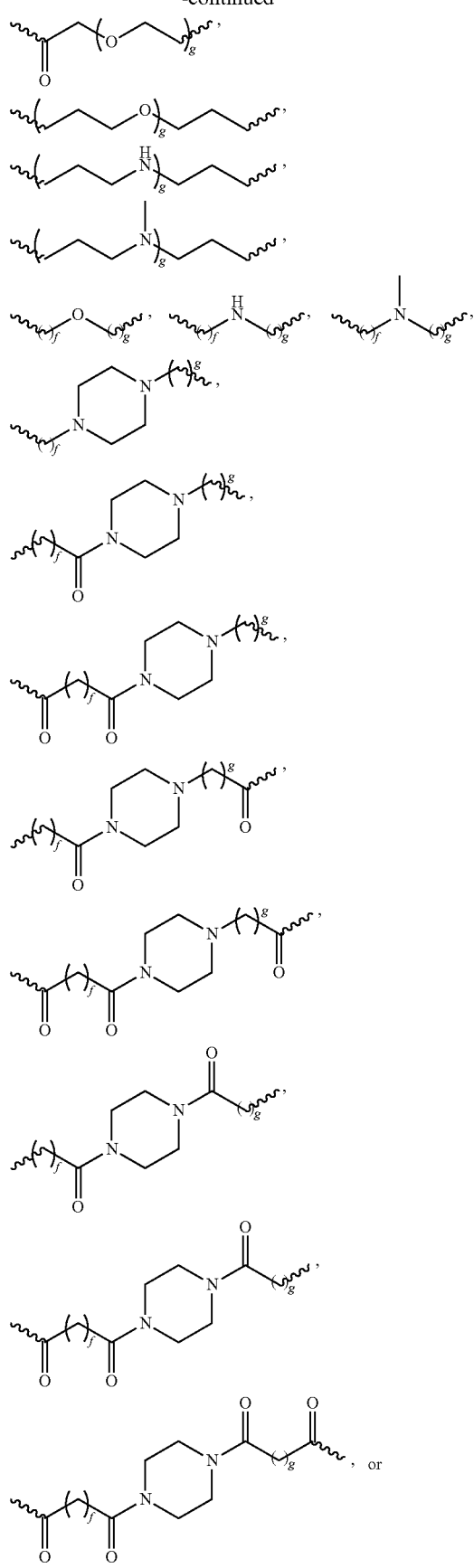

-continued
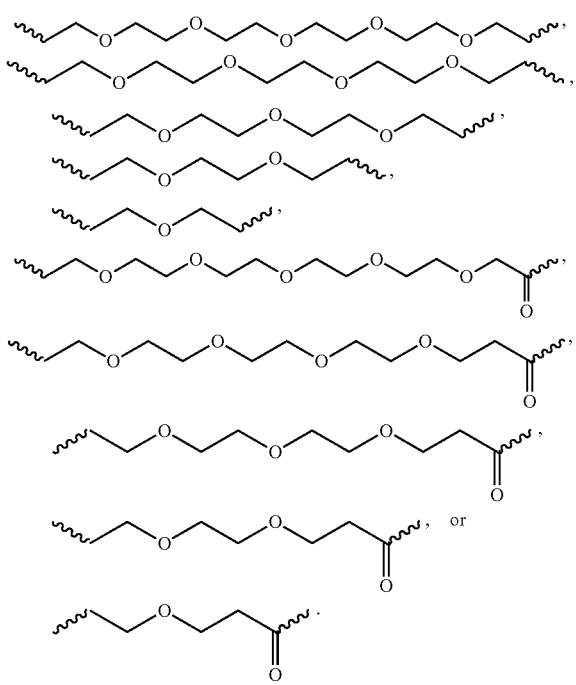
In certain embodiments, L2 is of the formula:
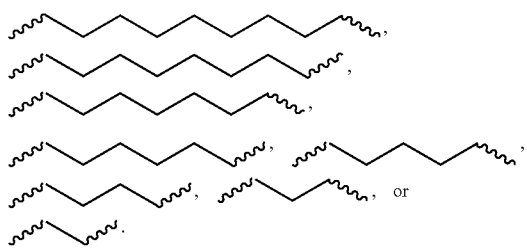
In certain embodiments, L2 is of the formula:
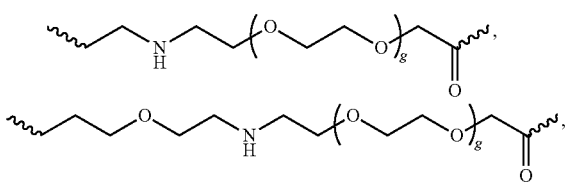
In certain embodiments, L2 is of the formula:
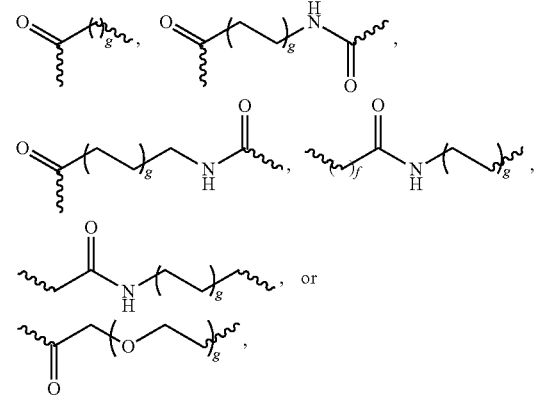
wherein g is 1, 2, 3, 4 or 5; h is 0, 1, 2, 3, 4 or 5; and f is 1, 2, 3, 4, 5, 6, 7 or 8.
In certain embodiments, L2 is of the formula:
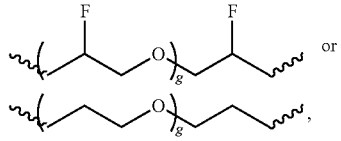
wherein g is 1, 2, 3, 4, 5, 6, 7 or 8; and f is 1, 2, 3, 4, 5, 6, 7 or 8.
In certain embodiments, L2 is of the formula:
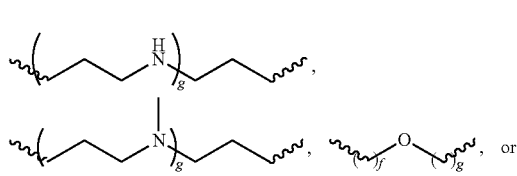
wherein g is 1, 2, 3, 4, 5, 6, 7 or 8.
In certain embodiments, L2 is of the formula:

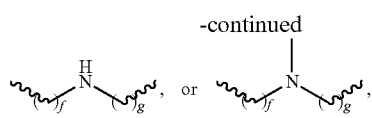
wherein g is 1, 2, 3, 4, 5, 6, 7 or 8; and f is 1, 2, 3, 4, 5, 6, 7 or 8.
In certain embodiments, L2 is of the formula:
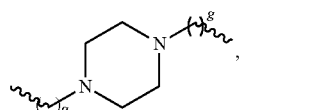
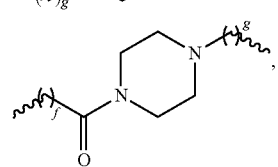
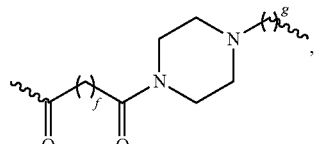
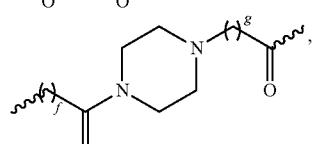
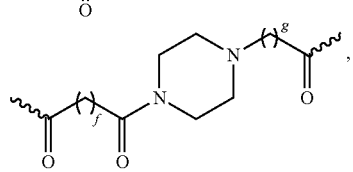
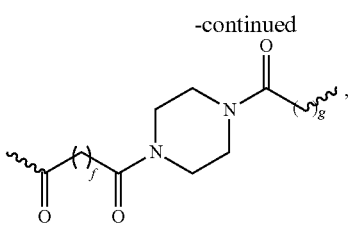
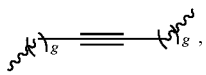, or
wherein g is 1, 2, 3, 4, 5, 6, 7 or 8; and f is 1, 2, 3, 4, 5, 6, 7 or 8.
In certain embodiments, L2 is of the formula:
wherein g is 1, 2, 3, 4, 5, 6, 7 or 8.
In certain embodiments, the compound of the disclosure is of any one of the structure as follows,
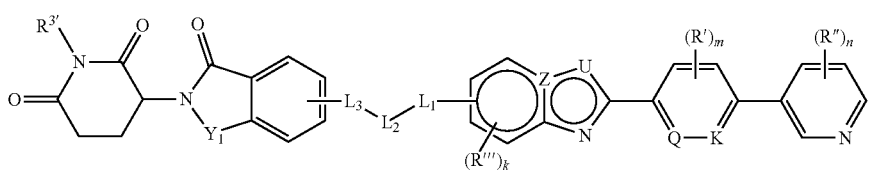
I-1
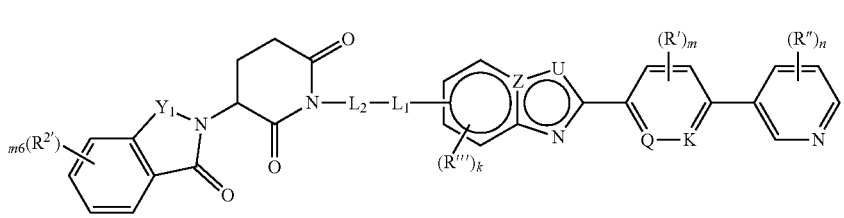
II-1

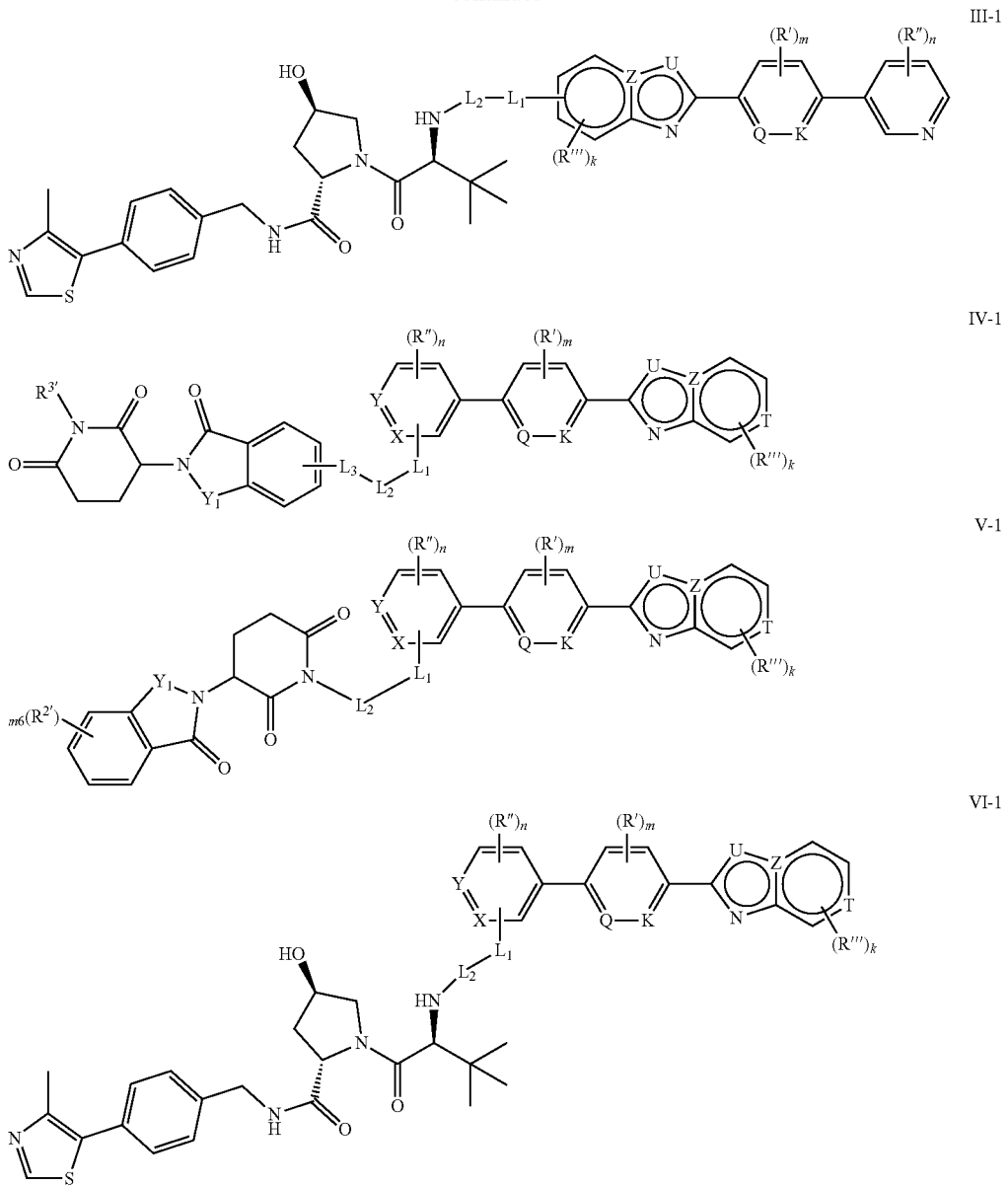

wherein, in Formula I-1, R³' is H or C₁₋₆ alkyl; Y₁ is CH₂ or

L₁ is a bond, —NR—, —O—, or —S—, wherein R is hydrogen, optionally substituted acyl, optionally substituted alkyl or a nitrogen protecting group; L3 is a bond, —NR—, —O—, or —S—, wherein R is hydrogen, optionally substituted acyl, optionally substituted alkyl or a nitrogen protecting group; L2 is a substituted or unsubstituted $C_{1-50}$ hydrocarbon chain; Z is C or N; U is O, S or CH; where Z and U are not heteroatoms at the same time; Q is CH or N; K is CH or N; where Q and K are not N at the same time; each occurrence of R''' is independently selected from the group consisting of H, OH, NH₂, C₁₋₆ alkyl, C₁₋₆ alkylamino, C₁₋₆ alkoxy and halogen; k is 0, 1, 2 or 3; each occurrence of R' is independently selected from the group consisting of H, halogen, OH, C₁₋₆ alkyl, C₁₋₆ haloalkyl and C₁₋₆ alkoxy; m is 0, 1, 2, 3 or 4; each occurrence of R'' is independently selected from the group consisting of H, halo, OH, NH₂, C₁₋₆ alkyl, C₁₋₆ alkoxy, C₁₋₆ haloalkyl, C₁₋₆ alkylamino, C₃₋₆ cycloalkyl, C₃₋₆ cycloalkylamino and C₃₋₆ heterocycloalkyl; n is 0, 1 or 2;

in Formula II-1, each occurrence of R²' is independently selected from the group consisting of H, OH, C₁₋₆ alkyl, C₁₋₆ alkoxy, C₁₋₆ alkylamino and NH₂; m6 is 0, 1, 2, 3 or 4; Y₁ is CH₂ or

$L_1$ is a bond, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; where Z and U are not heteroatoms at the same time; Q is CH or N; K is CH or N; where Q and K are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2;

in Formula III-1, L1 is a bond, —NR—, —O—, or —S—, wherein R is hydrogen, optionally substituted acyl, optionally substituted alkyl or a nitrogen protecting group; L3 is a bond, —NR—, —O—, or —S—, wherein R is hydrogen, optionally substituted acyl, optionally substituted alkyl or a nitrogen protecting group; L2 is a substituted or unsubstituted $C_{1-50}$ hydrocarbon chain; Z is C or N; U is O, S or CH; where Z and U are not heteroatoms at the same time; Q is CH or N; K is CH or N; where Q and K are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2;

in Formula IV-1, $R^{3'}$ is H or $C_{1-6}$ alkyl; $Y_1$ is $CH_2$ or

$L_1$ is a bond, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; T is CH or N; where only one of U, Z and T is heteroatom; Q is CH or N; K is CH or N; where Q and K are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; X is $CR^6$ or N; Y is $CR^6$ or N; where one of X and Y is N, while the other is $CR^6$; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula V-1, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

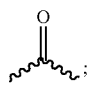

$L_1$ is a bond, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; T is CH or N; where only one of U, Z and T is heteroatom; Q is CH or N; K is CH or N; where Q and K are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; X is $CR^6$ or N; Y is $CR^6$ or N; where one of X and Y is N, while the other is $CR^6$; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula VI-1, $L_1$ is a bond, —NR—, —O—, or —S—, wherein R is hydrogen, optionally substituted acyl, optionally substituted alkyl or a nitrogen protecting group; $L_3$ is a bond, —NR—, —O—, or —S—, wherein R is hydrogen, optionally substituted acyl, optionally substituted alkyl or a nitrogen protecting group; $L_2$ is a substituted or unsubstituted $C_{1-50}$ hydrocarbon chain; Z is C or N; U is O, S or CH; T is CH or N; where only one of U, Z and T is heteroatom; Q is CH or N; K is CH or N; where Q and K are not N at the same time; each occurrence of R''' is independently selected from the group consisting of H, OH, $NH_2$, $C_{1-6}$ alkyl, $C_{1-6}$ alkylamino, $C_{1-6}$ alkoxy and halogen; k is 0, 1, 2 or 3; each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4; each occurrence of R'' is independently selected from the group consisting of H, halo, OH, $NH_2$, $C_{1-6}$ alkyl, $C_{1-6}$ alkoxy, $C_{1-6}$ haloalkyl, $C_{1-6}$ alkylamino, $C_{3-6}$ cycloalkyl, $C_{3-6}$ cycloalkylamino and $C_{3-6}$ heterocycloalkyl; n is 0, 1 or 2; X is $CR^6$ or N; Y is $CR^6$ or N; where one of X and Y is N, while the other is $CR^6$; $R^6$ is independently selected from the group consisting of H, $NH_2$, $C_{1-6}$ alkyl and $C_{1-6}$ alkoxy, wherein $NH_2$, $C_{1-6}$ alkyl or $C_{1-6}$ alkoxy is optionally substituted by 1 to 3 of $C_{1-3}$ alkyl, $C_{3-6}$ cycloalkyl and/or halo.

In certain embodiments, the compound of Formula I-1 is of the following Formula 1, 5, 6, 8, 10 or 13, An embodiment of the disclosure is the compound of Formula 1, wherein R' is H, $C_{1-3}$ haloalkyl or $C_{1-3}$ alkoxy, preferably H, $CF_3$, $CCl_3$, methoxy or ethoxy, more preferably H, CF or methoxy.

Formula 1

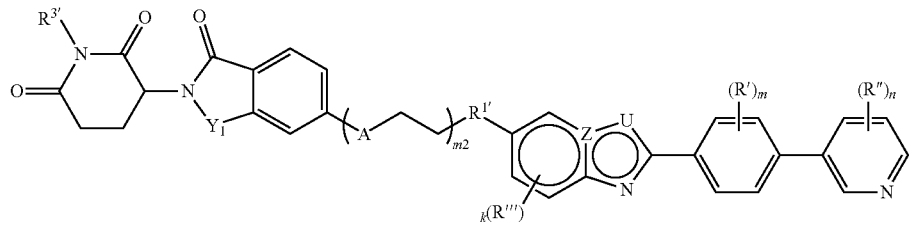

Formula 5

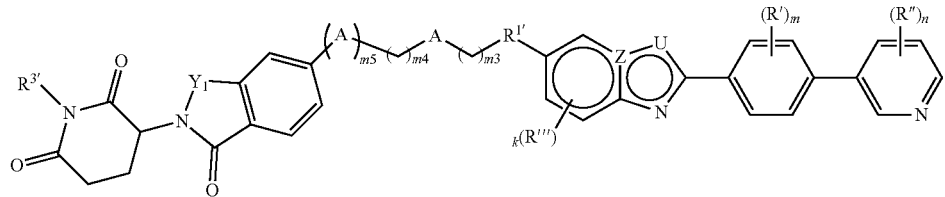

Formula 6

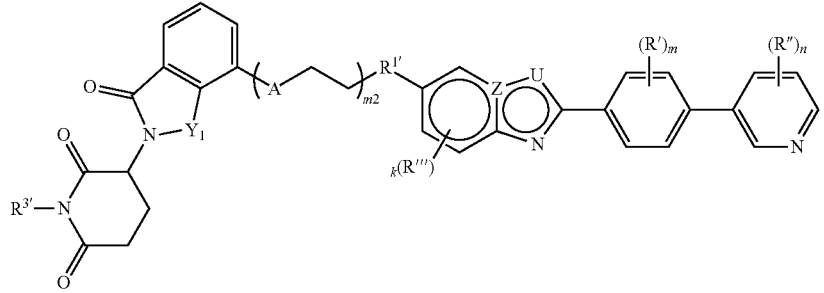

Formula 8

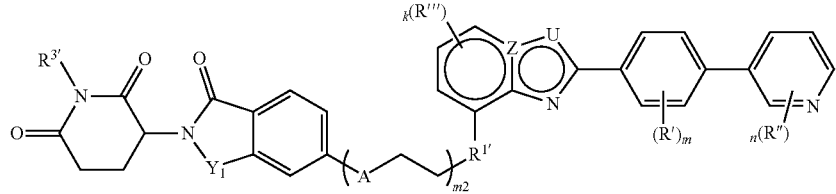

Formula 10

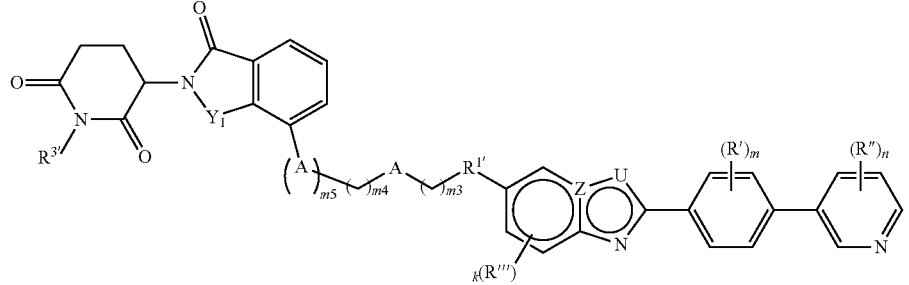

Formula 13

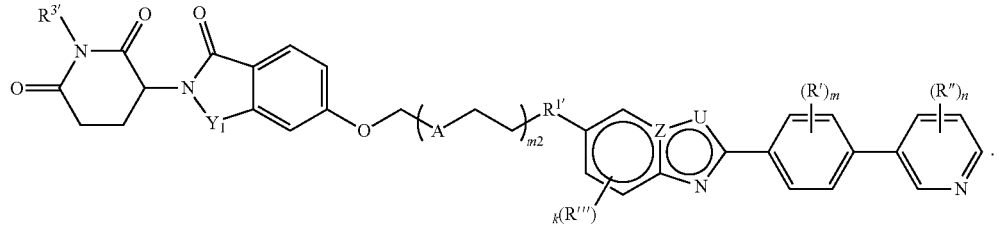

An embodiment of the disclosure is the compound of Formula 1, wherein m is 0, 1, 2, 3 or 4, preferably 0 or 1.

An embodiment of the disclosure is the compound of Formula 1, wherein R" is H, halo, OH, NH$_2$, C$_{1-3}$ alkoxy, C$_{1-3}$ alkylamino, C$_{3-5}$ cycloalkyl, C$_{3-5}$ cycloalkylamino and C$_{3-5}$ heterocycloalkyl, preferably H, F, Cl, NH$_2$, methoxy, ethoxy, methylamino, dimethylamino, ethylamino, diethylamino, cyclopropyl, cyclobutyl or cyclopentyl, more preferably H, F, dimethylamino or cyclopropyl.

An embodiment of the disclosure is the compound of Formula 1, wherein n is 0, 1 or 2, preferably 0 or 1.

An embodiment of the disclosure is the compound of Formula 1, wherein R' is H, OH or halogen, preferably H, OH, F or Cl, more preferably H.

An embodiment of the disclosure is the compound of Formula 1, wherein k is 0, 1, 2 or 3, preferably 0 or 1.

An embodiment of the disclosure is the compound of Formula 1, wherein R''' is O, NH,

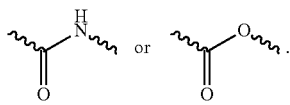

An embodiment of the disclosure is the compound of Formula 1, wherein A is O, NH,

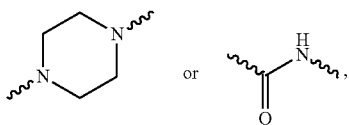

preferably O or

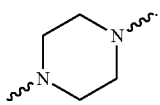

An embodiment of the disclosure is the compound of Formula 1, wherein m2 is 2, 3, 4 or 6, preferably 2 or 6.

An embodiment of the disclosure is the compound of Formula 1, wherein R$^{3'}$ is H or C$_{1-3}$ alkyl, preferably H or methyl, more preferably H.

An embodiment of the disclosure is the compound of Formula 1 having the structure as shown in Formula 1-1, In Formula 1-1, R$^{3'}$ is H or C$_{1-3}$ alkyl; Y$_1$ is CH$_2$ or

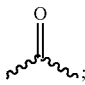

A is O, NH,

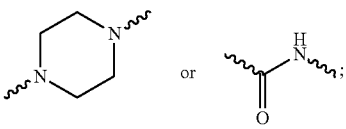

m2 is 1, 2, 3, 4, 5, 6 and 7; R$^{1'}$ is O, NH,

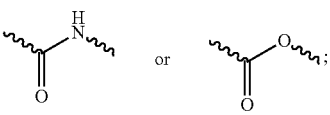

U is O, S or CH; Z is C or N; where U and Z are not heteroatoms at the same time; R' is H, C$_{1-3}$ haloalkyl or C$_{1-3}$ alkoxy; R" is H, F, Cl, OH, NH$_2$, C$_{1-3}$ alkoxy, methylamino, dimethylamino, diethylamino or cyclopropylamino; n is 0, 1 or 2.

An embodiment of the disclosure is the compound of Formula 1-1, wherein m2 is 2, 3, 4 or 6, preferably 2 or 6.

An embodiment of the disclosure is the compound of Formula 1-1, wherein R$^{3'}$ is H or methyl.

An embodiment of the disclosure is the compound of Formula 1-1, wherein A is O or

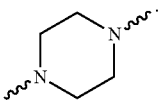

An embodiment of the disclosure is the compound of Formula 1-1, wherein R$^{1'}$ is O, NH or

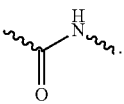

An embodiment of the disclosure is the compound of Formula 1-1, wherein Z is N, U is CH.

Formula 1-1

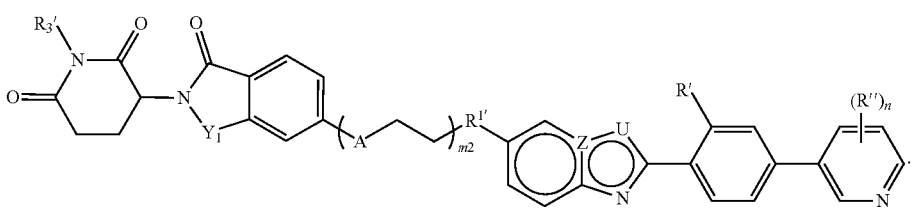

An embodiment of the disclosure is the compound of Formula 1-1, wherein Z is C, U is S or O.

An embodiment of the disclosure is the compound of Formula 1-1, wherein R" is H, F, Cl, OH, NH₂, methoxy, methylamino, dimethylamino, diethylamino, cyclopropyl or cyclopropylamino, preferably H, F, methylamino, dimethylamino or cyclopropylamino.

An embodiment of the disclosure is the compound of Formula 1-1, wherein R' is H, C$_{1-3}$ fluoroalkyl, methoxy or ethoxy, preferably R' is H, methoxy or CF₃.

An embodiment of the disclosure is the compound of Formula 5, wherein R$^{3'}$ is H or C$_{1-3}$ alkyl, preferably H or methyl.

An embodiment of the disclosure is the compound of Formula 5, wherein R" is H, halo, OH, NH₂, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, OH, NH₂, methyl, methoxy, CF₃, CCl₃, methylamino, cyclopropyl or dimethylamino, more preferably H, F, CF₃, cyclopropyl, cyclopropylamino or dimethylamino.

An embodiment of the disclosure is the compound of Formula 5, wherein n is 0, 1 or 2, preferably 0 or 1.

An embodiment of the disclosure is the compound of Formula 5 having the structure as shown in Formula 5-1, Formula 5-1

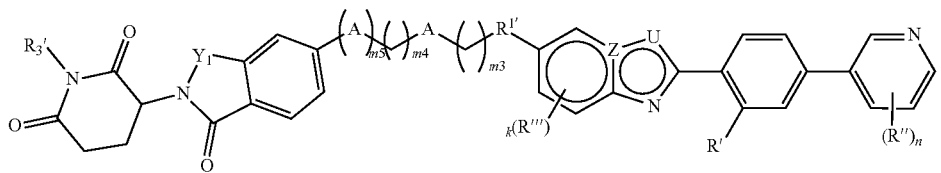

An embodiment of the disclosure is the compound of Formula 5, wherein A is O, NH or

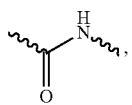

preferably O.

An embodiment of the disclosure is the compound of Formula 5, wherein m4 is 0, 1, 2, or 3, preferably 0 or 3.

An embodiment of the disclosure is the compound of Formula 5, wherein m5 is 0, 1, 2 or 3, preferably 0 or 1.

An embodiment of the disclosure is the compound of Formula 5, wherein m3 is 1, 2, 3, 4, 5 or 6, preferably 3 or 5.

An embodiment of the disclosure is the compound of Formula 5, wherein R$^{1'}$ is O, NH or

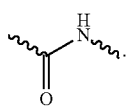

An embodiment of the disclosure is the compound of Formula 5, wherein R'" is H, OH, C$_{1-3}$ alkyl, C$_{1-3}$ alkoxy or halogen, preferably H, methyl, methoxy or F, more preferably H.

An embodiment of the disclosure is the compound of Formula 5, wherein k is 0, 1, 2 or 3, preferably 0 or 1.

An embodiment of the disclosure is the compound of Formula 5, wherein Z is C, U is O or S.

An embodiment of the disclosure is the compound of Formula 5, wherein Z is N, U is CH.

An embodiment of the disclosure is the compound of Formula 5, wherein R' is H, halogen, OH, C$_{1-3}$ alkyl, C$_{1-3}$ haloalkyl or C$_{1-3}$ alkoxy, preferably H, F, CF₃, CCl₃, methyl or methoxy, more preferably H or CF₃.

An embodiment of the disclosure is the compound of Formula 5, wherein m is 0, 1, 2 or 3, preferably 0 or 1.

In Formula 5-1, R$^{3'}$ is H or C$_{1-3}$ alkyl; Y₁ is CH₂ or

A is O, NH,

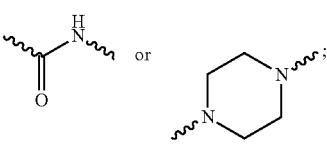

m5 is 0 or 1; m4 is 0, 1, 2, 3 or 4; m3 is 1, 2, 3, 4, 5 or 6; R$^{1'}$ is O, NH,

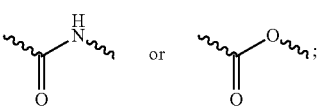

Z is C or N; U is O, S or CH; where Z and U are not heteroatoms at the same time; R'" is H, OH, C$_{1-3}$ alkyl, C$_{1-3}$ alkoxy or halogen; R' is H, halogen, OH, C$_{1-3}$ alkyl, C$_{1-3}$ haloalkyl or C$_{1-3}$ alkoxy; R" is H, halo, OH, NH₂, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino and C$_{3-5}$ heterocycloalkyl; n is 0, 1 or 2.

An embodiment of the disclosure is the compound of Formula 5-1, wherein A is O.

An embodiment of the disclosure is the compound of Formula 5-1, wherein m5 is 0 or 1.

An embodiment of the disclosure is the compound of Formula 5-1, wherein m4 is 0 or 3.

An embodiment of the disclosure is the compound of Formula 5-1, wherein m3 is 3, 5.

An embodiment of the disclosure is the compound of Formula 5-1, wherein R$^{1'}$ is O, NH or

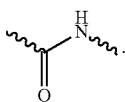

An embodiment of the disclosure is the compound of Formula 5-1, wherein Z is C, U is O or S.

An embodiment of the disclosure is the compound of Formula 5-1, wherein Z is N, U is CH.

An embodiment of the disclosure is the compound of Formula 5-1, wherein R' is H, halogen, $C_{1-3}$ alkyl, $C_{1-3}$ fluoroalkyl or $C_{1-3}$ alkoxy, preferably H, methyl, $CF_3$, methyl or methoxy, more preferably H or $CF_3$.

An embodiment of the disclosure is the compound of Formula 5-1, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, $CF_3$, amino, methylamino, dimethylamino, cyclopropyl or cyclopropylamino, more preferably H, F, $CF_3$, dimethylamino, cyclopropylamino or cyclopropyl.

An embodiment of the disclosure is the compound of Formula 6, wherein $R^{3'}$ is H or $C_{1-3}$ alkyl, preferably H or methyl.

An embodiment of the disclosure is the compound of Formula 6, wherein A is O, NH or

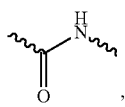

preferably O or NH.

An embodiment of the disclosure is the compound of Formula 6, wherein m2 is 1, 2, 3, 4, 5, 6 or 7, preferably 2 or 6.

An embodiment of the disclosure is the compound of Formula 6, wherein $R^{1'}$ is O, NH or

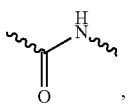

preferably O or NH.

An embodiment of the disclosure is the compound of Formula 6, wherein Z is C or N, and U is O, S or CH, where Z and U are not heteroatoms at the same time; preferably Z is C and U is S.

An embodiment of the disclosure is the compound of Formula 6, wherein R'" is H, OH, $C_{1-3}$ alkyl, $C_{1-3}$ alkoxy or halogen, preferably H, methyl, methoxy or F, more preferably H.

An embodiment of the disclosure is the compound of Formula 6, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 6, wherein m is 0, 1, 2 or 3, preferably 0 or 1.

An embodiment of the disclosure is the compound of Formula 6, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, cyclopropyl, cyclopropylamino or dimethylamino, more preferably H, F, $CF_3$, dimethylamino, cyclopropyl or cyclopropylamino.

An embodiment of the disclosure is the compound of Formula 6, wherein n is 0 or 1.

An embodiment of the disclosure is the compound of Formula 6 having the structure as shown in Formula 6-1, Formula 6-1

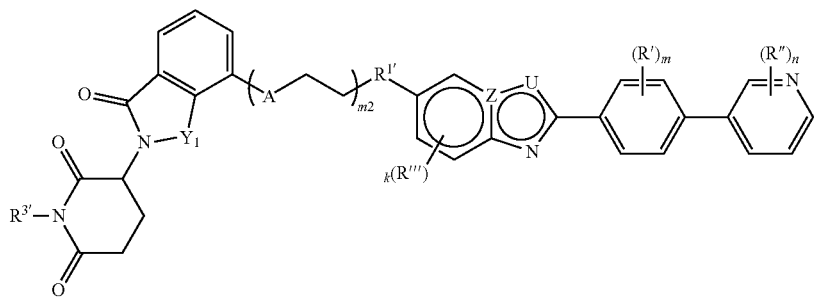

in Formula 6-1, $R^{3'}$ is H or $C_{1-3}$ alkyl; $Y_1$ is $CH_2$ or

A is O, NH,

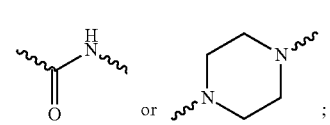

m2 is 1, 2, 3, 4, 5, 6 or 7; $R^{1'}$ is O, NH,

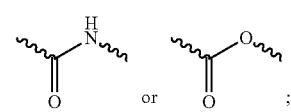

R'" is H, OH, $C_{1-3}$ alkyl, $C_{1-3}$ alkoxy or halogen; k is 0, 1, 2 or 3; Z is C or N; U is O, S or CH; where Z and U are not heteroatoms at the same time; R' is H, halogen, OH, $C_{1-3}$ alkyl, $C_{1-3}$ haloalkyl or $C_{1-3}$ alkoxy; m is 0, 1, 2 or 3; R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; n is 0, 1 or 2.

An embodiment of the disclosure is the compound of Formula 6-1, wherein $R^3$ is H or methyl.

An embodiment of the disclosure is the compound of Formula 6-1, wherein A is O or NH.

An embodiment of the disclosure is the compound of Formula 6-1, wherein m2 is 2 or 6.

An embodiment of the disclosure is the compound of Formula 6-1, wherein $R^{1'}$ is O, or NH.

An embodiment of the disclosure is the compound of Formula 6-1, wherein R' is H or $CF_3$.

An embodiment of the disclosure is the compound of Formula 6-1, wherein m is 0, 1, 2 or 3, preferably 0 or 1.

An embodiment of the disclosure is the compound of Formula 6-1, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, $CF_3$, methoxy, methyl, dimethylamino, cyclopropyl, cyclopropylamino or methylamino, more preferably H, $CF_3$, F, dimethylamino, cyclopropyl or cyclopropylamino, most preferably H, dimethylamino, cyclopropyl or cyclopropylamino.

An embodiment of the disclosure is the compound of Formula 6-1, wherein n is 0 or 1.

An embodiment of the disclosure is the compound of Formula 6-1, wherein R" substitutes at the adjacent position to the N atom.

An embodiment of the disclosure is the compound of Formula 8, wherein $R^{3'}$ is H or $C_{1-3}$ alkyl, preferably H or methyl.

An embodiment of the disclosure is the compound of Formula 8, wherein $Y_1$ is $CH_2$ or preferably $CH_2$.

An embodiment of the disclosure is the compound of Formula 8, wherein A is O, NH, preferably O.

An embodiment of the disclosure is the compound of Formula 8, wherein m2 is 1, 2, 3 or 4, preferably 2.

An embodiment of the disclosure is the compound of Formula 8, wherein $R^{1'}$ is O, NH, preferably O.

An embodiment of the disclosure is the compound of Formula 8, wherein R''' is H, OH, $C_{1-3}$ alkyl, $C_{1-3}$ alkoxy or halogen, preferably H, methyl, methoxy or F, more preferably H.

An embodiment of the disclosure is the compound of Formula 8, wherein k is 0 or 1.

An embodiment of the disclosure is the compound of Formula 8, wherein Z is C or N; U is O, S or CH; where Z and U are not heteroatoms at the same time; preferably Z is N and U is CH; preferably Z is C and U is S.

An embodiment of the disclosure is the compound of Formula 8, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 8, wherein m is 0, 1 or 2.

An embodiment of the disclosure is the compound of Formula 8, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 8, wherein n is 0, 1 or 2.

An embodiment of the disclosure is the compound of Formula 8 is

An embodiment of the disclosure is the compound of Formula 10, wherein $R^{3'}$ is H or $C_{1-3}$ alkyl, preferably H or methyl.

An embodiment of the disclosure is the compound of Formula 10, wherein $Y_1$ is $CH_2$ or preferably $CH_2$.

An embodiment of the disclosure is the compound of Formula 10, wherein A is O, NH, preferably

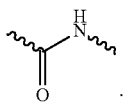

An embodiment of the disclosure is the compound of Formula 10, wherein m5 is 0 or 1.

An embodiment of the disclosure is the compound of Formula 10, wherein m4 is 0 or 1.

An embodiment of the disclosure is the compound of Formula 10, wherein m3 is 1, 2, 3, 4 or 5, preferably 4.

An embodiment of the disclosure is the compound of Formula 10, wherein $R^{1'}$ is O, NH,

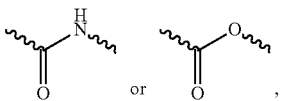

preferably O.

An embodiment of the disclosure is the compound of Formula 10, wherein R''' is H, OH, $C_{1-3}$ alkyl, $C_{1-3}$ alkoxy or halogen, preferably H, methyl, methoxy or F, more preferably H.

An embodiment of the disclosure is the compound of Formula 10, wherein k is 0 or 1.

An embodiment of the disclosure is the compound of Formula 10, wherein Z is C, U is S or O.

An embodiment of the disclosure is the compound of Formula 10, wherein Z is N, U is CH.

An embodiment of the disclosure is the compound of Formula 10, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 10, wherein m is 0 or 1.

An embodiment of the disclosure is the compound of Formula 10, wherein R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, cyclopropyl, cyclopropylamino or dimethylamino, more preferably H, F or $CF_3$.

An embodiment of the disclosure is the compound of Formula 10, wherein n is 0 or 1.

An embodiment of the disclosure is the compound of Formula 13, wherein $R^{3'}$ is H or $C_{1-3}$ alkyl, preferably H or methyl.

An embodiment of the disclosure is the compound of Formula 13, wherein $Y_1$ is $CH_2$ or

preferably $CH_2$.

An embodiment of the disclosure is the compound of Formula 13, wherein A is O, NH,

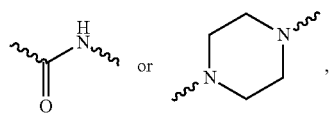

preferably

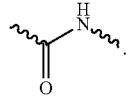

An embodiment of the disclosure is the compound of Formula 13, wherein m2 is 1, 2, 3 or 4, preferably 1.

An embodiment of the disclosure is the compound of Formula 13, wherein $R^{1'}$ is O, NH,

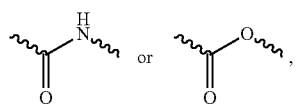

preferably NH.

An embodiment of the disclosure is the compound of Formula 13, wherein R''' is H, OH, $C_{1-3}$ alkyl, $C_{1-3}$ alkoxy or halogen, preferably H, methyl, methoxy or F, more preferably H.

An embodiment of the disclosure is the compound of Formula 13, wherein k is 0, 1, 2 or 3, preferably 0 or 1.

An embodiment of the disclosure is the compound of Formula 13, wherein Z is C, U is S or O.

An embodiment of the disclosure is the compound of Formula 13, wherein Z is N, U is CH.

An embodiment of the disclosure is the compound of Formula 13, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 13, wherein m is 0, 1, 2 or 3, preferably 0 or 1.

An embodiment of the disclosure is the compound of Formula 13, wherein R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, cyclopropyl, cyclopropylamino or dimethylamino, more preferably H, F, $CF_3$, dimethylamino, cyclopropyl or cyclopropylamino, most preferably dimethylamino.

An embodiment of the disclosure is the compound of Formula 13, wherein n is 0, 1 or 2, preferably 0 or 1.

An embodiment of the compound of Formula II-1 is of the following Formula 3,

Formula 3

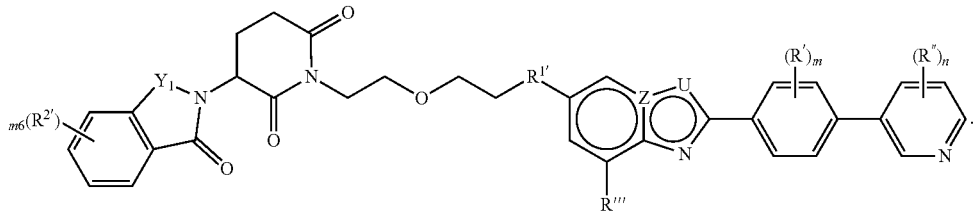

An embodiment of the disclosure is the compound of Formula 3, wherein $R^2$ is H, OH, $C_{1-3}$ alkyl, $C_{1-3}$ alkoxy, $C_{1-3}$ alkylamino or $NH_2$, preferably H, OH or $NH_2$.

An embodiment of the disclosure is the compound of Formula 3, wherein m6 is 0, 1, 2 or 3, preferably 0 or 1.

An embodiment of the disclosure is the compound of Formula 3, wherein $R^{1'}$ is O or NH.

An embodiment of the disclosure is the compound of Formula 3, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 3, wherein m is 0, 1, 2, 3 or 4, preferably 0 or 1.

An embodiment of the disclosure is the compound of Formula 3, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 3, wherein n is 0, 1, 2 or 3, preferably 0, 1 or 2.

An embodiment of the disclosure is the compound of Formula 3, wherein Z is C, U is O or S.

An embodiment of the disclosure is the compound of Formula 3, wherein Z is N, U is CH.

An embodiment of the disclosure is the compound of Formula 3, wherein R' is H, OH, $C_{1-3}$ alkyl, $C_{1-3}$ alkoxy or halogen, preferably H, F, methyl or methoxy, more preferably H.

An embodiment of the disclosure is the compound of Formula 3 having the structure as shown in Formula 3-1, $R^{1'}$ is O, NH,

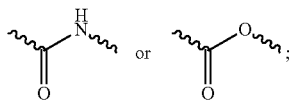

Z is C or N; U is O, S or CH;

where Z and U are not heteroatoms at the same time; R" is H, halo, OH, $NH_2$, $C_{1-3}$ alkoxy, $C_{1-3}$ haloalkyl, $C_{3-5}$ cycloalkyl, $C_{3-5}$ cycloalkylamino or $C_{1-3}$ alkylamino; n is 0, 1 or 2.

An embodiment of the disclosure is the compound of Formula 3-1, wherein $R^{2'}$ is H, $NH_2$ or OH.

An embodiment of the disclosure is the compound of Formula 3-1, wherein m6 is 0 or 1.

An embodiment of the disclosure is the compound of Formula 3-1, wherein when m6 is 1, $R^{2'}$ is substituted at the following position in the phenyl:

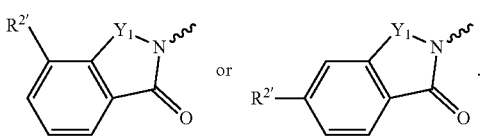

An embodiment of the disclosure is the compound of Formula 3-1, wherein $R^{1'}$ is O or NH.

Formula 3-1

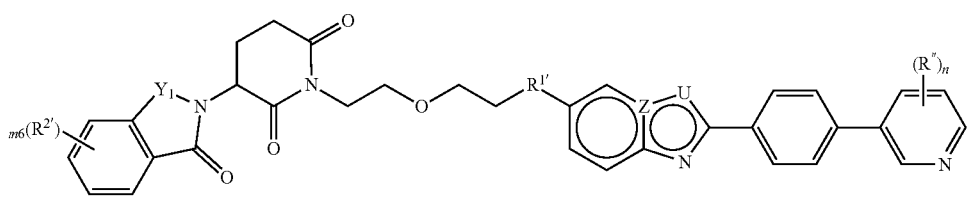

In Formula 3-1, $R^{2'}$ is H, OH, $C_{1-3}$ alkyl, $C_{1-3}$ alkoxy, $C_{1-3}$ alkylamino or $NH_2$; m6 is 0, 1, 2 or 3; $Y_1$ is $CH_2$ or

An embodiment of the disclosure is the compound of Formula 3-1, wherein R" is F, dimethylamino, methylamino, cyclopropyl or cyclopropylamino.

An embodiment of the disclosure is the compound of Formula 3-1, wherein n is 0, 1, or 2.

An embodiment of the compound of Formula III-1 is of the following Formula 15,

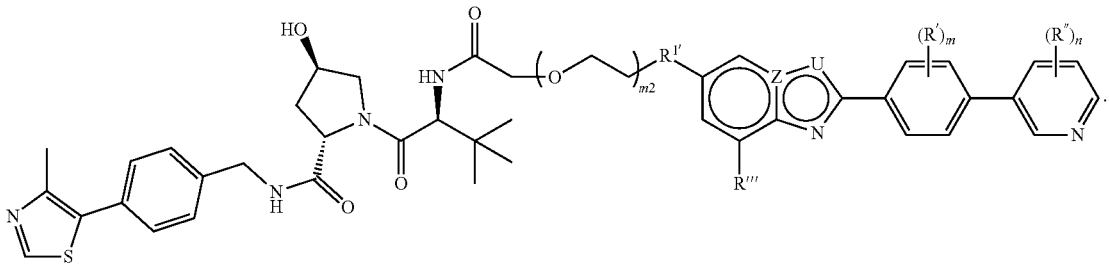

Formula 15

An embodiment of the disclosure is the compound of Formula 15, wherein m2 is 1, 2, 3, 4, 5, 6 or 7, preferably 1, 2, 3, 4, 5 or 6, more preferably 2 or 5.

An embodiment of the disclosure is the compound of Formula 15, wherein $R^{1'}$ is O, NH,

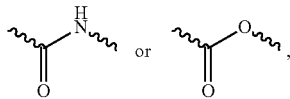

preferably O or NH.

An embodiment of the disclosure is the compound of Formula 15, wherein R''' is H, OH, $C_{1-3}$ alkyl, $C_{1-3}$ alkoxy or halogen, preferably H, F, methyl or methoxy, more preferably H.

An embodiment of the disclosure is the compound of Formula 15, wherein Z is C, U is O or S.

An embodiment of the disclosure is the compound of Formula 15, wherein Z is N, U is CH.

An embodiment of the disclosure is the compound of Formula 15, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H, $CF_3$ or F.

An embodiment of the disclosure is the compound of Formula 15, wherein m is 0, 1, 2 or 3, preferably 0, 1 or 2, more preferably 0 or 1.

An embodiment of the disclosure is the compound of Formula 15, wherein R'' is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F, methylamino, cyclopropylamino or dimethylamino, most preferably H or dimethylamino.

An embodiment of the disclosure is the compound of Formula 15, wherein n is 0, 1 or 2, preferably 0 or 1.

An embodiment of the compound of Formula IV-1 is of the following Formula 2, 7, 9, 11, 12 or 14,

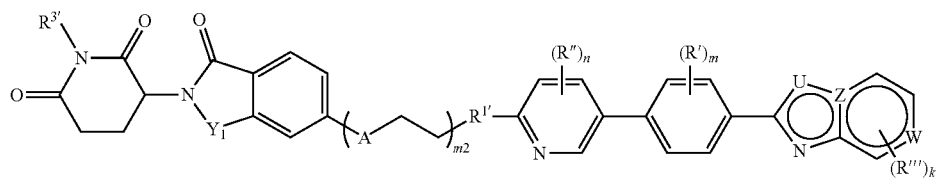

Formula 2

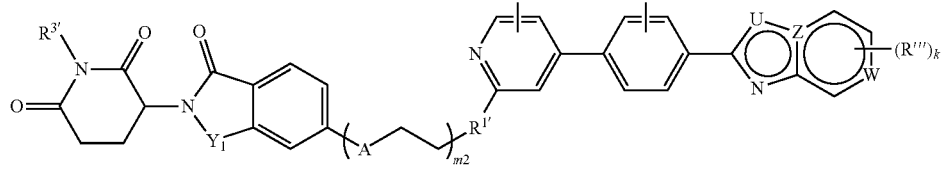

Formula 7

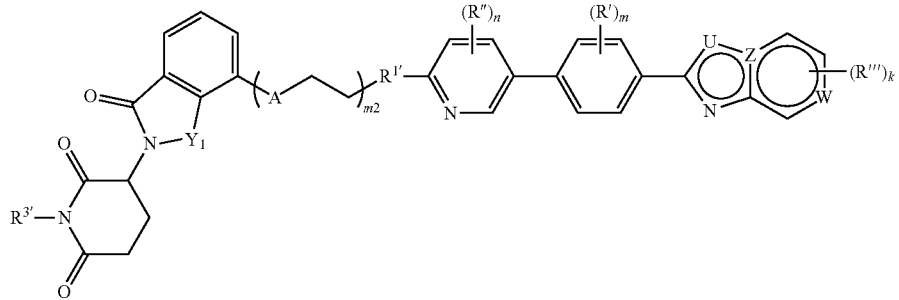

Formula 9

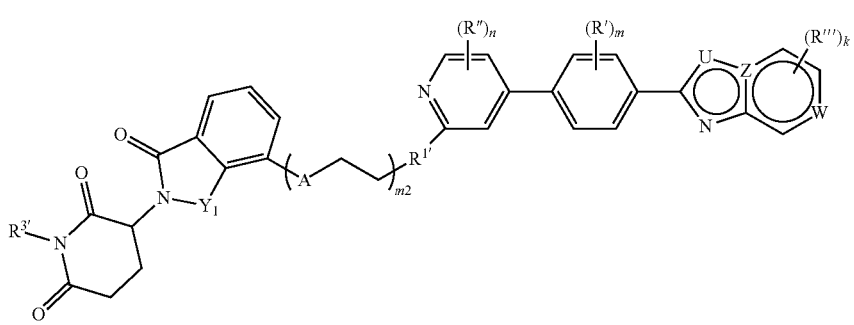

Formula 11

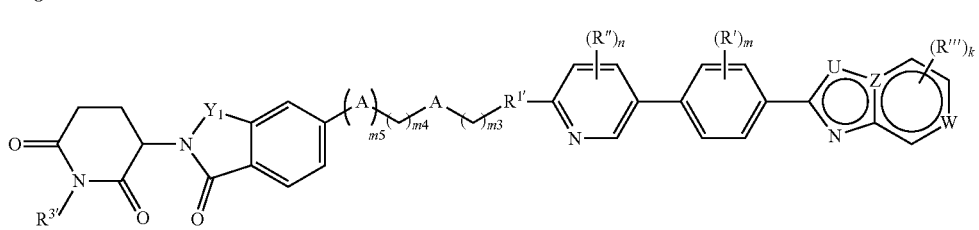

Formula 12

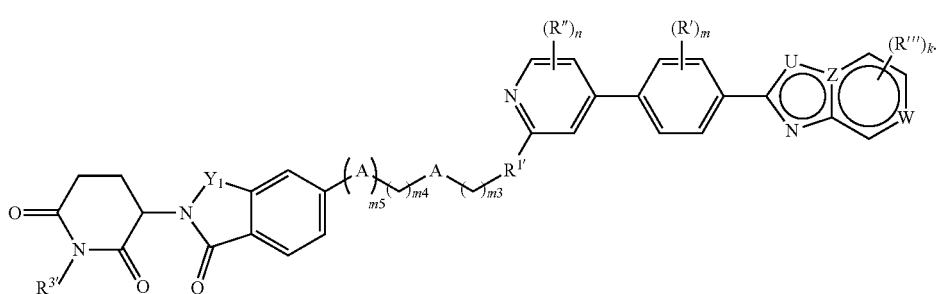

Formula 14

An embodiment of the disclosure is the compound of Formula 2, wherein $R^{3'}$ is H or $C_{1-3}$ alkyl, preferably H or methyl.

An embodiment of the disclosure is the compound of Formula 2, wherein $Y_1$ is $CH_2$ or

An embodiment of the disclosure is the compound of Formula 2, wherein A is O, NH,

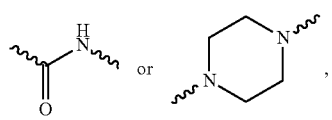

preferably O.

An embodiment of the disclosure is the compound of Formula 2, wherein m2 is 2, 3, 4, 5 or 6, preferably 2 or 6.

An embodiment of the disclosure is the compound of Formula 2, wherein $R^{1'}$ is O, NH, preferably NH.

An embodiment of the disclosure is the compound of Formula 2, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 2, wherein n is 0, 1 or 2, preferably 0 or 1.

An embodiment of the disclosure is the compound of Formula 2, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 2, wherein m is 0, 1, 2 or 3, preferably 0, 1 or 2.

An embodiment of the disclosure is the compound of Formula 2, wherein Z is C, U is O or S, W is CH.

An embodiment of the disclosure is the compound of Formula 2, wherein Z is N, U is CH, W is CH.

An embodiment of the disclosure is the compound of Formula 2, wherein Z is C, W is N, U is CH.

An embodiment of the disclosure is the compound of Formula 2, wherein R''' is H, OH, NH$_2$, C$_{1-3}$ alkyl, C$_{1-3}$ alkylamino, C$_{1-3}$ alkoxy or halogen, preferably H, F, methoxy, methylamino or dimethylamino.

An embodiment of the disclosure is the compound of Formula 2, wherein k is 0, 1, 2 or 3, preferably 0, 1 or 2, more preferably 0 or 1.

An embodiment of the disclosure is the compound of Formula 7, wherein R$^{3'}$ is H or C$_{1-3}$ alkyl, preferably H or methyl.

An embodiment of the disclosure is the compound of Formula 7, wherein Y$_1$ is CH$_2$ or

An embodiment of the disclosure is the compound of Formula 7, wherein A is O, NH,

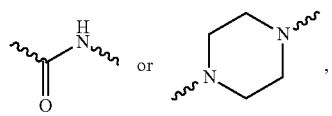

preferably O.

An embodiment of the disclosure is the compound of Formula 7, wherein m2 is 2, 3, 4, 5 or 6, preferably 2 or 3.

An embodiment of the disclosure is the compound of Formula 7, wherein R$^{1'}$ is O, NH,

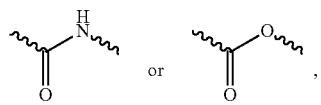

preferably NH.

An embodiment of the disclosure is the compound of Formula 7, wherein R'' is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, OH, NH$_2$, methyl, methoxy, CF$_3$, CCl$_3$, methylamino, dimethylamino, cyclopropyl or cyclopropylamino, more preferably H, F, CF$_3$, cyclopropyl or cyclopropylamino.

An embodiment of the disclosure is the compound of Formula 7, wherein n is 0, 1, or 2, preferably 0 or 1.

An embodiment of the disclosure is the compound of Formula 7, wherein R' is H, halogen, OH, C$_{1-3}$ alkyl, C$_{1-3}$ haloalkyl or C$_{1-3}$ alkoxy, preferably H, F, CF$_3$, CCl$_3$, methyl or methoxy, more preferably H or CF$_3$.

An embodiment of the disclosure is the compound of Formula 7, wherein m is 0, 1, 2 or 3, preferably 0, 1 or 2.

An embodiment of the disclosure is the compound of Formula 7, wherein Z is C, U is O or S, W is CH.

An embodiment of the disclosure is the compound of Formula 7, wherein Z is N, U is CH, W is CH.

An embodiment of the disclosure is the compound of Formula 7, wherein Z is C, W is N, U is CH.

An embodiment of the disclosure is the compound of Formula 7, wherein R''' is H, OH, NH$_2$, C$_{1-3}$ alkyl, C$_{1-3}$ alkylamino, C$_{1-3}$ alkoxy or halogen, preferably H, F, methoxy, methylamino or dimethylamino.

An embodiment of the disclosure is the compound of Formula 7, wherein k is 0, 1, 2 or 3, preferably 0, 1 or 2, more preferably 0 or 1.

An embodiment of the disclosure is the compound of Formula 9, wherein R$^{3'}$ is H or C$_{1-3}$ alkyl, preferably H or methyl.

An embodiment of the disclosure is the compound of Formula 9, wherein Y$_1$ is CH$_2$ or

An embodiment of the disclosure is the compound of Formula 9, wherein A is O, NH,

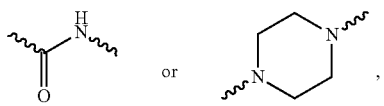

preferably O.

An embodiment of the disclosure is the compound of Formula 9, wherein m2 is 2, 3, 4, 5 or 6, preferably 2 or 3.

An embodiment of the disclosure is the compound of Formula 9, wherein R$^{1'}$ is O, NH,

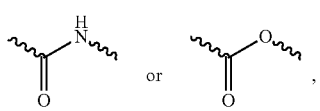

preferably NH.

An embodiment of the disclosure is the compound of Formula 9, wherein R'' is H, halo, OH, NH$_2$, C$_{1-3}$ alkyl, C$_{1-3}$ alkoxy, C$_{1-3}$ haloalkyl, C$_{1-3}$ alkylamino, C$_{3-5}$ cycloalkyl, C$_{3-5}$ cycloalkylamino or C$_{3-5}$ heterocycloalkyl, preferably H, F, OH, NH$_2$, methyl, methoxy, CF$_3$, CCl$_3$, methylamino, dimethylamino, cyclopropyl or cyclopropylamino, more preferably H, F, CF$_3$, cyclopropyl or cyclopropylamino.

An embodiment of the disclosure is the compound of Formula 9, wherein n is 0, 1, or 2, preferably 0 or 1.

An embodiment of the disclosure is the compound of Formula 9, wherein R' is H, halogen, OH, C$_{1-3}$ alkyl, C$_{1-3}$ haloalkyl or C$_{1-3}$ alkoxy, preferably H, F, CF$_3$, CCl$_3$, methyl or methoxy, more preferably H or CF$_3$.

An embodiment of the disclosure is the compound of Formula 9, wherein m is 0, 1, 2 or 3, preferably 0, 1 or 2.

An embodiment of the disclosure is the compound of Formula 9, wherein Z is C, U is O or S, W is CH.

An embodiment of the disclosure is the compound of Formula 9, wherein Z is N, U is CH, W is CH.

An embodiment of the disclosure is the compound of Formula 9, wherein Z is C, W is N, U is CH.

An embodiment of the disclosure is the compound of Formula 9, wherein R' is H, OH, NH$_2$, C$_{1-3}$ alkyl, C$_{1-3}$ alkylamino, C$_{1-3}$ alkoxy or halogen, preferably H, F, methoxy, methylamino or dimethylamino.

An embodiment of the disclosure is the compound of Formula 9, wherein k is 0, 1, 2 or 3, preferably 0, 1 or 2, more preferably 0 or 1.

An embodiment of the disclosure is the compound of Formula 11, wherein R$^{3'}$ is H or C$_{1-3}$ alkyl, preferably H or methyl.

An embodiment of the disclosure is the compound of Formula 11, wherein $Y_1$ is $CH_2$ or

An embodiment of the disclosure is the compound of Formula 11, wherein A is O, NH,

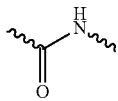 or 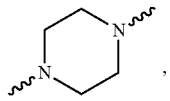, preferably O.

An embodiment of the disclosure is the compound of Formula 11, wherein m2 is 2, 3, 4, 5 or 6, preferably 2 or 3.

An embodiment of the disclosure is the compound of Formula 11, wherein $R^{1'}$ is O, NH,

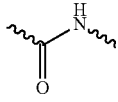 or 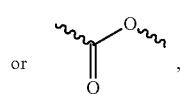, preferably NH.

An embodiment of the disclosure is the compound of Formula 11, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 11, wherein n is 0, 1 or 2, preferably 0 or 1.

An embodiment of the disclosure is the compound of Formula 11, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 11, wherein m is 0, 1, 2 or 3, preferably 0, 1 or 2.

An embodiment of the disclosure is the compound of Formula 11, wherein Z is C, U is O or S, W is CH.

An embodiment of the disclosure is the compound of Formula 11, wherein Z is N, U is CH, W is CH.

An embodiment of the disclosure is the compound of Formula 11, wherein Z is C, W is N, U is CH.

An embodiment of the disclosure is the compound of Formula 11, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 11, wherein k is 0, 1, 2 or 3, preferably 0, 1 or 2, more preferably 0 or 1.

An embodiment of the disclosure is the compound of Formula 12, wherein $R^{3'}$ is H or $C_{1-3}$ alkyl, preferably H or methyl.

An embodiment of the disclosure is the compound of Formula 12, wherein $Y_1$ is $CH_2$ or

, preferably $CH_2$.

An embodiment of the disclosure is the compound of Formula 12, wherein A is O, NH,

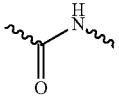 or 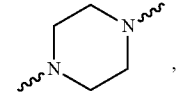, preferably O.

An embodiment of the disclosure is the compound of Formula 12, wherein m3 is 1, 2, 3, 4, 5 or 6, preferably 2 or 3.

An embodiment of the disclosure is the compound of Formula 12, wherein m4 is 0 or 1, 2 or 3, preferably 0 or 3.

An embodiment of the disclosure is the compound of Formula 12, wherein m5 is 0 or 1, 2 or 3, preferably 0 or 1.

An embodiment of the disclosure is the compound of Formula 12, wherein $R^{1'}$ is O, NH,

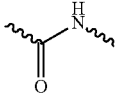 or 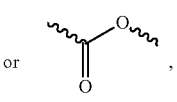, preferably NH.

An embodiment of the disclosure is the compound of Formula 12, wherein R" is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 12, wherein n is 0, 1 or 2, preferably 0 or 1.

An embodiment of the disclosure is the compound of Formula 12, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 12, wherein m is 0, 1, 2 or 3, preferably 0, 1 or 2.

An embodiment of the disclosure is the compound of Formula 12, wherein Z is C, U is O or S, W is CH.

An embodiment of the disclosure is the compound of Formula 12, wherein Z is N, U is CH, W is CH.

An embodiment of the disclosure is the compound of Formula 12, wherein Z is C, W is N, U is CH.

An embodiment of the disclosure is the compound of Formula 12, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 12, wherein k is 0, 1, 2 or 3, preferably 0, 1 or 2, more preferably 0 or 1.

An embodiment of the disclosure is the compound of Formula 14, wherein $R^{3'}$ is H or $C_{1-3}$ alkyl, preferably H or methyl.

An embodiment of the disclosure is the compound of Formula 14, wherein $Y_1$ is $CH_2$ or

, preferably $CH_2$.

An embodiment of the disclosure is the compound of Formula 14, wherein A is O, NH,

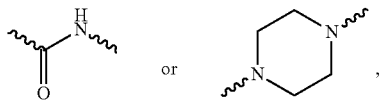

preferably O.

An embodiment of the disclosure is the compound of Formula 14, wherein m3 is 1, 2, 3, 4, 5 or 6, preferably 2, 3 or 4.

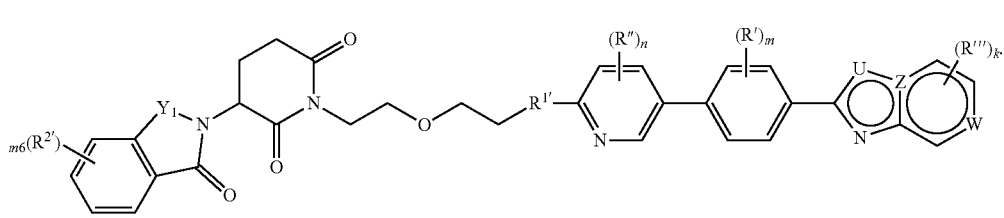

An embodiment of the disclosure is the compound of Formula 14, wherein m4 is 0, 1, 2, 3 or 4, preferably 0 or 3.

An embodiment of the disclosure is the compound of Formula 14, wherein m5 is 0 or 1, 2 or 3, preferably 0 or 1.

An embodiment of the disclosure is the compound of Formula 14, wherein $R^{1'}$ is O, NH,

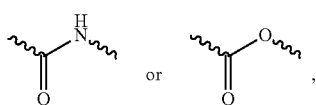

preferably

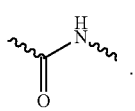

An embodiment of the disclosure is the compound of Formula 14, wherein R″ is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl, preferably H, F, OH, $NH_2$, methyl, methoxy, $CF_3$, $CCl_3$, methylamino, dimethylamino, cyclopropyl or cyclopropylamino, more preferably H, F, $CF_3$, cyclopropyl or cyclopropylamino.

An embodiment of the disclosure is the compound of Formula 14, wherein n is 0, 1, or 2, preferably 0 or 1.

An embodiment of the disclosure is the compound of Formula 14, wherein R' is H, halogen, OH, $C_{1-3}$ alkyl, $C_{1-3}$ haloalkyl or $C_{1-3}$ alkoxy, preferably H, F, $CF_3$, $CCl_3$, methyl or methoxy, more preferably H or $CF_3$.

An embodiment of the disclosure is the compound of Formula 14, wherein m is 0, 1, 2 or 3, preferably 0, 1 or 2.

An embodiment of the disclosure is the compound of Formula 14, wherein Z is C, U is O or S, W is CH.

An embodiment of the disclosure is the compound of Formula 14, wherein Z is N, U is CH, W is CH.

An embodiment of the disclosure is the compound of Formula 14, wherein Z is C, W is N, U is CH.

An embodiment of the disclosure is the compound of Formula 14, wherein R‴ is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 14, wherein k is 0, 1, 2 or 3, preferably 0, 1 or 2, more preferably 0 or 1.

An embodiment of the compound of Formula V-1 is of the following Formula 4,

An embodiment of the disclosure is the compound of Formula 4, wherein $R^2$ is H, OH, $C_{1-3}$ alkyl, $C_{1-3}$ alkoxy, $C_{1-3}$ alkylamino or $NH_2$, preferably H, OH or $NH_2$.

An embodiment of the disclosure is the compound of Formula 4, wherein m6 is 0, 1 or 2, preferably 0 or 1.

An embodiment of the disclosure is the compound of Formula 4, wherein $R^{1'}$ is O, NH,

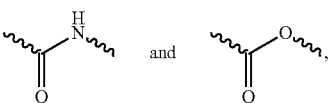

preferably O or NH.

An embodiment of the disclosure is the compound of Formula 4, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 4, wherein m is 0, 1, 2, 3 or 4, preferably 0 or 1.

An embodiment of the disclosure is the compound of Formula 4, wherein R″ is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 4, wherein n is 0, 1, or 2, preferably 0 or 1.

An embodiment of the disclosure is the compound of Formula 4, wherein Z is C, U is O or S, W is CH.

An embodiment of the disclosure is the compound of Formula 4, wherein Z is N, U is CH, W is CH.

An embodiment of the disclosure is the compound of Formula 4, wherein Z is C, U is CH, W is N.

An embodiment of the disclosure is the compound of Formula 4, wherein R‴ is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 4, wherein k is 0, 1, 2 or 3, preferably 0, 1 or 2, more preferably 0 or 1.

An embodiment of the disclosure is the compound of Formula 4 having the structure as shown in Formula 4-1,

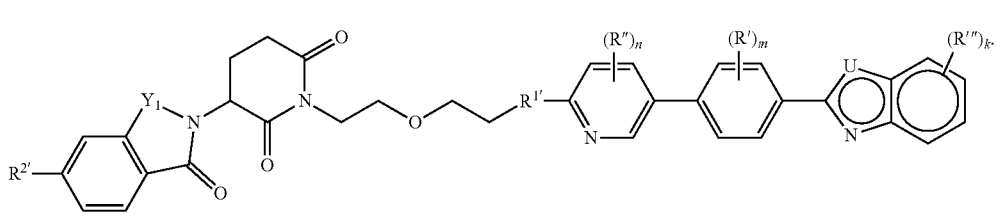
Formula 4-1

In Formula 4-1, $R^{2'}$ is H, OH, $C_{1-3}$ alkyl, $C_{1-3}$ alkoxy, $C_{1-3}$ alkylamino or $NH_2$; $Y_1$ is $CH_2$ or

$R^{1'}$ is O, NH,

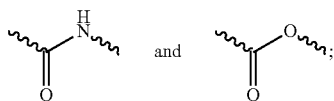

R" is H, halo, OH, $NH_2$, $C_{1-3}$ alkoxy, $C_{1-3}$ haloalkyl, $C_{1-3}$ alkylamino or $C_{3-5}$ heterocycloalkyl; n is 0, 1 or 2; R' is H, halogen, OH, $C_{1-3}$ alkyl, $C_{1-3}$ haloalkyl or $C_{1-3}$ alkoxy; m is 0, 1 or 2; U is O or S; R'" is H, OH, $NH_2$, $C_{1-3}$ alkyl, $C_{1-3}$ alkylamino, $C_{1-3}$ alkoxy or halogen; k is 0, 1, 2, 3 or 4.

An embodiment of the disclosure is the compound of Formula 4-1, wherein $R^{1'}$ is NH.

An embodiment of the disclosure is the compound of Formula 4-1, wherein R" is H.

An embodiment of the disclosure is the compound of Formula 4-1, wherein R' is H.

An embodiment of the disclosure is the compound of Formula 4-1, wherein $R^{2'}$ is OH.

An embodiment of the disclosure is the compound of Formula 4-1, wherein R'" is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 4, wherein k is 0, 1, 2 or 3, preferably 0, 1 or 2, more preferably 0 or 1.

An embodiment of the disclosure is the compound of Formula 4, wherein U is S.

An embodiment of the compound of Formula VI-1 is of the following Formula 16 or 17,

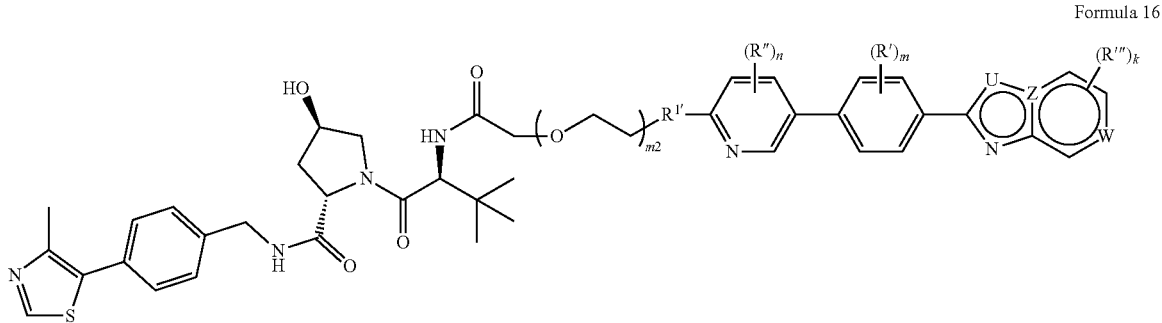
Formula 16

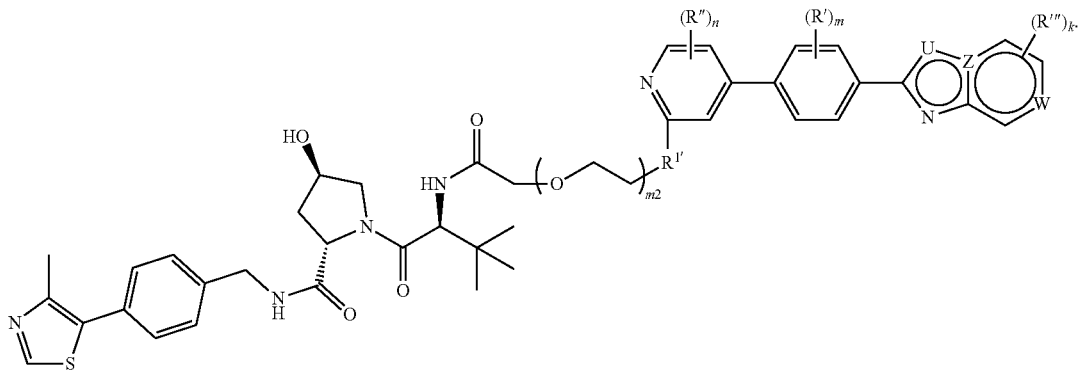
Formula 17

An embodiment of the disclosure is the compound of Formula 16, wherein m2 is 1, 2, 3, 4, 5 or 6, preferably 2 or 5.

An embodiment of the disclosure is the compound of Formula 16, wherein $R^{1'}$ is O, NH,

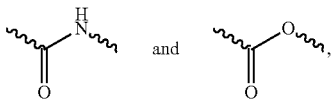 and , preferably NH.

An embodiment of the disclosure is the compound of Formula 16, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 16, wherein m is 0, 1, 2, 3 or 4, preferably 0 or 1.

An embodiment of the disclosure is the compound of Formula 16, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 16, wherein n is 0, 1, or 2, preferably 0 or 1.

An embodiment of the disclosure is the compound of Formula 16, wherein Z is C, U is O or S, W is CH.

An embodiment of the disclosure is the compound of Formula 16, wherein Z is N, U is CH, W is CH.

An embodiment of the disclosure is the compound of Formula 16, wherein Z is C, U is CH, W is N.

An embodiment of the disclosure is the compound of Formula 16, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 16, wherein k is 0, 1, 2 or 3, preferably 0, 1 or 2, more preferably 0 or 1.

An embodiment of the disclosure is the compound of Formula 17, wherein m2 is 1, 2, 3, 4, 5 or 6, preferably 2 or 5.

An embodiment of the disclosure is the compound of Formula 17, wherein $R^{1'}$ is O, NH,

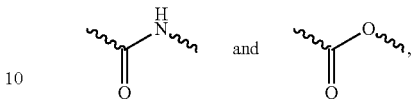 and , preferably NH.

An embodiment of the disclosure is the compound of Formula 17, wherein R' is H, halogen, OH, $C_{1-3}$ alkyl, $C_{1-3}$ haloalkyl or $C_{1-3}$ alkoxy, preferably H, halogen or $C_{1-3}$ fluoroalkyl, more preferably H or F.

An embodiment of the disclosure is the compound of Formula 17, wherein m is 0, 1, 2, 3 or 4, preferably 0 or 1.

An embodiment of the disclosure is the compound of Formula 17, wherein R" is H, halo, OH, $NH_2$, $C_{1-3}$ alkoxy, $C_{3-5}$ cycloalkyl, $C_{3-5}$ cycloalkylamino or $C_{1-3}$ alkylamino, preferably H, halo, methylamino, dimethylamino, cyclopropylamino or cyclopropyl, more preferably H, F or dimethylamino.

An embodiment of the disclosure is the compound of Formula 17, wherein n is 0, 1, or 2, preferably 0 or 1.

An embodiment of the disclosure is the compound of Formula 17, wherein Z is C, U is O or S, W is CH.

An embodiment of the disclosure is the compound of Formula 17, wherein Z is N, U is CH, W is CH.

An embodiment of the disclosure is the compound of Formula 17, wherein Z is C, U is CH, W is N.

An embodiment of the disclosure is the compound of Formula 17, wherein R''' is H, OH, $NH_2$, $C_{1-3}$ alkyl, $C_{1-3}$ alkylamino, $C_{1-3}$ alkoxy or halogen, preferably H, F, methoxy, methylamino or dimethylamino.

An embodiment of the disclosure is the compound of Formula 17, wherein k is 0, 1, 2 or 3, preferably 0, 1 or 2, more preferably 0 or 1.

Some embodiments of the disclosure are the compounds having a structure depicted in Table 1.

TABLE 1

| 159985 | 160273 | 160275 | 160313 | 160383 |

TABLE 1-continued
| 170350 | 161177 | 160219 | 170351 | 160744 |
|---|---|---|---|---|
| 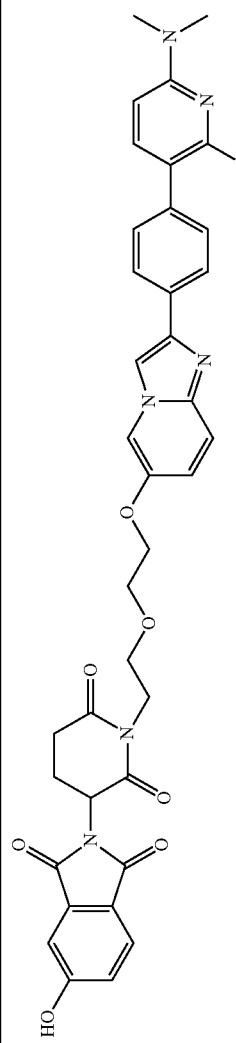 | 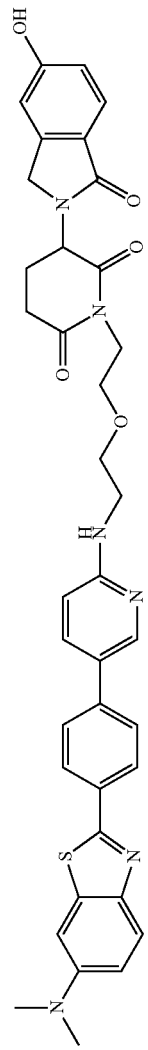 | 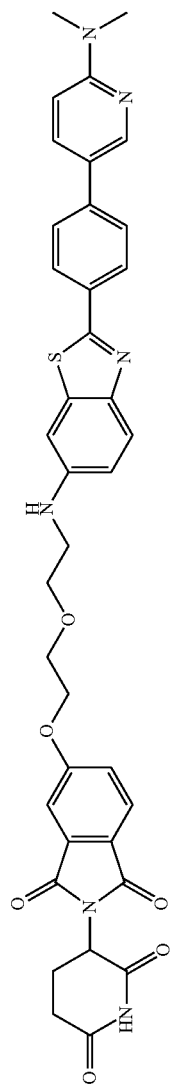 | 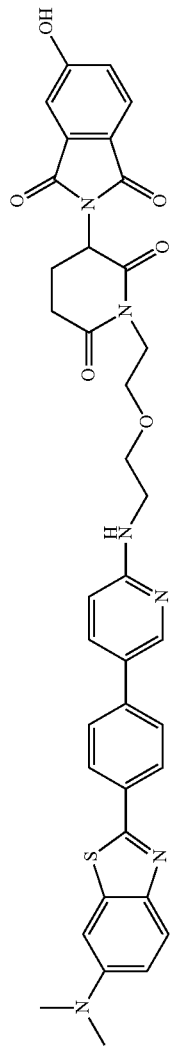 | 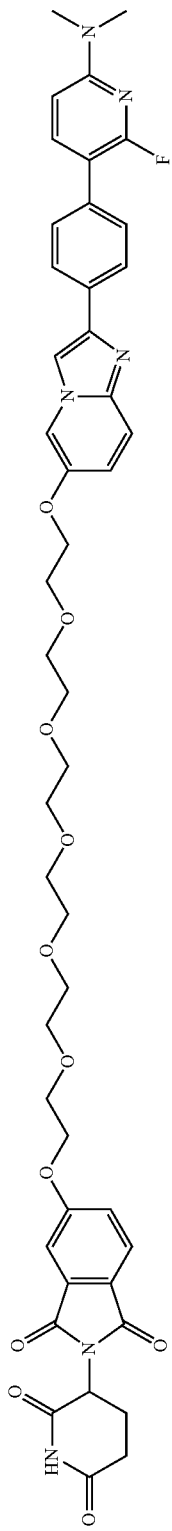 |

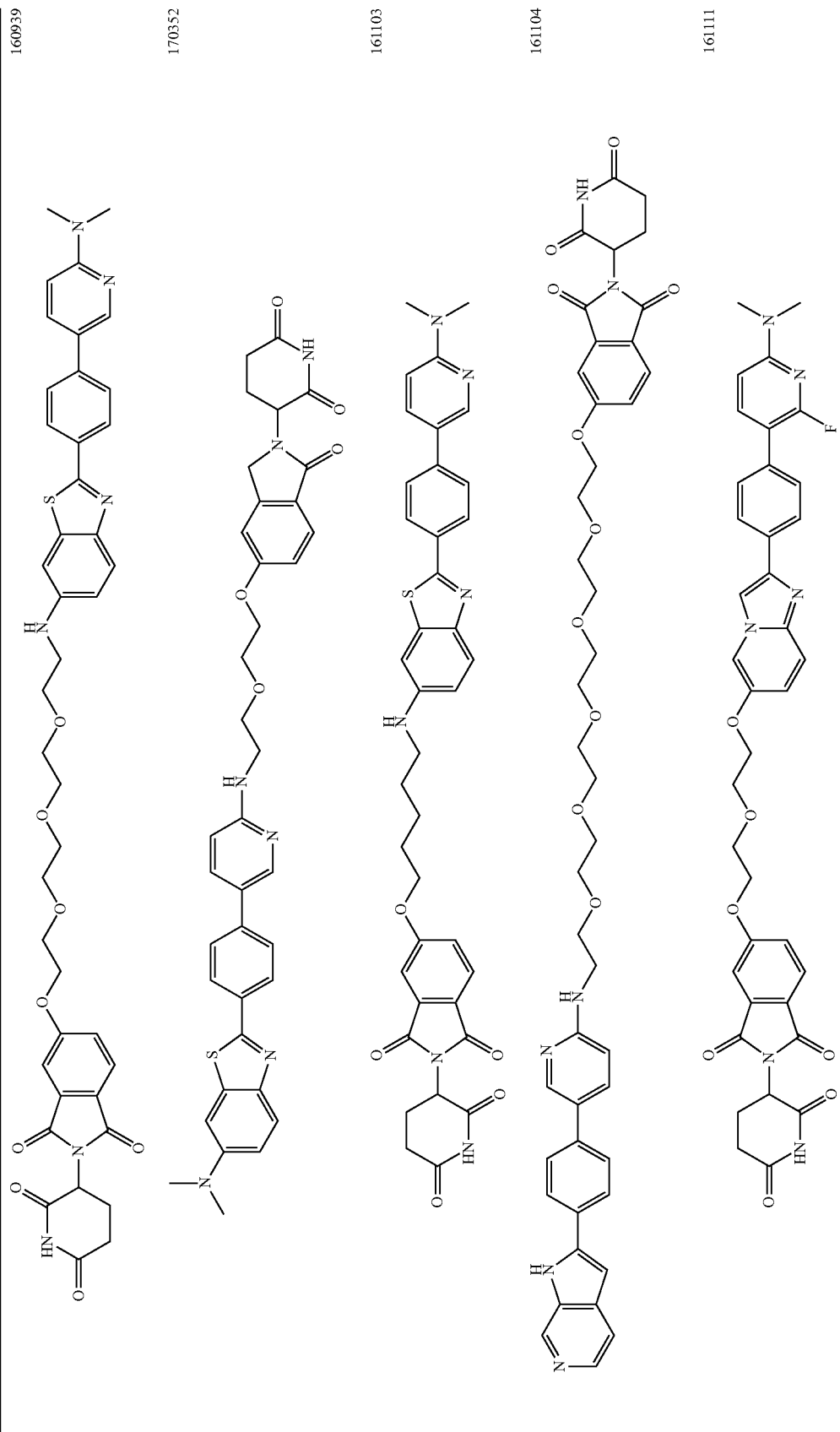

TABLE 1-continued
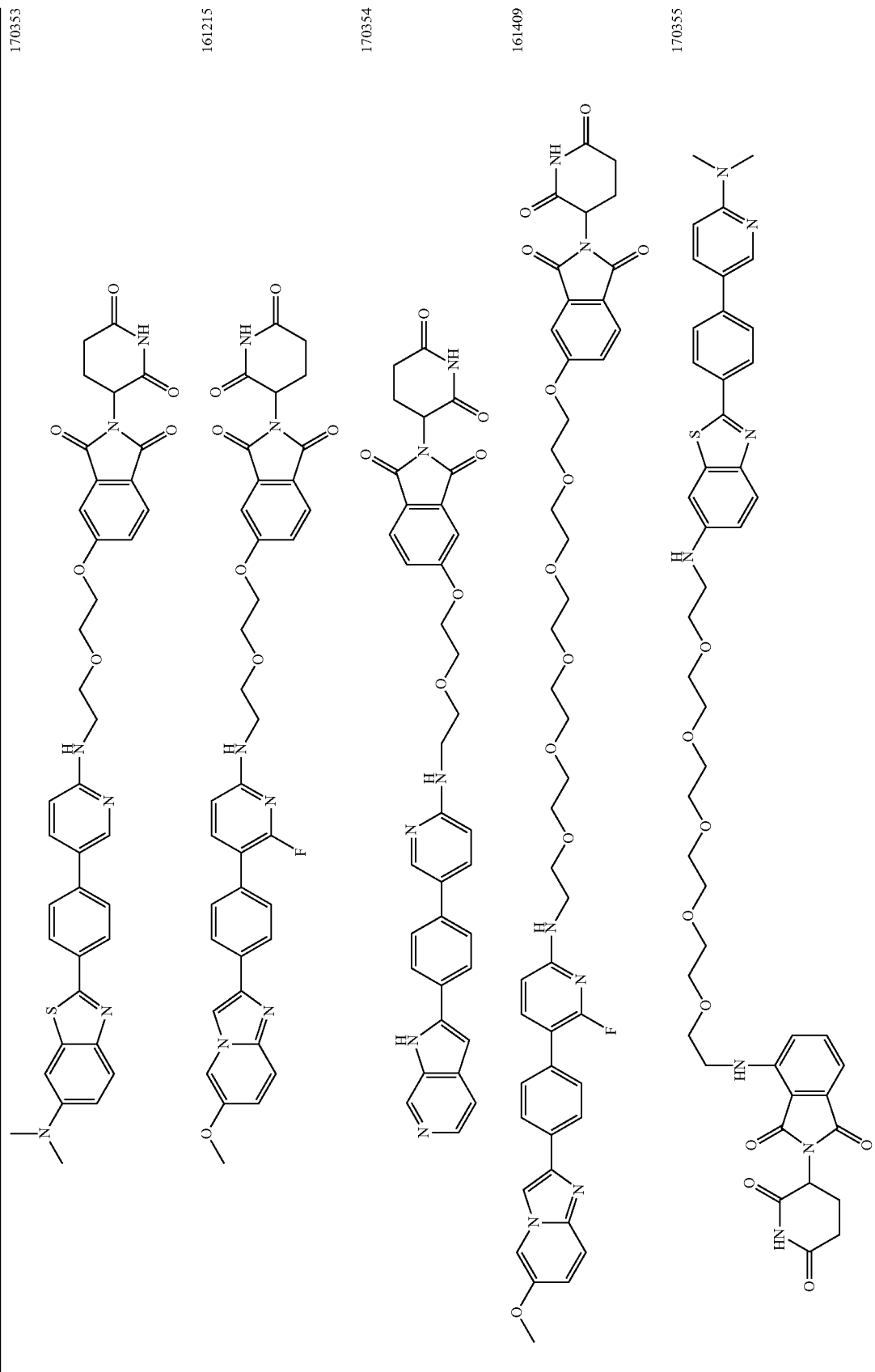

TABLE 1-continued
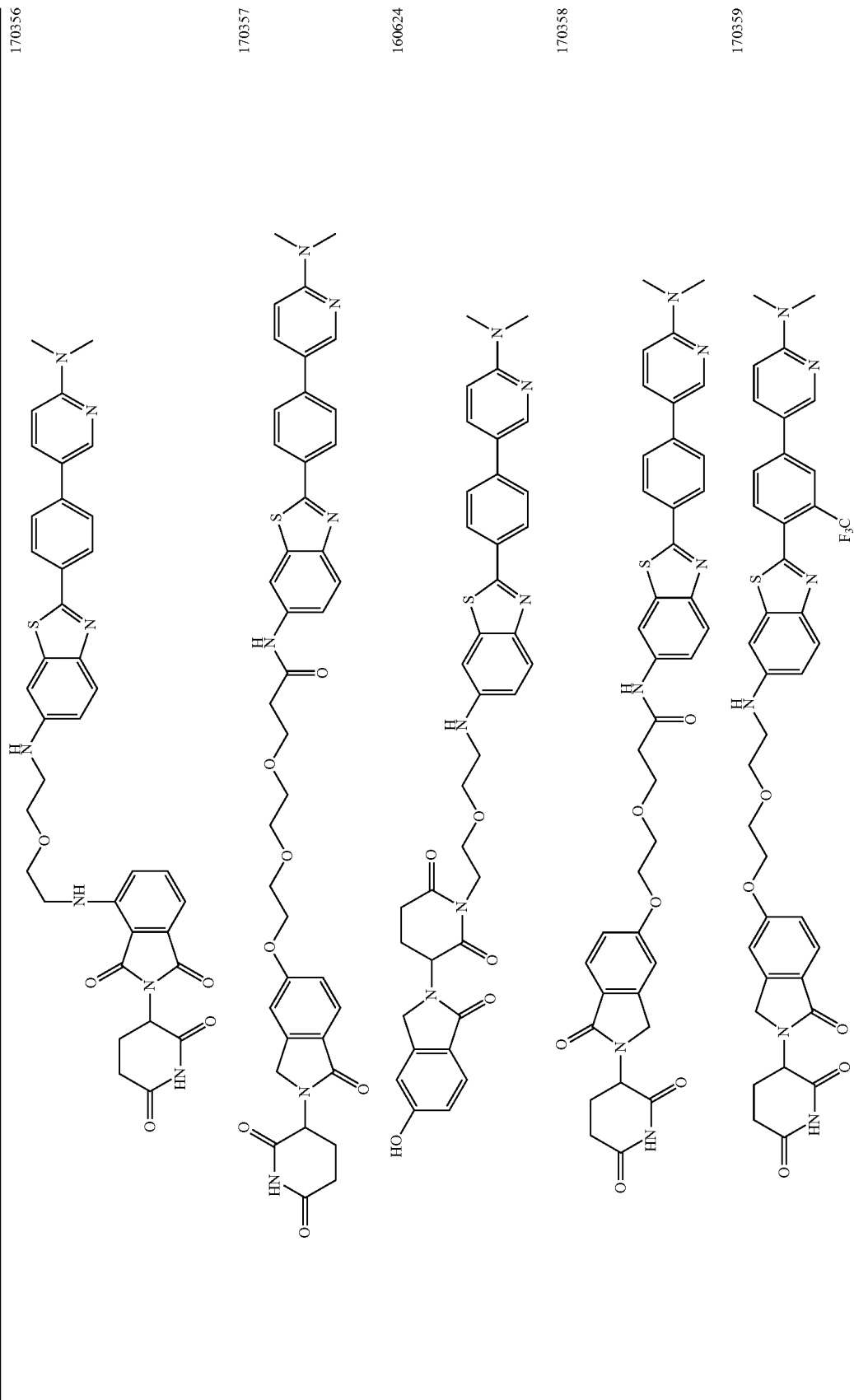

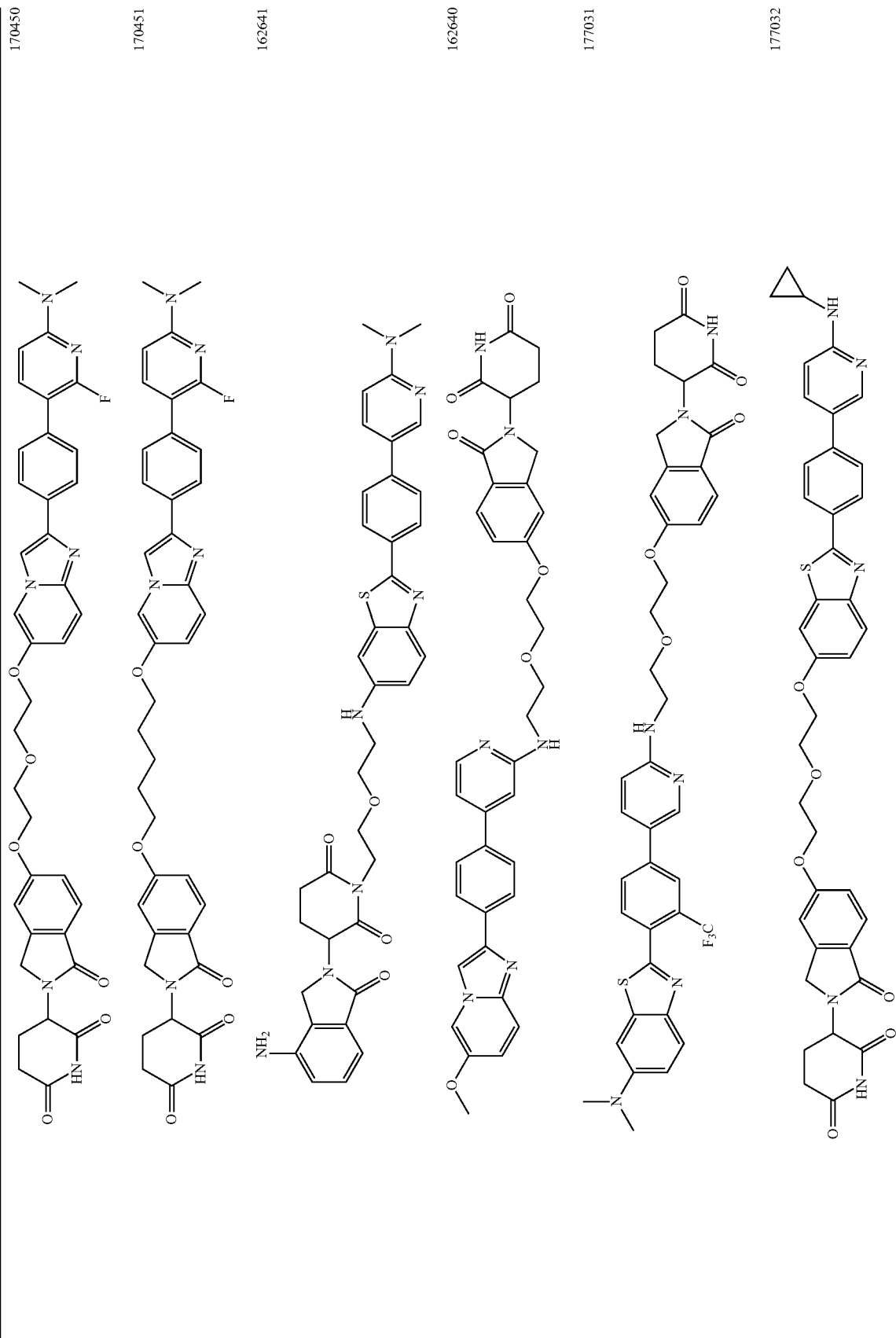

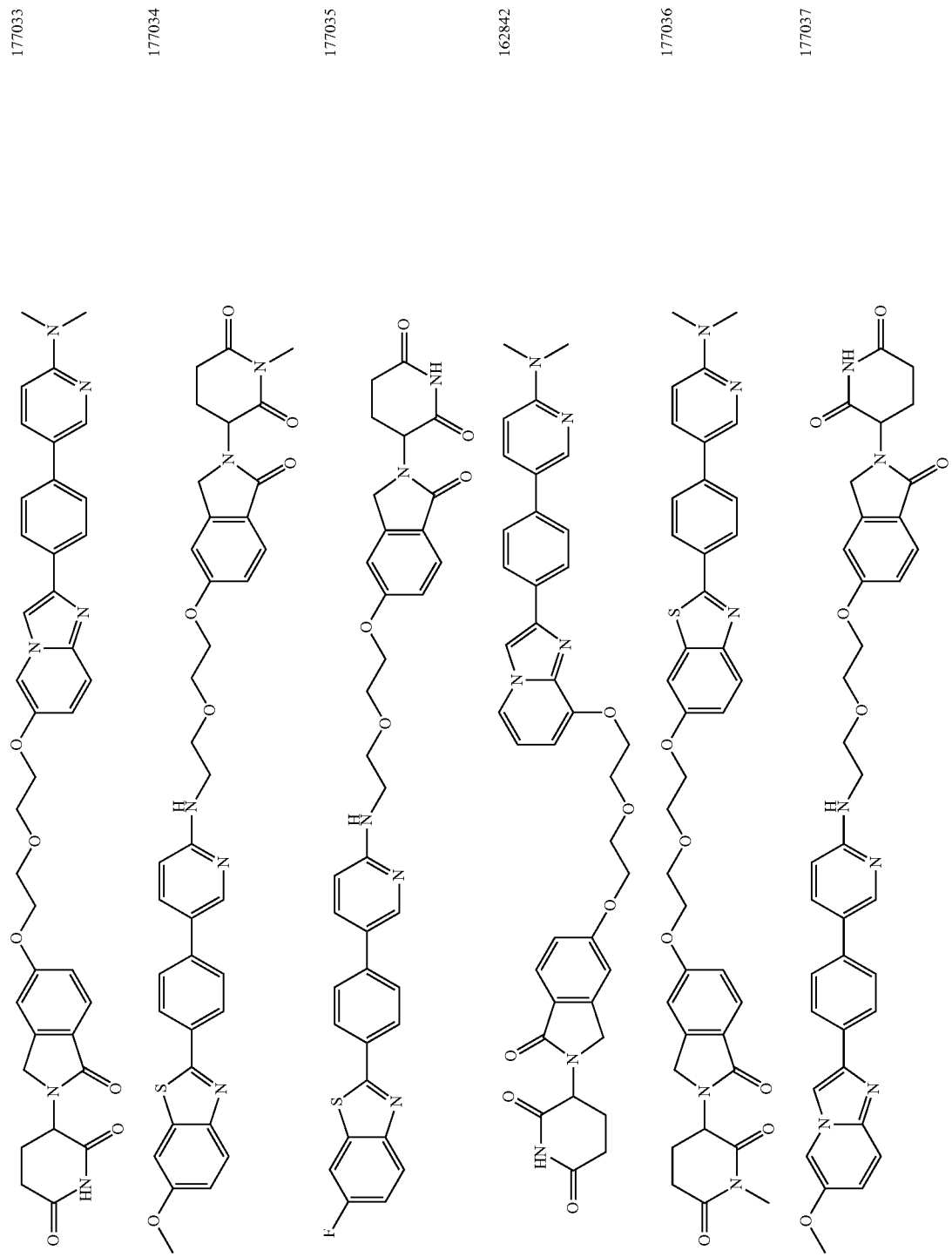

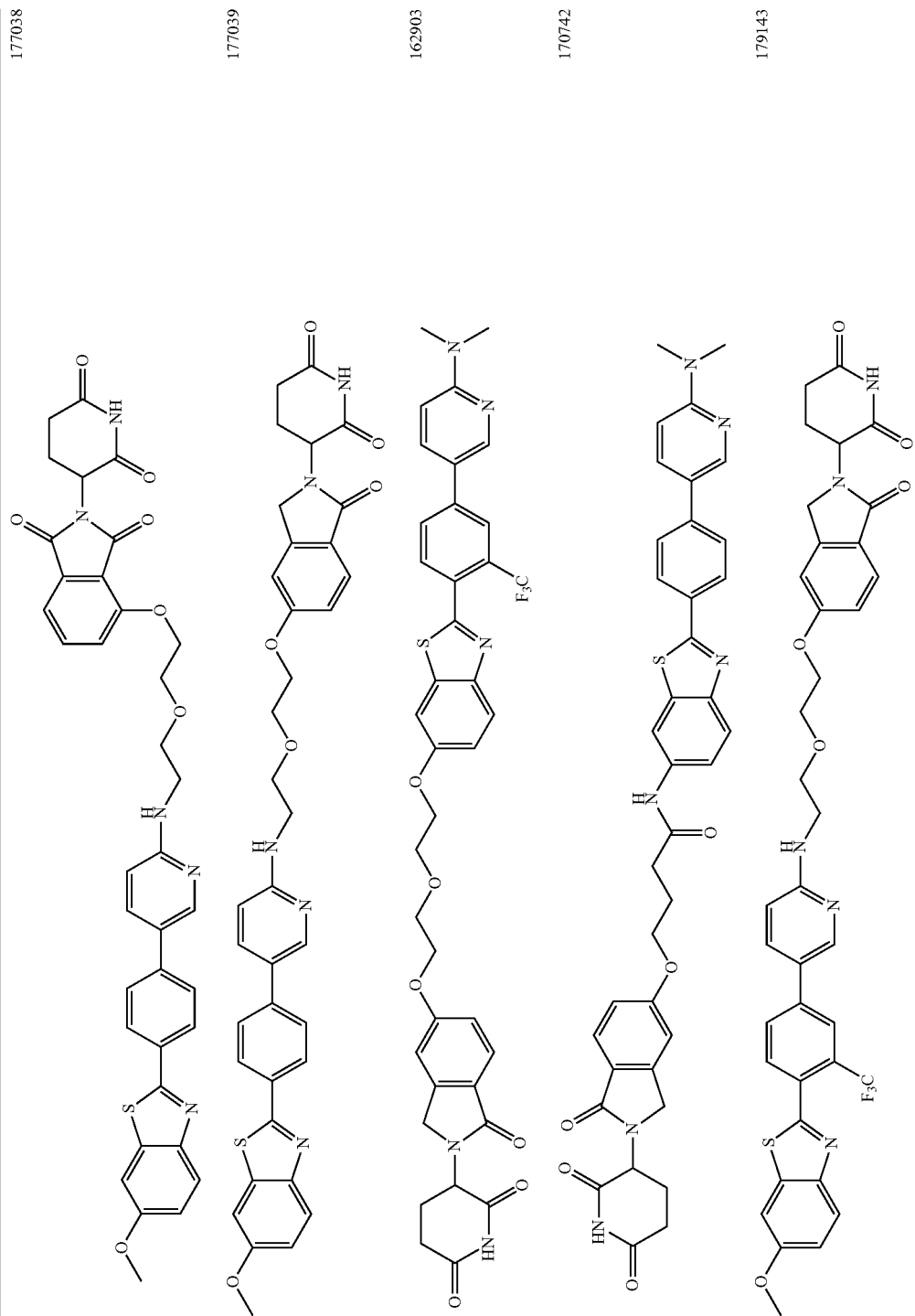

TABLE 1-continued
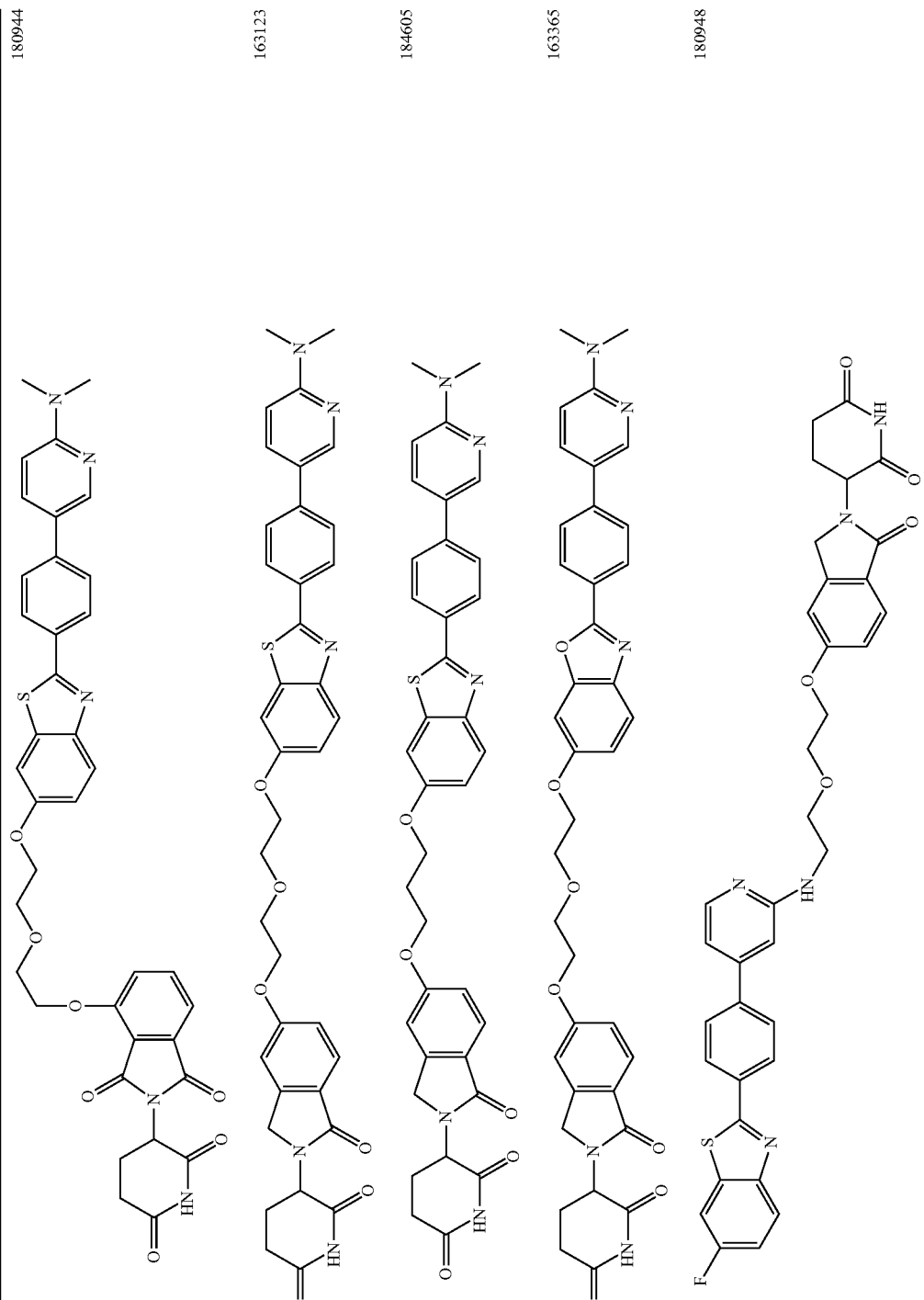

TABLE 1-continued
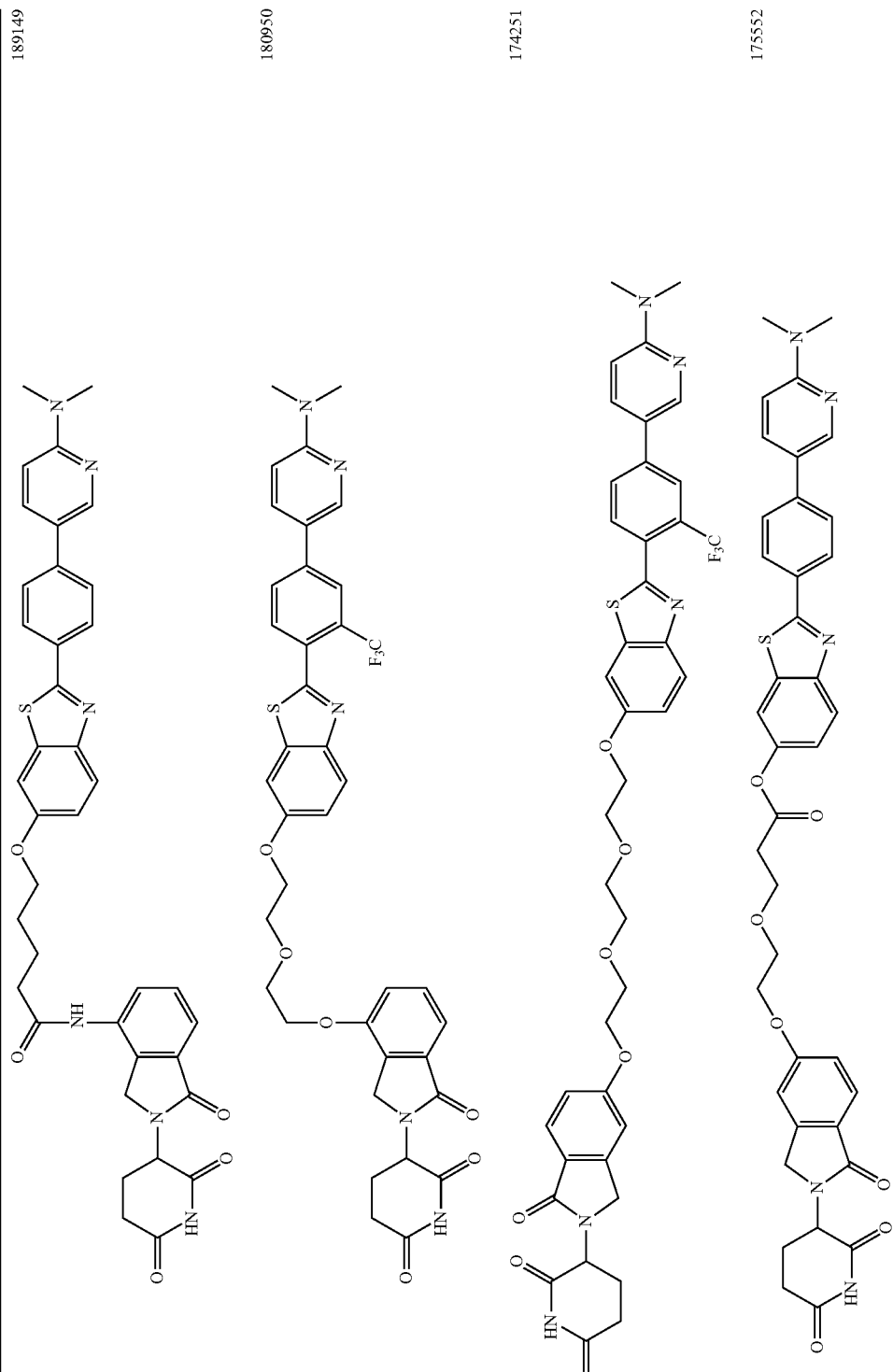

TABLE 1-continued
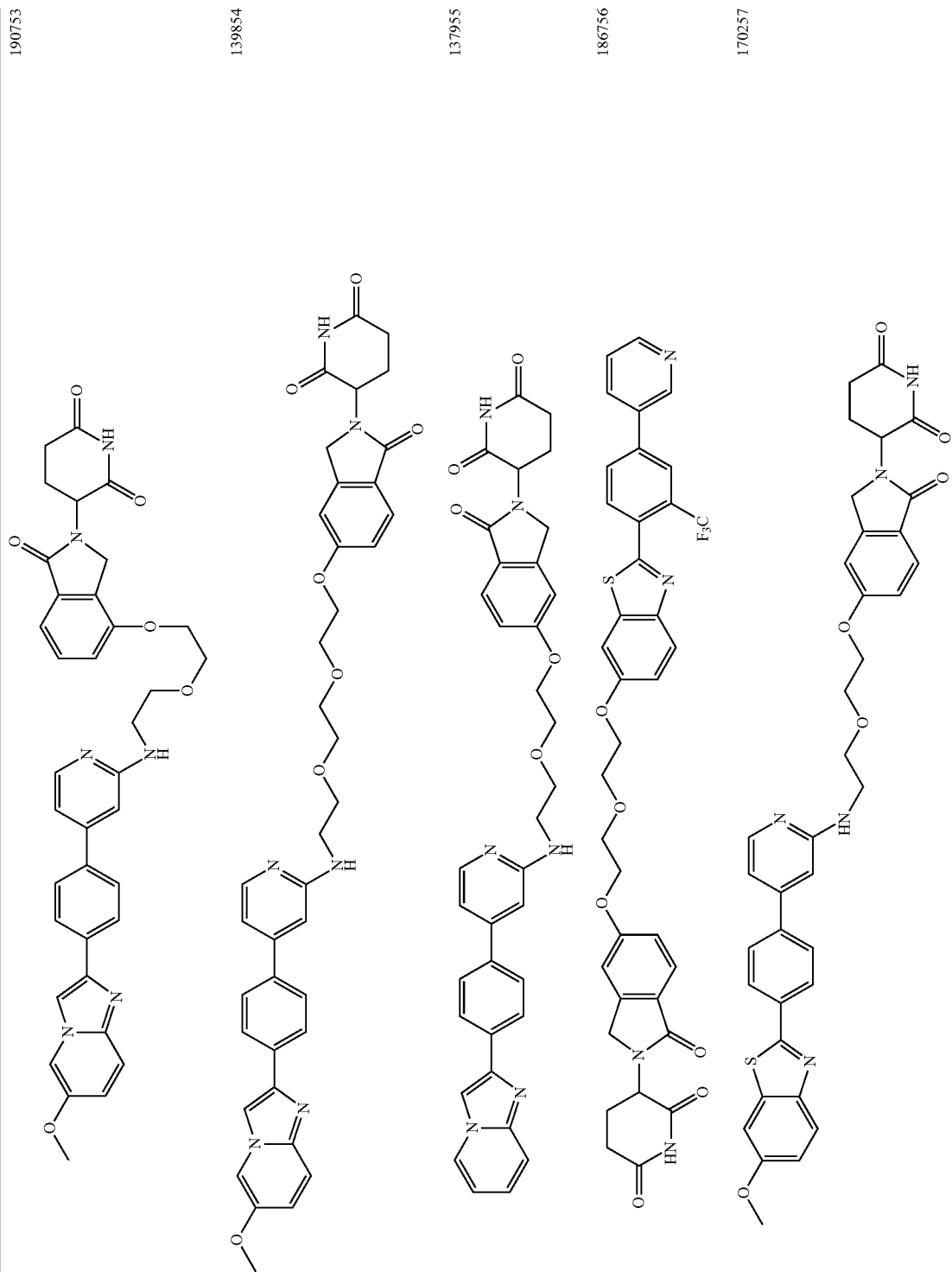

TABLE 1-continued
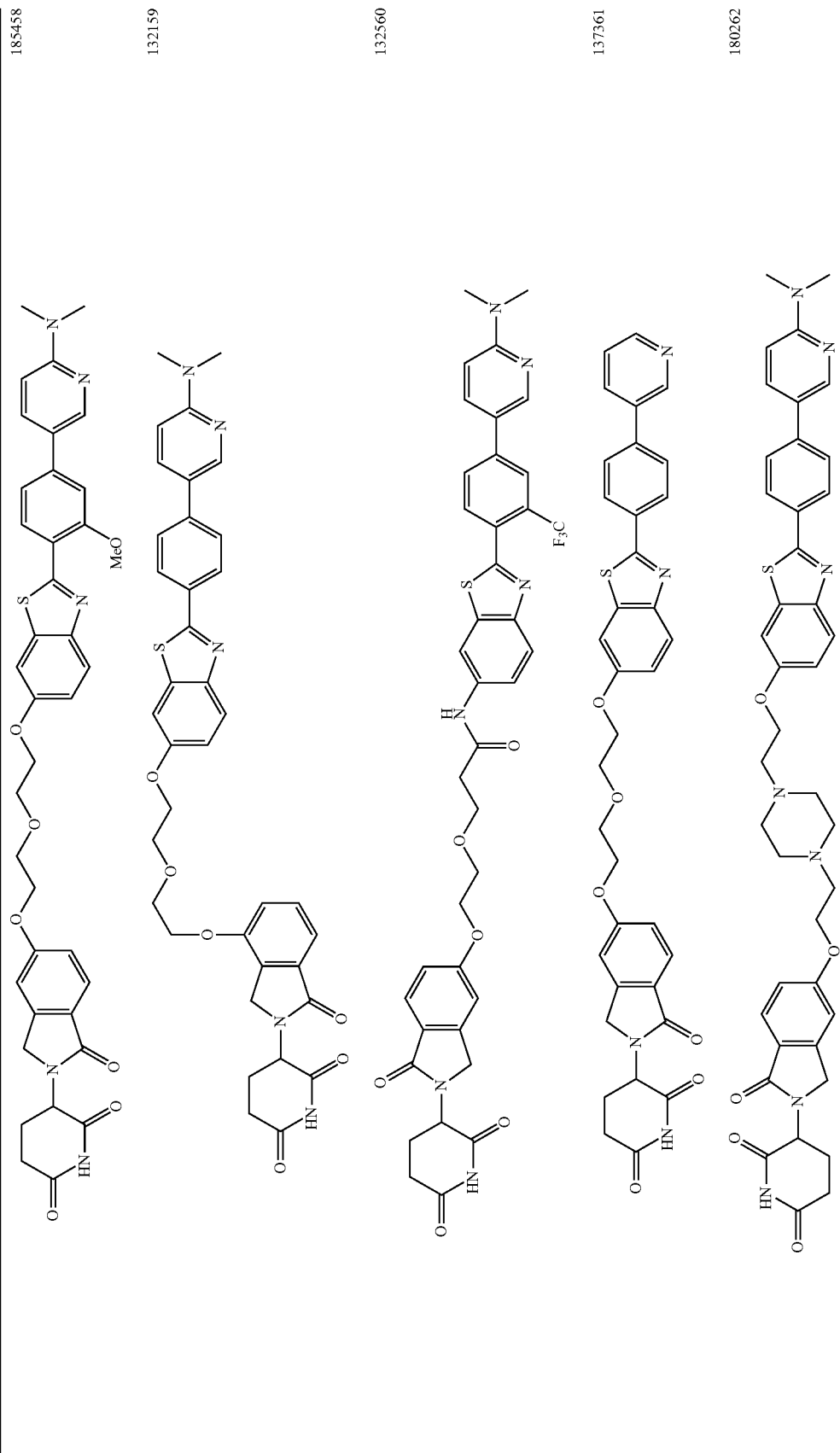

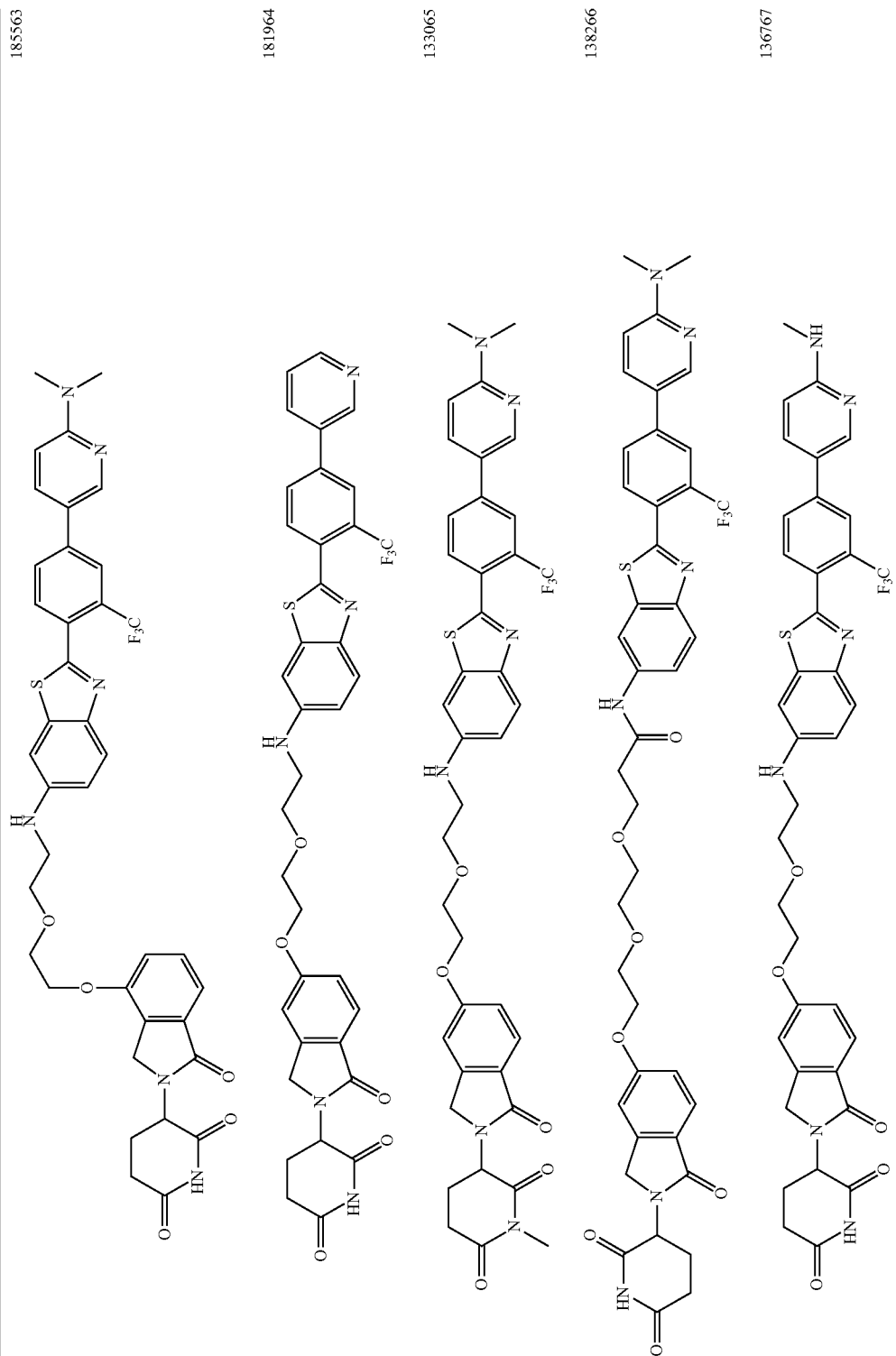

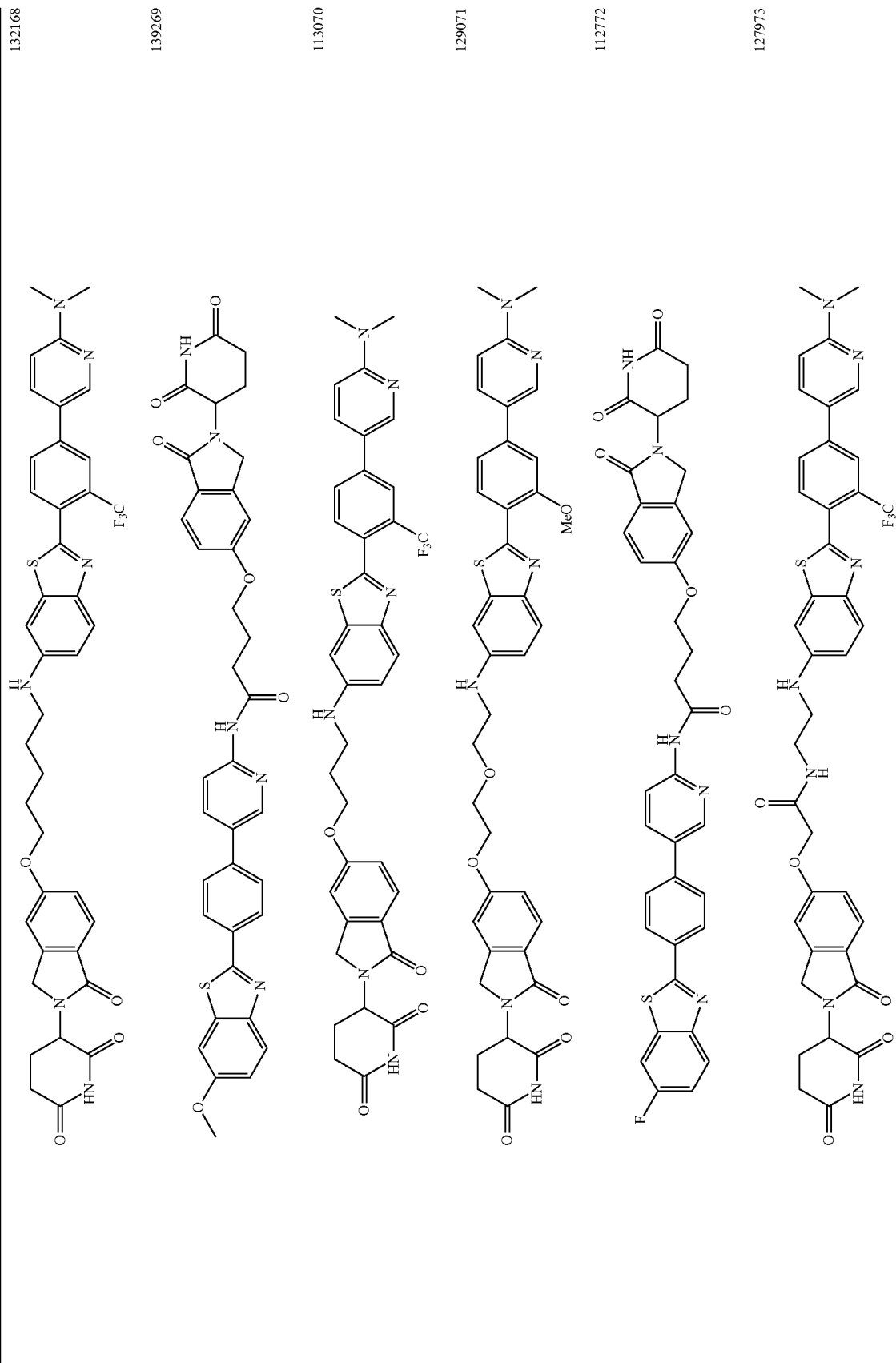

TABLE 1-continued
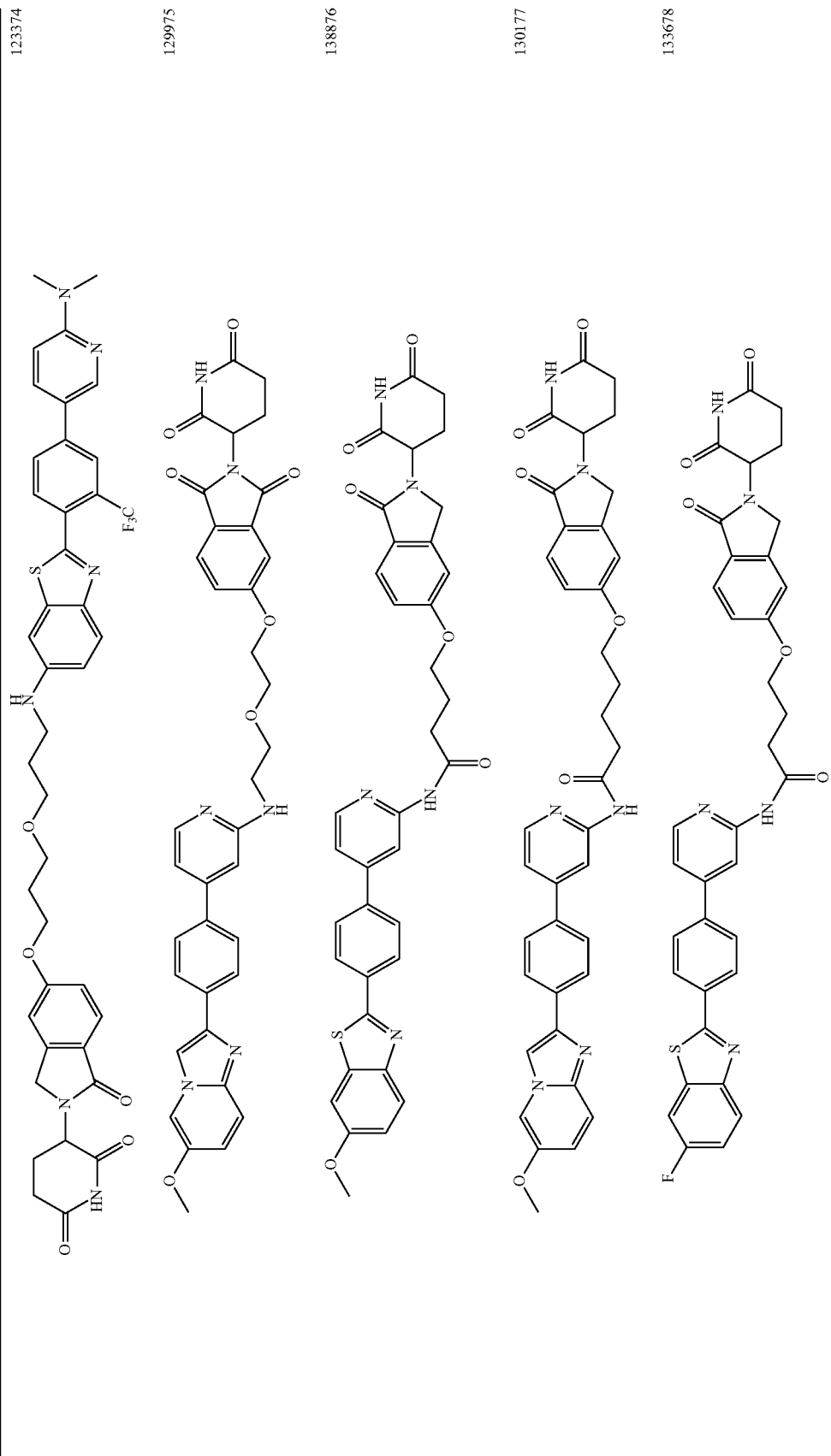

TABLE 1-continued
| 190279 | 133380 | 120581 | 161247 |
|---|---|---|---|
| 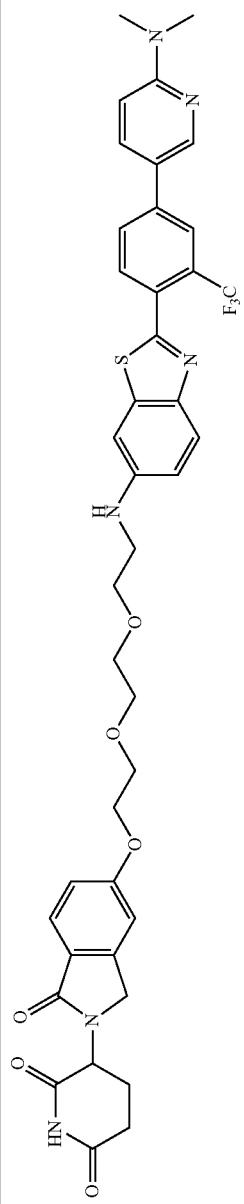 | 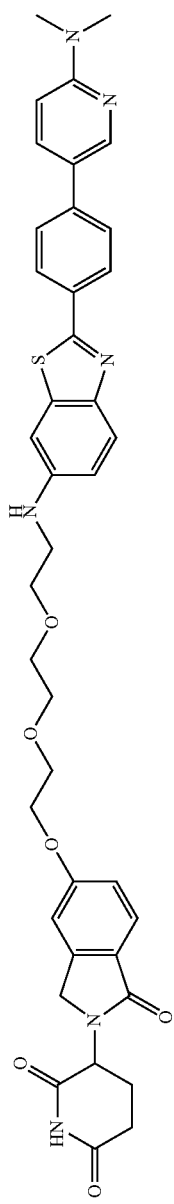 | 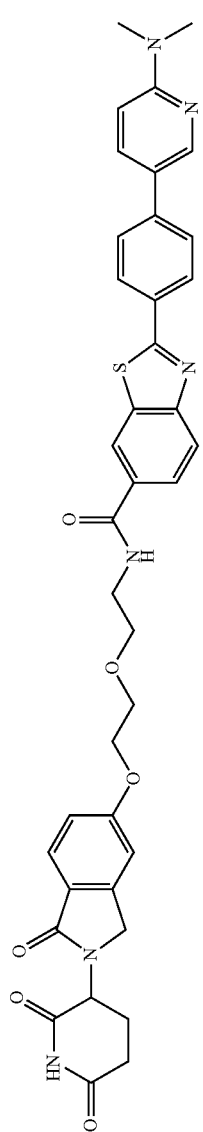 | 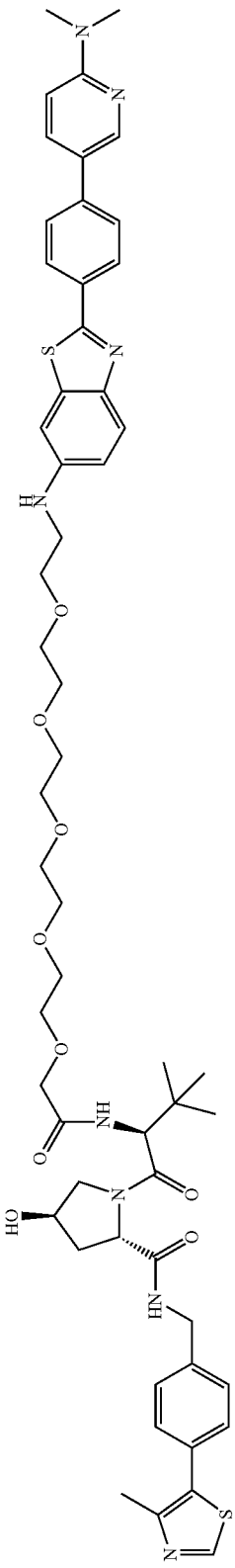 |

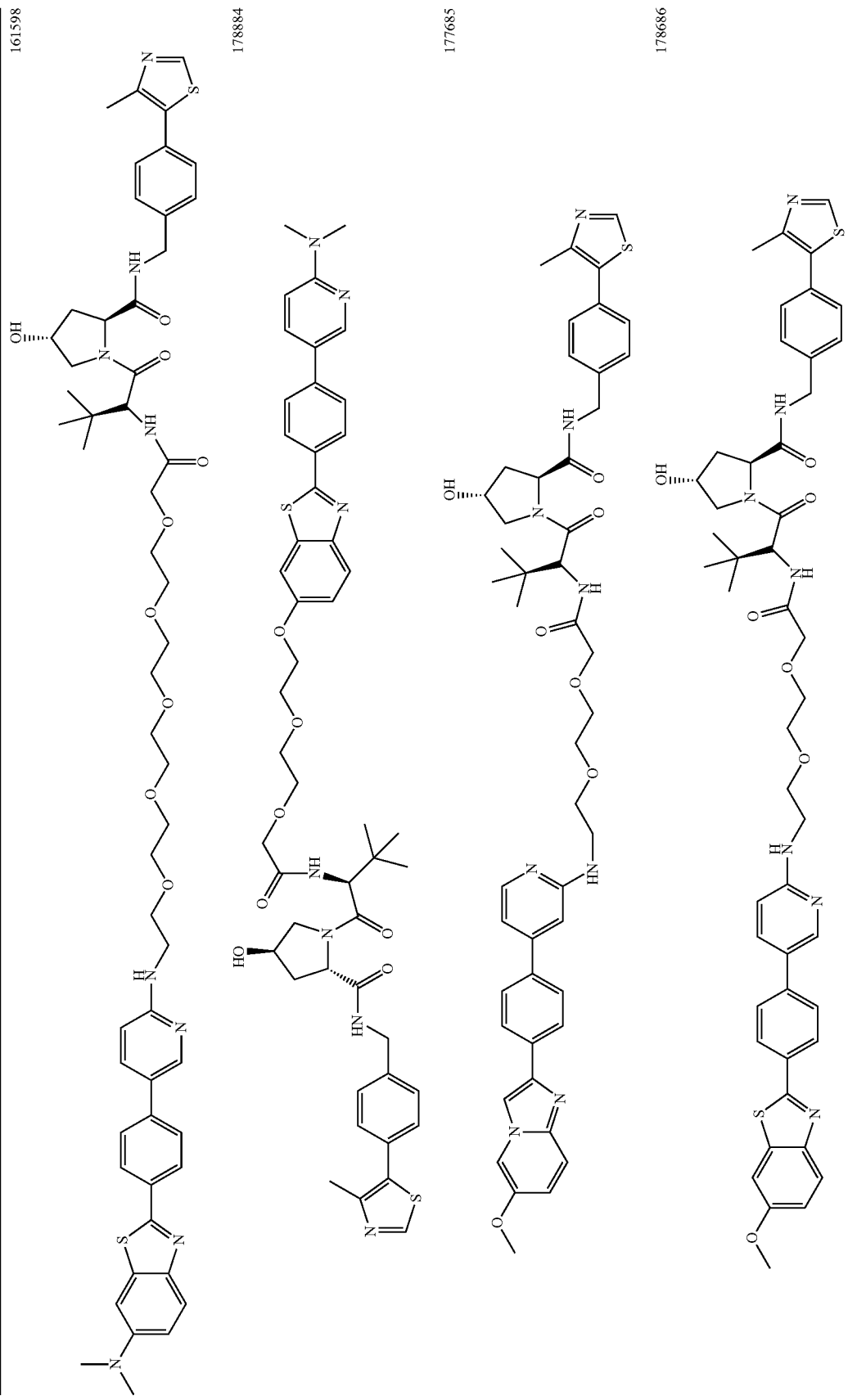

TABLE 1-continued

| 180187 | 190222 | 190083 | 129804 | 134555 |

TABLE 1-continued
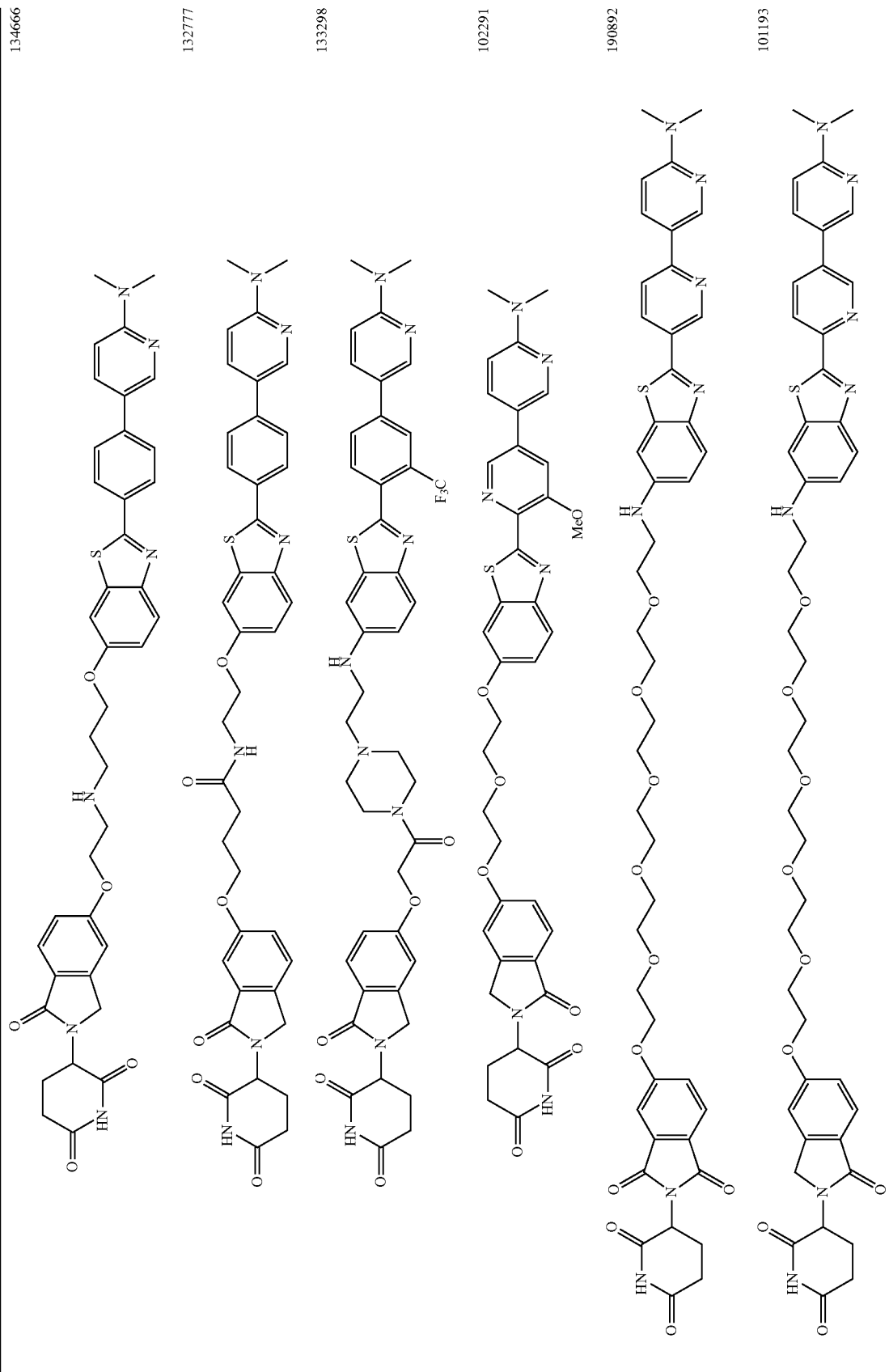

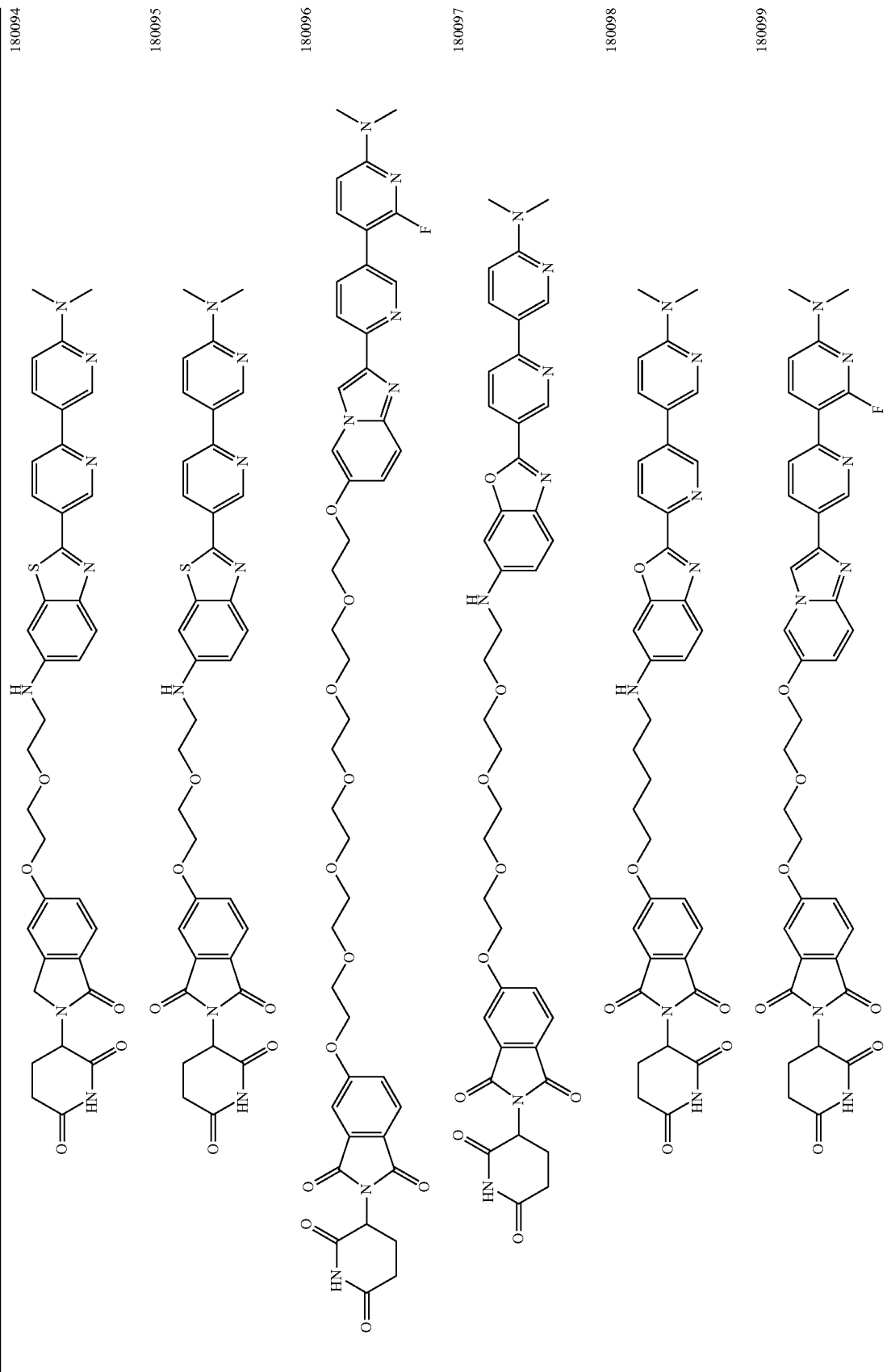

TABLE 1-continued
| 180194 | 180195 | 180196 | 180197 | 180198 |
|---|---|---|---|---|
| 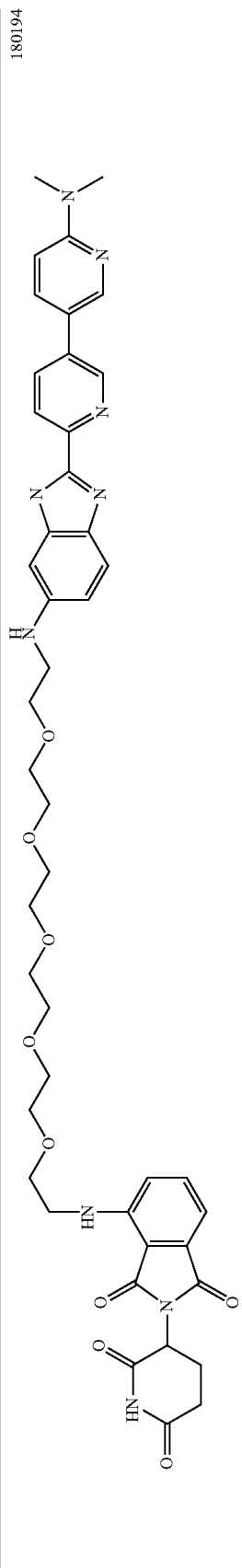 | 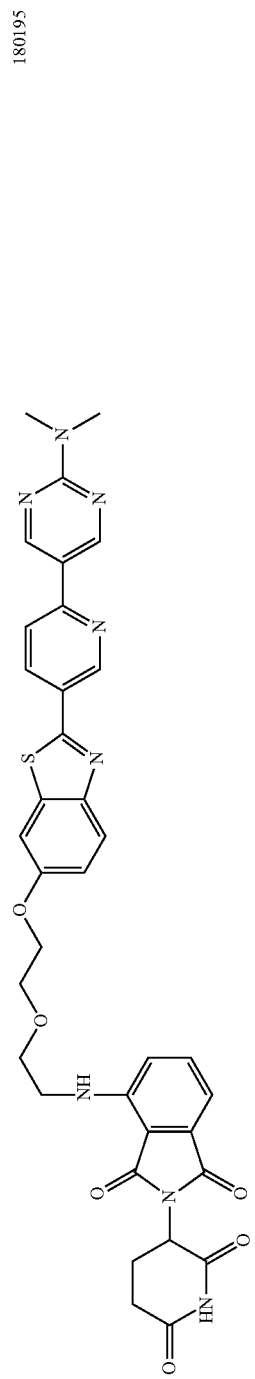 | 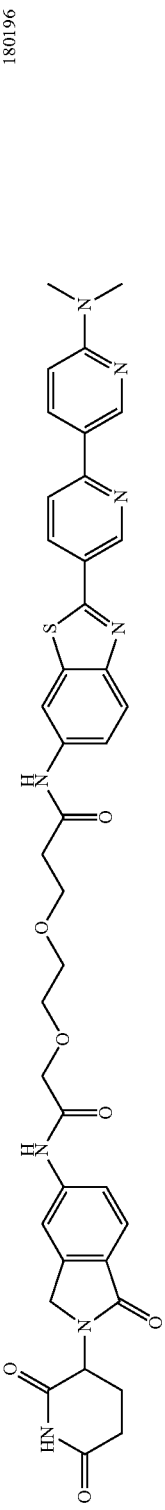 | 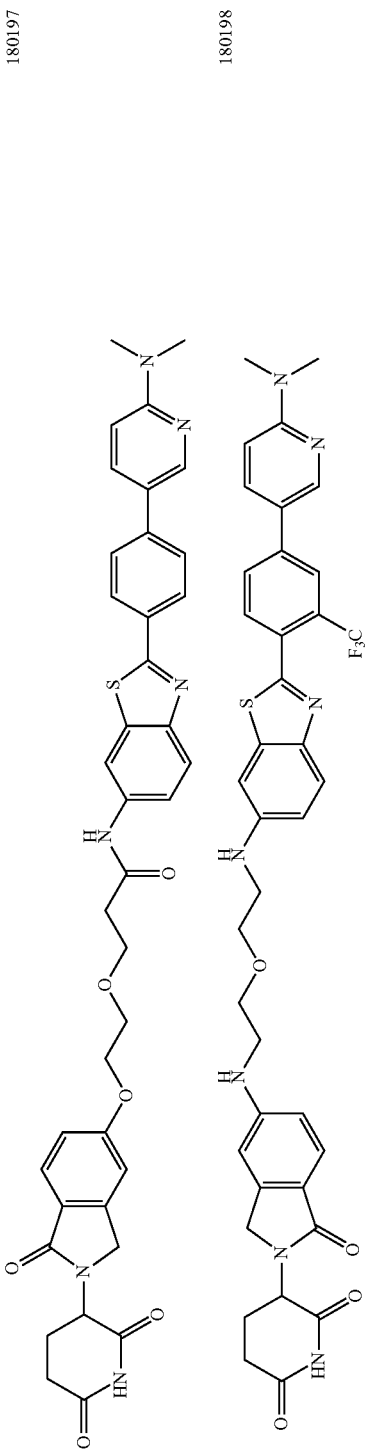 | |

TABLE 1-continued
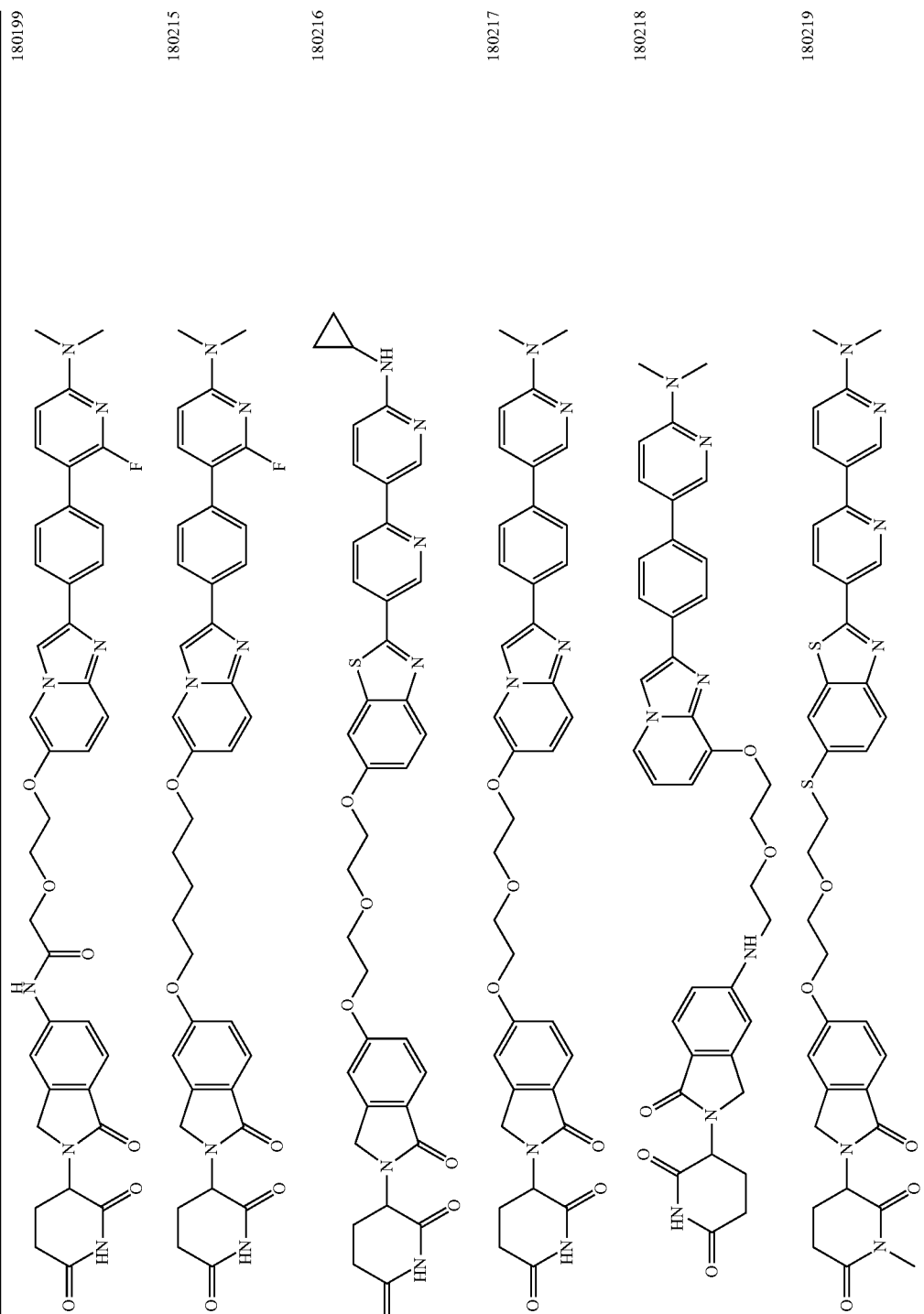

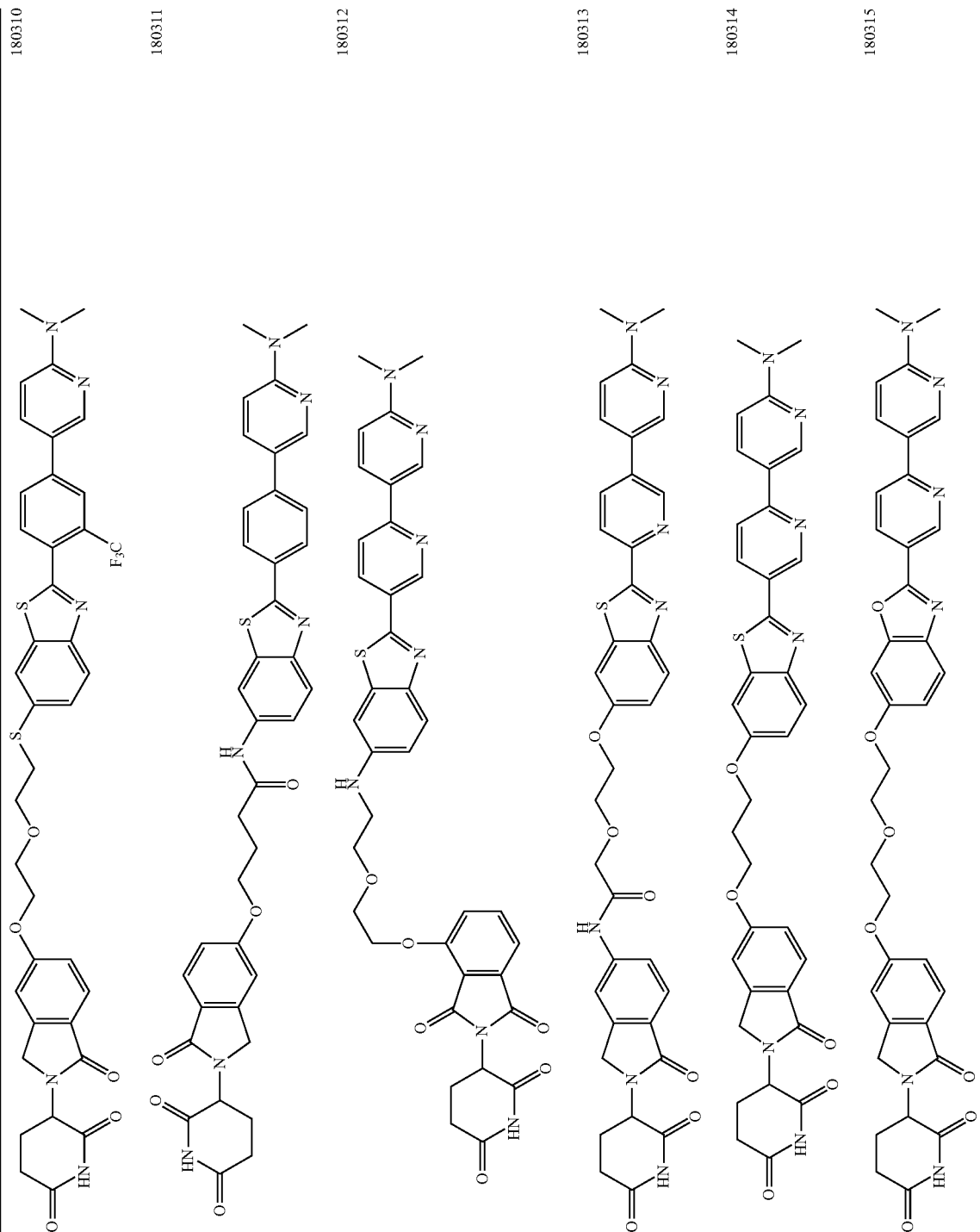

TABLE 1-continued
| 180316 | 180317 | 180318 | 120010 | 120011 |
|---|---|---|---|---|
| 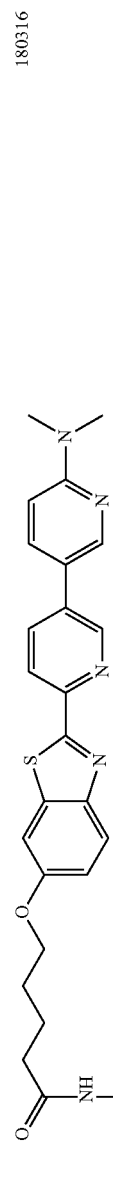 | 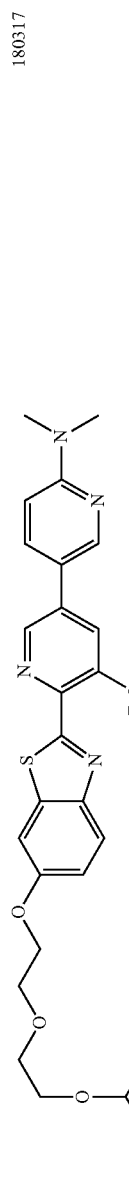 | 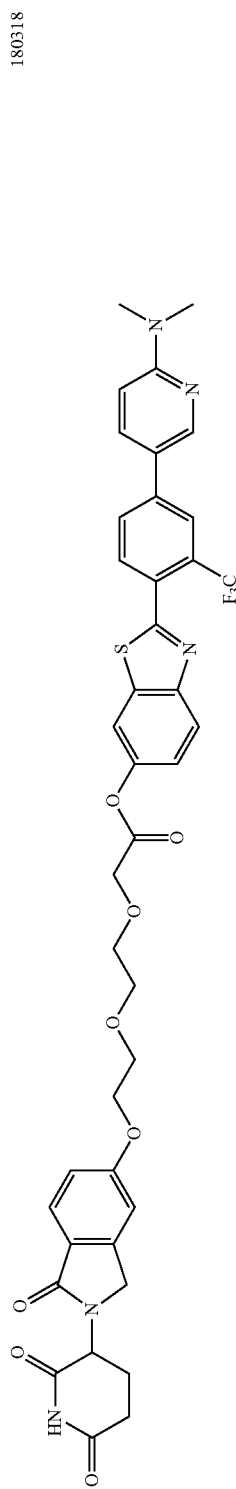 | 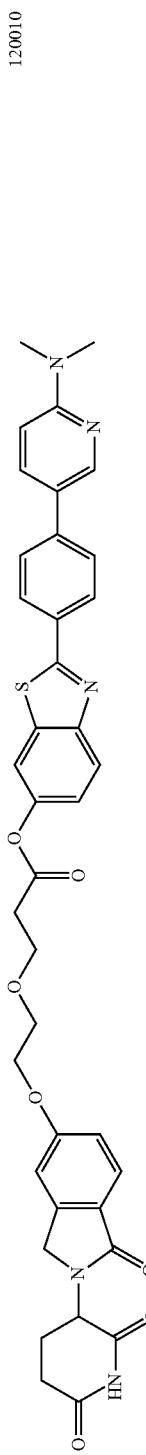 | 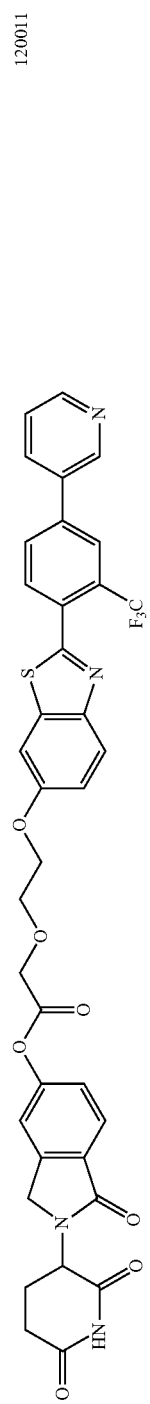 |

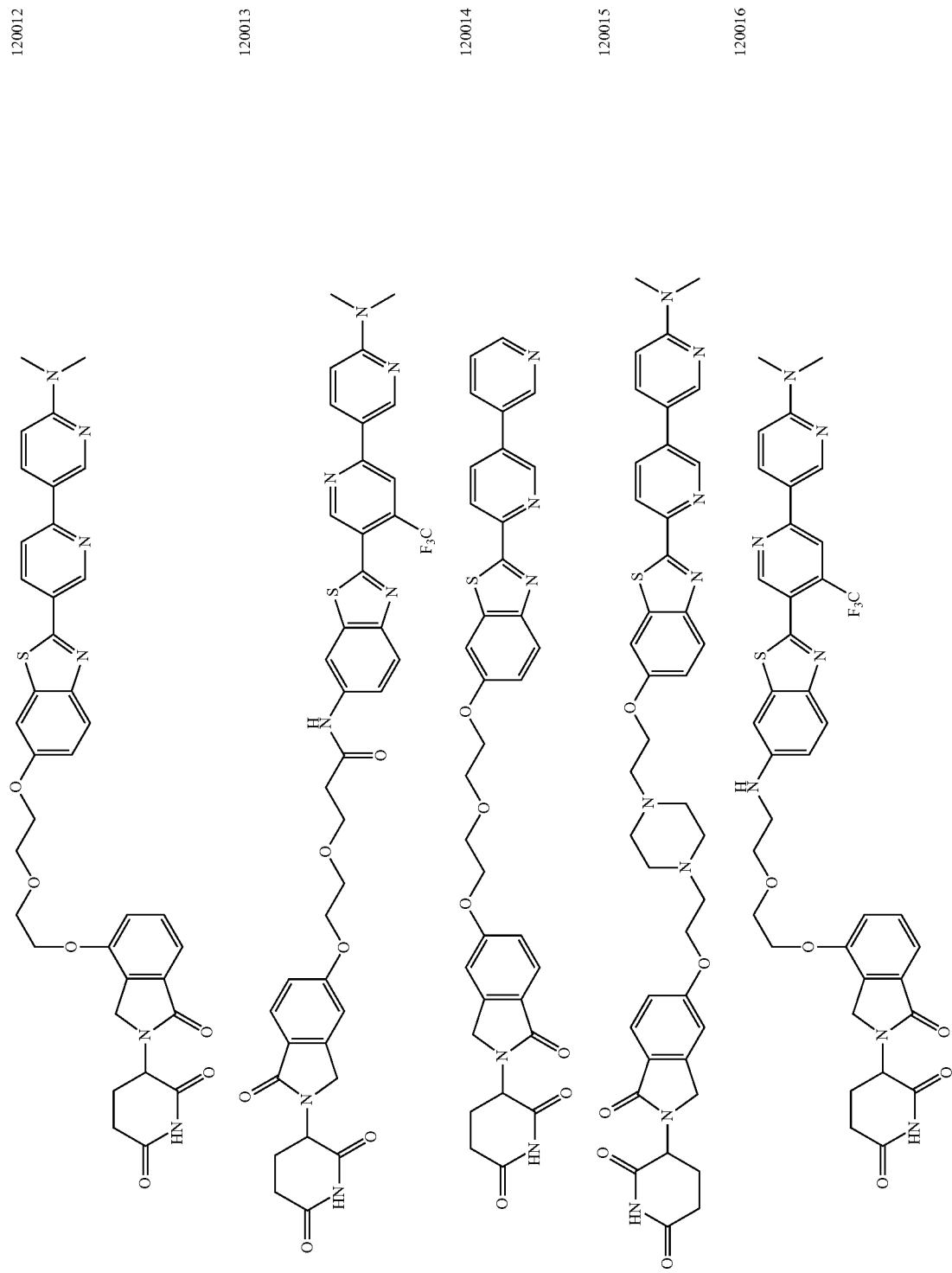

TABLE 1-continued

TABLE 1-continued
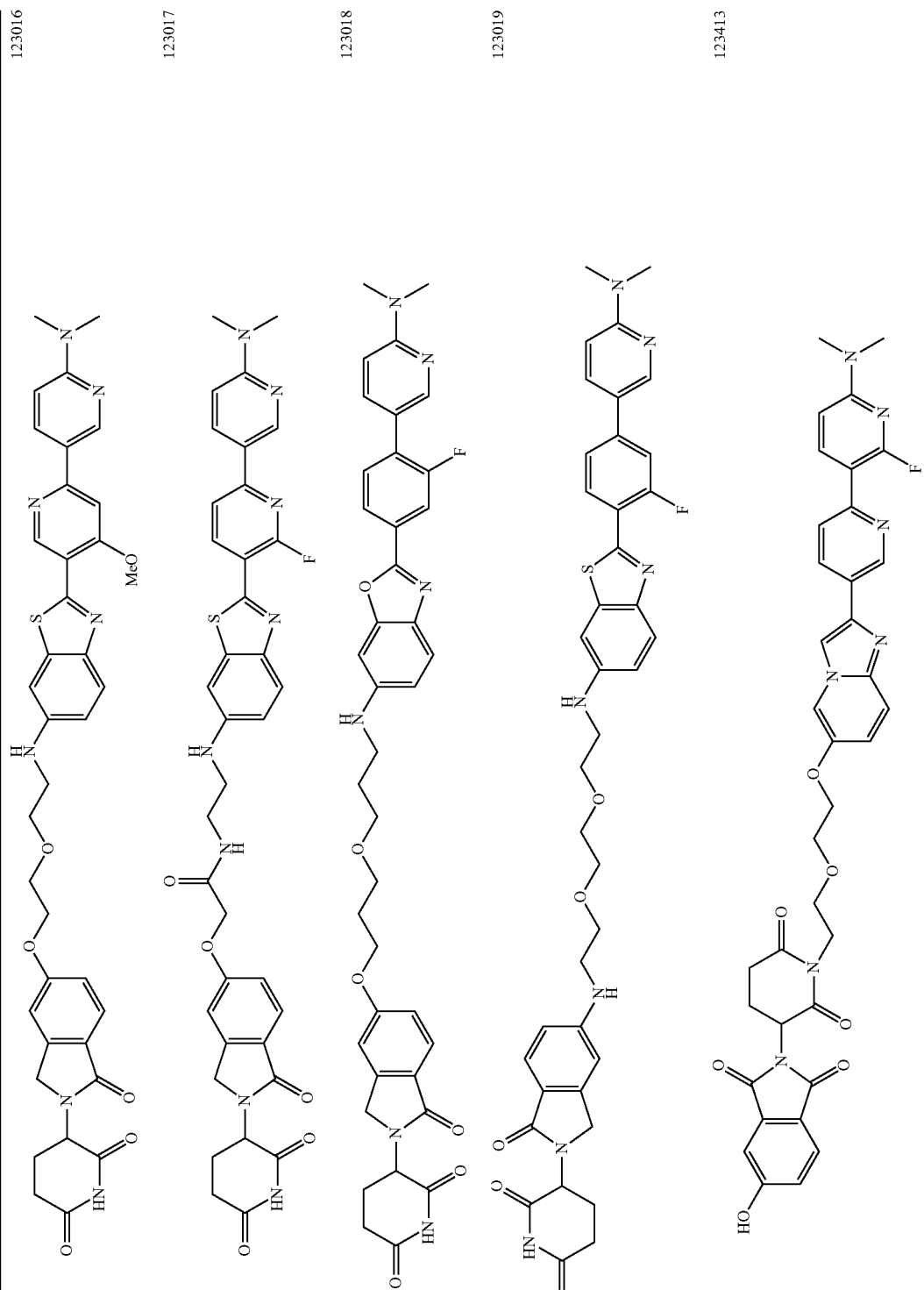

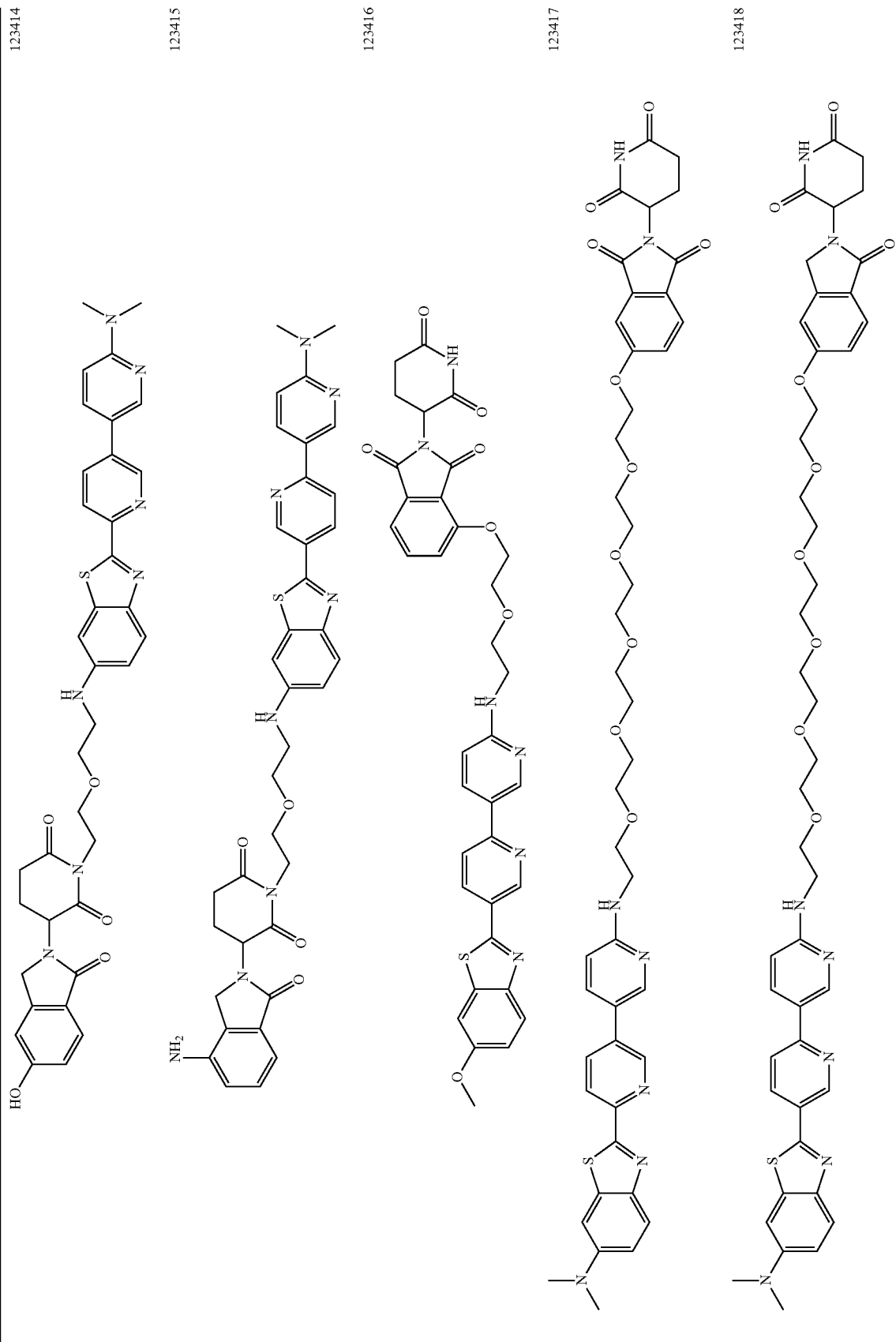

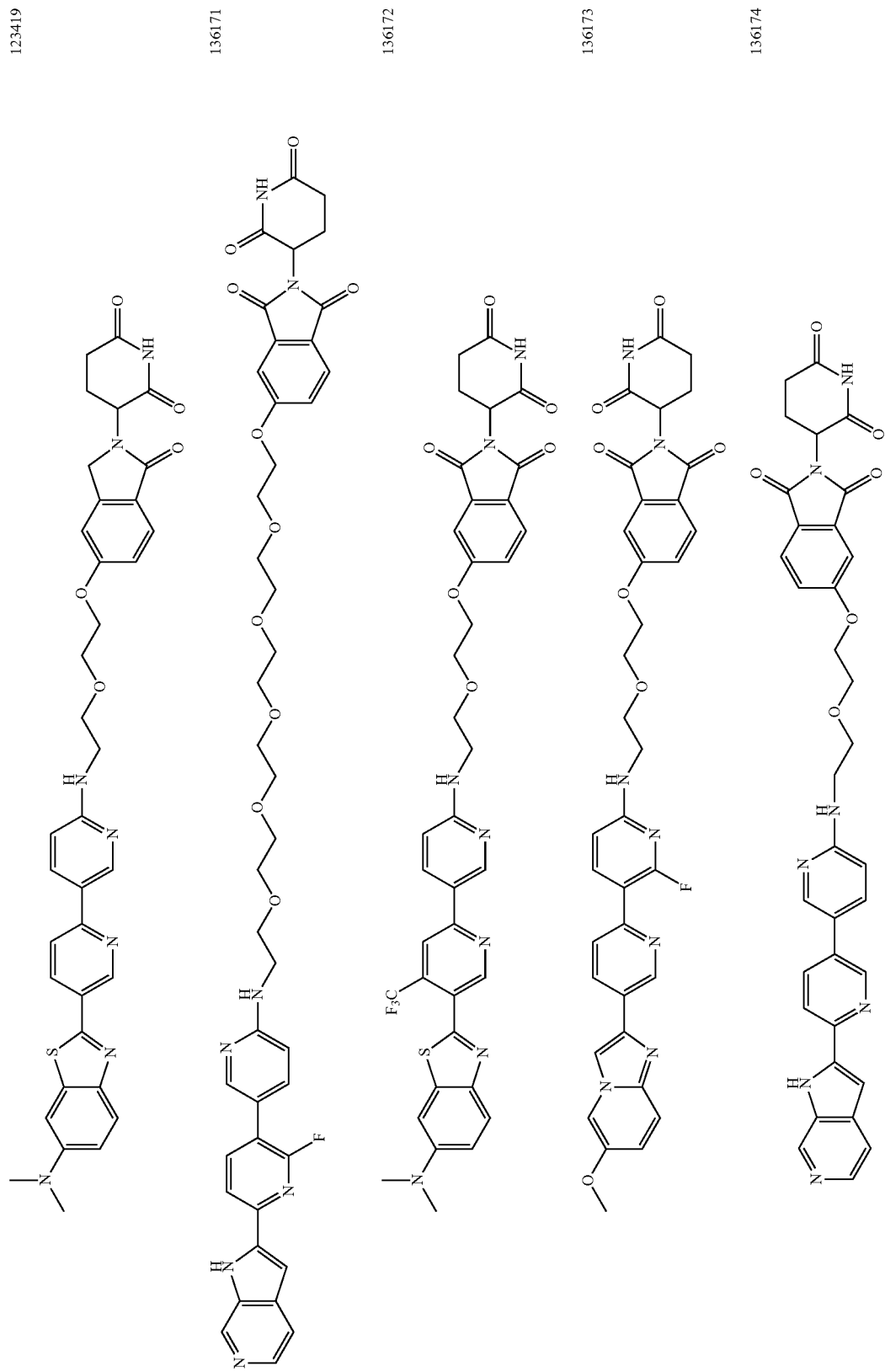

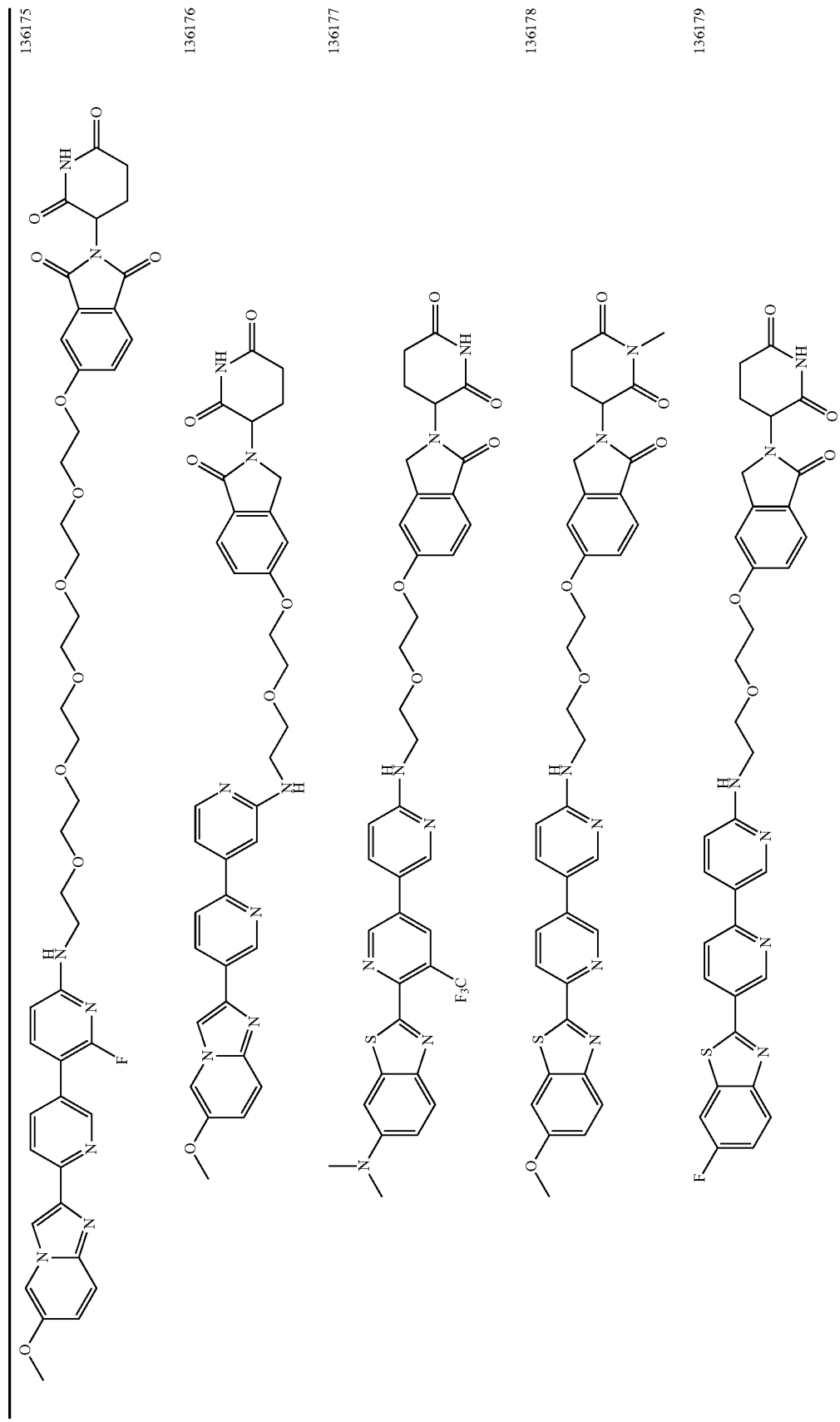

TABLE 1-continued
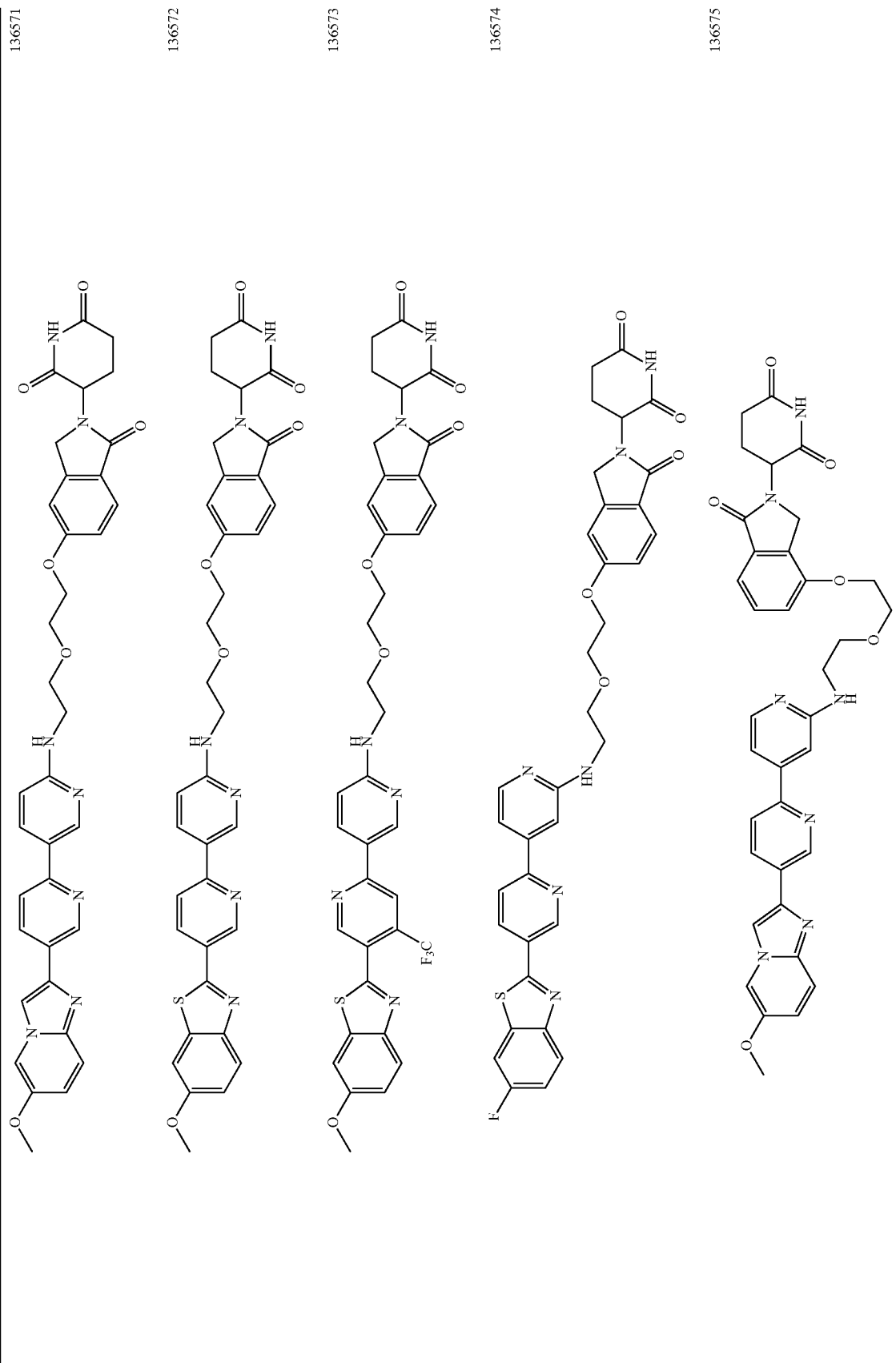

TABLE 1-continued
| 136576 | 136577 | 136578 | 136579 | 139571 |
|---|---|---|---|---|
| 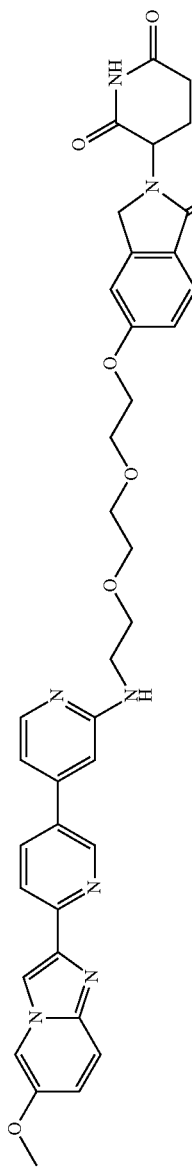 | 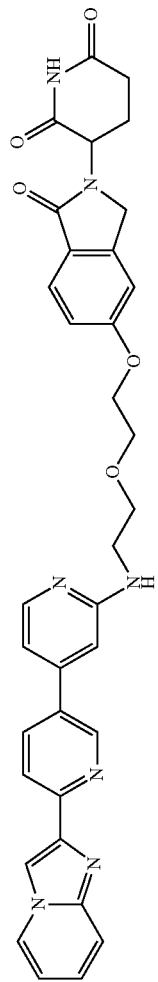 | 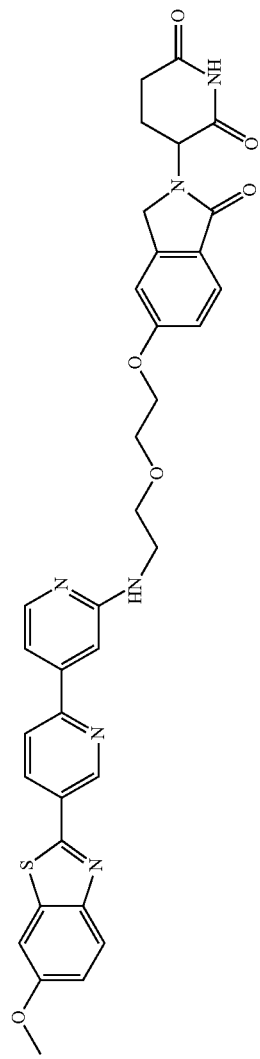 | 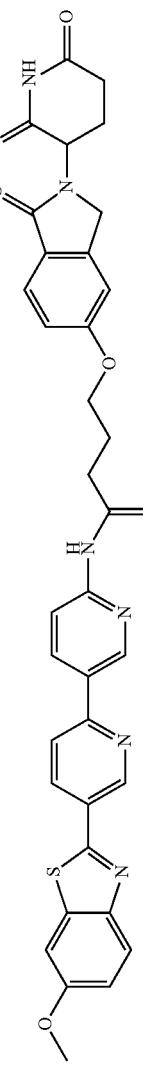 | 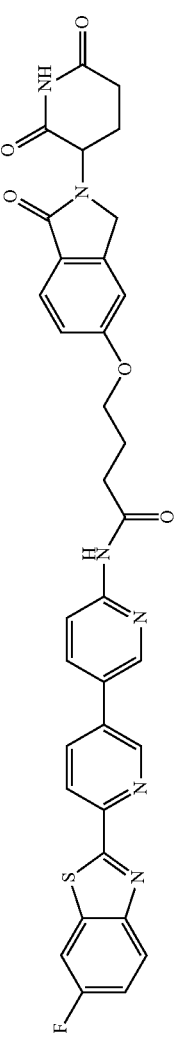 |

TABLE 1-continued
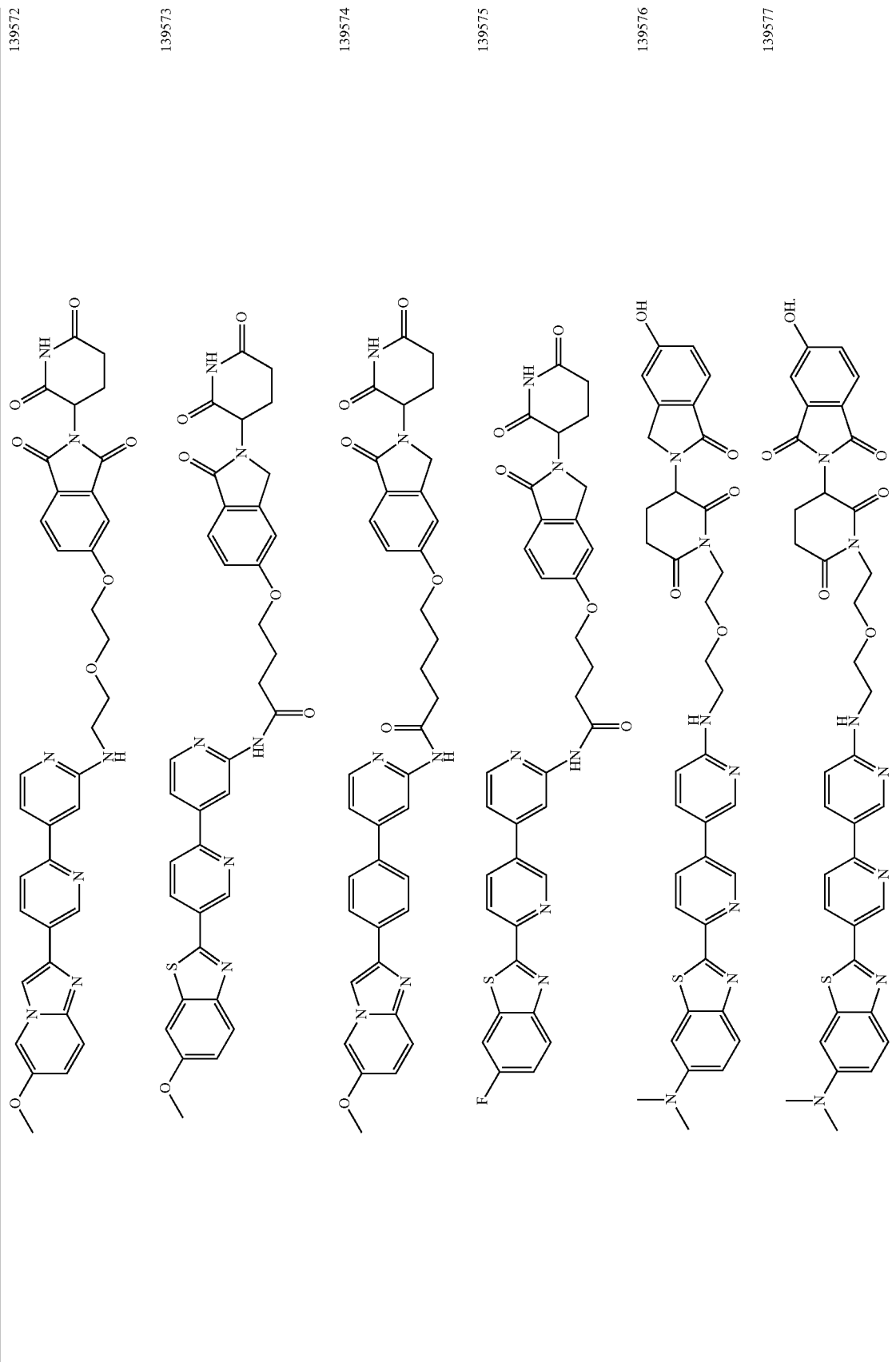

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the FIGURE, can be arranged, substituted, combined, and designed in a wide variety of different configurations, all of which are explicitly contemplated and make part of this application.

An embodiment is the compound wherein the compound is isotopically labeled or radiolabeled. An embodiment is a solvate, hydrate, salt, or ester or the compound of the disclosure.

An aspect of the disclosure is a composition, comprising a compound of the disclosure and a pharmaceutically acceptable excipient.

An aspect of the disclosure is a method for aiding in the treatment of a tauopathy in a subject, the method comprising administering an effective amount of a compound of the disclosure, or the composition of the disclosure, wherein the compound or the composition treats the subject.

In some embodiments, the tauopathy is a neurodegenerative tauopathy. In some embodiments, the tauopathy is selected from the group consisting of Alzheimer's Disease (AD), amyotrophic lateral sclerosis (ALS), Huntington's disease (HD), Parkinson's disease (PD), Creutzfeldt-Jacob disease, Dementia pugilistica, Down's Syndrome, Gerstmann-Straussler-Scheinker disease, British dementia, Danish dementia, inclusion-body myositis, prion protein cerebral amyloid angiopathy, traumatic brain injury, Guam Parkinsonism-dementia complex, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallervorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle-only dementia, White matter tauopathy with globular glial inclusions, Frontotemporal dementia, Postencephalitic Parkinsonism, Parkinsonism linked to chromosome 17, and Myotonic dystrophy. In some embodiments, the tauopathy is Alzheimer's disease (AD), progressive supranuclear palsy (PSP), corticobasal degeneration (CBD), or Pick's disease (PiD).

In some embodiments, according to any of the methods described above, the method further comprises administering to the subject at least one additional therapy. In some embodiments, the at least one additional therapy is selected from neurological drugs, anti-Tau antibodies, Tau inhibitors, anti-amyloid beta antibodies, beta-amyloid aggregation inhibitors, anti-BACE1 antibodies, and BACE1 inhibitors.

In some embodiments, according to any of the methods described above, the subject is diagnosed as having or being at risk of developing a Tau protein-associated disease. In some embodiments, the subject is diagnosed as having or being at risk of developing a tauopathy selected from the group consisting of Alzheimer's disease (AD), progressive supranuclear palsy (PSP), corticobasal degeneration (CBD), and Pick's disease (PiD).

In another aspect, provided herein is a method of reducing pathological human Tau in a sample. The method comprises a step of contacting the sample with a bispecific conjugate according to any of the embodiments described above. In some embodiments, the pathological human Tau is from a tauopathy selected from the group consisting of Alzheimer's disease (AD), progressive supranuclear palsy (PSP), corticobasal degeneration (CBD), and Pick's disease (PiD). In some embodiments, the pathological human Tau is Tau Type 1A, IB, 11A, or MB; misordered Tau; mis-disordered Tau; sarkosyl-insoluble Tau; an extracellular Tau deposit; a Tau aggregate; paired helical filaments; a neurofibrillary pathology; or a hyperphosphorylated form of truncated Tau or full-length Tau. In some embodiments, the pathological human Tau is hyperphosphorylated and sarkosyl-insoluble Tau. In some embodiments, the sample is a brain sample, a cerebrospinal fluid sample, or a blood sample. In some embodiments, the detecting comprising producing a readout comprising information about the presence of pathological human Tau in the sample. In some embodiments, the sample is from a subject and the method further comprises diagnosing whether the subject has a tauopathy or is likely to develop a tauopathy based on the readout.

In another aspect, provided herein is a method of reducing the level of Tau protein in a subject having, or at risk of developing, a Tau protein-associated disease, comprising administering to the subject a compound according to any of the embodiments described above, or a pharmaceutical composition according to any of the embodiments described above, wherein a) the level of non-phosphorylated Tau protein, phosphorylated Tau protein, and/or hyperphosphorylated Tau protein is reduced in the subject as compared to their levels in the subject prior to administration of the compound; and/or b) the level of a pathological Tau species is reduced in the subject as compared to its level in the subject prior to administration of the compound.

In another aspect, provided herein is a method of retaining or increasing cognitive memory capacity or slowing memory loss in a subject having or at risk of developing a Tau protein-associated disease, comprising administering to the subject a compound according to any of the embodiments described above or a pharmaceutical composition according to any of the embodiments described above.

In another aspect, provided herein is a method of inhibiting and/or reversing the propagation of Tau aggregation in a subject having or at risk of developing a Tau protein-associated disease, comprising administering to the subject a compound according to any of the embodiments described above or a pharmaceutical composition according to any of the embodiments described above.

In another aspect, provided herein is a method of inhibiting and/or reversing Tau seeding in a subject having or at risk of developing a Tau protein-associated disease, comprising administering to the subject a compound according to any of the embodiments described above or a pharmaceutical composition according to any of the embodiments described above.

Definitions

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein. When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having indicated number of carbon atoms. In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), amyl ($C_5$), neopentyl ($C_5$), 3-methyl-2-butyl ($C_5$), tertiary amyl ($C_5$), and n-hexyl ($C_6$).

"Alkenyl" refers to an alkyl group with one or more carbon-carbon double bonds at any position of the chain, which can be monosubstituted or polysubstituted, and can be monovalent, divalent or multivalent. Examples of the alkenyl group include a vinyl group, a propenyl group, a butenyl group, a pentenyl group, a hexenyl group, a butadienyl group, a pentadienyl group, a hexadienyl group, etc.

"Alkynyl" refers to an alkyl group with one or more carbon-carbon triple bonds at any position of the chain, which can be monosubstituted or polysubstituted, and can be monovalent, divalent or multivalent. Examples of alkynyl groups include ethynyl, propynyl, butynyl, pentynyl, etc.

"Cycloalkyl" includes any stable cyclic or polycyclic hydrocarbon group and any carbon atom which is saturated, which can be monosubstituted or polysubstituted, and can be monovalent, divalent or multivalent. Examples of such cycloalkyl groups include, but are not limited to, cyclopropyl, norbornyl, [2.2.2]bicyclooctane, [4.4.0]bicyclononane, etc.

"Optionally" means that an event or situation described subsequently may, but not necessarily, occur, and the description includes the occurrence of the event or situation mentioned above and the absence of the event or situation described therein.

"Substituted" means that any one or more hydrogen atoms on a particular atom are replaced with substituents, including deuterium and hydrogen variants, as long as the valence of a particular atom is normal and the substituted compound is stable. When the substituent is a keto (i.e., =O), it means that two hydrogen atoms are substituted. Ketone substitution does not occur on aromatic groups. The term "optionally substituted" means that it may or may not be substituted. Unless otherwise specified, the type and number of substituents may be arbitrary on the basis of being chemically achievable.

When any variable (e.g. R) occurs more than one time in any constituents or formula for a compound, its definition at each occurrence is independent of its definition at every other occurrence. Thus, for example, if a group is shown to be substituted by 0-2 of R, then said group may optionally be substituted by up to two R groups and R at each occurrence is selected independently from the definition of R. Also, combinations of substituents and/or variables are permissible only if such combinations result in stable compounds.

When the number of a bonding group is zero, for example, -(A)$_0$-, then this bonding group is a single bond.

"Alkoxy" refers to refers to said alkyl group with a specified number of carbon atoms attached through an oxygen bridge. Unless otherwise specified, $C_{1-6}$ alkoxy includes $C_1$, $C_2$, $C_3$, $C_4$, $C_5$ and $C_6$ alkoxy group. Examples of alkoxy groups include, but are not limited to, methoxy, ethoxy, n-propoxy, isopropoxy, n-butoxy, sec-butoxy, tert-butoxy, n-pentyloxy and S-pentyloxy.

"Aryl" refers to a polyunsaturated, aromatic hydrocarbon substituent which can be monosubstituted or polysubstituted, and can be monovalent, divalent or polyvalent, and can be monocyclic or polycyclic (e.g., 1 to 3 rings; at least one of which is aromatic). They are fused together or covalently linked.

"Halo" or "halogen" by itself or as part of another substituent refers to a fluorine, chlorine, bromine or iodine atom.

"Haloalkyl" includes both monohaloalkyl and polyhaloalkyl. For example, the term "halo($C_{1-4}$)alkyl" includes, but is not limited to, trifluoromethyl, 2,2,2-trifluoroethyl, 4-chlorobutyl, 3-bromopropyl, etc. Unless otherwise specified, examples of haloalkyl include, but are not limited to, trifluoromethyl, trichloromethyl, pentafluoroethyl, and pentachloroethyl.

"Heterocyclo" refers to a radical of a 3- to 10-membered non-aromatic ring or aromatic ring system having indicated ring carbon atoms (such as 2 to 6 ring carbon atoms) and 1 to 4 ring heteroatoms, wherein each heteroatom is independently selected from nitrogen, oxygen and sulfur ("$C_{2-6}$ heterocyclo"). In heterocyclo groups that contain one or more nitrogen atoms, the point of attachment can be a carbon or nitrogen atom, as valency permits. A heterocyclo group can either be monocyclic ("monocyclic heterocyclo") or a fused, bridged or spiro ring system such as a bicyclic system ("bicyclic heterocyclo"), and can be saturated or partially unsaturated. Heterocyclo bicyclic ring systems can include one or more heteroatoms in one or both rings. "Heterocyclo" also includes ring systems wherein the heterocyclic ring, as defined above, is fused with one or more carbocyclic groups wherein the point of attachment is either on the carbocyclic or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

"Nitrogen protecting group" refers to a protecting group for preventing side reactions at the amino nitrogen position. Representative amino protecting groups include, but are not limited to formyl; acyl, such as alkanoyl (e.g., acetyl, trichloroacetyl or trifluoroacetyl); alkoxycarbonyl, such as tert-butoxycarbonyl (Boc); Arylmethoxycarbonyl, such as benzyloxycarbonyl (Cbz) and 9-fluorenylmethoxycarbonyl (Fmoc); arylmethyl, such as benzyl (Bn), trityl (Tr), 1, 1-di-(4'-methoxyphenyl)methyl; silyl groups such as trimethylsilyl (TMS) and tert-butyldimethylsilyl (TBS), etc.

In some embodiments, a heterocyclo group is a 5-10 membered non-aromatic ring system or aromatic ring system having indicated ring carbon atoms and 1-4 ring heteroatoms, wherein each heteroatom is independently selected from nitrogen, oxygen, and sulfur. In some embodiments, a heterocyclo group is a 5-6 membered non-aromatic ring system or aromatic ring system having indicated ring carbon atoms and 1-4 ring heteroatoms, wherein each heteroatom is independently selected from nitrogen, oxygen, and sulfur ("5-6 membered heterocyclo"). In some embodiments, the 5-6 membered heterocyclo has 1-3 ring heteroatoms selected from nitrogen, oxygen, and sulfur. In some embodiments, the 5-6 membered heterocyclo has 1-2 ring heteroatoms selected from nitrogen, oxygen, and sulfur. In some embodiments, the 5-6 membered heterocyclo has one ring heteroatom selected from nitrogen, oxygen, and sulfur.

Exemplary 3-membered heterocyclo groups containing one heteroatom include, without limitation, aziridinyl, oxiranyl, and thioranyl. Exemplary 4-membered heterocyclo groups containing one heteroatom include, without limitation, azetidinyl, oxetanyl, and thietanyl. Exemplary 5-membered heterocyclo groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclo groups containing two heteroatoms include, without limitation, dioxolanyl, oxasulfuranyl, disulfuranyl, and oxazolidin-2-one. Exemplary 5-membered heterocyclo groups containing three heteroatoms include, without limitation, triazolinyl, oxadiazolinyl, and thiadiazolinyl. Exemplary 6-membered heterocyclo groups containing one heteroatom include, without limitation, piperidinyl, tetrahydropyranyl, dihydropyridinyl, and thianyl. Exemplary 6-membered heterocyclo groups containing two heteroatoms include, without limitation, piperazinyl, morpholinyl, dithianyl, and dioxanyl. Exemplary 6-membered heterocyclo groups containing two heteroatoms include, without limitation, triazinanyl. Exemplary 7-membered heterocyclo groups containing one heteroatom include, without limitation, azepanyl, oxepanyl, and thiepanyl. Exemplary 8-membered heterocyclo groups containing one heteroatom include, without limitation, azocanyl, oxecanyl, and thiocanyl. Exemplary 5-membered heterocyclo groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclo groups fused to an aryl ring (also referred to herein as a 6,6-bicyclic heterocyclic ring) include, without limitation, tetrahydroquinolinyl, tetrahydroisoquinolinyl, and the like.

The term "pharmaceutically acceptable salt" means a salt that is not harmful to mammals, especially humans. Pharmaceutically acceptable salts can be formed using non-toxic acids or bases, including mineral acids or inorganic bases, or organic acids or organic bases. Examples of pharmaceutically acceptable salts include metal salts formed with aluminum, calcium, lithium, magnesium, potassium, sodium, zinc and so on, and organic salts formed with lysine, N, N'-dibenzylethylenediamine, chloroprocaine, choline, diethanolamine, ethylenediamine, meglumine (N-methylglucamine), procaine and so on. Also, pharmaceutically acceptable salts contain acid-addition salts and base-addition salts.

The term "pharmaceutically acceptable excipient" means pharmaceutically acceptable materials, compositions, or vehicles such as physiological saline solutions, liquid or solid fillers, diluents, solvents, or encapsulants. Examples of pharmaceutically acceptable excipients include water, saline water, physiological saline water or phosphate buffered saline water (PBS), sodium chloride injection solution, Ringer's injection solution, isotonic dextrose injection solution, sterile water injection solution, dextrose, and lactated Ringer's injection solution.

"Effective amount" means enough amount of medicine or agent which can achieve the desired affect without toxin. For the oral preparation in this invention, "effective amount" of a kind of active substance in compositions means the amount needed to achieve the desired affect when combining with another active substance in compositions. The effective amount varies with each individual, and depends on ages of receptors and general situations, also specific active substances.

The term "solvate" means a solvent-containing compound that is formed by association of one or a plurality of solvent molecules to the compounds of the present invention. Solvates include, for example, monosolvates, disolvates, trisolvates, and tetrasolvates. Also, solvates include hydrates. The term "hydrate" means a compound further containing a stoichiometric or a non-stoichiometric amount of water constrained by non-covalent bonding intermolecular force, or a salt thereof. Hydrates include monohydrates, dihydrates, trihydrates, tetrahydrates, and the like.

The term "effective dose" refers to the amount of a compound or a composition which will have a targeted effect. For example, in some embodiments, the effective dose may refer to the amount of a compound or a composition which will enable tau imaging.

The term "tau imaging" means imaging tau proteins that accumulate in the brain. This imaging may be performed by positron emission tomography (PET), fluorescence microscopy measurement, multi-photon imaging, two-photon imaging, near-infrared fluorescence imaging, autoradiography, and single-photon emission computed tomography (SPECT).

The terms "treatment," "treat," and "treating" refer to reversing, alleviating, delaying the onset of, or inhibiting the progress of a disease. In some embodiments, treatment is administered after one or more signs or symptoms of the disease have developed or have been observed. In other embodiments, treatment may be administered in the absence of signs or symptoms of the disease. For example, treatment may be administered to a susceptible subject prior to the onset of symptoms (for example, in light of a history of symptoms or a known genetic predisposition). Treatment may also be continued after symptoms have resolved, for example, to delay or prevent recurrence.

The compounds of the present invention can be prepared by a variety of synthetic methods well known to those skilled in the art, including the embodiments listed below, combinations thereof with other chemical synthesis methods, and equivalent alternatives known to those skilled in the art. Preferred embodiments include, but are not limited to, the embodiments of the invention.

Synthesis of Compounds

The following synthetic procedures are provided as examples, using which one of ordinary skill in the art can synthesize the compounds of the disclosure.

Compounds of Formula (I)

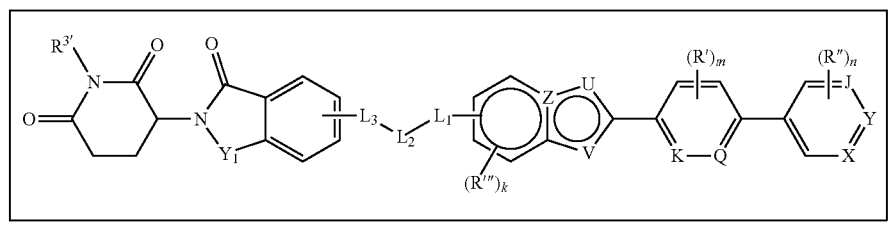

Formula I

Compounds of the general formula (I) are prepared as set forth in the Scheme below:

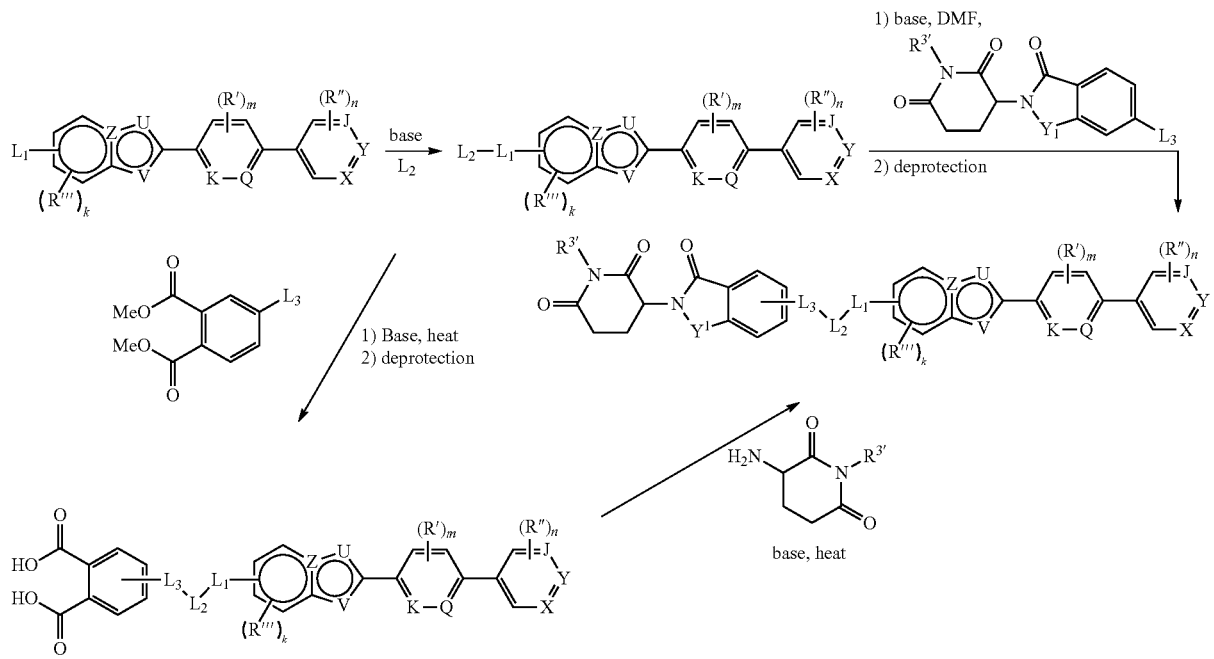

Compounds of Formula (II)
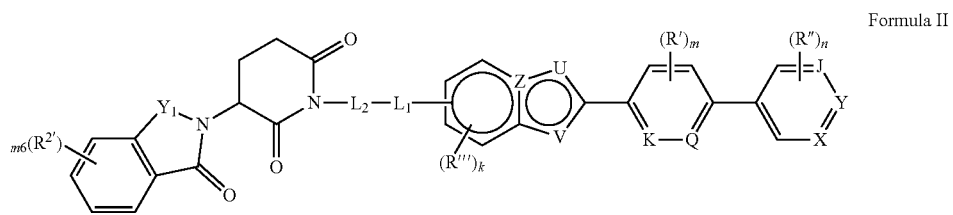
Formula II
Compounds of the general formula (II) are prepared as set forth in the Scheme below:
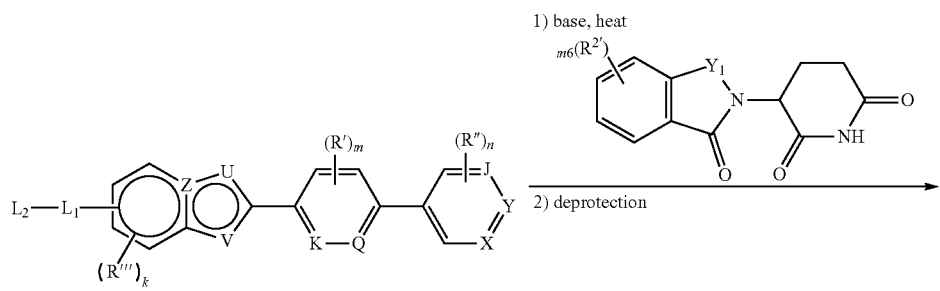
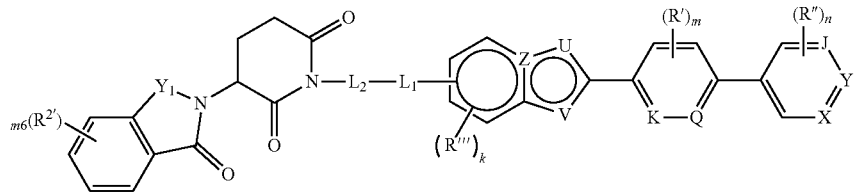
Compounds of Formula (III)
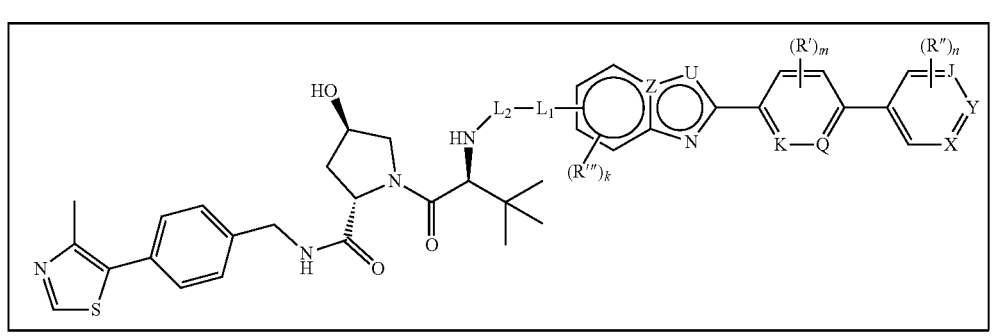
Formula III Compounds of the general formula (III) are prepared as set forth in the Scheme below:
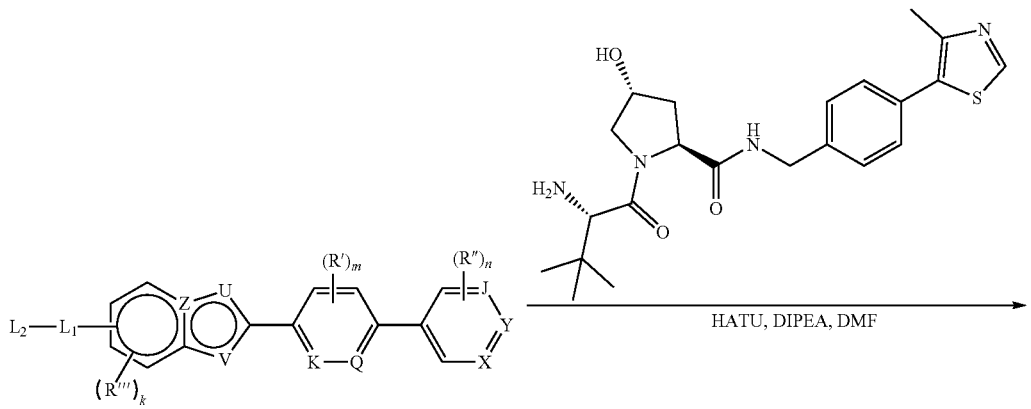
Compounds of Formula (IV)
Formula IV
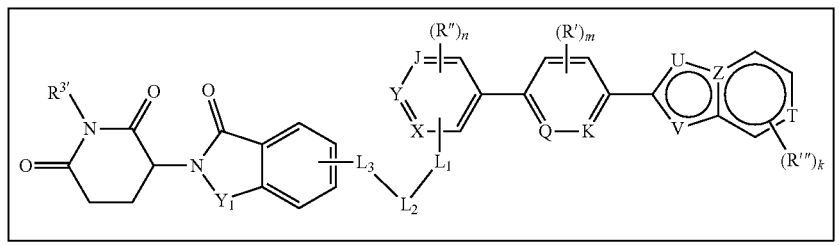
Compounds of the general formula (IV) are prepared as set forth in the Scheme below:

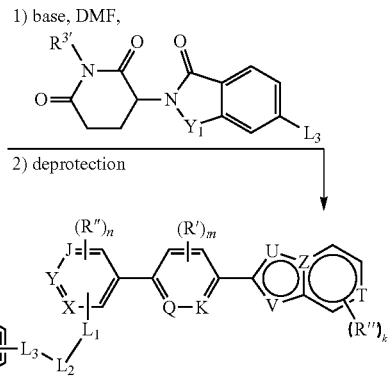
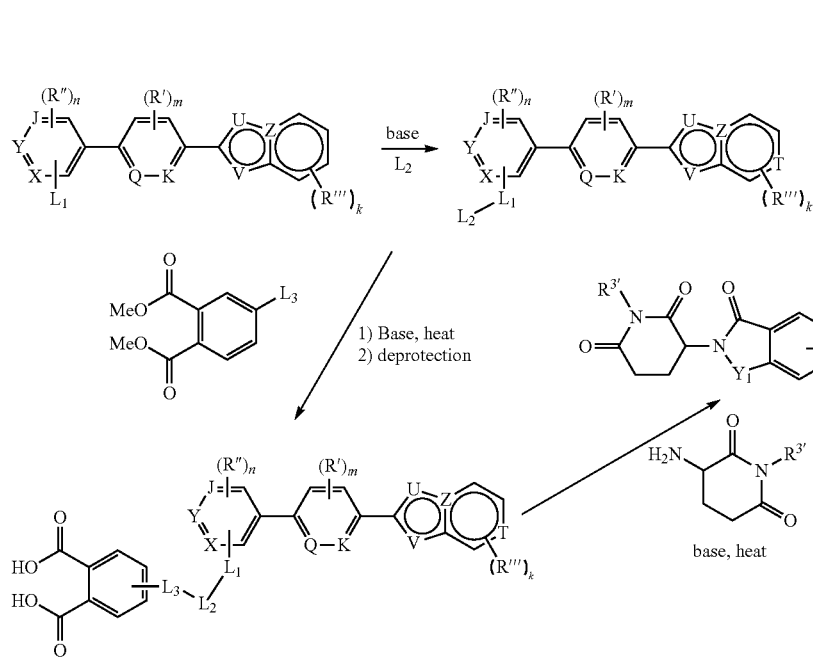
Compounds of Formula (V)
Formula V
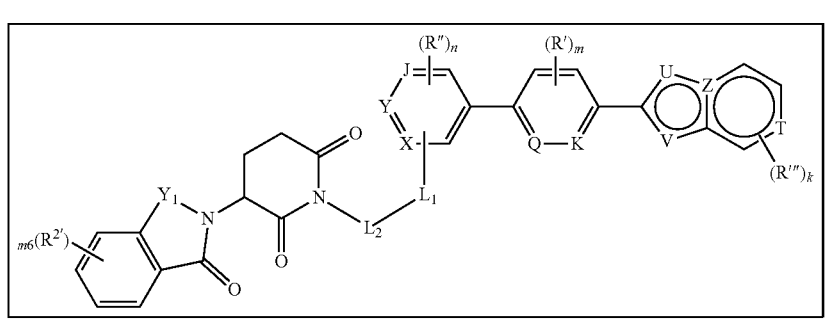
Compounds of the general formula (V) are prepared as set forth in the Scheme below:
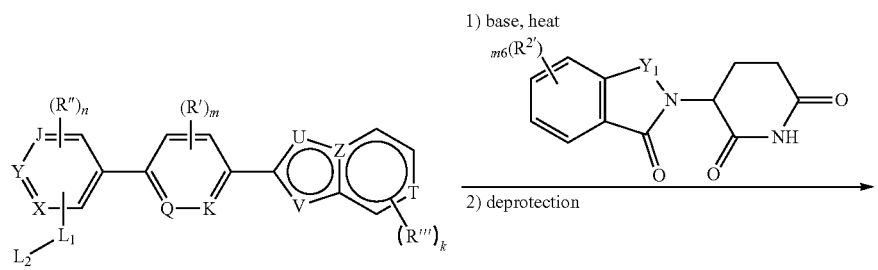

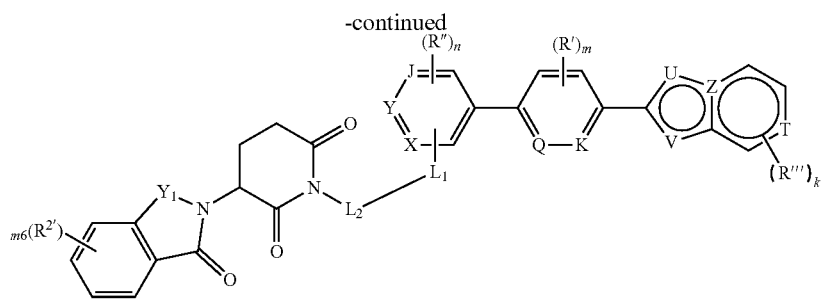
Compounds of Formula (VI)
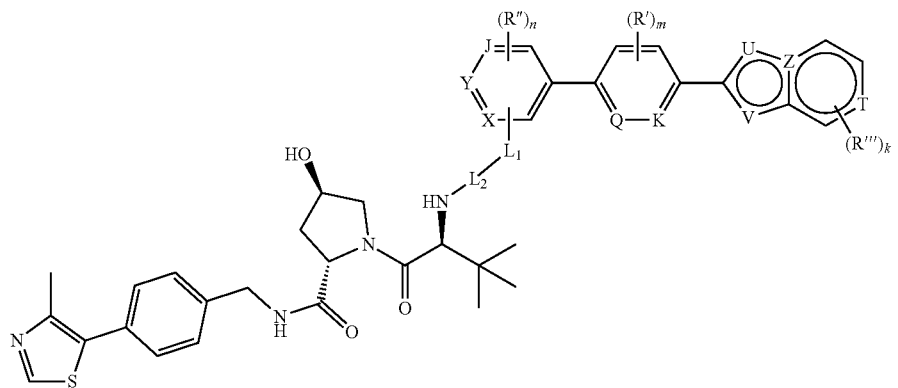
Formula VI
Compounds of the general formula (VI) are prepared as set forth in the Scheme below:
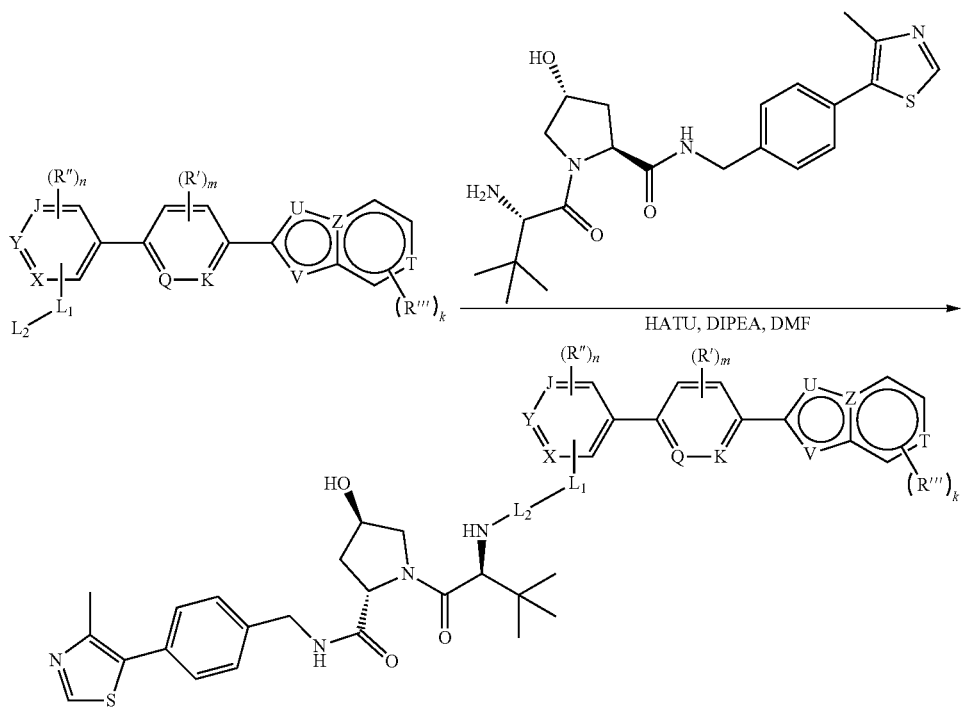

Other compounds within the scope of the disclosure are synthesized by methods like these, and by analogy with methods set forth in the Examples below. Additional synthetic methods can be found in WO2019214681, WO2018102067 and WO2019014429, all of which are incorporated herein by reference in full.

Methods of Treatment

Compounds of the disclosure are administered to a subject in order to treat a tauopathy, a disorder or disease associated with the accumulation of tau protein aggregates and/or neurofibrillary tangles. Tauopathies include Alzheimer's Disease (AD), amyotrophic lateral sclerosis (ALS), Huntington's disease (HD), Parkinson's disease (PD), Creutzfeldt-Jacob disease, Dementia pugilistica, Down's Syndrome, Gerstmann-Straussler-Scheinker disease, British dementia, Danish dementia, inclusion-body myositis, prion protein cerebral amyloid angiopathy, traumatic brain injury, Guam Parkinsonism-dementia complex, Non-Guamanian motor neuron disease with neurofibrillary tangles, argyrophilic grain dementia, corticobasal degeneration, diffuse neurofibrillary tangles with calcification, frontotemporal dementia, frontotemporal dementia with parkinsonism linked to chromosome 17, Hallervorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis, Tangle-only dementia, White matter tauopathy with globular glial inclusions, Frontotemporal dementia, Postencephalitic Parkinsonism, Parkinsonism linked to chromosome 17, and Myotonic dystrophy. In some embodiments, the tauopathy is Alzheimer's disease (AD), progressive supranuclear palsy (PSP), corticobasal degeneration (CBD), and Pick's disease (PiD).

A. Administration

After formulation with an appropriate pharmaceutically acceptable excipient in a desired dosage, the pharmaceutical compositions of this invention can be administered to humans and other animals orally, parenterally, intracisternally, intraperitoneally, intrathecally, intraventricularly, topically, bucally, or the like, depending on the disease or condition being treated.

In certain embodiments, a pharmaceutical composition comprising a compound of the disclosure is administered orally or parenterally, at dosage levels sufficient to deliver from about 0.001 mg/kg to about 200 mg/kg in one or more doses for one or several days. In some embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In some embodiments, the compounds described herein are at dosages sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic and/or prophylactic effect. The desired dosage may be delivered three times a day, twice a day, once a day, every other day, every third day, every week, every two weeks, every three weeks, or every four weeks. In some embodiments, the dosage is delivered using multiple administrations (e.g., two, three, four, five, six, seven, eight, nine, ten, eleven, twelve, thirteen, fourteen, or more administrations). In some embodiments, the composition described herein is administered at a dose that is below the dose at which the agent causes non-specific effects.

In some embodiments, at least one additional therapy is administered to the subject. In some embodiments, the additional therapy is a neurological drug, anti-Tau antibody, Tau inhibitor, anti-amyloid beta antibody, beta-amyloid aggregation inhibitor, anti-BACE1 antibody, or BACE1 inhibitor.

In some embodiments, the subject is diagnosed as having or being at risk of developing a Tau protein-associated disease. In some embodiments, the subject is diagnosed as having or being at risk of developing a tauopathy selected from the group consisting of Alzheimer's disease (AD), progressive supranuclear palsy (PSP), corticobasal degeneration (CBD), and Pick's disease (PiD).

B. Compositions

Pharmaceutical compositions described herein can be prepared by methods generally known in the art of pharmacology. In general, such methods include the steps of combining the compound of the disclosure with a carrier and/or one or more other accessory ingredients, and then shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Pharmaceutically acceptable excipients used in the manufacture of pharmaceutical compositions include inert diluents, dispersing and/or granulating agents, surface active agents and/or emulsifiers, disintegrating agents, binding agents, preservatives, stabilizers, buffering agents, lubricating agents, and/or oils. Excipients such as cocoa butter and suppository waxes, coloring agents, coating agents, sweetening, flavoring, and perfuming agents may also be present in the composition.

Suitable diluents include calcium carbonate, sodium carbonate, calcium phosphate, calcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Suitable granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

C. Kits

In some embodiments, a kit described herein further includes instructions for using the kit. A kit described herein may also include information as required by a regulatory agency such as the U.S. Food and Drug Administration (FDA). In some embodiments, the information included in the kits is prescribing information. In some embodiments, the kits and instructions provide for treating a disease (e.g., neurological disorder, neurodegenerative disease, or tauopathy) in a subject in need thereof. In some embodiments, the kits and instructions provide for preventing a disease (e.g., neurological disorder, neurodegenerative disease, or tauopathy) in a subject in need thereof. In certain embodiments, the kits and instructions provide for reducing the risk of developing a disease (e.g., neurological disorder, neurodegenerative disease, or tauopathy) in a subject in need thereof. In some embodiments, the kits and instructions provide for promoting the degradation of tau protein in a subject or cell. In some embodiments, the kits and instructions provide for diagnosing a neurological disorder in the central nervous system (e.g., through use of a radiolabeled compound of the disclosure). In some embodiments, the kits and instructions provide for imaging and/or detecting a neurological disorder in the central nervous system (e.g., through use of a radiolabeled compound of the disclosure). In some embodiments, the kits and instructions provide for imaging and/or detecting pathological aggregation of tau protein in the central nervous system (e.g., through use of a radiolabeled compound of the disclosure). A kit described herein may include one or more additional pharmaceutical agents described herein as a separate composition.

D. Diagnostics

The compounds of the disclosure provide a method of detecting and imaging tau aggregates. This imaging can be performed by molecular imaging methods such as positron emission tomography (PET), fluorescence microscopy measurement, multi-photon imaging, two-photon imaging, near-infrared fluorescence imaging, autoradiography, and single-photon emission computed tomography (SPECT). Also, this imaging includes in vitro, ex vivo, and in vivo imaging.

The imaging method comprises administering a radiolabeled compound of the disclosure to a subject, and detecting said radiolabeled compound of the invention in said subject. The present invention further provides a method of detecting Tau aggregates in vitro or in vivo using a radiolabeled compound of the disclosure, as described herein. Hence, the present invention provides useful tools for early detection and diagnosis of Alzheimer's disease. The present invention also provides useful tools for monitoring the progression of Alzheimer's disease and the effect of treatment.

In general, the imaging method can comprise the steps of (a) administering to a subject a radiolabeled compound of the disclosure; (b) allowing the radiolabeled compound to bind to Tau in the subject; (c) detecting signals emitted by the radioisotope in the bound radiolabeled compound; (d) generating an image representative of the location and/or amount of the signals; and (e) determining the distribution and extent of Tau aggregates in the subject.

The step of "administering" a radiolabeled compound of the invention is often carried out parenterally, such as intravenously. The intravenous route represents an efficient way to deliver the compound throughout the body of the subject. Intravenous administration neither represents a substantial physical intervention nor a substantial health risk to the subject. The radiolabeled compound can be administered as a radiopharmaceutical composition. The administration step is not required for a complete definition of the imaging method of the invention. As such, the imaging method of the invention can also be understood as comprising the above-defined steps (b)-(e) carried out on a subject to whom a radiolabeled compound of the invention has been pre-administered.

The "detecting" step of the method involves detection of signals emitted by the radioisotope in the radiolabeled compound of the invention, by means of a detector sensitive to the signals, e.g., a PET camera. This detection step can also be understood as the acquisition of signal data.

The "generating" step of the method of the invention is carried out by a computer which applies a reconstruction algorithm to the acquired signal data to yield a dataset. This dataset is then manipulated to generate images showing the location and/or amount of signals emitted by the radioisotope. The signals emitted directly correlate with the amount of enzyme or neoplastic tissue such that the "determining" step can be made by evaluating the generated image.

An amount of the isotopically labeled derivative and radiolabeled derivative of the compound for administration one or more times a day to a 70 kg adult human may comprises about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of the compound per unit dosage form.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

The following examples are provided as a further guide for those of ordinary skill in the art, and are not intended to limit the scope of the claimed invention in any way.

In general in the examples below, chemicals were purchased from Sinopharm Chemical Reagent Co. (SCRC), Sigma-Aldrich, Alfa, or other vendors. $^{1}$H NMR and $^{19}$F NMR spectra were recorded on a Bruker AVIII 400 or Bruker AVIII 500 spectrometer.

LCMS measurement was run on an Agilent 1200 HPLC/6100 SQ System using the following conditions: Method A: Mobile Phase: A: Water (0.01% TFA) B: CAN (0.01% TFA); Gradient Phase: 5% B increasing to 95% B within 1.4 min, 95% B with 1.6 min (total runtime: 3 min); Flow Rate: 2.3 mL/min; Column: SunFire C18, 4.6*50 mm, 3.5 μm; Column Temperature: 50° C. Detectors: ADC ELSD, DAD (214 nm and 254 nm), ES-API. Method B: Mobile Phase: A: Water (10 mM $NH_4HCO_3$) B: Acetonitrile; Gradient Phase: 5% to 95% B within 1.5 min, 95% B with 1.5 min (total runtime: 3 min); Flow Rate: 2.0 mL/min; Column: XBridge C18, 4.6*50 mm, 3.5 μm; Column Temperature: 40° C. Detectors: ADC ELSD, DAD (214 nm and 254 nm), MSD (ES-API). Method C: Mobile Phase: A: Water (10 mM $NH_4HCO_3$) B: Acetonitrile; Gradient Phase: 5% to 95% B within 1.5 min, 95% B with 1.5 min (total runtime: 3 min); Flow Rate: 2.0 mL/min; Column: XBridge C18, 4.6*50 mm, 3.5 μm; Column Temperature: 40° C. Detectors: ADC ELSD, DAD (214 nm and 254 nm), MSD (ES-API).

Abbreviations: THF—tetrahydrofuran; DMF—N,N-dimethylformamide; EtOAc—ethyl acetate; DCM—dichloromethane; MeOH—methanol; EtOH—ethanol; TEA—triethanol-amine; TFA—trifluoroacetic acid; RT—room temperature.

Additional embodiments are disclosed in further detail in the following examples, which are provided by way of illustration and are not in any way intended to limit the scope of this disclosure or the claims. While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

Example 1: Synthesis of Compound 159985

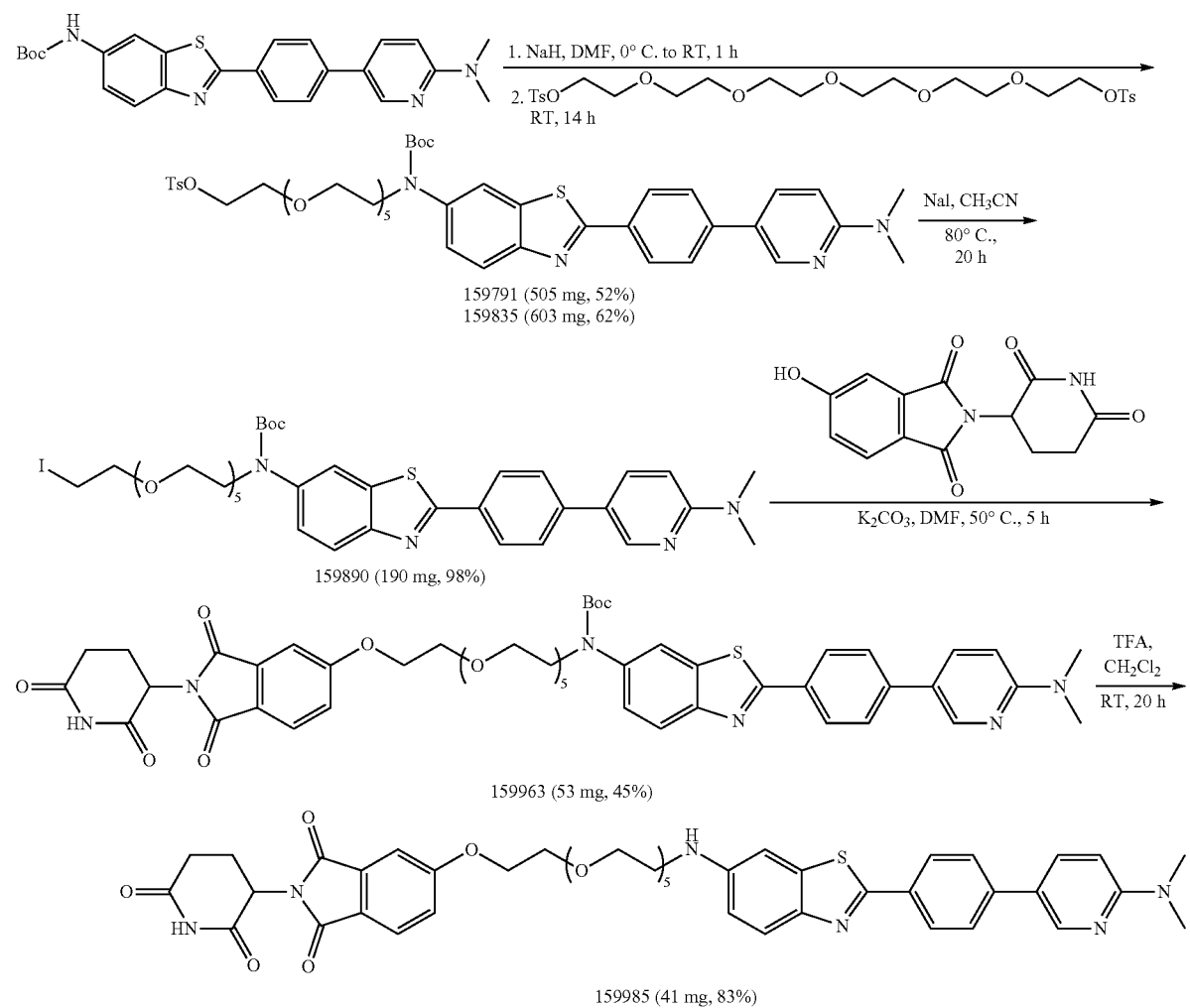

(A) 2-[2-[2-[2-[2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethoxy]ethoxy]ethoxy]ethoxy]ethyl 4-methylbenzenesulfonate To a solution of tert-butyl N-[2-[4-[6-(dimethylamino)pyridin-3-yl]-phenyl]-1,3-benzothiazol-6-yl]carbamate (500 mg, 1.12 mmol) in DMF (10 mL) was added with NaH (107.49 mg, 4.48 mmol) at 0° C. and stirred at RT for 1 h. 2-[2-[2-[2-[2-[2-(4-methyl-phenyl)sulfonyloxyethoxy]

ethoxy]ethoxy]ethoxy]ethoxy]ethyl 4-methylbenzenesulfonate (2.65 g, 4.48 mmol) in DMF (10 mL) was added to the reaction mixture and stirred at RT for 14 h. The mixture was quenched by adding water at 0° C. and then extracted with EtOAc (200 mL). The organic layer was washed with water (100 mL), brine (100 mL), dried over $Na_2SO_4$, concentrated and purified by column chromatography (DCM:MeOH=10:1, Rf=0.7) to give 2-[2-[2-[2-[2-[2-[[2-[4-[6-(dimethylamino)pyridin-3-yl]phenyl]-1,3-benzothiazol-6-yl]-[(2-m ethylpropan-2-yl)oxycarbonyl]amino]ethoxy]ethoxy]ethoxy]ethoxy]ethoxy]ethyl 4-methylbenzenesulfonate (compound 159835, 603 mg, 0.70 mmol, 62% yield) as a pale-yellow solid.

(B) tert-butyl N-[2-[4-[6-(dimethylamino)pyridin-3-yl]phenyl]-1,3-benzothiazol-6-yl]-N-[2-[2-[2-[2-[2-(2-iodoethoxy)ethoxy]ethoxy]ethoxy]ethyl]carbamate A mixture of 2-[2-[2-[2-[2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethoxy]ethoxy]ethoxy]ethyl 4-methyl-benzenesulfonate (200 mg, 0.23 mmol) and NaI (42 mg, 0.28 mmol) in $CH_3CN$ (5 mL) was heated at 80° C. for 20 h. The residue was taken up in DCM (50 mL) and water (50 mL). The organic layer was washed with water (50 mL), brine (50 mL) dried over $Na_2SO_4$ and concentrated to give tert-butyl N-[2-[4-[6-(dimethylamino)pyridin-3-yl]phenyl]-1,3-benzo-thiazol-6-yl]-N-[2-[2-[2-[2-(2-iodoethoxy)ethoxy]ethoxy]ethoxy]ethyl]carbamate (compound 159890, 185.1 mg, 0.23 mmol, 98% yield) as a yellow solid.

(C) tert-butyl N-[2-[2-[2-[2-[2-[2-[2-[2,6-bis(oxo)piperidin-3-yl]-1,3-bis(oxo)isoindol-5-yl]oxyethoxy]ethoxy]ethoxy]ethoxy]ethyl]-N-[2-[4-[6-(dimethylamino)pyridin-3-yl]-phenyl]-1,3-benzothiazol-6-yl]carbamate A mixture of 2-[2,6-bis(oxo)piperidin-3-yl]-5-hydroxy-isoindole-1,3-dione (67 mg, 0.24 mmol), $K_2CO_3$ (51 mg, 0.37 mmol) and tert-butyl N-[2-[4-[6-(dimethylamino)pyridin-3-yl]phenyl]-1,3-benzothiazol-6-yl]-N-[2-[2-[2-[2-(2-iodoethoxy)ethoxy]ethoxy]ethoxy]ethyl]carbamate (100 mg, 0.12 mmol) in DMF (5 mL) was heated at 50° C. for 5 h. The mixture was quenched with water and then extracted with DCM (200 mL). The organic layer was dried over $Na_2SO_4$, concentrated, and purified by column chromatography on silica gel (DCM:MeOH=20:1, Rf=0.52) to give tert-butyl N-[2-[2-[2-[2-[2-[2-[2-[2,6-bis(oxo)piperidin-3-yl]-1,3-bis(oxo)isoindol-5-yl]oxyethoxy]ethoxy]ethoxy]-ethoxy]ethyl]-N-[2-[4-[6-(dimethylamino)pyridin-3-yl]phenyl]-1,3-benzothiazol-6-yl]-carbamate (53 mg, 0.05 mmol, 45% yield) as a pale-yellow solid.

(D) 2-[2,6-bis(oxo)piperidin-3-yl]-5-[2-[2-[2-[2-[2-[[2-[4-[6-(dimethylamino)-pyridin-3-yl]phenyl]-1,3-benzothiazol-6-yl]amino]ethoxy]ethoxy]ethoxy]ethoxy]-ethoxy]isoindole-1,3-dione To a solution of tert-butyl N-[2-[2-[2-[2-[2-[2-[2-[2,6-bis(oxo)-piperidin-3-yl]-1,3-bis(oxo)isoindol-5-yl]oxyethoxy]ethoxy]ethoxy]ethoxy]ethyl]-N-[2-[4-[6-(dimethylamino)pyridin-3-yl]phenyl]-1,3-benzothiazol-6-yl]carbamate (52 mg, 0.05 mmol) in DCM (5 mL) was added TFA (0.08 mL, 1.08 mmol) and stirred at RT for 20 h. The mixture was poured into ice water and neutralized with sat. $NaHCO_3$ solution to pH 8. The residue was taken up in DCM (20 mL) and water (10 mL). The organic layer was washed with water (10 mL), brine (10 mL), dried over $Na_2SO_4$ and concentrated to dryness to give 2-[2,6-bis(oxo)piperidin-3-yl]-5-[2-[2-[2-[2-[2-[[2-[4-[6-(dimethylamino)-pyridin-3-yl]phenyl]-1,3-benzothiazol-6-yl]amino]ethoxy]ethoxy]ethoxy]ethoxy]-ethoxy]isoindole-1,3-dione (compound 159985, 41 mg, 0.05 mmol, 83% yield) as a yellow solid. $^1$H NMR (400 MHz, DMSO-$d_6$). MS (ESI) m/z 867 (M+H)$^+$.

Example 2: Synthesis of Compound 160219

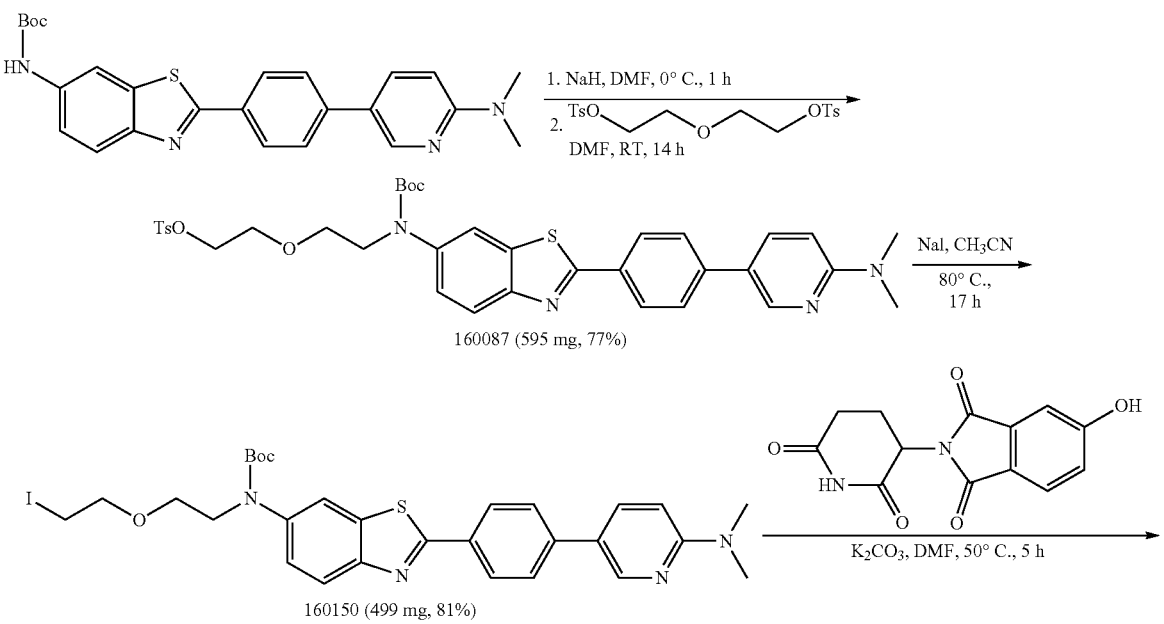

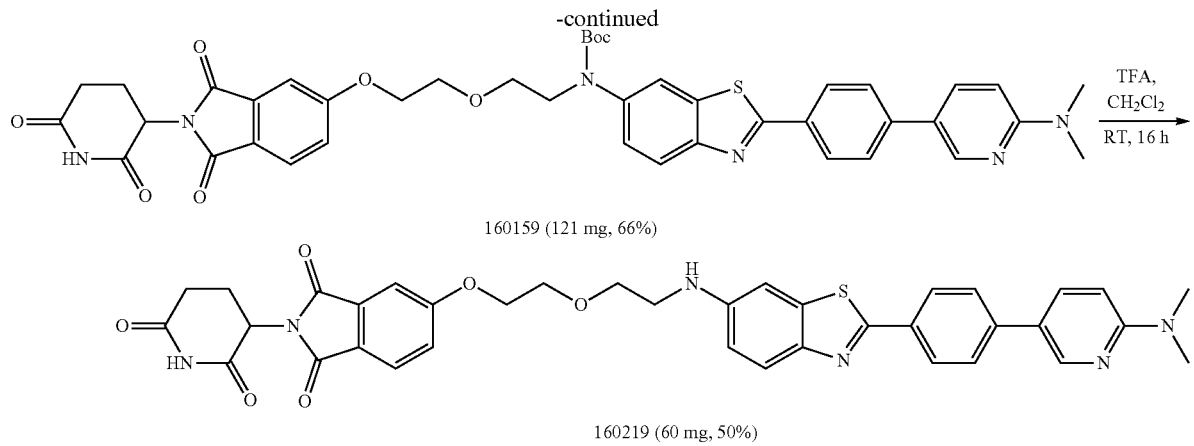

160159 (121 mg, 66%)

160219 (60 mg, 50%)

(A) Compound 160087:

To a solution of tert-butyl N-[2-[4-[6-(dimethylamino)pyridin-3-yl]phenyl]-1,3-benzothiazol-6-yl]carbamate (500 mg, 1.12 mmol) in DMF (10 mL) was added NaH (107 mg, 4.48 mmol) at 0° C. and stirred at room temperature for 1 h. 2-[2-(4-Methylphenyl)sulfonyloxyethoxy]ethyl 4-methylbenzenesulfonate (1.86 g, 4.48 mmol) in DMF (10 mL) was added to the reaction mixture and stirred at room temperature for 14 h. The mixture was cooled to 0° C. and quenched with water. The precipitation was collected by filtration, washed with water and purified by column chromatography (DCM:MeOH=20:1, Rf=0.68) to give 2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethyl 4-methylbenzenesulfonate (595 mg, 0.86 mmol, 77% yield) as a yellow solid.

(B) Compound 160150:

A mixture of 2-[2-[[2-[4-[6-(dimethylamino)pyridin-3-yl]-phenyl]-1,3-benzothiazol-6-yl]-[(2-methylpropan-2-yl)oxycarbonyl]amino]ethoxy]ethyl 4-methylbenzenesulfonate (595 mg, 0.86 mmol), NaI (156 mg, 1.04 mmol) in MeCN (15 mL) was heated at 80° C. for 17 h. The residue was taken up in DCM (50 mL) and water (50 mL). The organic layer was washed with water (50 mL), brine (50 mL), dried over Na₂SO₄ and concentrated to give tert-butyl N-[2-[4-[6-(dimethylamino)pyridin-3-yl]phenyl]-1,3-benzo-thiazol-6-yl]-N-[2-(2-iodoethoxy)ethyl]carbamate (449 mg, 0.70 mmol, 81% yield) as a yellow solid.

(C) Compound 160159:

A mixture of 2-[2,6-bis(oxo)piperidin-3-yl]-5-hydroxy-isoindole-1,3-dione (96 mg, 0.35 mmol), K₂CO₃ (96 mg, 0.70 mmol), tert-butyl N-[2-[4-[6-(di-methylamino)pyridin-3-yl]phenyl]-1,3-benzothiazol-6-yl]-N-[2-(2-iodoethoxy)ethyl]-carbamate (150 mg, 0.23 mmol) in DMF (5 mL) was heated at 50° C. for 5 h. Water (10 mL) was added to the mixture and the resulting precipitation was collected by filtration. The residue was purified by column chromatography (DCM:EtOAc=5:2, Rf=0.32) to give tert-butyl N-[2-[2-[2-[2,6-bis(oxo)piperidin-3-yl]-1,3-bis(oxo)isoindol-5-yl]-oxyethoxy]ethyl]-N-[2-[4-[6-(dimethylamino)pyridin-3-yl]phenyl]-1,3-benzothiazol-6-yl]-carbamate (121 mg, 0.15 mmol, 66% yield) as a yellow solid.

(D) Compound 160219:

To a solution of tert-butyl N-[2-[2-[2-[2,6-bis-(oxo)piperidin-3-yl]-1,3-bis(oxo)isoindol-5-yl]oxyethoxy]ethyl]-N-[2-[4-[6-(dimethylamino) pyridin-3-yl]phenyl]-1,3-benzothiazol-6-yl]carbamate (120 mg, 0.15 mmol) in DCM (5 mL) was added TFA (0.23 mL, 3.03 mmol), and the mixture stirred at room temperature for 20 h. The mixture was poured into ice water and neutralized with sat. NaHCO₃ to pH 8. The residue was taken up in DCM (20 mL) and water (10 mL). The organic layer was washed with water (10 mL), brine (10 mL), dried over Na₂SO₄, and concentrated to dryness to give 2-[2,6-bis(oxo)piperidin-3-yl]-5-[2-[2-[[2-[4-[6-(dimethylamino)pyridin-3-yl]phenyl]-1,3-benzothiazol-6-yl]amino]ethoxy]ethoxy]isoindole-1,3-dione (21 mg, 0.03 mmol, 18% yield) as a yellow solid.

Example 3: Synthesis of Compound 160939

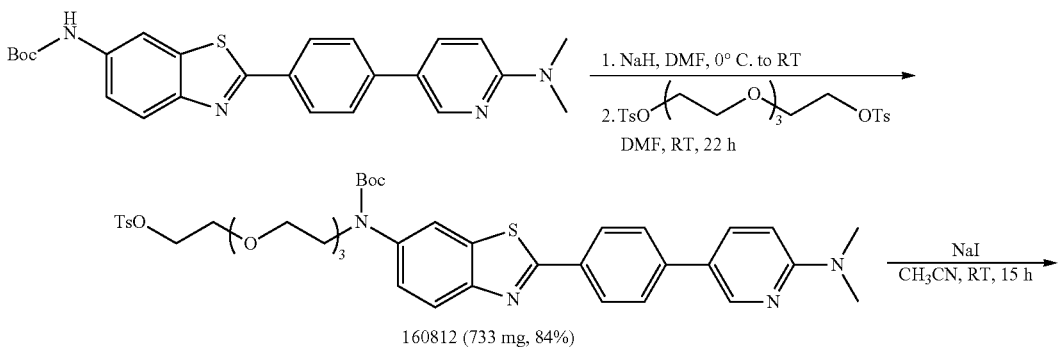

160812 (733 mg, 84%)

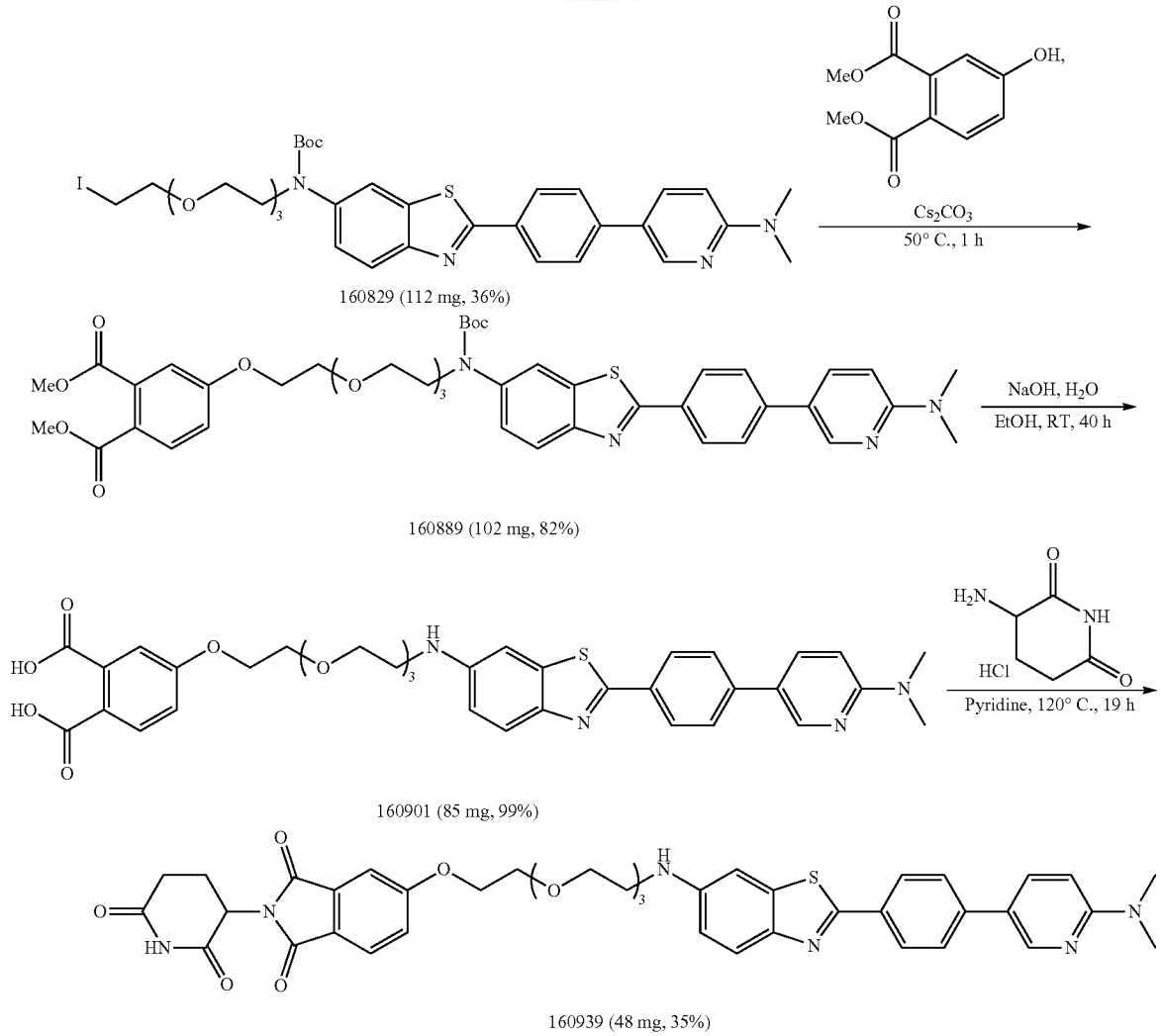

160829 (112 mg, 36%)

160889 (102 mg, 82%)

160901 (85 mg, 99%)

160939 (48 mg, 35%)

(A) Compound 160812:

To a solution of tert-butyl N-[2-[4-[6-(dimethylamino)pyridin-3-yl]phenyl]-1,3-benzothiazol-6-yl]carbamate (500 mg, 1.12 mmol) in DMF (10 mL) was added NaH (107 mg, 4.48 mmol) at 0° C. and stirred at RT for 1 h. 2-[2-[2-[2-(4-methylphenyl)sulfonyloxyethoxy]ethoxy]ethoxy]ethyl 4-methylbenzenesulfonate (1125 mg, 2.24 mmol) in DMF (5 mL) was added to the reaction mixture and stirred at RT for 22 h. The mixture was taken up in water (50 mL) and DCM (50 mL). The organic layer was washed with water (50 mL), brine (50 mL) dried over $Na_2SO_4$, concentrated and purified by column chromatography on silica gel (EtOAc:DCM=1:5, Rf=0.13) to give 2-[2-[2-[2-[[2-[4-[6-(dimethylamino)pyridin-3-yl]-phenyl]-1,3-benzothiazol-6-yl]-[(2-methylpropan-2-yl)oxycarbonyl]amino]ethoxy]ethoxy]-ethoxy]ethyl 4-methylbenzenesulfonate (733 mg, 0.94 mmol, 84% yield) as a yellow solid.

(B) Compound 160829:

A mixture of 2-[2-[2-[2-[[2-[4-[6-(dimethylamino)pyridin-3-yl]-phenyl]-1,3-benzothiazol-6-yl]-[(2-methylpropan-2-yl)oxycarbonyl]amino]ethoxy]ethoxy]ethoxy]ethyl 4-methylbenzenesulfonate (333 mg, 0.43 mmol) and NaI (109 mg, 0.73 mmol) in $CH_3CN$ (10 mL) was heated at 80° C. for 15 h. The solvent was removed by vacuo and the residue was re-dissolved in EtOAc. The mixture was washed with water (50 mL), brine (50 mL), dried over $MgSO_4$ and concentrated to give tert-butyl N-[2-[4-[6-(dimethylamino)pyridin-3-yl]-phenyl]-1,3-benzothiazol-6-yl]-N-[2-[2-[2-(2-iodoethoxy)ethoxy]ethoxy]ethyl]carbamate (112 mg, 0.15 mmol, 36% yield) as a yellow solid.

(C) Compound 160889:

A mixture of tert-butyl N-[2-[4-[6-(dimethylamino)pyridin-3-yl]-phenyl]-3a,7a-dihydro-1,3-benzothiazol-6-yl]-N-[2-[2-[2-(2-iodoethoxy)ethoxy]ethoxy]-ethyl]carbamate (112 mg, 0.15 mmol), $Cs_2CO_3$ (149.09 mg, 0.46 mmol) and dimethyl 4-hydroxybenzene-1,2-dicarboxylate (64 mg, 0.30 mmol) in DMF (2 mL) was stirred at 50° C. for 1 h. The mixture was cooled to RT and added with water. The precipitation was collected by filtration and then purified by column chromatography (EtOAc:DCM=1:1, Rf=0.33) to give dimethyl 4-[2-[2-[2-[2-[[2-[4-[6-(dimethylamino)pyridin-3-yl]phenyl]-1,3-benzo-thiazol-6-yl]-[(2-methylpropan-2-yl)oxycarbonyl]amino]ethoxy]ethoxy]ethoxy]-ethoxy]benzene-1,2-dicarboxylate (102 mg, 0.13 mmol, 82% yield) as a yellow solid.

(D) Compound 160901:

To a solution of dimethyl 4-[2-[2-[2-[2-[[2-[4-[6-(dimethyl-amino)pyridin-3-yl]phenyl]-1,3-benzothiazol-6-yl]-

[(2-methylpropan-2-yl)oxycarbonyl]-amino]ethoxy]ethoxy]ethoxy]ethoxy]benzene-1,2-dicarboxylate (102 mg, 0.13 mmol) in EtOH (2 mL) was added NaOH (40 mg, 1 mmol) in water (2 mL). The resulting mixture was stirred at RT for 40 h. The reaction was diluted with EtOAc (10 mL) and acidified with 1N HCl solution to pH 1. The organic layer was washed with water (10 mL), brine (10 mL) dried over Na₂SO₄ and concentrated to dryness to give 4-[2-[2-[2-[2-[[2-[4-[6-(dimethylamino)pyridin-3-yl]-phenyl]-1,3-benzothiazol-6-yl]amino]ethoxy]ethoxy]ethoxy]ethoxy]phthalic acid (86 mg, 0.13 mmol, 99.9% yield) as an orange solid.

(E) Compound 160939:

A mixture of 4-[2-[2-[2-[2-[[2-[4-[6-(dimethylamino)pyridin-3-yl]phenyl]-1,3-benzothiazol-6-yl]amino]ethoxy]ethoxy]ethoxy]ethoxy]phthalic acid (122 mg, 0.18 mmol) and 3-aminopiperidine-2,6-dione hydrochloride (32 mg, 0.20 mmol) in pyridine (5 mL) was heated at 120° C. for 19 h. The mixture was cooled to RT, diluted with DCM (100 mL) and washed with water (50 mL) and brine (50 mL). The organic layer was collected, dried over Na₂SO₄, concentrated and purified by column chromatography (MeOH:DCM=1:10, Rf=0.73) to afford 2-[2,6-bis(oxo)piperidin-3-yl]-5-[2-[2-[2-[2-[[2-[4-[6-(dimethylamino)pyridin-3-yl]-phenyl]-1,3-benzothiazol-6-yl]amino]ethoxy]ethoxy]ethoxy]ethoxy]isoindole-1,3-dione (49 mg, 0.06 mmol, 35% yield) as a yellow solid.

Example 4: Synthesis of Compound 161103

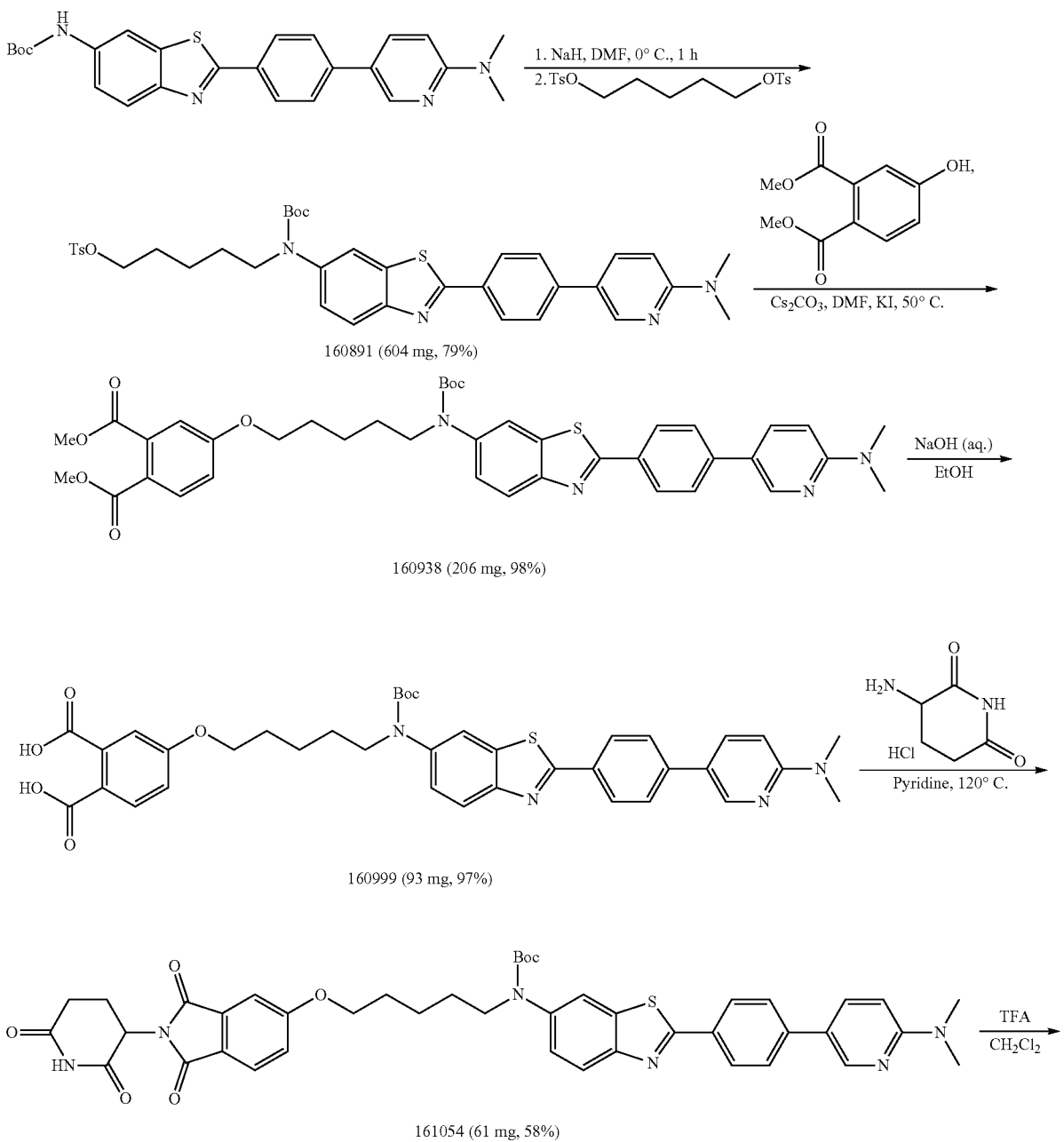

153 154

-continued

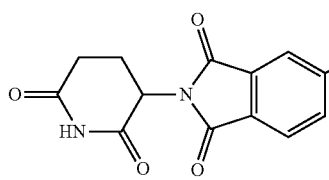 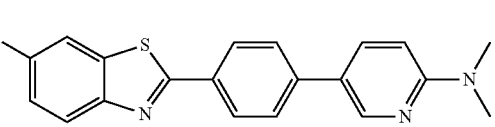

161103 (44 mg, 80%)

(A) Compound 160891:

To a solution of tert-butyl N-[2-[4-[6-(dimethylamino)pyridin-3-yl]phenyl]-1,3-benzothiazol-6-yl]carbamate (500 mg, 1.12 mmol) in DMF (10 mL) was added NaH (107 mg, 4.48 mmol) at 0° C. and stirred at RT for 1 h. 5-(4-methylphenyl)sulfonyloxypentyl 4-methylbenzenesulfonate (1.85 g, 4.48 mmol) in DMF (10 mL) was added to the reaction mixture and stirred at RT for 17 h. The mixture was cooled to 0° C. and quenched with water. The resulting precipitation was collected by filtration and purified by column chromatography (DCM:EtOAc=4:1, Rf=0.7) to give 5-[[2-[4-[6-(dimethylamino)pyridin-3-yl]phenyl]-1,3-benzothiazol-6-yl]-[(2-methylpropan-2-yl)oxycarbonyl]amino]pentyl 4-methylbenzenesulfonate (604 mg, 0.88 mmol, 79% yield) as a yellow solid.

(B) Compound 160938:

A mixture of dimethyl 4-hydroxybenzene-1,2-dicarboxylate (122 mg, 0.58 mmol), $Cs_2CO_3$ (285 mg, 0.87 mmol), KI (5 mg, 0.03 mmol) and 5-[[2-[4-[6-(di-methyl-amino)pyridin-3-yl]phenyl]-1,3-benzothiazol-6-yl]-[(2-methylpropan-2-yl)oxycarbonyl]-amino]pentyl 4-methylbenzenesulfonate (200 mg, 0.29 mmol) in DMF (2 mL) was heated at 50° C. for 2 h. The reaction was quenched with water. The resulting solid was collected by filtration and washed with water to give dimethyl 4-[5-[[2-[4-[6-(dimethylamino)pyridin-3-yl]phenyl]-1,3-benzothiazol-6-yl]-[(2-methylpropan-2-yl)oxycarbonyl]amino]pentoxy]benzene-1,2-dicarboxylate (206 mg, 0.28 mmol, 98% yield) as a yellow solid.

(C) Compound 160999:

A solution of dimethyl 4-[5-[[2-[4-[6-(dimethylamino)pyridin-3-yl]phenyl]-1,3-benzothiazol-6-yl]-[(2-methylpropan-2-yl)oxycarbonyl]amino]-pentoxy]benzene-1,2-dicarboxylate (100 mg, 0.14 mmol) in EtOH (2 mL) was added NaOH (110 mg, 2.76 mmol) in water (2 mL) and stirred at RT for 40 h. The reaction was neutralized to pH 1 with 1N HCl solution. The precipitation was collected by filtration and washed with water to afford 4-[5-[[2-[4-[6-(dimethylamino)pyridin-3-yl]phenyl]-1,3-benzothiazol-6-yl]-[(2-methylpropan-2-yl)oxycarbonyl]amino]pentoxy]phthalic acid (93 mg, 0.13 mmol, 97% yield) as a yellow solid.

(D) Compound 161054:

A mixture of 4-[5-[[2-[4-[6-(dimethylamino)pyridin-3-yl]-phenyl]-1,3-benzothiazol-6-yl]-[(2-methylpropan-2-yl)oxycarbonyl]amino]pentoxy]phthalic acid (93 mg, 0.13 mmol), and 3-aminopiperidine-2,6-dione hydrochloride (48 mg, 0.29 mmol) in pyridine (3 mL) was heated at 120° C. for 40 h. Water was then added to the mixture. The precipitate was collected by filtration and purified by column chromatography (DCM:EtOAc=4:1, Rf=0.28) to afford tert-butyl N-[5-[2-[2,6-bis(oxo)piperidin-3-yl]-1,3-bis(oxo)isoindol-5-yl]oxypentyl]-N-[2-[4-[6-(dimethylamino)pyridin-3-yl]phenyl]-1,3-benzothiazol-6-yl]carba mate (61 mg, 0.08 mmol, 58% yield) as a yellow solid.

(E) Compound 161103:

A solution of tert-butyl N-[5-[2-[2,6-bis(oxo)piperidin-3-yl]-1,3-bis(oxo)isoindol-5-yl]oxypentyl]-N-[2-[4-[6-(dimethylamino)pyridin-3-yl]phenyl]-1,3-benzothiazol-6-yl]carbamate (61 mg, 0.08 mmol) in DCM (5 mL) was added TFA (0.12 mL, 1.55 mmol) and stirred at RT for 6 h. The mixture was poured into iced water and neutralized with sat. $NaHCO_3$ solution to pH 8. The residue was taken up in DCM (20 mL) and water (10 mL). The organic layer was washed with water (10 mL), brine (10 mL), dried over $Na_2SO_4$, and concentrated to dryness to give 2-[2,6-bis(oxo)piperidin-3-yl]-5-[5-[[2-[4-[6-(dimethyl-amino)pyridin-3-yl]phenyl]-1,3-benzothiazol-6-yl]amino]pentoxy]isoindole-1,3-dione (44 mg, 0.06 mmol, 80% yield) as a yellow solid.

Example 5: Synthesis of Compound 160273

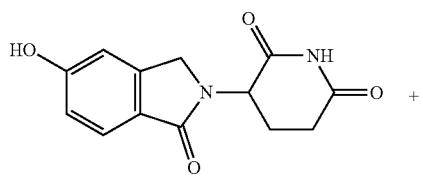

+

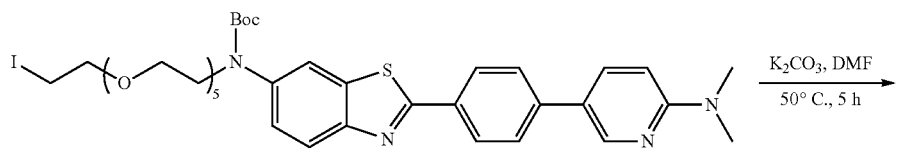

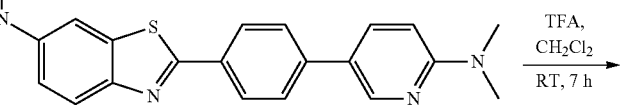
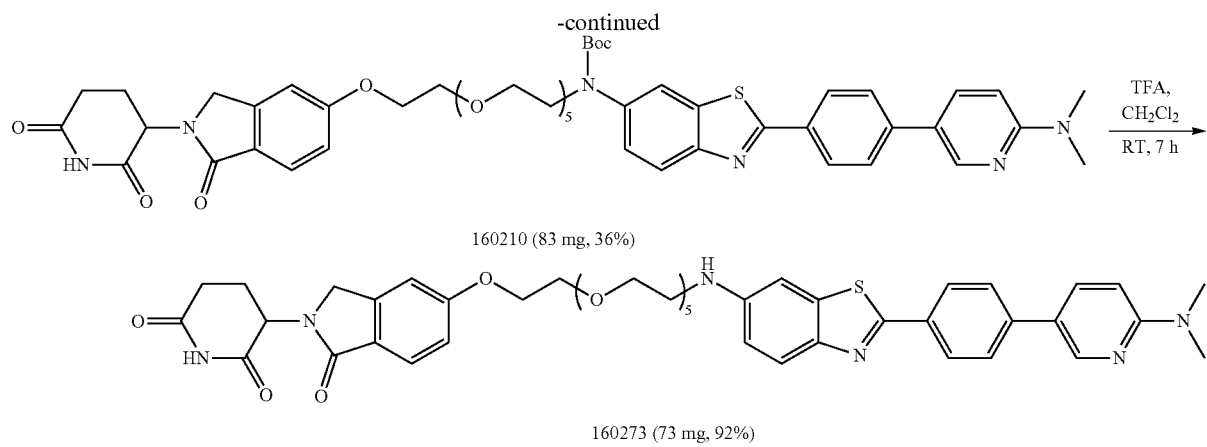

160210 (83 mg, 36%)

160273 (73 mg, 92%)

(A) Compound 160210:

A mixture of 3-(6-hydroxy-3-oxo-1H-isoindol-2-yl)piperidine-2,6-dione (95 mg, 0.37 mmol), $K_2CO_3$ (101 mg, 0.73 mmol), tert-butyl N-[2-[4-[6-(dimethylamino)pyridin-3-yl]phenyl]-1,3-benzothiazol-6-yl]-N-[2-[2-[2-[2-[2-(2-iodoethoxy)ethoxy]ethoxy]ethoxy]ethyl]carbamate (200 mg, 0.24 mmol) in DMF (5 mL) was heated at 50° C. for 5 h. The mixture was quenched with water and extracted with DCM (200 mL). The organic layer was collected, dried over $Na_2SO_4$, concentrated and purified by column chromatography (DCM:MeOH=20:1, Rf=0.48) to give tert-butyl N-[2-[2-[2-[2-[2-[2-[[2-[2,6-bis(oxo)piperidin-3-yl]-1-oxo-3H-isoindol-5-yl]-oxy]ethoxy]ethoxy]ethoxy]ethoxy]ethoxy]ethyl]-N-[2-[4-[6-(dimethylamino)pyridin-3-yl]phenyl]-1,3-benzothiazol-6-yl]carbamate (83 mg, 0.09 mmol, 36% yield) as a pale-yellow solid.

(B) Compound 160273:

To a solution of tert-butyl N-[2-[2-[2-[2-[2-[2-[[2-[2,6-bis-(oxo)piperidin-3-yl]-1-oxo-3H-isoindol-5-yl]oxy]ethoxy]ethoxy]ethoxy]ethoxy]ethoxy]-ethyl]-N-[2-[4-[6-(dimethylamino)pyridin-3-yl]phenyl]-1,3-benzothiazol-6-yl]carbamate (83 mg, 0.09 mmol) in DCM (5 mL) was added TFA (0.13 mL, 1.74 mmol) and stirred at RT for 7 h. The mixture was poured into ice water and neutralized with sat. $NaHCO_3$ solution to pH 8. The residue was taken up in DCM (20 mL) and water (10 mL). The organic layer was washed with water (10 mL), brine (10 mL) dried over $Na_2SO_4$ and concentrated to dryness to give 3-[6-[2-[2-[2-[2-[2-[2-[[2-[4-[6-(dimethylamino)pyridin-3-yl]phenyl]-1,3-benzothiazol-6-yl]-amino]ethoxy]ethoxy]ethoxy]ethoxy]ethoxy]-3-oxo-1H-isoindol-2-yl]piperidine-2,6-dione (73 mg, 0.08 mmol, 92% yield) as a yellow solid.

Example 6: Synthesis of Compound 160313

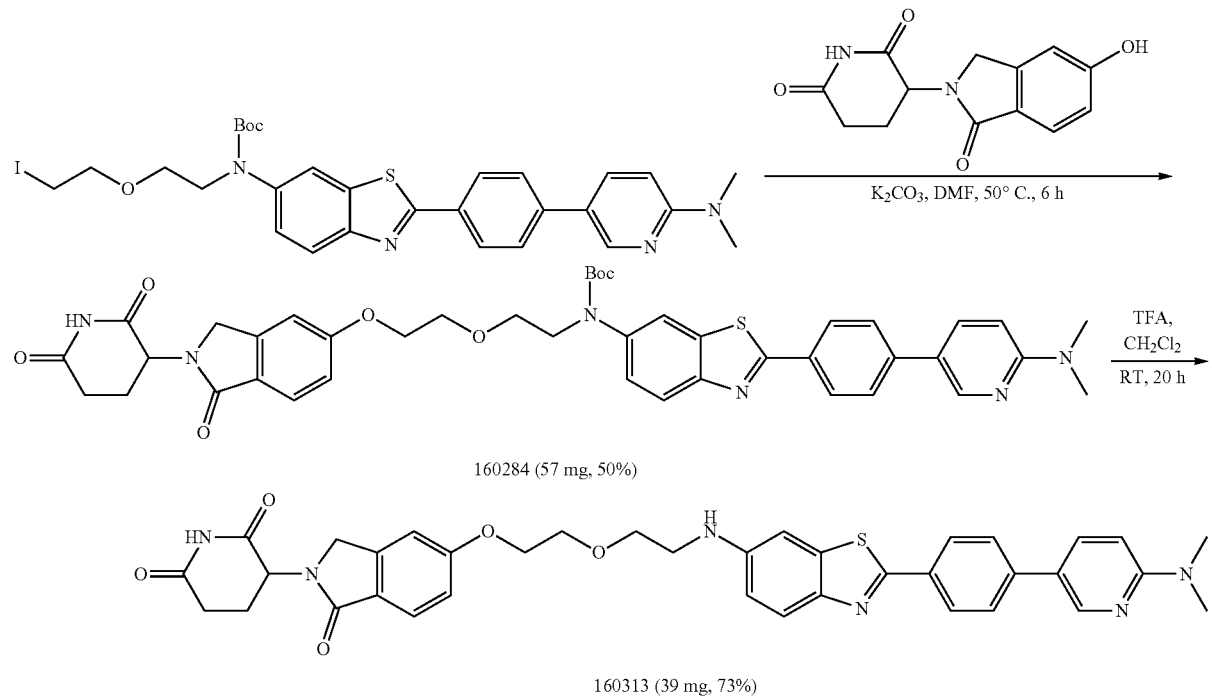

160284 (57 mg, 50%)

160313 (39 mg, 73%)

(A) Compound 160284:

A mixture of 3-(6-hydroxy-3-oxo-1H-isoindol-2-yl)-piperidine-2,6-dione (58 mg, 0.22 mmol), $K_2CO_3$ (61 mg, 0.44 mmol), tert-butyl N-[2-[4-[6-(dimethylamino)pyridin-3-yl]phenyl]-1,3-benzothiazol-6-yl]-N-[2-(2-iodoethoxy)ethyl]carbamate (95 mg, 0.15 mmol) in DMF (2 mL) was heated at 50° C. for 5 h. Water (10 mL) was added to the mixture. The resulting precipitate was collected by filtration and then purified by column chromatography (DCM:MeOH=20:1, Rf=0.52) to give tert-butyl N-[2-[2-[[2-[2,6-bis(oxo)piperidin-3-yl]-1-oxo-3H-isoindol-5-yl]oxy]ethoxy]-ethyl]-N-[2-[4-[6-(dimethylamino)pyridin-3-yl]phenyl]-1,3-benzothiazol-6-yl]carbamate (57 mg, 0.07 mmol, 50% yield) as a yellow solid.

(B) Compound 160313:

To a solution of tert-butyl N-[2-[2-[[2-[2,6-bis(oxo)piperidin-3-yl]-1-oxo-3H-isoindol-5-yl]oxy]ethoxy]ethyl]-N-[2-[4-[6-(dimethylamino)pyridin-3-yl]phenyl]-1,3-benzothiazol-6-yl]carbamate (54 mg, 0.07 mmol) in DCM (5 mL) was added TFA (0.11 mL, 1.39 mmol), and the mixture stirred at room temperature for 20 h. The mixture was poured into ice water and neutralized with sat. $NaHCO_3$ solution to pH 8. The residue was taken up in DCM (20 mL) and water (10 mL). The organic layer was washed with water (10 mL), brine (10 mL), dried over $Na_2SO_4$, and concentrated to dryness to give 3-[6-[2-[2-[[2-[4-[6-(dimethylamino)pyridin-3-yl]phenyl]-1,3-benzothiazol-6-yl]amino]ethoxy]ethoxy]-3-oxo-1H-isoindol-2-yl]piperidine-2,6-dione (39 mg, 0.05 mmol, 77% yield) as a yellow solid.

Example 7: Synthesis of Compound 162640

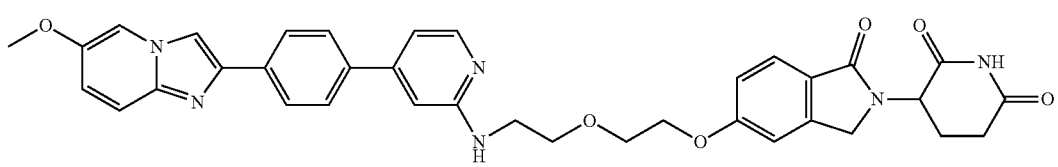

Compound 162640 were synthesized according to methods similar to Example 6.

$^1$H NMR (600 MHz, DMSO-d6) δ 10.97 (s, 1H), 8.36 (s, 1H), 8.24 (d, J=2.3 Hz, 1H), 8.01-8.05 (m, 4H), 7.72 (d, J=8.4 Hz, 2H), 7.62 (d, J=8.4 Hz, 1H), 7.52 (d, J=9.7 Hz, 1H), 7.17 (d, J=1.7 Hz, 1H), 7.05-7.09 (m, 2H), 6.81-6.85 (m, 2H), 6.61 (t, J=5.8 Hz, 1H), 5.07 (dd, J=13.2, 5.1 Hz, 1H), 4.36 (d, J=17.2 Hz, 1H), 4.19-4.27 (m, 4H), 3.79-3.85 (m, 7H), 3.66 (t, J=5.8 Hz, 3H), 3.48-3.54 (m, 3H), 2.85-2.93 (m, 1H), 1.92-1.99 (m, 1H).

Example 8: Synthesis of Compound 162842

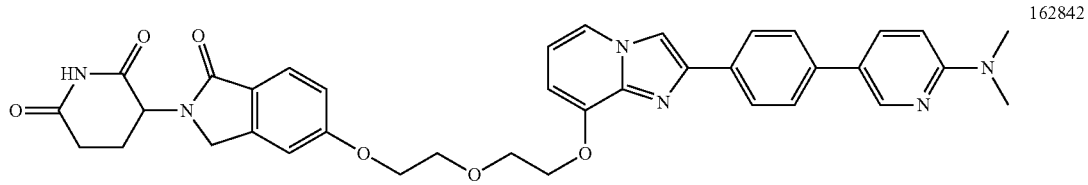

Compound 162842 were synthesized according to methods similar to Example 6.

$^1$H NMR (600 MHz, DMSO-d6) δ 10.96 (s, 1H), 8.50 (d, J=2.5 Hz, 1H), 8.40 (s, 1H), 8.13 (d, J=6.6 Hz, 1H), 7.99 (d, J=8.2 Hz, 2H), 7.89 (dd, J=8.9, 2.5 Hz, 1H), 7.68 (d, J=8.2 Hz, 2H), 7.60 (d, J=8.4 Hz, 1H), 7.19 (s, 1H), 7.08 (d, J=8.4 Hz, 1H), 6.79 (t, J=7.4 Hz, 1H), 6.75 (d, J=8.9 Hz, 1H), 6.70 (d, J=7.4 Hz, 1H), 5.06 (dd, J=13.2, 5.1 Hz, 1H), 4.35-4.38 (m, 2H), 4.32 (d, J=17.2 Hz, 1H), 4.28 (dd, J=8.2, 4.5 Hz, 2H), 4.20 (d, J=17.2 Hz, 1H), 3.96-3.99 (m, 2H), 3.92-3.95 (m, 2H), 3.08 (s, 7H), 2.85-2.93 (m, 1H), 2.26-2.37 (m, 2H), 1.91-1.98 (m, 2H).

Example 9: Synthesis of Compound 162903

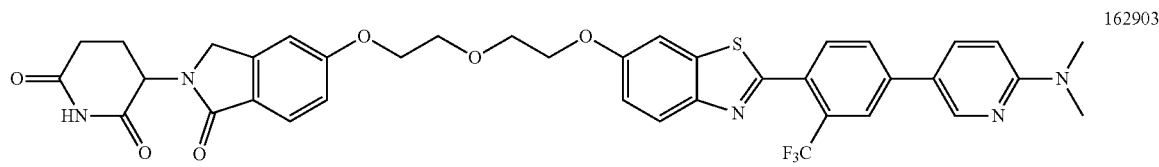

162903

Compound 162903 were synthesized according to methods similar to Example 6.

¹H NMR (600 MHz, DMS-d6) δ 10.97 (s, 1H), 8.63 (d, J=2.4 Hz, 1H), 8.12 (s, 1H), 8.08 (d, J=8.0 Hz, 1H), 8.03 (dd, J=8.9, 2.6 Hz, 1H), 7.99 (d, J=8.9 Hz, 1H), 7.87 (d, J=8.0 Hz, 1H), 7.78 (d, J=2.4 Hz, 1H), 7.63 (d, J=8.4 Hz, 1H), 7.18-7.21 (m, 1H), 7.08 (dd, J=8.4, 2.4 Hz, 1H), 6.79 (d, J=8.8 Hz, 1H), 5.08 (dd, J=13.4, 5.1 Hz, 1H), 4.38 (d, J=17.2 Hz, 1H), 4.22-4.29 (m, 4H), 3.89 (dd, J=9.2, 5.0 Hz, 3H), 3.11 (s, 3H), 2.56-2.63 (m, 1H), 2.33-2.40 (m, 1H).

Example 10: Synthesis of Compound 163123

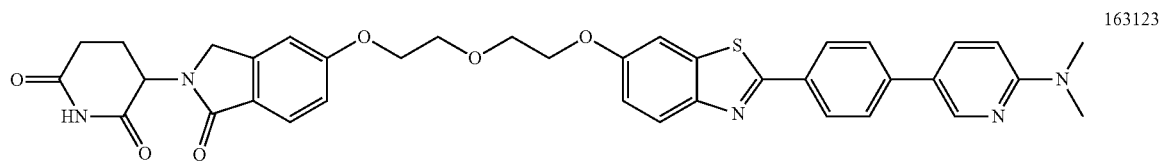

163123

Compound 163123 were synthesized according to methods similar to Example 6.

¹H NMR (600 MHz, DMSO-d6) δ 10.97 (s, 1H), 8.56 (d, J=2.5 Hz, 1H), 8.06 (d, J=8.4 Hz, 2H), 7.92-7.96 (m, 2H), 7.82 (d, J=8.4 Hz, 2H), 7.74 (d, J=2.5 Hz, 1H), 7.62 (d, J=8.4 Hz, 1H), 7.13-7.18 (m, 2H), 7.07 (dd, J=8.4, 2.1 Hz, 1H), 6.77 (d, J=9.0 Hz, 1H), 5.07 (dd, J=13.4, 5.2 Hz, 1H), 4.35 (d, J=17.1 Hz, 1H), 4.22-4.27 (m, 6H), 3.85-3.91 (m, 5H), 3.10 (s, 7H), 2.85-2.96 (m, 1H), 2.55-2.63 (m, 2H), 2.31-2.42 (m, 2H).

Example 11: Synthesis of Compound 163365

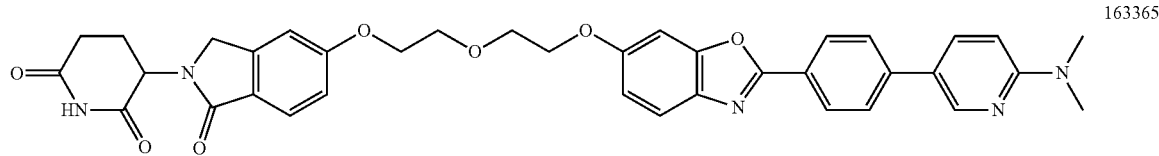

163365

Compound 163365 were synthesized according to methods similar to Example 6.

¹H NMR (600 MHz, DMSO-d6) δ 10.96 (s, 1H), 8.57 (d, J=2.5 Hz, 1H), 8.16 (d, J=8.4 Hz, 2H), 8.09 (s, 1H), 7.96 (dd, J=8.9, 2.4 Hz, 1H), 7.86 (d, J=8.4 Hz, 2H), 7.68 (d, J=8.7 Hz, 1H), 7.62 (d, J=8.4 Hz, 1H), 7.45 (d, J=2.1 Hz, 1H), 7.18 (s, 1H), 7.08 (d, J=8.3 Hz, 1H), 7.02 (dd, J=8.7, 2.2 Hz, 1H), 6.77 (d, J=8.9 Hz, 1H), 5.07 (dd, J=13.3, 5.2 Hz, 1H), 4.36 (d, J=17.2 Hz, 1H), 4.22-4.28 (m, 5H), 3.86-3.91 (m, 3H), 3.10 (s, 5H), 2.84-2.94 (m, 2H).

Example 12: Synthesis of Compound 161247

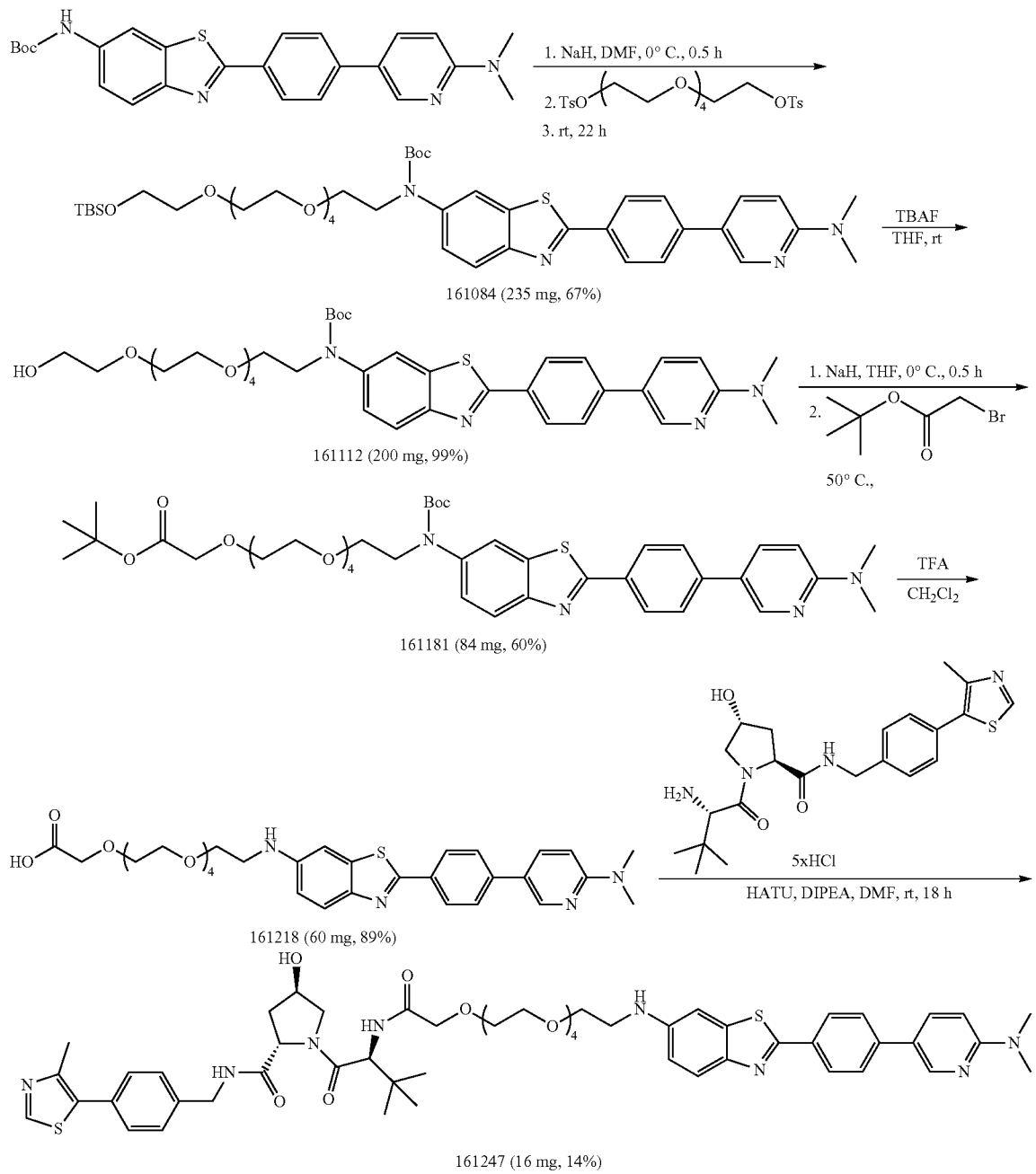

(A) Compound 161084:

To a solution of tert-butyl N-[2-[4-[6-(dimethylamino)pyridin-3-yl]phenyl]-1,3-benzothiazol-6-yl]carbamate (200 mg, 0.45 mmol) in DMF (3 mL) was added NaH (32 mg, 1.34 mmol) at 0° C. The resulting mixture was stirred at RT for 1 h. 2-[2-[2-[2-[2-[tert-butyl(dimethyl)silyl]oxyethoxy]ethoxy]ethoxy]ethoxy]ethyl 4-methylbenzenesulfonate (454 mg, 0.90 mmol) was added to the reaction mixture and stirred at RT for 22 h. The mixture was quenched with water. The precipitation was collected by filtration and purified by column chromatography (EtOAC:DCM=2:3, Rf=0.48) to give tert-butyl N-[2-[2-[2-[2-[2-[tert-butyl-(dimethyl)silyl]oxyethoxy]ethoxy]ethoxy]ethoxy]ethyl]-N-[2-[4-[6-(dimethylamino)pyridin-3-yl]phenyl]-1,3-benzothiazol-6-yl]carbamate (235 mg, 0.30 mmol, 67% yield) as a yellow solid.

(B) Compound 161112:

To a solution of tert-butyl N-[2-[2-[2-[2-[2-[tert-butyl-(dimethyl)-silyl]oxyethoxy]ethoxy]ethoxy]ethoxy]ethyl]-N-[2-[4-[6-(dimethylamino)pyridin-3-yl]-phenyl]-1,3-benzothiazol-6-yl]carbamate (235 mg, 0.30 mmol) in THF (5 mL) was added 1 M TBAF solution in THF (1.81 mL, 1.81 mmol) dropwise. The reaction mixture was stirred at RT for 7 h. The reaction mixture was concentrated to dryness and the residue was taken up in EtOAc (100 mL). The mixture was washed with water (100 mL) and brine (100 mL). The organic layer was collected, dried over $Na_2SO_4$ and concentrated to give tert-butyl N-[2-[4-[6-(dimethylamino)-pyridin-3-yl]phenyl]-1,3-benzothiazol-6-yl]-N-[2-[2-[2-[2-(2-hydroxyethyloxy)ethoxy]-ethoxy]ethoxy]ethyl]carbamate (200 mg, 0.30 mmol, 99.7% yield) as a yellow solid.

(C) Compound 161181:

To a solution of tert-butyl N-[2-[4-[6-(dimethylamino) pyridin-3-yl]phenyl]-1,3-benzothiazol-6-yl]-N-[2-[2-[2-[2-(2-hydroxyethyloxy)ethoxy]ethoxy]ethoxy]ethyl]carbamate (120 mg, 0.18 mmol) in THF (3 mL) was added NaH (9 mg, 0.36 mmol) at 0° C. and stirred for 30 min. tert-Butyl 2-bromoethanoate (0.08 mL, 0.54 mmol) was then added and the mixture was heated at 50° C. for 8 h. The solvent was removed by vacuum. The residue was purified by column chromatography (EtOAc:DCM=2:3, Rf=0.35) to afford tert-butyl 2-[2-[2-[2-[2-[2-[[2-[4-[6-(dimethylamino)pyridin-3-yl]phenyl]-1,3-benzothiazol-6-yl]-[(2-m ethylpropan-2-yl)oxycarbonyl]amino]ethoxy]ethoxy]ethoxy]ethoxy]ethoxy] ethanoate (84 mg, 0.11 mmol, 60% yield) as a yellow solid.

(D) Compound 161218:

A mixture of tert-butyl 2-[2-[2-[2-[2-[2-[[2-[4-[6-(dimethylamino)pyridin-3-yl]phenyl]-1,3-benzothiazol-6-yl]-[(2-methylpropan-2-yl)oxycarbonyl]amino]ethoxy]ethoxy] ethoxy]ethoxy]ethoxy]ethanoate (84 mg, 0.11 mmol) and TFA (0.12 mL, 1.61 mmol) in DCM (2 mL) was stirred at RT for 23 h. The mixture was acidified to pH 1 with 1N HCl solution. The mixture was extracted with DCM. The organic layer was washed with brine, dried over $Na_2SO_4$ and was concentrated to dryness to afford 2-[2-[2-[2-[2-[2-[[2-[4-[6-(dimethyl-amino)pyridin-3-yl]phenyl]-1,3-benzothiazol-6-yl]amino]ethoxy]ethoxy]ethoxy]ethoxy]-ethoxy]ethanoic acid (60 mg, 0.10 mmol, 89% yield) as a yellow solid.

(E) Compound 161247:

A mixture of (2S,4R)-1-[(2S)-2-amino-3,3-dimethyl-butanoyl]-N-[[4-(4-methyl-1,3-thiazol-5-yl)phenyl]m ethyl]-4-hydroxy-pyrrolidine-2-carboxamide (45 mg, 0.11 mmol), 2-[2-[2-[2-[2-[2-[[2-[4-[6-(dimethylamino)pyridin-3-yl] phenyl]-1,3-benzothiazol-6-yl]-amino]ethoxy]ethoxy] ethoxy]ethoxy]ethanoic acid (60 mg, 0.10 mmol), DIPEA (0.03 mL, 0.14 mmol) and HATU (73 mg, 0.19 mmol) in anhydrous DMF (3 mL) was stirred at RT for 18 h. The mixture was diluted with DCM, washed with water and brine, dried over $Na_2SO_4$, concentrated and purified by column chromatography on NH silica gel (MeOH: DCM=97:3, Rf=0.48) to give rac-(2R,4S)—N-[[4-(4-methyl-1,3-thiazol-5-yl)phenyl]methyl]-4-hydroxy-1-[rac-(2R)-2-[2-[2-[2-[2-[2-[2-[[2-[4-[6-(dimethylamino)pyridin-3-yl]phenyl]-1,3-benzothiazol-6-yl]-amino]ethoxy]ethoxy]-ethoxy]ethoxy]ethoxy]ethanoylamino]-3,3-dimethyl-butanoyl]pyrrolidine-2-carboxamide (16 mg, 0.01 mmol, 14% yield) as a yellow solid.

Example 13: Synthesis of Compound 160275

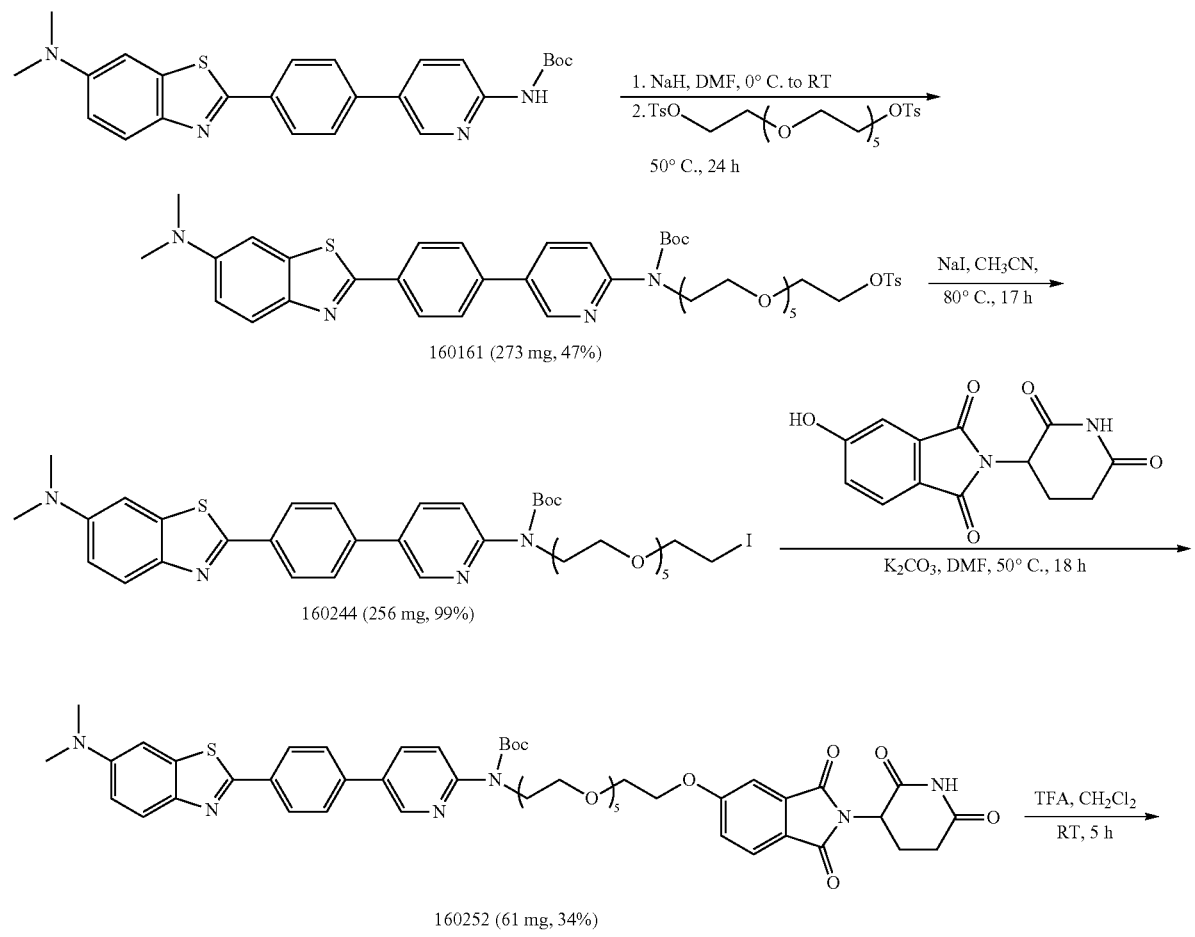

160161 (273 mg, 47%)

160244 (256 mg, 99%)

160252 (61 mg, 34%)

-continued

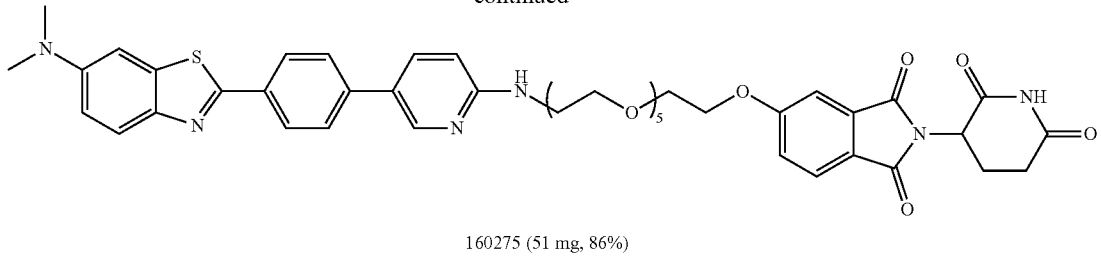

160275 (51 mg, 86%)

(A) Compound 160161:

To a solution of NaH (81 mg, 2.02 mmol) in DMF (1 mL) was added tert-butyl N-[5-[4-[6-(dimethylamino)-1,3-benzothiazol-2-yl]phenyl]pyridin-2-yl]-carbamate (300 mg, 0.67 mmol) in DMF (6 mL) at 0° C. and stirred at 25° C. for 30 min. 2-[2-[2-[2-[2-[2-(4-methylphenyl)sulfonyloxy-ethoxy]ethoxy]ethoxy]ethoxy]ethyl 4-methylbenzenesulfonate (794 mg, 1.34 mmol) in DMF (3 mL) was added to the reaction mixture and heated at 50° C. for 2 h. The mixture was quenched with saturated NH₄Cl solution and extracted with DCM. The organic layer was washed with brine, dried over MgSO₄, concentrated and purified by column chromatography (MeOH:DCM=3:97, Rf=0.3) to afford 2-[2-[2-[2-[2-[2-[[5-[4-[6-(dimethylamino)-1,3-benzothiazol-2-yl]phenyl]pyridin-2-yl]-[(2-m ethylpropan-2-yl)oxycarbonyl]amino]ethoxy]ethoxy]ethoxy]ethoxy]ethyl 4-methylbenzenesulfonate (273 mg, 0.32 mmol, 47% yield) as a yellow oil.

(B) Compound 160244:

A mixture of 2-[2-[2-[2-[2-[2-[[5-[4-[6-(dimethylamino)-1,3-benzothiazol-2-yl]phenyl]pyridin-2-yl]-[(2-methylpropan-2-yl)oxycarbonyl]amino]ethoxy]ethoxy]ethoxy]ethoxy]ethyl 4-methylbenzenesulfonate (270 mg, 0.31 mmol) and NaI (56.18 mg, 0.37 mmol) in CH₃CN (5 mL) was heated at 80° C. for 19 h. The mixture was diluted with DCM and extracted with water (50 mL) and brine (50 mL). The organic layer was dried over MgSO₄ and concentrated to dryness to afford tert-butyl N-[5-[4-[6-(dimethylamino)-1,3-benzothiazol-2-yl]phenyl]pyridin-2-yl]-N-[2-[2-[2-[2-[2-(2-iodoethoxy)ethoxy]ethoxy]ethoxy]ethyl]carbamate (256 mg, 0.31 mmol, 99.9% yield) as an orange oil.

(C) Compound 160252:

A mixture of 2-[2,6-bis(oxo)piperidin-3-yl]-5-hydroxy-isoindole-1,3-dione (102 mg, 0.37 mmol), K₂CO₃ (77 mg, 0.56 mmol) and tert-butyl N-[5-[4-[6-(di-methylamino)-1,3-benzothiazol-2-yl]phenyl]pyridin-2-yl]-N-[2-[2-[2-[2-[2-(2-iodoethoxy)-ethoxy]ethoxy]ethoxy]ethyl]carbamate (153 mg, 0.19 mmol) in DMF (4 mL) was heated at 50° C. for 18 h. The mixture was diluted with DCM (200 mL) and extracted with water. The organic layer was collected, dried over MgSO₄, concentrated and purified by column chromatography (MeOH:DCM=5:95, Rf=0.3) to give tert-butyl N-[2-[2-[2-[2-[2-[2-[2-[2,6-bis(oxo)piperidin-3-yl]-1,3-bis(oxo)isoindol-5-yl]oxyethoxy]-ethoxy] ethoxy]ethoxy]ethoxy]ethyl]-N-[5-[4-[6-(dimethylamino)-1,3-benzothiazol-2-yl]-phenyl]pyridin-2-yl]carbamate (61 mg, 0.06 mmol, 34% yield) as a yellow solid.

(D) Compound 160275:

To a solution of tert-butyl N-[2-[2-[2-[2-[2-[2-[2-[2,6-bis-(oxo)piperidin-3-yl]-1,3-bis(oxo)isoindol-5-yl]oxyethoxy] ethoxy]ethoxy]ethoxy]-ethoxy]ethyl]-N-[5-[4-[6-(dimethyl-amino)-1,3-benzothiazol-2-yl]phenyl]pyridin-2-yl]-carbamate (61 mg, 0.06 mmol) in DCM (1 mL) was added TFA (0.5 mL, 6.53 mmol) at 0° C. The resulting mixture was stirred at RT for 5 h. The solution was neutralized with saturated NaHCO₃ solution at 0° C. and extracted with DCM. The organic layer was washed with brine, dried over MgSO₄, concentrated and purified by column chromatography on NH silica gel (MeOH:DCM=99:1, Rf=0.3) to afford 2-[2,6-bis(oxo)piperidin-3-yl]-5-[2-[2-[2-[2-[2-[2-[[5-[4-[6-(dimethylamino)-1,3-benzothiazol-2-yl]phenyl]pyridin-2-yl]amino]ethoxy]ethoxy]-ethoxy]ethoxy]ethoxy]ethoxy] isoindole-1,3-dione (51 mg, 0.05 mmol, 86% yield) as a yellow solid.

Example 14: Synthesis of Compound 161177

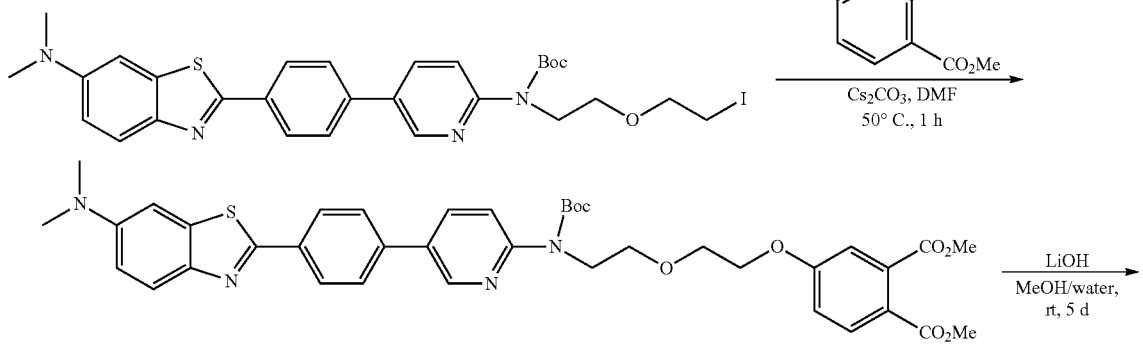

161026 (148 mg, 66%)

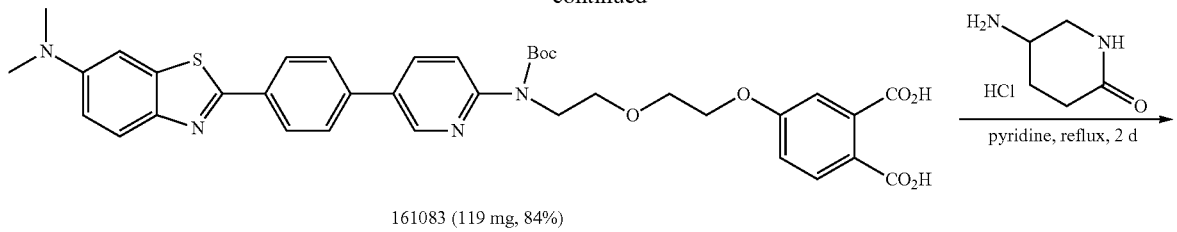

161083 (119 mg, 84%)

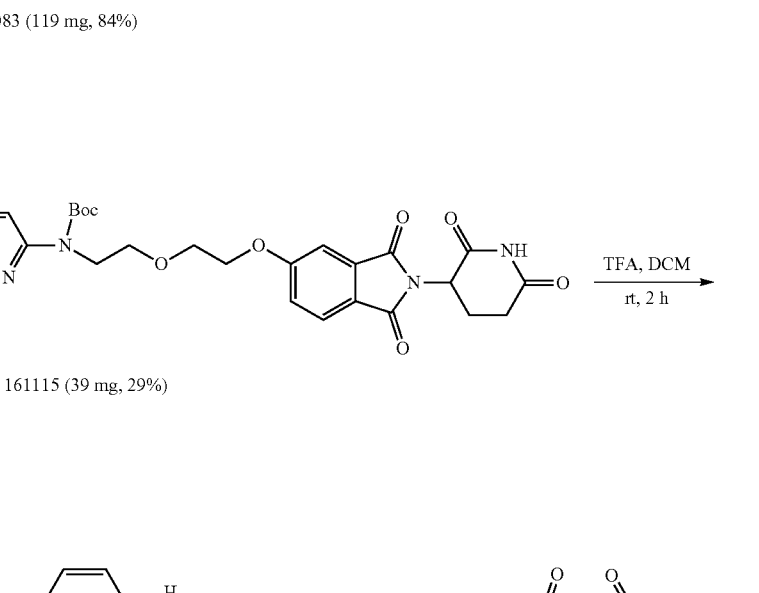

161115 (39 mg, 29%)

161177 (11 mg, 31%)

(A) Compound 161026: A mixture of dimethyl 4-hydroxyphthalate (139 mg, 0.62 mmol), $Cs_2CO_3$ (303 mg, 0.93 mmol), tert-butyl N-[5-[4-[6-(dimethylamino)-1,3-benzothiazol-2-yl]-phenyl]pyridin-2-yl]-N-[2-(2-iodoethoxy)ethyl] carbamate (200 mg, 0.31 mmol) in DMF (5 mL) was heated at 50° C. for 1 h. The mixture was quenched with water and extracted with DCM. The organic layer was dried over $MgSO_4$, concentrated and purified by column chromatography (EtOAc:Hex=1:1, Rf=0.4) to give dimethyl 4-[2-[2-[[5-[4-[6-(dimethylamino)-1,3-benzo-thiazol-2-yl]phenyl]pyridin-2-yl]-[(2-methylpropan-2-yl)oxycarbonyl]amino] ethoxy]ethoxy]-benzene-1,2-dicarboxylate (148 mg, 0.20 mmol, 66% yield) as a yellow solid.

(B) Compound 161083:

To a solution of dimethyl 4-[2-[2-[[5-[4-[6-(dimethyl-amino)-1,3-benzothiazol-2-yl]phenyl]pyridin-2-yl]-[(2-methylpro pan-2-yl)oxycarbonyl]amino]ethoxy]ethoxy] benzene-1,2-dicarboxylate (148 mg, 0.20 mmol) in MeOH (1 mL) and water (1 mL) was added LiOH (39 mg, 1.63 mmol). The reaction mixture was stirred at RT for 5 days. The solution was acidified with 1N HCl to pH 4-5. The resulting precipitate was collected by filtration, washed with water and dried over vacuo to afford 4-[2-[2-[[5-[4-[6-(dimethylamino)-1,3-benzothiazol-2-yl]phenyl]pyridin-2-yl]-[(2-methylpro pan-2-yl)oxycarbonyl]amino]ethoxy] ethoxy]phthalic acid (119 mg, 0.17 mmol, 84% yield) as a yellow solid.

(C) Compound 161115:

A mixture of 4-[2-[2-[[5-[4-[6-(dimethylamino)-1,3-benzo-thiazol-2-yl]phenyl]pyridin-2-yl]-[(2-methylpropan-2-yl)oxycarbonyl]amino]ethoxy]ethoxy]-phthalic acid (119 mg, 0.17 mmol) and 3-aminopiperidine-2,6-dione hydrochloride (31 mg, 0.19 mmol) in pyridine (2 mL) was heated at 120° C. for 2 days. The mixture was concentrated to dryness and purified by column chromatography (MeOH:DCM=5:95, Rf=0.3) to afford tert-butyl N-[2-[2-[2-[2,6-bis(oxo)piperidin-3-yl]-1,3-bis(oxo)isoindol-5-yl]oxyethoxy] ethyl]-N-[5-[4-[6-(dimethylamino)-1,3-benzothiazol-2-yl] phenyl]pyridin-2-yl]carbamate (39 mg, 0.05 mmol, 29% yield) as a yellow solid.

(D) Compound 161177:

To a solution of tert-butyl N-[2-[2-[2-[2,6-bis(oxo)-piperidin-3-yl]-1,3-bis(oxo)isoindol-5-yl]oxyethoxy]ethyl]-N-[5-[4-[6-(dimethyl-amino)-1,3-benzothiazol-2-yl]phenyl] pyridin-2-yl]carbamate (39 mg, 0.05 mmol) in DCM (1 mL) was added TFA (1 mL, 13.06 mmol) at 0° C. The resulting mixture was stirred at RT for 2 h. The solution was neutralized with sat. $NaHCO_3$ solution and extracted with DCM. The organic layer was washed with brine, dried over $MgSO_4$, concentrated and purified by chromatography (MeOH:DCM=1:99, Rf=0.1) to afford 2-[2,6-bis(oxo)-piperidin-3-yl]-5-[2-[2-[[5-[4-[6-(dimethylamino)-1,3-benzo-thiazol-2-yl]phenyl]pyridin-2-yl]amino]ethoxy]ethoxy] isoindole-1,3-dione (11 mg, 0.02 mmol, 31% yield) as a yellow solid.

Example 15: Synthesis of Compound 160383

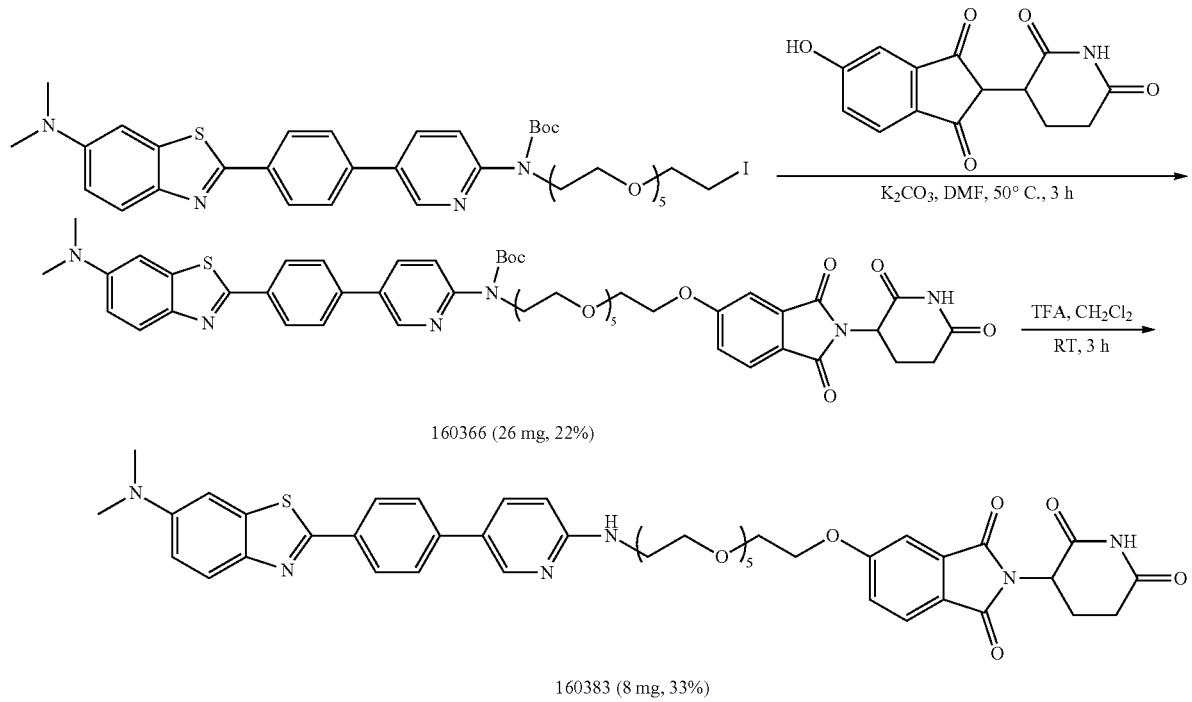

(A) Compound 160366:
A mixture of 3-(6-hydroxy-3-oxo-1H-isoindol-2-yl)piperidine-2,6-dione (63 mg, 0.24 mmol), K$_2$CO$_3$ (51 mg, 0.37 mmol), tert-butyl N-[5-[4-[6-(dimethyl-amino)-1,3-benzothiazol-2-yl]phenyl]pyridin-2-yl]-N-[2-[2-[2-[2-[2-(2-iodoethoxy)ethoxy]-ethoxy]ethoxy]ethoxy]ethyl]carbamate (100 mg, 0.12 mmol) in DMF (2 mL) was heated at 50° C. for 3 h. The mixture was quenched with water, extracted with DCM (200 mL) dried over MgSO$_4$, concentrated and purified by chromatography (MeOH:DCM=5:95, Rf=0.3) to afford tert-butyl N-[2-[2-[2-[2-[2-[2-[[2-[2,6-bis(oxo)piperidin-3-yl]-1-oxo-3H-isoindol-5-yl]oxy]ethoxy]-ethoxy]ethoxy]ethoxy]ethoxy]ethyl]-N-[5-[4-[6-(dimethylamino)-1,3-benzothiazol-2-yl]-phenyl]pyridin-2-yl]carbamate (26 mg, 0.03 mmol, 22% yield) as a yellow solid.

(B) Compound 160383:
To a solution of tert-butyl N-[2-[2-[2-[2-[2-[2-[[2-[2,6-bis-(oxo)piperidin-3-yl]-1-oxo-3H-isoindol-5-yl]oxy]ethoxy]ethoxy]ethoxy]-ethoxy]ethoxy]ethyl]-N-[5-[4-[6-(dimethylamino)-1,3-benzothiazol-2-yl]phenyl]pyridin-2-yl]carbamate (26 mg, 0.03 mmol) in DCM (1 mL) was added TFA (0.5 mL, 6.53 mmol) at 0° C. and the mixture was stirred at RT for 3 h. The solution was neutralized with sat. NaHCO$_3$ solution at 0° C. and then extracted with DCM. The organic layer was washed with brine, dried over MgSO$_4$, concentrated and purified by chromatography (MeOH:DCM=5:95, Rf=0.2) to afford 3-[6-[2-[2-[2-[2-[2-[2-[[5-[4-[6-(dimethylamino)-1,3-benzothiazol-2-yl]-phenyl]pyridin-2-yl]amino]ethoxy]ethoxy]ethoxy]ethoxy]-ethoxy]ethoxy]-3-oxo-1H-isoindol-2-yl]piperidine-2,6-dione (9 mg, 0.01 mmol, 33% yield) as a yellow solid.

Example 16: Synthesis of Compound 160744

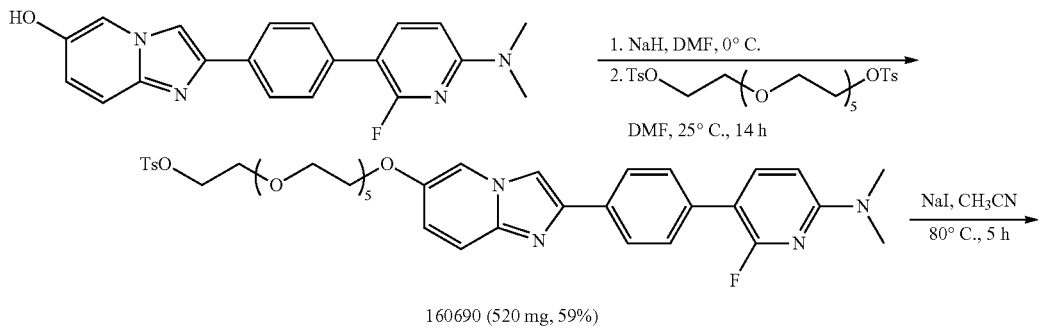

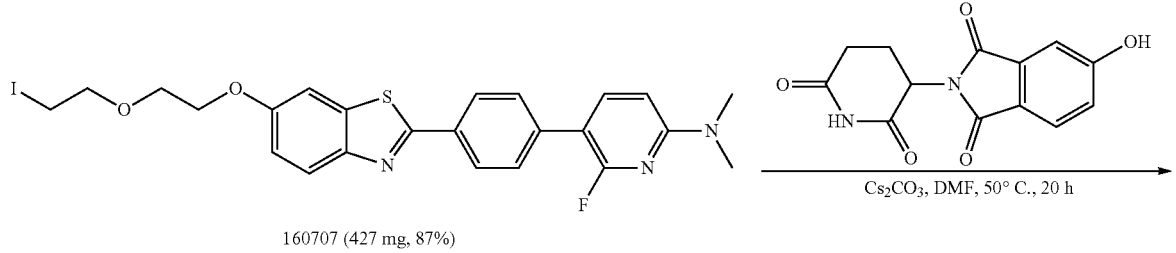

160707 (427 mg, 87%)

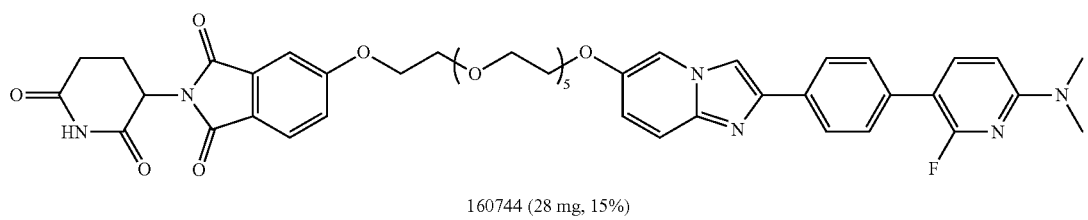

160744 (28 mg, 15%)

(A) Compound 160690:

To a solution of 2-[4-[6-(dimethylamino)-2-fluoro-pyridin-3-yl]phenyl]imidazo[1,2-a]pyridin-6-ol (400 mg, 1.15 mmol) in DMF (10 mL) was added NaH (184 mg, 4.59 mmol) at 0° C. and stirred at RT for 1 h. 2-[2-[2-[2-[2-[2-(4-methylphenyl)sulfonyloxyethoxy]ethoxy]ethoxy]ethoxy]ethyl 4-methylbenzenesulfonate (2 mL, 4.13 mmol) was added to the mixture and stirred at RT for 14 h under argon. The mixture was diluted with DCM (10 mL), washed with water (10 mL) and brine (10 mL). The organic layer was collected, dried over $Na_2SO_4$, concentrated and purified by column chromatography (DCM:MeOH=50:1, Rf=0.29) to give 2-[2-[2-[2-[2-[2-[2-[4-[6-(dimethylamino)-2-fluoro-pyridin-3-yl]phenyl]imidazo-[1,2-a]pyridin-6-yl]oxyethoxy]ethoxy]ethoxy]ethoxy]ethyl 4-methylbenzenesulfonate (520 mg, 0.68 mmol, 59% yield) as pale yellow solid.

(B) Compound 160707:

A mixture of 2-[2-[2-[2-[2-[2-[2-[4-[6-(dimethylamino)-2-fluoro-pyridin-3-yl]phenyl]imidazo[1,2-a]pyridin-6-yl]oxyethoxy]ethoxy]ethoxy]ethoxy]ethyl 4-methylbenzenesulfonate (520 mg, 0.68 mmol) and NaI (122 mg, 0.81 mmol) in $CH_3CN$ (6 mL) was heated at 80° C. for 5 h. The mixture was added water and extracted with DCM. The organic layer was washed with water (20 mL), brine (20 mL), dried over $Na_2SO_4$, concentrated and purified by chromatography (MeOH:DCM=1:50, Rf=0.39) to give 6-fluoro-5-[4-[6-[2-[2-[2-[2-[2-(2-iodoethoxy)ethoxy]ethoxy]ethoxy]ethoxy]ethoxy]imidazo-[1,2-a]pyridin-2-yl]phenyl]-N,N-dimethyl-pyridin-2-amine (427 mg, 0.59 mmol, 87% yield) as pale-yellow solid.

(C) Compound 160744:

A mixture of 2-[2,6-bis(oxo)piperidin-3-yl]-5-hydroxy-isoindole-1,3-dione (114 mg, 0.41 mmol), $Cs_2CO_3$ (202 mg, 0.62 mmol) and 6-fluoro-5-[4-[6-[2-[2-[2-[2-[2-(2-iodoethoxy)ethoxy]ethoxy]ethoxy]ethoxy]ethoxy]-3,8a-dihydro-imidazo[1,2-a]pyridin-2-yl]phenyl]-N,N-dimethyl-pyridin-2-amine (150 mg, 0.21 mmol) in DMF (3 mL) was heated at 50° C. for 20 h. The mixture was quenched with water and the resulting precipitation was collected by filtration. The residue was purified by column chromatography (MeOH:DCM=1:20, Rf=0.34) to give 2-[2,6-bis(oxo)piperidin-3-yl]-5-[2-[2-[2-[2-[2-[2-[2-[4-[6-(dimethyl-amino)-2-fluoro-pyridin-3-yl]phenyl]imidazo[1,2-a]pyridin-6-yl]oxyethoxy]ethoxy]-ethoxy]ethoxy]ethoxy]isoindole-1,3-dione (28 mg, 0.03 mmol, 15% yield) as brown solid.

$^1H$ NMR (400 MHz, DMSO-d6) δ 11.09 (s, 1H), 8.28 (s, 1H), 8.23 (d, J=2.3 Hz, 1H), 7.97 (d, J=7.8, 2H), 7.87 (dd, J=10.8, 8.4 Hz, 1H), 7.81 (d, J=8.4 Hz, 1H), 7.57 (d, J=7.8 Hz, 2H), 7.50 (d, J=9.7 Hz, 1H), 7.43 (d, J=2.3 Hz, 1H), 7.34 (dd, J=8.4, 2.3 Hz, 1H), 7.05 (dd, J=9.7, 2.3 Hz, 1H), 6.63 (dd, J=8.4, 2.0 Hz, 1H), 5.11 (dd, J=12.9, 5.5 Hz, 1H), 4.25-4.32 (m, 2H), 4.06-4.14 (m, 2H), 3.74-3.79 (m, 4H), 3.47-3.63 (m, 18H), 3.06 (s, 6H), 2.80-2.96 (m, 2H).

Example 17: Synthesis of Compound 161111

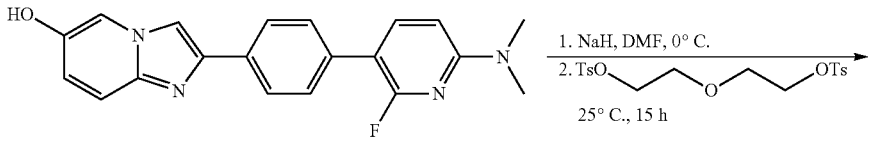

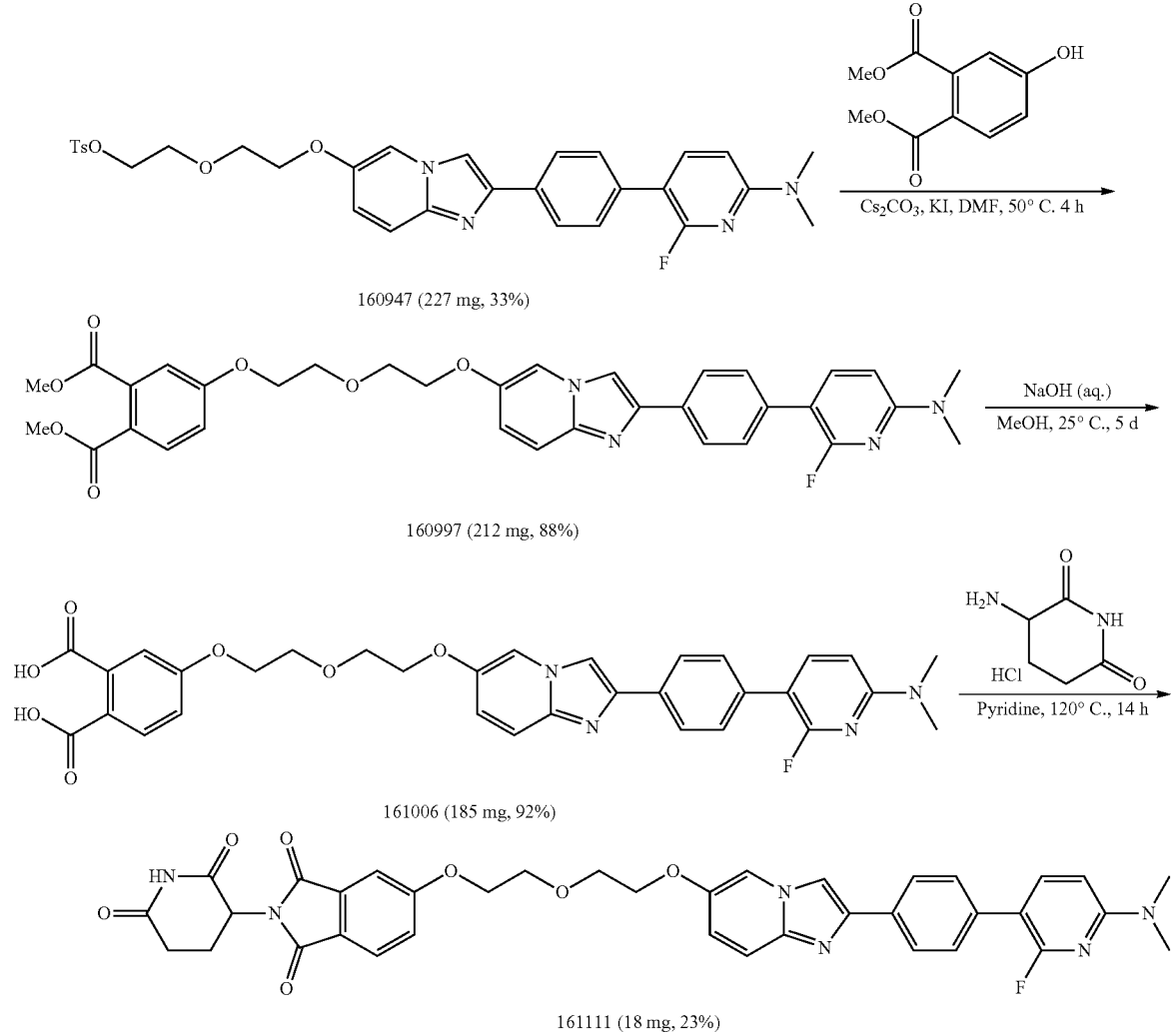

(A) Compound 160947:
To a solution of 2-[4-[6-(dimethylamino)-2-fluoro-pyridin-3-yl]phenyl]imidazo[1,2-a]pyridin-6-ol (400 mg, 1.15 mmol) in dry DMF (8 mL) was added NaH (0.14 g, 3.44 mmol) at 0° C. and stirred at RT for 1 h. 2-[2-(4-methylphenyl)sulfonyloxyethoxy]ethyl 4-methylbenzenesulfonate (1.43 g, 3.44 mmol) was added to the mixture and stirred at the same temperature for 16 h. The reaction was quenched with water and extracted with DCM. The organic layer was washed with water, brine, dried over Na$_2$SO$_4$, concentrated and purified by column chromatography on silica gel (EtOAc:DCM=1:5, Rf=0.33) to give 2-[2-[2-[4-[6-(di-methylamino)-2-fluoro-pyridin-3-yl]phenyl]imidazo[1,2-a]pyridin-6-yl]oxyethoxy]ethyl 4-methylbenzenesulfonate (227 mg, 0.38 mmol, 33% yield) as orange solid.

(B) Compound 160997:
A mixture of dimethyl 4-hydroxybenzene-1,2-dicarboxylate (161 mg, 0.77 mmol), Cs$_2$CO$_3$ (374.2 mg, 1.15 mmol), KI (6 mg, 0.04 mmol) and 2-[2-[2-[4-[6-(dimethylamino)-2-fluoro-pyridin-3-yl]phenyl]imidazo[1,2-a]pyridin-6-yl]oxyethoxy]ethyl 4-methylbenzenesulfonate (226 mg, 0.38 mmol) in DMF (4 mL) was heated at 50° C. for 4 h. The mixture was quenched with water and the resulting precipitation was collected by filtration and washed with water to give dimethyl 4-[2-[2-[2-[4-[6-(dimethylamino)-2-fluoro-pyridin-3-yl]-phenyl]imidazo[1,2-a]pyridin-6-yl]oxyethoxy]ethoxy]benzene-1,2-dicarboxylate (212 mg, 0.34 mmol, 88% yield) as an orange solid.

(C) Compound 161006:
To a solution of dimethyl 4-[2-[2-[2-[4-[6-(dimethylamino)-2-fluoro-pyridin-3-yl]phenyl]imidazo[1,2-a]pyridin-6-yl]oxyethoxy]ethoxy]benzene-1,2-dicarboxylate (211 mg, 0.34 mmol) in MeOH (2 mL) was added NaOH (443 mg, 11.08 mmol) in water (2 mL) and stirred at RT for 5 days. The reaction was diluted with EtOAc (50 mL) and acidified with 1N HCl solution to pH 1. The organic layer was washed with water (50 mL), brine (50 mL) dried over Na$_2$SO$_4$ and concentrated to give 4-[2-[2-[2-[4-[6-(dimethylamino)-2-fluoro-pyridin-3-yl]phenyl]imidazo[1,2-a]pyridin-6-yl]-oxyethoxy]ethoxy]phthalic acid (185 mg, 0.31 mmol, 92% yield) as a yellow solid.

(D) Compound 161111:
A mixture of 4-[2-[2-[2-[4-[6-(dimethylamino)-2-fluoro-pyridin-3-yl]phenyl]imidazo[1,2-a]pyridin-6-yl]oxyethoxy]ethoxy]phthalic acid (67 mg, 0.11 mmol), and 3-aminopiperidine-2,6-dione hydrochloride (20 mg, 0.15 mmol) in pyridine (3 mL) was heated at 120° C. for 14 h. The solvent was removed by vacuum. The residue was redissolved in DCM and water was added. The resulting precipitate was collected by filtration and purified by column chromatography (MeOH:DCM=1:100, Rf=0.19) to afford 2-[2,6-bis(oxo)-piperidin-3-yl]-5-[2-[2-[2-[4-[6-(dimethylamino)-2-fluoro-pyridin-3-yl]phenyl]imidazo[1,2-a]pyridin-6-yl]oxyethoxy]ethoxy]isoindole-1,3-dione (18 mg, 0.02 mmol, 22% yield) as a yellow solid.

Example 18: Synthesis of Compound 161215

(A) Compound 160806:
To a solution of NaH (138 mg, 3.45 mmol) in DMF (2 mL) was added tert-butyl N-[6-fluoro-5-[4-(6-methoxyimidazo[1,2-a]pyridin-2-yl)phenyl]pyridin-2-yl]carbamate (500 mg, 1.15 mmol) in DMF (10 mL) at 0° C. The resulting mixture was stirred at room temperature for 30 min. 2-[2-(4-Methylphenyl)sulfonyloxyethoxy]ethyl 4-methylbenzenesulfonate (954 mg, 2.30 mmol) in DMF (3 mL) was added to the reaction mixture and stirred at room temperature for 21 h. The mixture was quenched with saturated NH4Cl

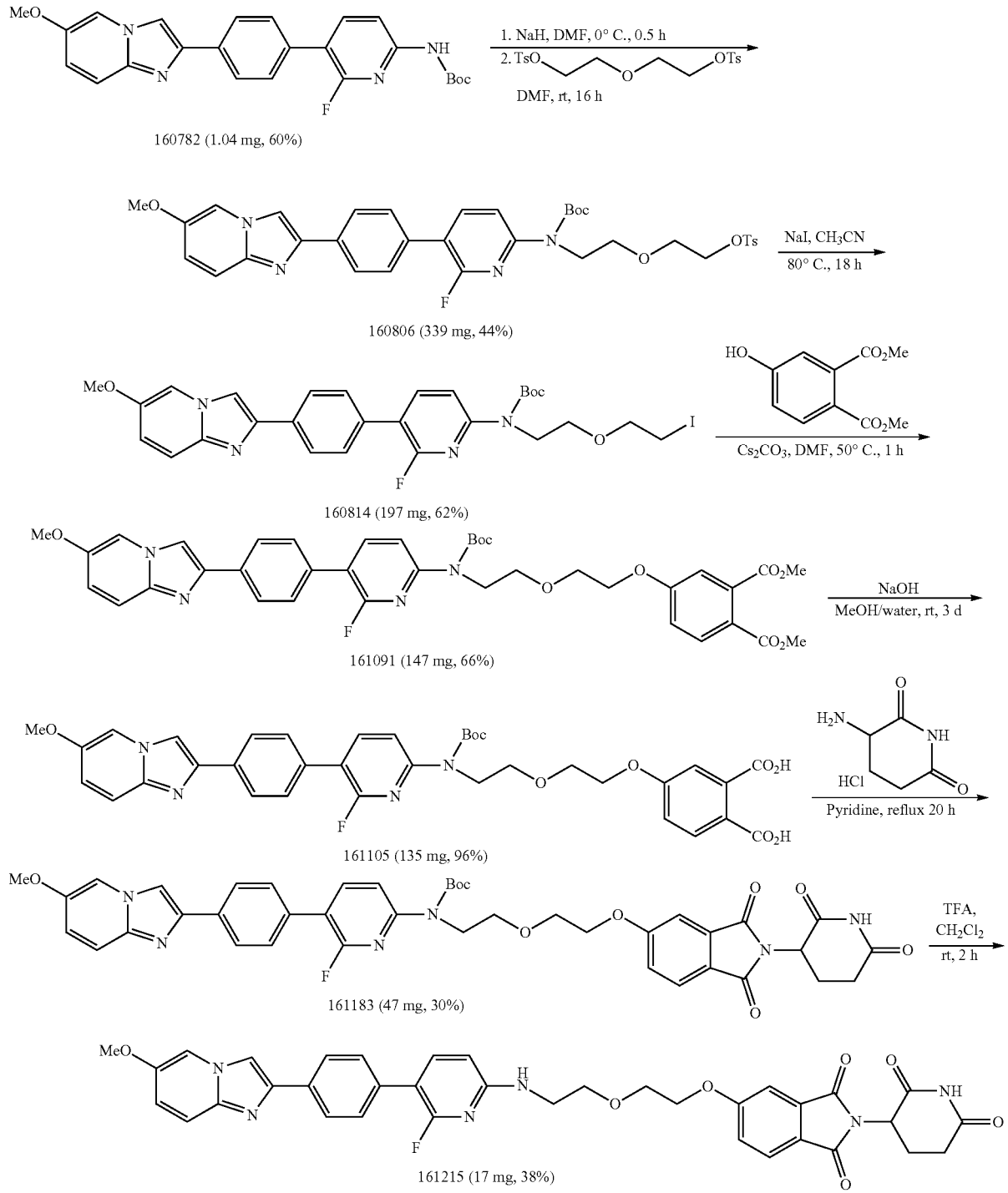

solution and extracted with EtOAc. The organic layer was washed with brine, dried over MgSO₄, concentrated and purified by column chromatography (EtOAc:DCM=3:17, Rf=0.3) to afford 2-[2-[[6-fluoro-5-[4-(6-methoxyimidazo[1,2-a]pyridin-2-yl)phenyl]pyridin-2-yl]-[(2-methyl-propan-2-yl)oxycarbonyl]amino]ethoxy]ethyl 4-methylbenzenesulfonate (339 mg, 0.50 mmol, 44% yield) as a yellow solid.

(B) Compound 160814:

A mixture of 2-[2-[[6-fluoro-5-[4-(6-methoxyimidazo[1,2-a]-pyridin-2-yl)phenyl]pyridin-2-yl]-[(2-methylpropan-2-yl)oxycarbonyl]amino]ethoxy]ethyl 4-methylbenzenesulfonate (339 mg, 0.50 mmol) and NaI (90 mg, 0.60 mmol) in MeCN (10 mL) was heated at 80° C. for 19 h. The mixture was added to water and extracted with EtOAc. The organic layer was washed with water (50 mL), brine (50 mL), dried over MgSO₄, concentrated, and purified by column chromatography (EtOAc:DCM=1:9, Rf=0.3) to afford tert-butyl N-[6-fluoro-5-[4-(6-methoxyimidazo[1,2-a]pyridin-2-yl)phenyl]pyridin-2-yl]-N-[2-(2-iodoethoxy)ethyl]carbamate (197 mg, 0.31 mmol, 62% yield) as a yellow solid.

(C) Compound 161091:

A mixture of dimethyl 4-oxybenzene-1,2-dicarboxylate (131 mg, 0.62 mmol), Cs₂CO₃ (305 mg, 0.93 mmol), tert-butyl N-[6-fluoro-5-[4-(6-methoxyimidazo-[1,2-a]pyridin-2-yl)phenyl]pyridin-2-yl]-N-[2-(2-iodoethoxy)ethyl]carbamate (197 mg, 0.31 mmol) in DMF (5 mL) was heated at 50° C. for 1 h. The mixture was quenched with water, extracted with DCM, dried over MgSO₄, concentrated, and purified by column chromatography (EtOAc:hexane=1:1, Rf=0.3) to give dimethyl 4-[2-[2-[[6-fluoro-5-[4-(6-methoxyimidazo-[1,2-a]pyridin-2-yl)phenyl]pyridin-2-yl]-[(2-methylpropan-2-yl)oxycarbonyl]amino]ethoxy]-ethoxy]benzene-1,2-dicarboxylate (147 mg, 0.21 mmol, 66% yield) as a yellow solid.

(D) Compound 161105:

To a solution of dimethyl 4-[2-[2-[[6-fluoro-5-[4-(6-methoxy-imidazo[1,2-a]pyridin-2-yl)phenyl]pyridin-2-yl]-[(2-methylpropan-2-yl)oxycarbonyl]amino]-ethoxy]ethoxy]benzene-1,2-dicarboxylate (147 mg, 0.21 mmol) in MeOH (2 mL) was added NaOH (66 mg, 1.65 mmol) in water (2 mL), and the mixture stirred at room temperature for 3 days. The reaction was neutralized with 1N HCl solution to pH 1. The precipitate was collected by filtration and washed with water to give 4-[2-[2-[[6-fluoro-5-[4-(6-methoxyimidazo[1,2-a]-pyridin-2-yl)phenyl]pyridin-2-yl]-[(2-methylpropan-2-yl)oxycarbonyl]amino]ethoxy]-ethoxy]phthalic acid (135 mg, 0.20 mmol, 96% yield) as a white solid.

(E) Compound 161183:

A mixture of 4-[2-[2-[[6-fluoro-5-[4-(6-methoxyimidazo[1,2-a]-pyridin-2-yl)phenyl]pyridin-2-yl]-[(2-methylpropan-2-yl)oxycarbonyl]amino]ethoxy]-ethoxy]phthalic acid (135 mg, 0.20 mmol) and 3-aminopiperidine-2,6-dione hydrochloride (49 mg, 0.29 mmol) in pyridine (2 mL) was heated at 120° C. for 20 h. The mixture was concentrated to dryness, and purified by column chromatography on NH silica gel (MeOH:DCM=1:99, Rf=0.1) to afford tert-butyl N-[2-[2-[2-[2,6-bis(oxo)piperidin-3-yl]-1,3-bis(oxo)isoindol-5-yl]oxyethoxy]ethyl]-N-[6-fluoro-5-[4-(6-methoxyimidazo[1,2-a]pyridin-2-yl)phenyl]pyridin-2-yl]-carbamate (47 mg, 0.06 mmol, 30% yield) as a yellow solid.

(F) Compound 161215:

To a solution of tert-butyl N-[2-[2-[2-[2,6-bis(oxo)piperidin-3-yl]-1,3-bis(oxo)isoindol-5-yl]oxyethoxy]ethyl]-N-[6-fluoro-5-[4-(6-methoxyimidazo[1,2-a]pyridin-2-yl)phenyl]pyridin-2-yl]carbamate (47 mg, 0.06 mmol) in DCM (1 mL) was added TFA (1 mL, 13 mmol) at 0° C., and the mixture stirred at room temperature for 2 h. The solution was neutralized with saturated NaHCO₃ solution and extracted with DCM. The organic layer was washed with brine, dried over MgSO₄, concentrated and purified by chromatography on NH silica gel (MeOH:DCM=1:99, Rf=0.1) to afford 2-[2,6-bis(oxo)piperidin-3-yl]-5-[2-[2-[[6-fluoro-5-[4-(6-methoxyimidazo[1,2-a]pyridin-2-yl) phenyl]pyridin-2-yl]amino]ethoxy]ethoxy]isoindole-1,3-dione (17 mg, 0.02 mmol, 38% yield) as a yellow solid. ¹H NMR (400 MHz, DMSO-d6) δ 11.07 (s, 1H), 8.28 (s, 1H), 8.19 (d, J=2.3 Hz, 1H), 7.92 (d, J=8.3 Hz, 2H), 7.79 (d, J=8.3 Hz, 1H), 7.70 (dd, J=10.3, 8.2 Hz, 1H), 7.46-7.52 (m, 3H), 7.43 (d, J=2.2 Hz, 1H), 7.34 (dd, J=8.2, 2.3 Hz, 1H), 7.14 (t, J=5.7 Hz, 1H), 7.01 (dd, J=10.3, 2.2 Hz, 1H), 6.49 (d, J=8.5 Hz, 1H), 5.08 (dd, J=13.1, 5.3 Hz, 1H), 4.34-4.28 (m, 2H), 3.75-3.83 (m, 5H), 3.62 (t, J=5.5 Hz, 2H), 3.39-3.44 (m, 2H), 2.77-2.91 (m, 1H), 2.49-2.66 (m, 2).

Example 19: Synthesis of Compound 161409

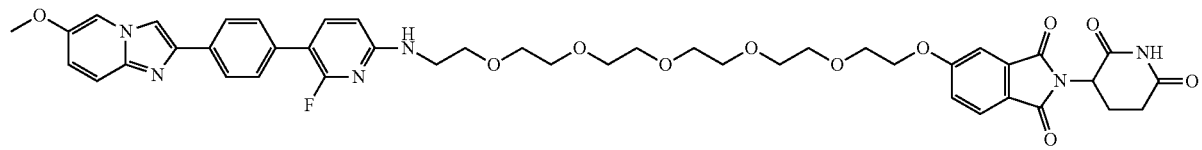

161409

Compound 161409 could be synthesized by method similar to example 19. ¹H NMR (400 MHz, DMSO-d6) δ 11.09 (s, 1H), 8.27 (s, 1H), 8.19 (d, J=2.5 Hz, 1H), 7.92 (d, J=8.0 Hz, 2H), 7.78 (d, J=8.4 Hz, 1H), 7.71 (dd, J=10.2, 8.6 Hz, 1H), 7.45-7.53 (m, 3H), 7.41 (d, J=2.0 Hz, 1H), 7.32 (dd, J=8.6, 2.1 Hz, 1H), 7.13 (t, J=5.3 Hz, 1H), 7.00 (dd, J=9.7, 1.6 Hz, 1H), 6.49 (d, J=9.2 Hz, 1H), 5.07 (dd, J=12.8, 5.3 Hz, 1H), 4.24-4.29 (m, 2H), 3.77 (s, 3H), 3.72-3.76 (m, 2H), 3.44-3.58 (m, 20H), 3.34-3.41 (m, 3H), 2.77-2.91 (m, 2H).

Example 20: Synthesis of Compound 161104

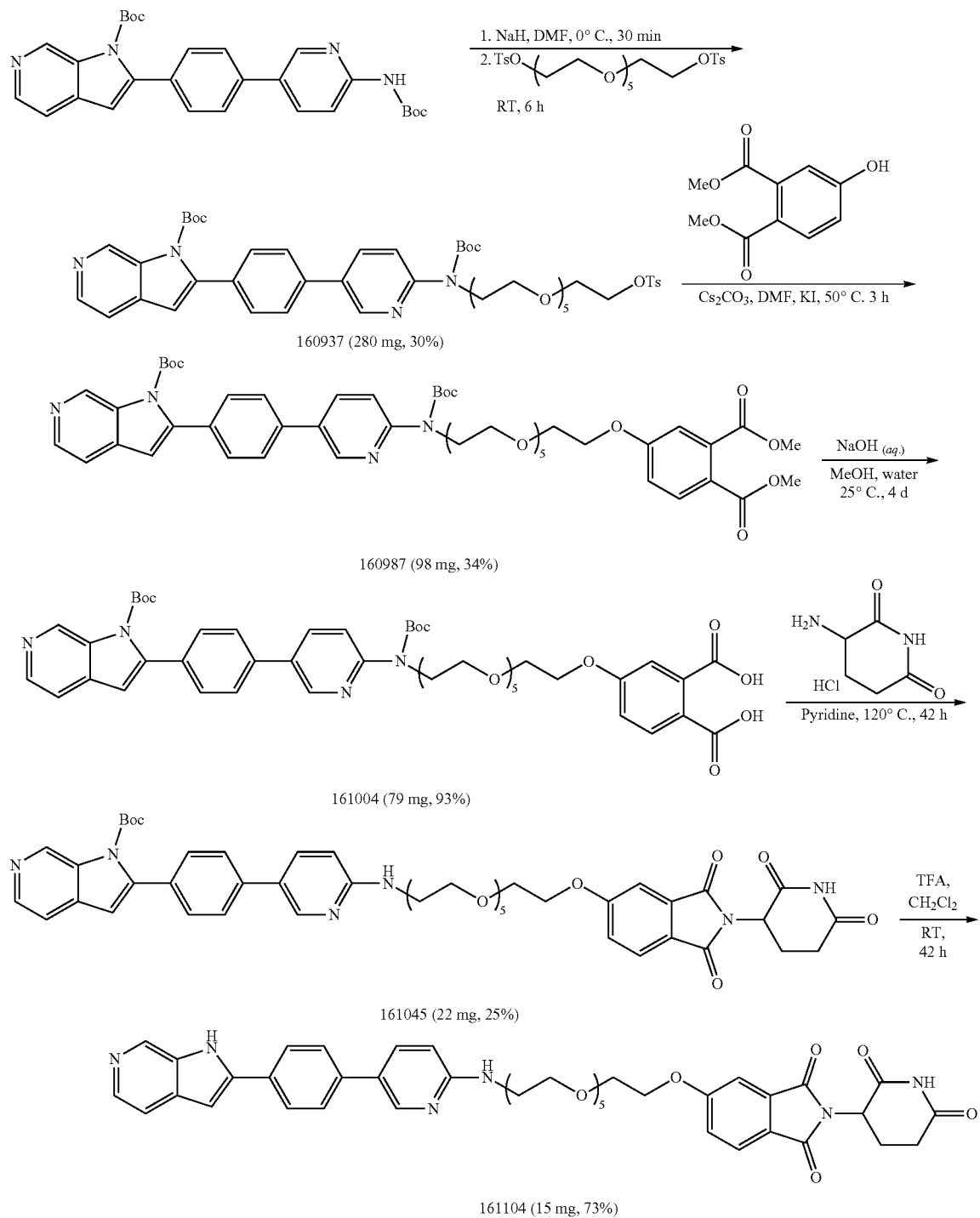

(A) Compound 160937:

To a solution of tert-butyl 2-[4-[6-[(2-methylpropan-2-yl)-oxycarbonylamino]pyridin-3-yl]phenyl]pyrrolo[2,3-c]-pyridine-1-carboxylate (500 mg, 1.03 mmol) in DMF (10 mL) was added NaH (49 mg, 1.23 mmol) at 0° C. and stirred at RT for 30 min. 2-[2-[2-[2-[2-[2-(4-methylphenyl)sulfonyloxyethoxy]ethoxy]ethoxy]ethoxy]-ethoxy]ethyl 4-methylbenzenesulfonate (789 mg, 1.34 mmol) was added to the reaction mixture and stirred at RT for 6 h. The mixture was quenched with sat. NH₄Cl solution and extracted with DCM. The organic layer was washed with brine, dried over MgSO₄, concentrated and purified by column chromatography (EtOAc:DCM=1:4, Rf=0.33) to afford tert-butyl 2-[4-[6-[2-[2-[2-[2-[2-(4-methylphenyl)sulfonyloxyethoxy]

ethoxy]ethoxy]-ethoxy]ethoxy]ethyl-[(2-methylpropan-2-yl)oxycarbonyl]amino]pyridin-3-yl]phenyl]pyrrolo-[2,3-c]pyridine-1-carboxylate (280 mg, 0.31 mmol, 30% yield) as pale-yellow oil.

(B) Compound 160987:

A solution of dimethyl 4-hydroxybenzene-1,2-dicarboxylate (130.05 mg, 0.62 mmol), $Cs_2CO_3$ (303 mg, 0.93 mmol), and tert-butyl 2-[4-[6-[2-[2-[2-[2-[2-[2-(4-methylphenyl)sulfonyloxyethoxy]ethoxy]ethoxy]ethoxy]ethoxy]ethyl-[(2-methylpropan-2-yl)oxycarbonyl]amino]pyridin-3-yl]phenyl]pyrrolo[2,3-c]pyridine-1-carboxylate (280 mg, 0.31 mmol) in DMF (3 mL) was heated at 50° C. for 3 h. The mixture was quenched with water and the resulting precipitation was collected by filtration. The solid was then purified by column chromatography (EtOAc:DCM=4:1, Rf=0.32) to provide dimethyl 4-[2-[2-[2-[2-[2-[2-[(2-methylpropan-2-yl)oxycarbonyl-[5-[4-[1-[(2-methylpropan-2-yl)oxycarbonyl]pyrrolo[2,3-c]-pyridin-2-yl]phenyl]pyridin-2-yl]amino]ethoxy]ethoxy]ethoxy]ethoxy]ethoxy]ethoxy]benzene-1,2-dicarboxylate (98 mg, 0.10 mmol, 34% yield) as pale-yellow oil.

(C) Compound 161004:

To a solution of dimethyl 4-[2-[2-[2-[2-[2-[2-[(2-methylpropan-2-yl)oxycarbonyl-[5-[4-[1-[(2-methylpropan-2-yl)oxycarbonyl]pyrrolo[2,3-c]pyridin-2-yl]-phenyl]pyridin-2-yl]amino]ethoxy]ethoxy]ethoxy]ethoxy]ethoxy]ethoxy]benzene-1,2-dicarboxylate (98 mg, 0.10 mmol) in EtOH (5 mL) was added NaOH (33 mg, 0.83 mmol) in water (5 mL) and stirred at RT for 4 days. The reaction was diluted with DCM (10 mL) and acidified with 1N HCl solution to pH 1. The organic layer was washed with water (10 mL), brine (10 mL) dried over $Na_2SO_4$ and concentrated to dryness to give 4-[2-[2-[2-[2-[2-[2-[[5-[4-[1-[(2-methyl-propan-2-yl)oxycarbonyl]pyrrolo[2,3-c]pyridin-2-yl]phenyl]pyridin-2-yl]amino]ethoxy]-ethoxy]ethoxy]ethoxy]ethoxy]phthalic acid (79 mg, 0.10 mmol, 93% yield) as pale-yellow solid.

(D) Compound 161045:

A mixture of 4-[2-[2-[2-[2-[2-[2-[[5-[4-[1-[(2-methyl-propan-2-yl)oxycarbonyl]pyrrolo[2,3-c]pyridin-2-yl]phenyl]pyridin-2-yl]amino]ethoxy]-ethoxy]ethoxy]ethoxy]ethoxy]phthalic acid (79 mg, 0.10 mmol) and 3-aminopiperidine-2,6-dione HCl (18 mg, 0.11 mmol) in pyridine (3 mL) was heated at 120° C. for 42 h. The solvent was removed in vacuo. The residue was re-dissolved in with DCM (10 mL), washed with brine, dried over $Na_2SO_4$, concentrated and purified by column chromatography (MeOH:DCM=1:19, Rf=0.3) to give tert-butyl 2-[4-[6-[2-[2-[2-[2-[2-[2-[2,6-bis(oxo)piperidin-3-yl]-1,3-bis(oxo)-isoindol-5-yl]oxyethoxy]ethoxy]ethoxy]ethoxy]ethoxy]ethylamino]pyridin-3-yl]phenyl]-pyrrolo[2,3-c]pyridine-1-carboxylate (22 mg, 0.02 mmol, 25% yield) as a yellow solid.

(E) Compound 161104:

To a solution of tert-butyl 2-[4-[6-[2-[2-[2-[2-[2-[2-[2,6-bis(oxo)-piperidin-3-yl]-1,3-bis(oxo)isoindol-5-yl]oxyethoxy]ethoxy]ethoxy]ethoxy]ethoxy]ethylamino]pyridin-3-yl]phenyl]pyrrolo[2,3-c]pyridine-1-carboxylate (22 mg, 0.02 mmol) in DCM (3 mL) was added TFA (0.03 mL, 0.36 mmol), and the mixture stirred at RT for 42 h. The mixture was neutralized with sat. $NaHCO_3$ to pH 8 and extracted with DCM (10 mL). The organic layer was washed with brine, dried over $Na_2SO_4$ and concentrated to dryness to give 2-[2,6-bis(oxo)piperidin-3-yl]-5-[2-[2-[2-[2-[2-[2-[[5-[4-(1H-pyrrolo-[2,3-c]pyridin-2-yl)phenyl]pyridin-2-yl]amino]ethoxy]ethoxy]ethoxy]ethoxy]ethoxy]-ethoxy]isoindole-1,3-dione (15 mg, 0.02 mmol, 73% yield) as a yellow solid.

Example 21: Synthesis of Compound 160624

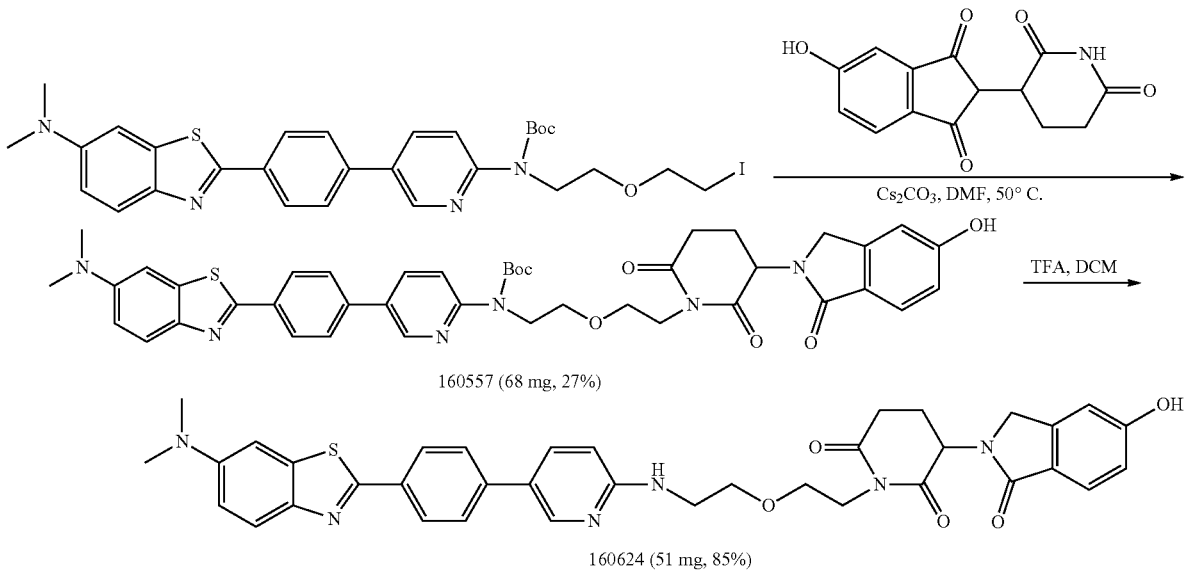

160557 (68 mg, 27%)

160624 (51 mg, 85%)

Compound 160557:

A mixture of 3-(6-oxidanyl-3-oxidanylidene-1H-isoindol-2-yl)piperidine-2,6-dione (169 mg, 0.65 mmol), $Cs_2CO_3$ (317 mg, 0.97 mmol), tert-butyl N-[5-[4-[6-(dimethylamino)-1,3-benzothiazol-2-yl]phenyl]pyridin-2-yl]-N-[2-(2-iodanylethoxy)ethyl]carbamate (209 mg, 0.32 mmol) in DMF (5 mL) was heated at 50° C. for 1 h. The mixture was quenched with water, extracted with DCM, dried over $MgSO_4$, concentrated and purified by column chromatography (solvent gradient 0% to 3% MeOH in DCM, Rf=0.2) to give tert-butyl (5-(4-(6-(dimethylamino)benzo[d]thiazol-2-yl)phenyl)pyridin-2-yl)(2-(2-(3-(5-hydroxy-1-oxoisoindolin-2-yl)-2,6-dioxopiperidin-1-yl)ethoxy)ethyl)carbamate (68 mg, 0.09 mmol, 27% yield) as a yellow solid.

Compound 160624:

To a solution of tert-butyl (5-(4-(6-(dimethylamino)benzo[d]thiazol-2-yl)phenyl)pyridin-2-yl)(2-(2-(3-(5-hydroxy-1-oxoisoindolin-2-yl)-2,6-dioxopiperidin-1-yl)ethoxy)ethyl)carbamate (68 mg, 0.09 mmol) in DCM (2 mL) was added TFA (1 mL, 13.06 mmol) at 0° C. and stirred at room temperature for 6 h. The solution was neutralized with saturated NaHCO₃ solution at 0° C. and the solution was extracted with DCM. The organic layer was washed with brine, dried over MgSO₄ and concentrated to dryness to afford 1-(2-(2-((5-(4-(6-(dimethylamino)benzo[d]thiazol-2-yl)phenyl)pyridin-2-yl)amino)ethoxy)eth yl)-3-(5-hydroxy-1-oxoisoindolin-2-yl)piperidine-2,6-dione (51 mg, 0.07 mmol, 85% yield) as a yellow solid.

Example 22: Synthesis of Compound 162641

(101 mg, 0.31 mmol) and heated at 80° C. for 3 h. The mixture was diluted with DCM, washed with water and brine, dried over Na₂SO₄, concentrated and purified by column chromatography (MeOH:DCM=1:20, Rf=0.3) to give tert-butyl N-[2-[2-[3-(7-azanyl-3-oxidanylidene-1H-isoindol-2-yl)-2,6-bis(oxidanylidene)piperidin-1-yl]ethoxy]ethyl]-N-[2-[4-[6-(dimethylamino)pyridin-3-yl]phenyl]-1,3-benzothiazol-6-yl]carba mate (70 mg, 0.09 mmol, 58% yield) as a yellow solid.

Compound 162641:

To a solution of tert-butyl N-[2-[2-[3-(7-azanyl-3-oxidanylidene-1H-isoindol-2-yl)-2,6-bis(oxidanylidene)piperidin-1-yl]ethoxy]ethyl]-N-[2-[4-[6-(dimethylamino)pyridin-3-yl]phenyl]-1,3-benzothiazol-6-yl]carba mate (70 mg, 0.09 mmol) in DCM (2 mL) was added TFA (0.1 mL, 1.35 mmol) and stirred at room temperature for 20 h. The mixture was neutralized with sat. NaHCO₃ solution to pH 8. The residue was taken up in DCM (20 mL) and water (10 mL). The

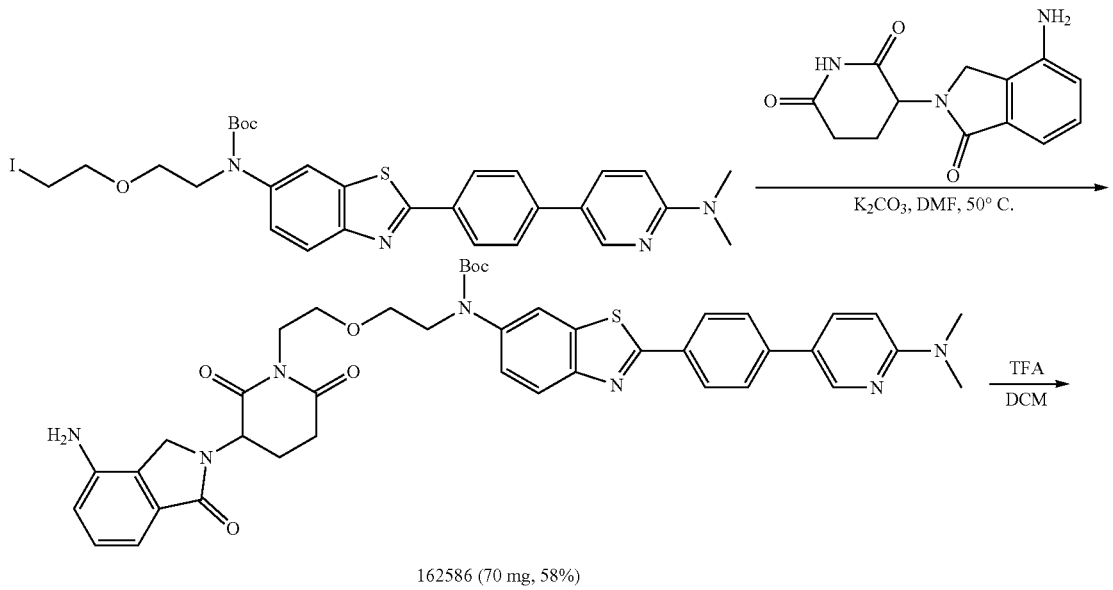

162586 (70 mg, 58%)

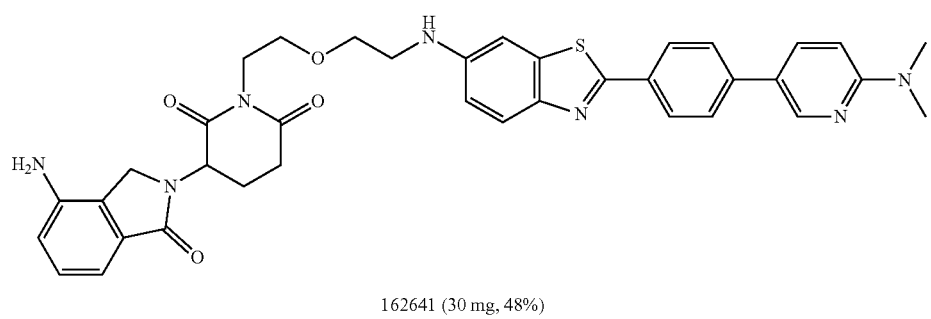

162641 (30 mg, 48%)

Compound 162586:

A solution of tert-butyl N-[2-[4-[6-(dimethylamino)pyridin-3-yl]phenyl]-1,3-benzothiazol-6-yl]-N-[2-(2-iodanylethoxy)ethyl]carbamate (100 mg, 0.16 mmol) in DMF (5 mL) was added 3-(7-azanyl-3-oxidanylidene-1H-isoindol-2-yl)piperidine-2,6-dione (48 mg, 0.19 mmol) and K₂CO₃ organic layer was washed with water (10 mL) and brine (10 mL), dried over Na₂SO₄ and concentrated to give 3-(7-azanyl-3-oxidanylidene-1H-isoindol-2-yl)-1-[2-[2-[[2-[4-[6-(dimethylamino)pyridin-3-yl]phenyl]-1,3-benzothiazol-6-yl]amino]ethoxy]ethyl]piperidine-2,6-dione (30 mg, 0.04 mmol, 46% yield) as a yellow solid.

Example 23: Synthesis of Compound 161598

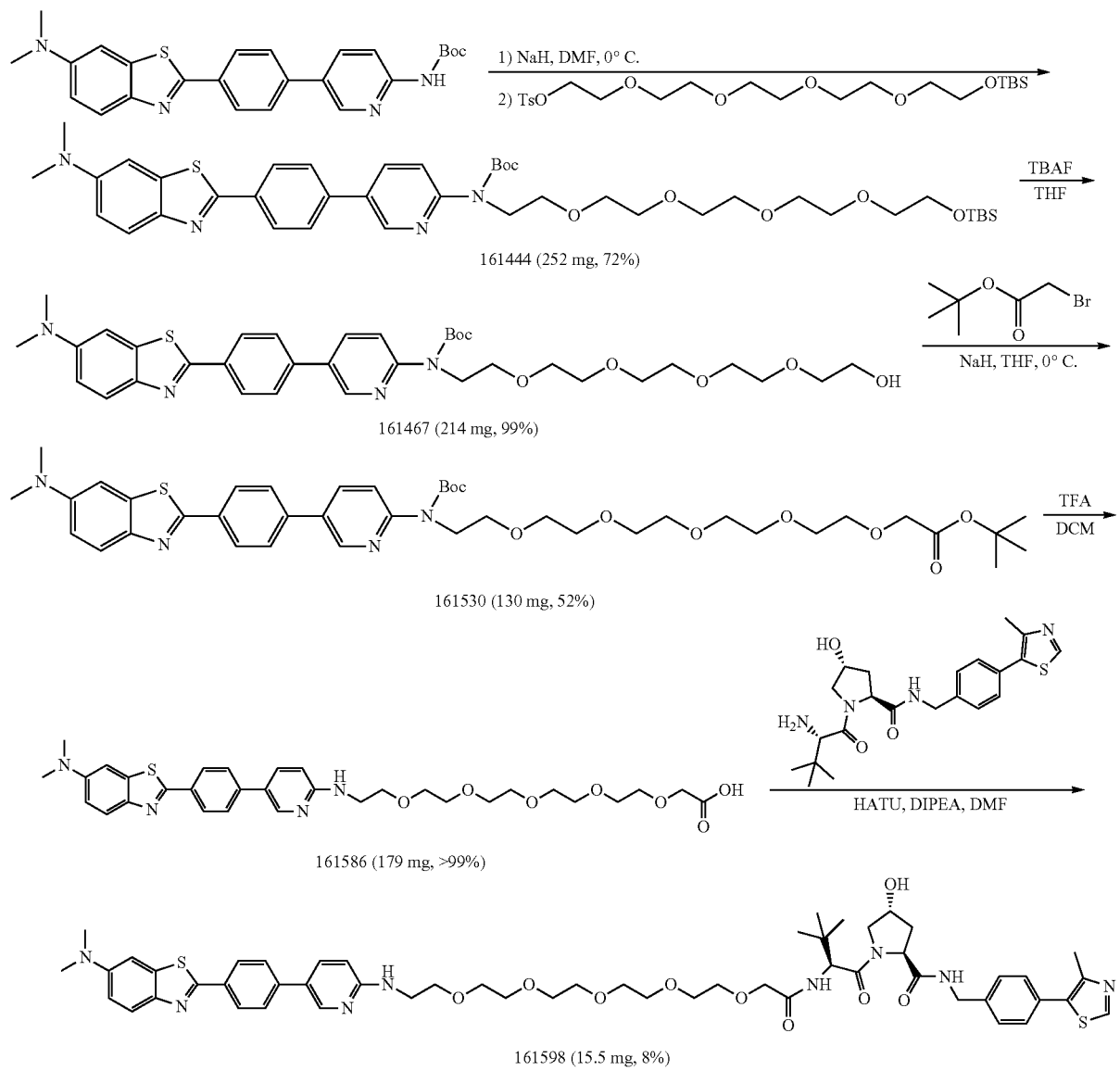

Compound 161444:

To a solution of tert-butyl N-[5-[4-[6-(dimethylamino)-1,3-benzothiazol-2-yl]phenyl]pyridin-2-yl]carbamate (200 mg, 0.45 mmol) in DMF (5 mL) was added NaH (43 mg, 1.79 mmol) at 0° C. and stirred at room temperature for 1 h. The mixture was added 2-[2-[2-[2-[2-[tert-butyl(dimethyl)silyl]oxyethoxy]ethoxy]ethoxy]ethoxy]ethyl 4-methylbenzenesulfonate (681 mg, 1.34 mmol) and stirred at the same temperature for 24 h. The reaction was quenched by adding water. The resulting solid was collected by filtration and purified by column chromatography (EtOAc:DCM=7:3, Rf=0.4) to give tert-butyl N-[2-[2-[2-[2-[2-[tert-butyl(dimethyl)silyl]oxyethoxy]ethoxy]ethoxy]ethoxy]ethyl]-N-[5-[4-[6-(dimethylamino)-1,3-benzothiazol-2-yl]phenyl]pyridin-2-yl]carbamate (252 mg, 0.32 mmol, 72% yield) as a yellow oil.

Compound 161467:

A solution of tert-butyl N-[2-[2-[2-[2-[2-[tert-butyl(dimethyl)silyl]oxyethoxy]ethoxy]ethoxy]ethoxy]ethyl]-N-[5-[4-[6-(dimethylamino)-1,3-benzothiazol-2-yl]phenyl]pyridin-2-yl]carbamate (252 mg, 0.32 mmol) in THF (5 mL) was added TBAF (1 M in THF, 1.94 mL, 1.94 mmol) dropwisely and stirred at room temperature for 19 h. The reaction mixture was concentrated to dryness and the residue was taken up in EtOAc (50 mL). The mixture was washed with water (50 mL) and brine (50 mL), dried over Na$_2$SO$_4$. And concentrated to dryness to give tert-butyl N-[5-[4-[6-(dimethylamino)-1,3-benzothiazol-2-yl]phenyl]pyridin-2-yl]-N-[2-[2-[2-[2-(2-hydroxyethyloxy)ethoxy]ethoxy]ethoxy]ethyl]carbamate (214 mg, 0.32 mmol, 99% yield) as a yellow oil.

Compound 161530:

A mixture of tert-butyl N-[5-[4-[6-(dimethylamino)-1,3-benzothiazol-2-yl]phenyl]pyridin-2-yl]-N-[2-[2-[2-[2-(2-hydroxyethyloxy)ethoxy]ethoxy]ethoxy]ethyl]carbamate (214 mg, 0.32 mmol) and tert-butyl 2-bromanylethanoate (0.14 mL, 0.96 mmol) in THF (3 mL) was added NaH (19 mg, 0.80 mmol) at 0° C. and stirred at room temperature for 42 h. The reaction was quenched by adding water. The mixture was diluted with DCM (50 mL), washed with water (50 mL) and brine (50 mL), dried over Na$_2$SO$_4$, concentrated to dryness and purified by column chromatography (EtOAc:Hex=1:1, Rf=0.35) to afford tert-butyl 2-[2-[2-[2-[2-[2-[[5-[4-[6-(dimethylamino)-1,3-benzothiazol-2-yl]phenyl]pyridin-2-yl]-[(2-m ethylpropan-2-yl)oxycarbonyl]amino]ethoxy]ethoxy]ethoxy]ethoxy]ethanoate (130 mg, 0.17 mmol, 52% yield) as a yellow oil.

Compound 161586:

To a solution of tert-butyl 2-[2-[2-[2-[2-[2-[[5-[4-[6-(dimethylamino)-1,3-benzothiazol-2-yl]phenyl]pyridin-2-yl]-[(2-m ethylpropan-2-yl)oxycarbonyl]amino]ethoxy]ethoxy]ethoxy]ethoxy]ethanoate (130 mg, 0.17 mmol) in DCM (2 mL) was added TFA (0.38 mL, 4.99 mmol) and stirred at room temperature for 22 h. The mixture was concentrated to dryness to afford 2-[2-[2-[2-[2-[2-[[5-[4-[6-(dimethylamino)-1,3-benzothiazol-2-yl]phenyl]pyridin-2-yl]amino]ethoxy]ethoxy]ethoxy]ethoxy]ethoxy]ethanoic acid TFA salt (179 mg, 0.29 mmol, >99% yield) as an orange oil.

Compound 161598:

A mixture of (2S,4R)-1-[(2S)-2-azanyl-3,3-dimethyl-butanoyl]-N-[[4-(4-methyl-1,3-thiazol-5-yl)phenyl]m ethyl]-4-oxidanyl-pyrrolidine-2-carboxamide (79 mg, 0.18 mmol), 2-[2-[2-[2-[2-[2-[[5-[4-[6-(dimethylamino)-1,3-benzothiazol-2-yl]phenyl]pyridin-2-yl]amino]ethoxy]ethoxy]ethoxy]ethoxy]ethoxy]ethanoic acid (104 mg, 0.17 mmol), DIPEA (0.04 mL, 0.25 mmol) and HATU (127 mg, 0.33 mmol) in anhydrous DMF (3 mL) was stirred at room temperature for 18 h. The mixture was taken up in DCM, washed with water and brine, dried over anhydrous Na$_2$SO$_4$, concentrated and purified by column chromatography (MeOH:DCM=3:100, Rf=0.32) to give rac-(2R,4S)—N-[[4-(4-methyl-1,3-thiazol-5-yl)phenyl]methyl]-4-oxidanyl-1-[rac-(2R)-2-[2-[2-[2-[2-[2-[[5-[4-[6-(dimethylamino)-1,3-benzothiazol-2-yl]phenyl]pyridin-2-yl]amino]eth oxy]ethoxy]ethoxy]ethoxy]ethanoylamino]-3,3-dimethyl-butanoyl]pyrrolidine-2-carb oxamide (16 mg, 0.01 mmol, 8% yield) as a yellow solid.

Example 24: In Vitro Fluorescence-Based Recombinant Tau Binding Assay (A) Expression and Purification of Human Tau:

1 mM IPTG (Sangon Biotech, Cat. No A100487) was used to induce production of tau by bacteria (BL21, Invitrogen, Cat. No C600003) transformed with a full-length 2N4R tau expression plasmid. After 3 hours, cell pellet was resuspended in lysis buffer (100 mM PIPES, 1 mM EGTA, 1 mM MgSO4, pH 6.8) and lysed by sonication followed by centrifugation (15,000 rpm, 15 min, 4° C.). The supernatant was then placed in a boiling water bath for 20 min, followed by centrifugation (15,000 rpm, 15 min, 4° C.). Supernatant was loaded onto a Q-Sepharose® Fast Flow column (GE healthcare, Cat. No 17-0510-01), the flow-through fraction was loaded onto an SP-Sepharose® Fast Flow column (GE healthcare, Cat. No 17-0729-01), and tau protein was eluted with elution buffer (100 mM PIPES, 1 M NaCl, 1 mM EGTA, 1 mM MgSO$_4$, 0.2 M NaCl, pH 6.8). Collected fractions of tau-containing eluates were pooled, concentrated and dialyzed against HEPES buffer (25 mM HEPES, 0.1 mM EDTA, 0.5 mM DTT, 100 mM NaCl, pH 7.2) and stored at −80° C. in small aliquots until use. Protein concentration was determined by UV absorption.

(B) Preparation of Heparin-Induced Aggregated Tau (aTau):

2 μM of tau prepared in 30 mM Tris-HCl, pH 7.5 buffer was incubated in tube with 15 μM heparin (Sigma, Cat. No H3149) at 37° C. for 24 hours.

(C) Compound Fluorescent Spectra Scanning Assay:

Compounds were dissolved in 100% DMSO, and 40 nM aTau was incubated with 10 μM of each compound in 2% DMSO in 96 well plate (Corning, Cat. No 3573) at 37° C. for 1 hour. Emission and excitation of the compound was scanned by microplate spectrometer (EnSpire 2300, PerkinElmer).

(D) In Vitro Fluorometric aTau Binding Assays:

2 μM aTau was diluted to 0.04 μM with 30 mM Tris-HCl (pH 6.8), and then incubated with serially diluted compound (three-fold serial dilutions, from 10 to 0.00017 μM) in a 96-well plate (Corning, Cat. No 3573) at 37° C. for 1 hour. Fluorescence intensity (excitation/emission=370/500 nm) of APN-0729 was read by microplate spectrometer (EnSpire 2300, PerkinElmer). Compound Kd values were calculated using the following equation: $Y=B_{max}*X/(Kd+X)$, where X is the concentration of compound; Y is the fluorescence signal of (compound+aTau)−(compound+DMSO); and $B_{max}$ is the maximum signal. The results are shown in Table 2 below.

TABLE 2

Competition Assay with PBB5

| Compound | Ex/Em (nm) | Kd (μ M) | PBB5 (μ M) | Bmax (%) |
|---|---|---|---|---|
| 159985 | 375/485 | 0.10 | 0.32 | 71 |
| 160219 | 375/480 | 0.11 | 0.15 | 69 |
| 160273 | 375/495 | 0.47 | 0.27 | 59 |
| 160313 | 370/500 | 0.08 | 0.22 | 64 |
| 160275 | 375/505 | 0.23 | 1.29 | 96 |
| 160703 | 390/500 | 0.10 | 1.00 | =100 |
| 160383 | 375/525 | 0.55 | 0.27 | 80 |
| 160624 | 380/500 | 0.12 | 0.55 | =100 |
| 160744 | 355/405 | 0.15 | 5.96 | 113 |
| 160570 | 350/520 | 0.36 | 2.26 | =100 |
| 160371 | 300/400 | 0.29 | >10 | =100.0 |

(E) PBB5 Competition Assay:

2 μM of aTau was diluted to 0.12 μM by with mM Tris-HCl (pH 6.8) and then incubated with 0.1 μM 2-(4-(2-(methylamino)pyridine-5-yl)-1,3-butadiene-1-yl)benzothiazole-6-ol (PBB5) and serially diluted compound (three-fold serial dilution, from 10 to 0.00017 μM) in a 96-well plate (Corning, Cat. No 3573) at 37° C. for 1 hour. Fluorescence intensity (excitation/emission=530/690 nm) of PBB5 was read by microplate spectrometer (EnSpire 2300, PerkinElmer). Percentage of competition was calculated using the following equation: (Max−well of compound alone)/(Max−Min)*100%, where Max=(Tau+PBB5) signals−(buffer+PBB5) signals; and Min=(buffer+PBB5) signals−(buffer+PBB5) signals.

The IC$_{50}$ value of each compound was calculated with GraphPad Prism software using the "4 Parameter Logistic Model or Sigmoidal Dose-Response Model":

$Y=\text{Bottom}+(\text{Top}-\text{Bottom})/(1+(\text{IC}50/X)^{\text{HillSlope}})$ To examine tau binding ability of the compounds, we performed fluorescence-based in vitro tau binding assay. All compounds retained tau binding ability as well as competitive nature with PBB5.

Example 25: Cell-Based Tau Binding Assay (A) Mouse brain lysate preparation as the source of tau seeds: Three months old WT and rTg4510 mouse were sacrificed by cervical dislocation. The brains were quickly removed from the skulls, weighed, the cerebellums discarded, and the remaining brains dissected along the midline on ice. Half of each cerebrum was placed into a homogenization tube (MP Biomedicals) and kept on ice. Ice-cold homogenization buffer was added, 5-fold volumes to brain weight. The homogenate was vortexed by FastPrep-24™ 5G (MP biomedicals) for 40 second in 6 m/s rate, and then centrifuged (Eppendorf) at 13,000×g for 15 min at 4° C. The supernatant of brain lysate was transferred into a new microfuge tube and stored at −80° C.

Because the homogenization buffer caused minor toxicity to HEK cells, the brain lysate underwent a buffer exchange from Tris-based buffer to PBS. The brain lysate was thawed on ice. Sterile PBS was added into a 2-ml centrifugal filter tube (10K cut-off, Amicon), and then centrifuged at 4500×g for 2 min at 4° C. to rinse the tube. The thawed lysate was added into the filter tube, and filled with sterile 1×PBS to 2 mL. The tube was centrifuged at 4500×g for 60 min at 4° C. The PBS wash step was repeated. After the centrifugation step, 300 µL of supernatant in the bottom of centrifuged tube was collected and kept on ice. The rest of the supernatant was repeated to fill the buffer and centrifuged for 20 min again. The second collected supernatant was combined with the previous one. The protein concentration was measured by Bradford assay (Bio-Red). The mouse brain lysate exchanged buffer was diluted with sterile 1×PBS to 3 mg/mL, aliquoted to 90 and 180 µL in microfuge tubes and stored at −80° C.

(B) Cell Culture:

Tau RD(LM)-eGFP HEK293 cells were cultured in two kinds of culture media. For cell maintenance, the cells were cultured in DMEM/F-12 (Gibco) supplemented with 10% FBS (Gibco), 1% PS (Gibco) and 6 µg/mL puromycin (Gibco) and plated by 1×10$^6$ cells/well in 6 well plate (Greiner). Cells were sub-cultured twice per week. For tau binding tests, the cells were cultured in DMEM/F-12 supplemented with 1.25% FBS, 1% PS and 6 µg/mL puromycin (binding medium) and plated by 1.5×10$^4$ cells/well in a 96 well plate pre-coated with poly-D-lysine (BD Biosciences).

(C) Compound Treatment: Frozen mouse brain lysate was thawed on ice and diluted to 1 µg/µL with 1×PBS. Diluted brain lysate or 1×PBS were added into each well of a 96-well plate containing cells cultured for 24 hrs. After 24 hours of incubation, the culture medium was replaced with fresh binding medium. On the third day after tau seeding, 10 mM of the compound stock solution were serially diluted two folds down from 1000, 500, 250, 125, 62.5, 31.25, 15.63, 7.8 nM in fresh binding medium and the DMSO (Sigma) concentration was maintained at 0.1% for all wells. The media in the 96-well plate were then replaced with the medium containing various concentrations of the compound. The plate was placed back to the incubator for 2 hours, and medium was replaced with binding medium containing 8% NucRed 647 (Thermo Fisher) to stain the nucleus for 30 minutes. The cells were fixed with 4% PFA (Electron Microscopy Sciences) for 20 minutes at RT then changed to 1×PBS for image acquisition.

(D) Image acquisition and analysis: All images were taken by ImageXpress Micro Confocal (Molecular devices) using a 20× objective lens, and excitation/emission settings were defined by the DAPI, FITC20 & Cy5 channels for APN-0729, Tau-eGFP & Nucleus, respectively. All images were processed for tau binding analysis using a customized module of MetaXpress software (Molecular devices). The module is capable of measuring: (1) total cell numbers (=nuclei numbers); (2) tau aggregate numbers; (3) tau positive cell numbers; (4) tau aggregate average area; (5) tau and compound double-positive aggregate numbers; (6) tau and compound double-positive cell numbers; (7) compound average intensity in tau aggregates; (8) tau and compound double-positive area in tau aggregates.

Example 26: Tau Degradation Assay (A). Cell-based model of Tau inclusion formation: Six month old rTg4510 mouse brain lysates were used as the source of tau seeds, prepared as described in Example 26 above. P301L-Tau-FL-GFP HEK293 cells represent HEK293 cells express full-length human tau T40 (2N4R) carrying the P301L mutation with a GFP tag (P301L-Tau-FL-GFP). 1×10$^6$ of P301L-Tau-FL-GFP HEK293 cells were cultured on a 6-well plate in culture medium containing DMEM/F-12 (Gibco) supplemented with 10% fetal bovine serum (FBS) (Gibco), 1% Penicillin-Streptomycin (Gibco) and 0.5 mg/ml geneticin (Thermo Fisher Scientific) for 24 hours to reach 70-90% confluency, indicating the cells were ready for transfection. 50 µg of 6-month-old rTg4510 mouse brain lysate was diluted in 400 µL of serum free medium and mixed with 16 µL of lipofectamine 3000 reagent (Thermo Fisher Scientific) diluted in 400 µl of serum free medium. A solution mixture of rTg4510 brain lysate and lipofectamine 3000 was incubated at room temperature for 25 mins. The culture media were removed, and then a solution mixture of rTg4510 lysate and lipofectamine 3000 was added to the cells for transfection. The solution mixture was incubated at room temperature for five hours, followed by medium change to 10% fetal bovine serum (FBS). After two-day incubation, Tau aggregates (Tau spots) were induced and images were acquired by ImageXpress Micro Confocal high-content imaging system (Molecular Devices) as described in Example 52 above. Analysis was performed by two customized modules in MetaXpress software (Molecular Devices) for aggregated tau analysis. Output included cell numbers, numbers of tau spots, average intensity of tau spots, and average size of tau spots.

(B). Compound treatment: 100 µL of 3×10$^4$ cells comprising Tau aggregates, prepared as described above in step (A), were plated on a 96-well plate coated with poly-D-lysine (BD Biosciences) and cultured for 24 hours. Compounds to be tested were dissolved in culture medium containing 0.1% DMSO. Each of test compounds in the concentration of 1, 0.2 and 0.04 µM was added to the cells comprising Tau aggregates and incubated at 37° C. for 24 hours. After that, culture medium was removed, cells were washed with PBS solution and then lysed using 30 µL of lysis buffer (PBS containing 0.3% Triton X-100 and 400 mM NaCl) for one hour at 4° C., and then cell lysate was diluted by 170 µl of PBS containing 400 mM NaCl. Cell lysate was filtrated by a 0.45 µM filtration plate (Pall) and applied for Tau aggregation assay.

(C). Control cell lysate: control cell lysate was collected from non-seeded cells.

(D). ELISA-based Tau aggregation assay: APNmAb005 ELISA kit for Tau aggregation assay was designed and developed to detect abnormal tau aggregates in buffered solution or cell lysate by using anti-Tau APNmab005 as capture and detection antibody. This antibody is a highly specific antibody bound to human tau aggregates accumulated in mammalian cells. APNmAb005 is recited in PCT Patent Application No. PCT/IB2020/057415, filed Aug. 5, 2020, which is incorporated herein by reference.

0.15 µg of APNmAb005 in 100 mM sodium carbonate buffer (pH 9.6) was coated on a high-binding polystyrene 96-well microplate (Greiner Bio-One) at 4° C. overnight. The microplate was washed with PBS followed by treatment with Intercept (PBS) blocking buffer (LI-COR) at room temperature for 2 hours. After that, the microplate was washed with PBS, and then the cell lysate with compound treatment, prepared as described above in step (C), was added into each well of the microplate and incubated at room temperature for 2 hours. The microplate was washed with PBS and then incubated with HRP-conjugated secondary antibody APNmAb005 at room temperature for 3 hours. HRP-conjugated secondary antibody APNmAb005 was prepared using HRP conjugation kit (Abcam, ab102890). The microplate was then washed with PBS and incubated with 100 µL of horseradish peroxidase (HRP) substrate at room temperature. After 20-min incubation, reactions were terminated by addition of 100 µL of stop solution (Cell Signaling Technology). Optical Density (O.D.) at 450 nm was measured using EnVision microplate reader (PerkinElmer).

The FIGURE shows the degradation of Tau aggregates measured by APNmAb005 ELISA assay. Upon treatment of 1 µM compound 162842, Optical Density (O.D.) 450 value decreases 20% compared to vehicle, reflecting the reduction of Tau aggregates.

Some embodiments of compounds were evaluated in Tau degradation assays. Results are summarized in Table 3.

TABLE 3

| Compound | Activity |
| --- | --- |
| 170350 | + |
| 160219 | − |
| 160313 | − |
| 160744 | + |
| 171177 | − |
| 161215 | + |
| 161409 | + |
| 160273 | − |
| 159985 | − |
| 162640 | + |
| 177031 | − |
| 162842 | ++ |
| 177038 | − |
| 174251 | − |
| 162903 | + |
| 160939 | − |
| 163123 | + |
| 160383 | − |
| 163365 | + |

Notes:
"++" indicates >20% reduction of tau aggregates upon treatment with 1 µM of compound
"+" indicates 10% to 20% reduction of tau aggregates upon treatment with 1 µM of compound
"−" indicates <10% reduction of tau aggregates upon treatment with 1 µM of compound Example 27: In Vivo Pharmacokinetic Study To determine whether the compounds of the present disclosure are capable of crossing the blood brain barrier (BBB), example compound 160313 was administered to mice in a pharmacokinetic study (1 mg/kg, intravenous) of plasma and brain tissue.

Animal Husbandry: Mice were housed at animal room environment with ventilation 15 times/hour, lighting 12 hours/day, temperature 20° C. to 24° C. and humidity 40% to 70%. The study rooms were disinfected and cleaned prior to the start of the study and the operation area was cleaned after each dosing or sampling during the study conduct. All animals had free access to food and water during the study. The animals had access to Certified Rodent Diet and water ad libitum. The nutritional composition and levels of contaminants of the diet and impurities and contaminants of the water were monitored by third organization. The health status of the animals was evaluated in accordance with accepted animal husbandry procedures and deemed suitable for experimental use.

Sample Collection & Processing: Approximately 110 µL of whole blood were collected from all animals via facial or cardiac puncture under anesthesia with Isoflurane into test tubes containing potassium ethylenediaminetetraacetate ($K_2$EDTA) at 0.25, 0.5, 1, 2, 4, 8 and 24 hr post dose. Brian samples were collected at 0.25, 0.5, 1, 2, 4, 8 and 24 hours post dose. A perfusion with pre-cold saline will be conducted via cardiac puncture before brain collection. Blood samples were centrifuged at 2000 g at 4° C. for 5 minutes to obtain plasma samples by transferring the supernatants into new tubes. All plasma and brain samples were stored at approximately −70° C. until analysis.

Bioanalytical Method Development: The concentrations of compound in plasma and brain samples were determined using a liquid chromatography with tandem mass spectrometry (LC-MS/MS) based method.

Results: The PK parameters were summarized in Table 4. Compound 160313 was able to penetrate BBB in short period of time. The brain/plasma ratio is about 0.31.

TABLE 4

| In vivo pharmacokinetic profile of Compound 160313 | | |
| --- | --- | --- |
| | Plasma | Brain |
| $AUC_{last}$ (hr * ng/mL) | 379 | 117 |
| $T_{1/2}$ (h) | 0.46 | 1.03 |
| $C_{max}$ (ng/mL) | — | 111 |
| $T_{max}$ (h) | — | 0.25 |

What is claimed is:

1. A compound of any one of Formula I to Formula VI,

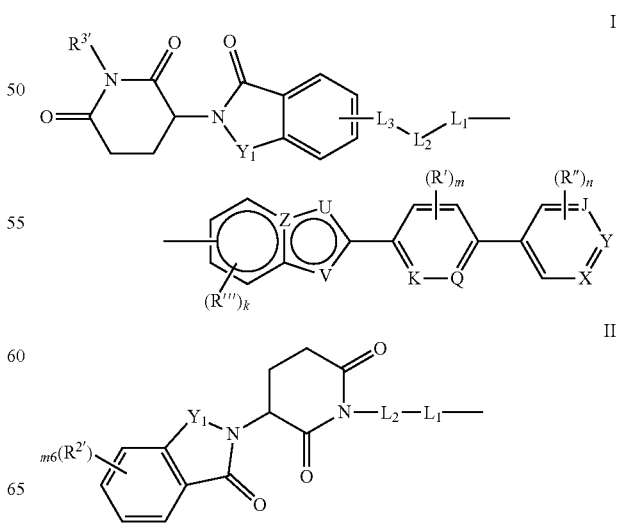

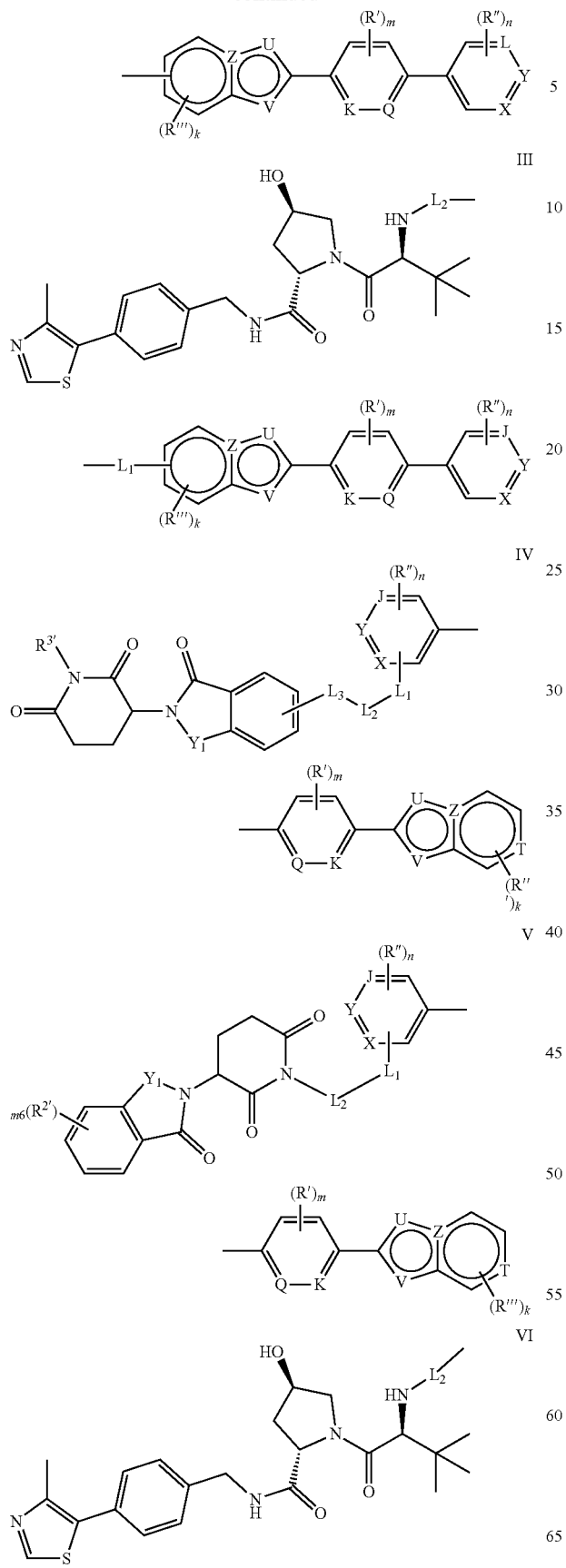
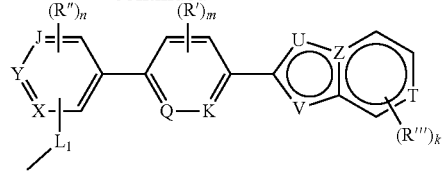

or, a pharmaceutical acceptable salt, an enantiomer, a tautomer, a racemate thereof, wherein, $L_1$ is a bond, —NR—, —O—, or —S—, wherein R is hydrogen, optionally substituted acyl, optionally substituted alkyl or a nitrogen protecting group;

$L_2$ is a substituted or unsubstituted $C_{1-50}$ hydrocarbon chain, wherein one or more chain atoms of the $C_{1-50}$ hydrocarbon chain are independently replaced with —C(=O)—, —O—, —NR$^{a1}$—, —S— or a cyclic moiety, wherein Rai is independently hydrogen, substituted or unsubstituted $C_{1-6}$ alkyl or a nitrogen protecting group;

Z is C or N; U is O, S or CH;

K is CH or N; Q is CH or N; where K and Q are not N at the same time;

each occurrence of R''' is independently selected from the group consisting of H, OH, NH$_2$, $C_{1-6}$ alkyl, $C_{1-6}$ alkylamino, $C_{1-6}$ alkoxy and halogen; k is 0, 1, 2 or 3;

each occurrence of R' is independently selected from the group consisting of H, halogen, OH, $C_{1-6}$ alkyl, $C_{1-6}$ haloalkyl and $C_{1-6}$ alkoxy; m is 0, 1, 2, 3 or 4;

each occurrence of R'' is independently selected from the group consisting of H, halo, OH, NH$_2$, $C_{1-6}$ alkyl, $C_{1-6}$ alkoxy, $C_{1-6}$ haloalkyl, $C_{1-6}$ alkylamino, $C_{3-6}$ cycloalkylamino, $C_{3-6}$ cycloalkyl and $C_{3-6}$ heterocycloalkyl; n is 0, 1 or 2;

J is CR$^6$ or N; X is CR$^6$ or N; Y is CR$^6$ or N; where at least one of J, X and Y is N, but J and Y are not N at the same time, X and Y are not N at the same time;

R$^6$ is independently selected from the group consisting of H, NH$_2$, $C_{1-6}$ alkyl and $C_{1-6}$ alkoxy, wherein NH$_2$, $C_{1-6}$ alkyl or $C_{1-6}$ alkoxy is optionally substituted by 1 to 3 of $C_{1-3}$ alkyl, $C_{3-6}$ cycloalkyl and/or halo;

in Formula I, $L_3$ is a bond, —NR—, —O—, or —S—, wherein R is hydrogen, optionally substituted acyl, optionally substituted alkyl or a nitrogen protecting group; R$^{3'}$ is H or $C_{1-6}$ alkyl; $Y_1$ is CH$_2$ or

V is N, where Z and U are not heteroatoms at the same time; in Formula II, each occurrence of R$^{2'}$ is independently selected from the group consisting of H, OH, $C_{1-6}$ alkyl, $C_{1-6}$ alkoxy, $C_{1-6}$ alkylamino and NH$_2$; m6 is 0, 1, 2, 3 or 4; $Y_1$ is CH$_2$ or

V is N, where Z and U are not heteroatoms at the same time;

in Formula III, V is N, where Z and U are not heteroatoms at the same time;

in Formula IV, $L_3$ is a bond, —NR—, —O—, or —S—, wherein R is hydrogen, optionally substituted acyl, optionally substituted alkyl or a nitrogen protecting group; $R^{3'}$ is H or $C_{1-6}$ alkyl; $Y_1$ is $CH_2$ or

V is N or NH; T is CH or N; where up to two of U, Z, V and T contain heteroatoms; in Formula V, each occurrence of $R^{2'}$ is independently selected from the group consisting of H, OH, $C_{1-6}$ alkyl, $C_{1-6}$ alkoxy, $C_{1-6}$ alkylamino and $NH_2$; m6 is 0, 1, 2, 3 or 4; $Y_1$ is $CH_2$ or

V is N or NH; T is CH or N; where up to two of U, Z, V and T contain heteroatoms; in Formula VI, V is N; T is CH or N; where up to two of U, Z, V and T contain heteroatoms.

2. The compound of claim 1, wherein $L_2$ is an optionally substituted $C_{1-45}$ hydrocarbon chain.

3. The compound of claim 1, wherein $L_2$ is selected from the group consisting of substituted or unsubstituted carbocyclylene, substituted or unsubstituted heterocyclylene, substituted or unsubstituted arylene, substituted or unsubstituted heteroarylene, or substituted or unsubstituted heteroalkylene, and combinations thereof, wherein one or more chain atoms of the substituted groups are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group.

4. The compound of claim 1, wherein $L_2$ comprises at least one instance selected from the group consisting of substituted or unsubstituted $C_{1-6}$ alkylene, substituted or unsubstituted $C_{2-6}$ alkenylene, substituted or unsubstituted $C_{2-6}$ alkynylene, substituted or unsubstituted hetero$C_{1-6}$alkylene, substituted or unsubstituted hetero$C_{2-6}$alkenylene, substituted or unsubstituted hetero$C_{2-6}$alkynylene, substituted or unsubstituted $C_{3-6}$carbocyclylene, substituted or unsubstituted 3-6 membered heterocyclylene, substituted or unsubstituted phenylene, and substituted or unsubstituted 5- to 6-membered heteroarylene, wherein one or more chain atoms of the substituted groups are independently replaced with —C(=O)—, —O—, —$NR^{a1}$—, —S— or a cyclic moiety, wherein $R^{a1}$ is independently hydrogen, substituted or unsubstituted $C_{1-6}$ alkyl or a nitrogen protecting group.

5. The compound of claim 1, wherein $L_2$ comprises at least one instance selected from the group consisting of substituted or unsubstituted methylene, ethylene, n-propylene, n-butylene, n-pentylene, n-hexylene, -$(CH_2)_2$—$O(CH_2)_2$—, —$OCH_2$—, —$O(CH_2)_2$—, —$O(CH_2)_3$—, —$O(CH_2)_4$—, —$O(CH_2)_5$—, —$O(CH_2)_6$—, and —NH—C(=O)—.

6. The compound of claim 3, wherein at least one chain atom of the hydrocarbon chain of $L_2$ is independently replaced with a 6-membered heterocyclyl group with 1-3 ring heteroatoms selected from the group consisting of nitrogen and oxygen.

7. The compound of claim 1 wherein $L_2$ is

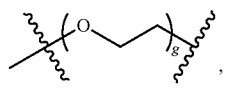

wherein g is 1, 2, 3, 4, 5, or 6.

8. The compound of claim 1, wherein $L_2$ includes the moiety —O—,

—NHC(=O)— or —NH—.

9. The compound of claim 1, wherein $L_2$ is selected from the group consisting of

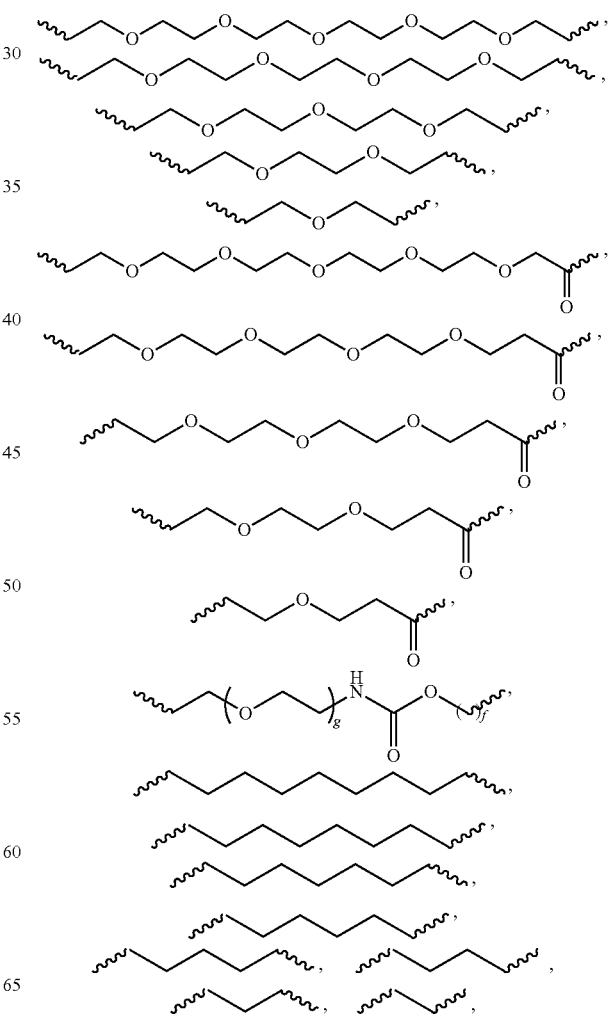

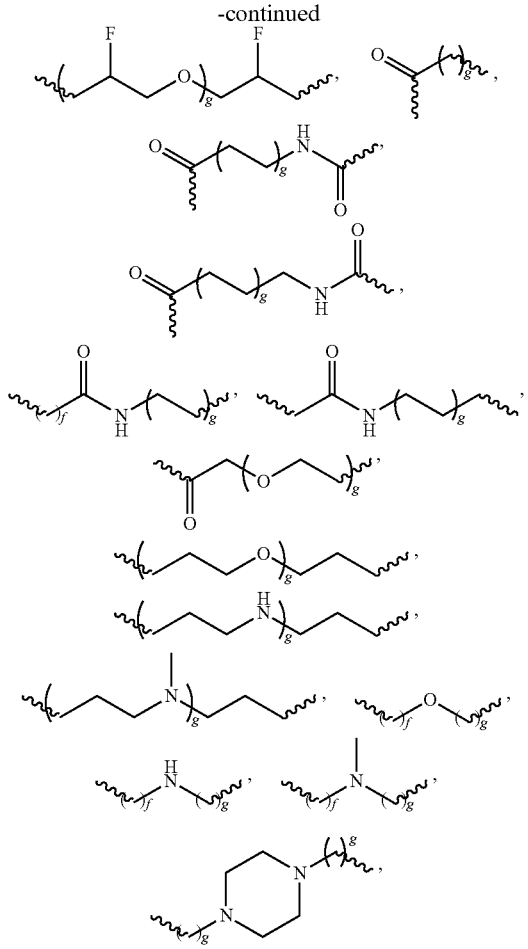
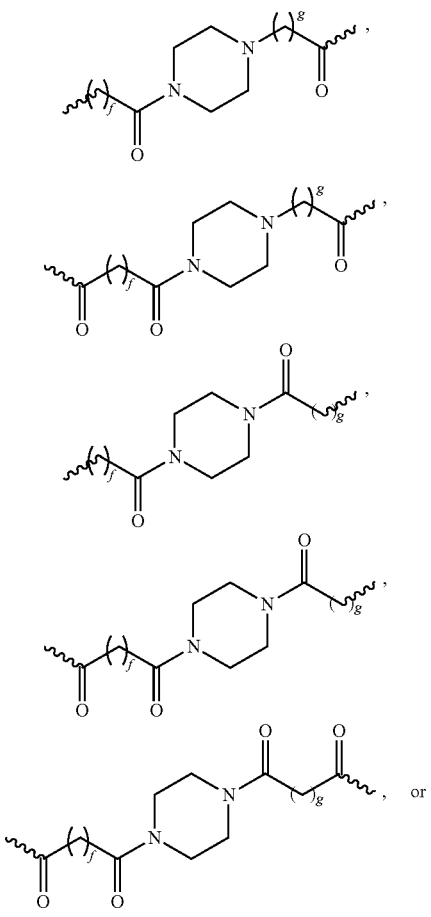
10. The compound of claim 1, wherein the compound of Formula I is of Formula I-1;
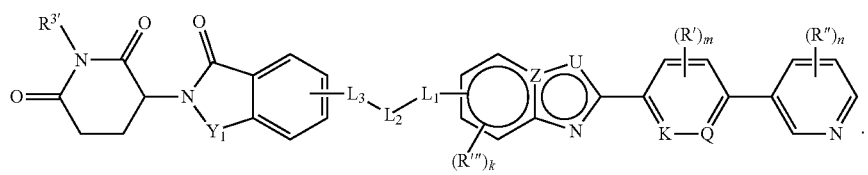
I-1

11. The compound of claim 1, wherein the compound of Formula II is of Formula II-1;
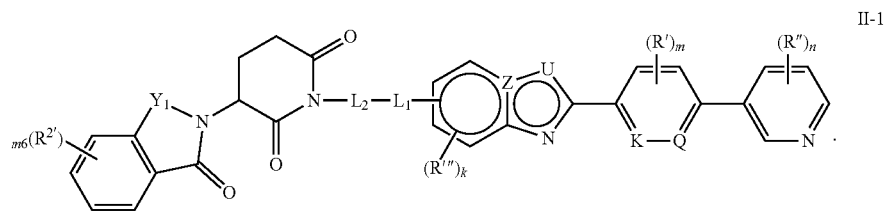
II-1
12. The compound of claim 1, wherein the compound of Formula III is of Formula III-1;
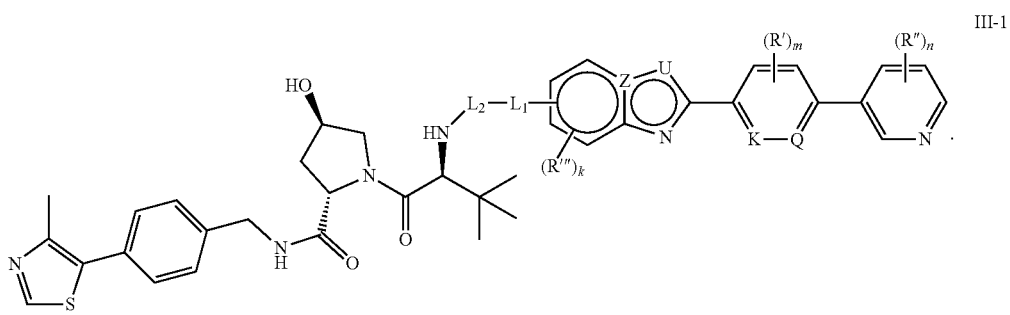
III-1
13. The compound of claim 1, wherein the compound of Formula IV is of Formula IV-1;
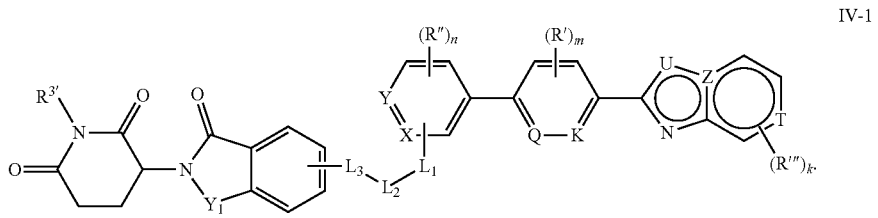
IV-1
14. The compound of claim 1, wherein the compound of Formula V is of Formula V-1;
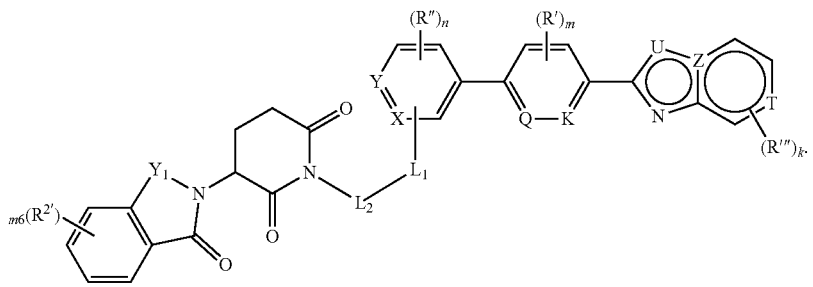
V-1

15. The compound of claim wherein the compound of Formula VI is of Formula VI-1;
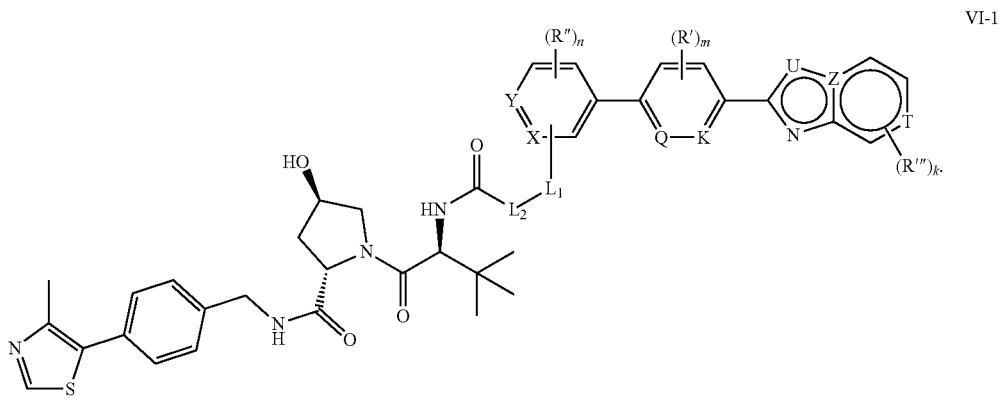
16. The compound of claim 13, wherein the compound is of Formula 2, 7, 9, 11, 12 or 14;
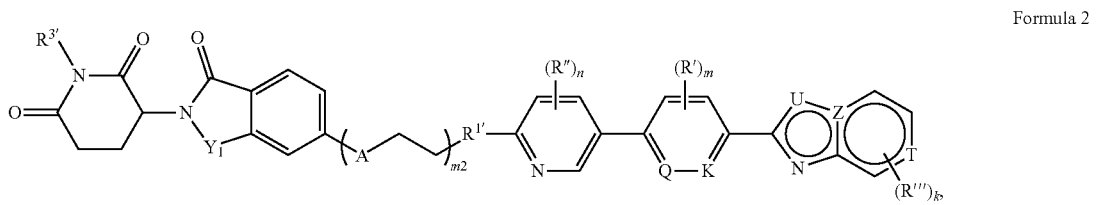
Formula 2
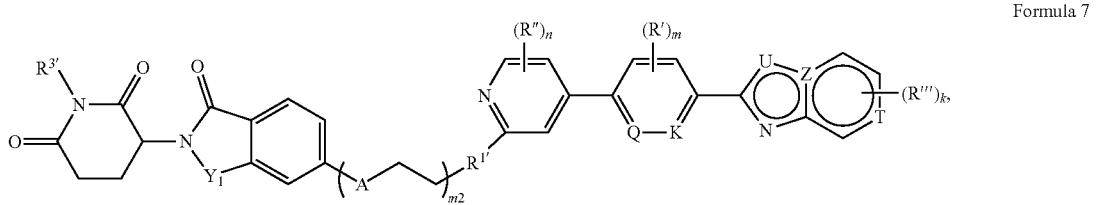
Formula 7
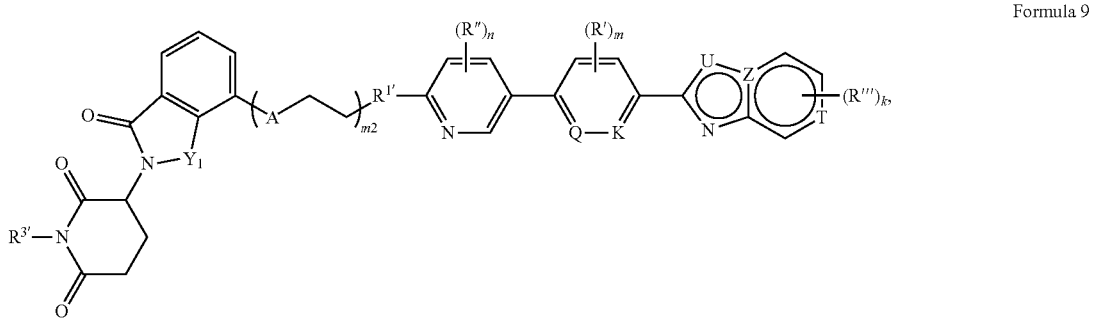
Formula 9
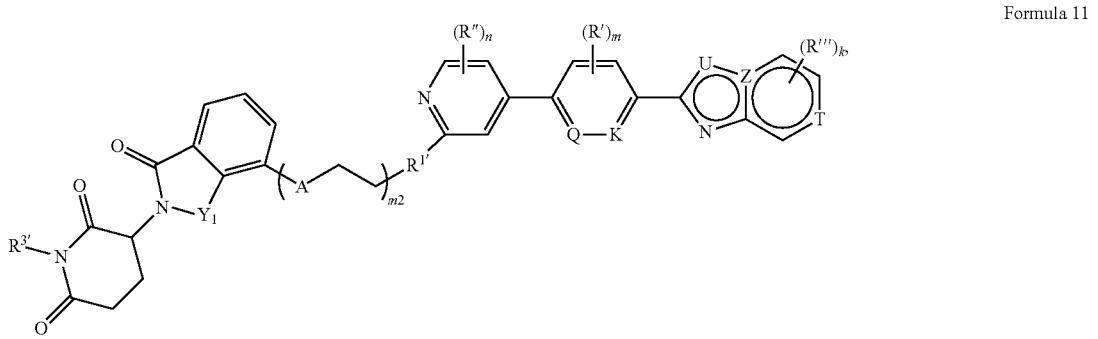
Formula 11

Formula 12

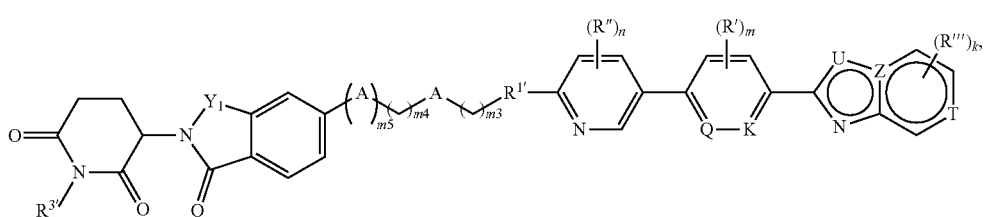

Formula 14

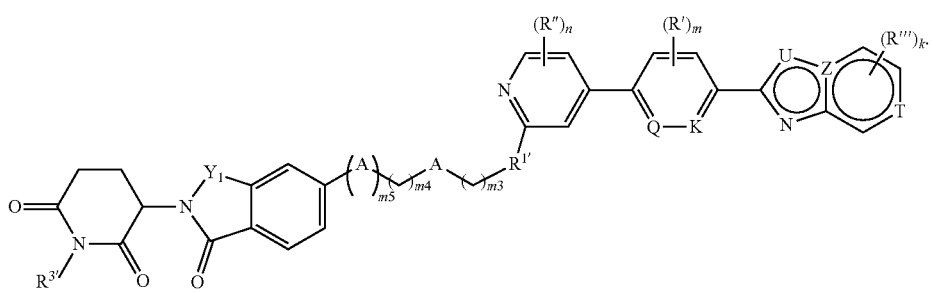

17. The compound of claim 16, wherein the compound is of Formula 2, and wherein $R^{3'}$ is H or $C_{1-3}$ alkyl; and/or, A is O, NH,

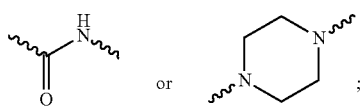

and/or, m2 is 2, 3, 4, 5 or 6; and/or, R''' is O, NH,

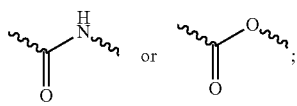

and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; and/or, R''' is H, OH, $NH_2$, $C_{1-3}$ alkyl, $C_{1-3}$ alkylamino, $C_{1-3}$ alkoxy or halogen.

18. The compound of claim 16, wherein the compound is of Formula 7, and wherein $R^{3'}$ is H or $C_{1-3}$ alkyl; and/or, A is O, NH,

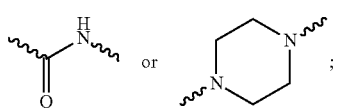

and/or, m2 is 2, 3, 4, 5 or 6; and/or, R''' is O, NH,

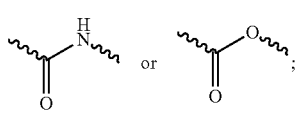

and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3.

19. The compound of claim 16, wherein the compound is of Formula 9, and wherein $R^{3'}$ is H or $C_{1-3}$ alkyl; and/or, A is O, NH,

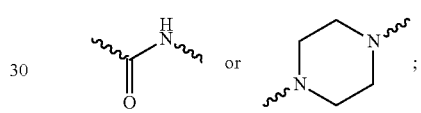

and/or, m2 is 2, 3, 4, 5 or 6; and/or, R''' is O, NH,

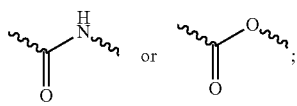

and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; and/or, R''' is H, OH, $NH_2$, $C_{1-3}$ alkyl, $C_{1-3}$ alkylamino, $C_{1-3}$ alkoxy or halogen.

20. The compound of claim 16, wherein the compound is of Formula 11, and wherein $R^{3'}$ is H or $C_{1-3}$ alkyl; and/or, A is O, NH,

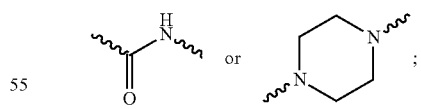

and/or, m2 is 2, 3, 4, 5 or 6; and/or, R''' is O, NH,

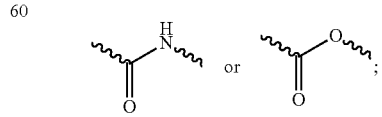

and/or, R'' is H, halo, OH, $NH_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; and/or, m is 0, 1, 2 or 3; and/or, R''' is H, OH, NH$_2$, $C_{1-3}$ alkyl, $C_{1-3}$ alkylamino, $C_{1-3}$ alkoxy or halogen.

21. The compound of claim 16, wherein the compound is of Formula 12, and wherein $R^{3'}$ is H or $C_{1-3}$ alkyl; A is O, NH,

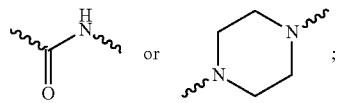

m3 is 1, 2, 3, 4, 5 or 6; m4 is 0 or 1, 2 or 3; m5 is 0 or 1, 2 or 3; $R^{1'}$ is O, NH,

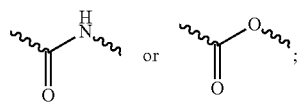

R" is H, halo, OH, NH$_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; R' is H, halogen, OH, $C_{1-3}$ alkyl, $C_{1-3}$ haloalkyl or $C_{1-3}$ alkoxy; m is 0, 1, 2 or 3; R''' is H, OH, NH$_2$, $C_{1-3}$ alkyl, $C_{1-3}$ alkylamino, $C_{1-3}$ alkoxy or halogen.

22. The compound of claim 16, wherein the compound is of Formula 14, and wherein $R^{3'}$ is H or $C_{1-3}$ alkyl; and/or, A is O, NH,

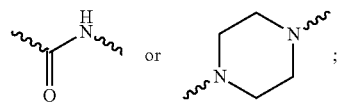

and/or, m3 is 1, 2, 3, 4, 5 or 6; and/or, m4 is 0, 1, 2, 3 or 4; and/or, m5 is 0 or 1, 2 or 3; and/or, R''' is O, NH,

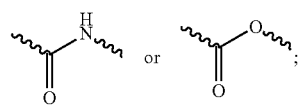

and/or, R" is H, halo, OH, NH$_2$, $C_{1-3}$ alkyl, $C_{1-3}$ alkoxy, $C_{1-3}$ haloalkyl, $C_{1-3}$ alkylamino, $C_{3-5}$ cycloalkyl, $C_{3-5}$ cycloalkylamino or $C_{3-5}$ heterocycloalkyl; and/or, R' is H, halogen, OH, $C_{1-3}$ alkyl, $C_{1-3}$ haloalkyl or $C_{1-3}$ alkoxy; m is 0, 1, 2 or 3; and/or, R''' is H, OH, NH$_2$, $C_{1-3}$ alkyl, $C_{1-3}$ alkylamino, $C_{1-3}$ alkoxy or halogen.

23. The compound of claim 1, wherein the compound is of Formula 4;

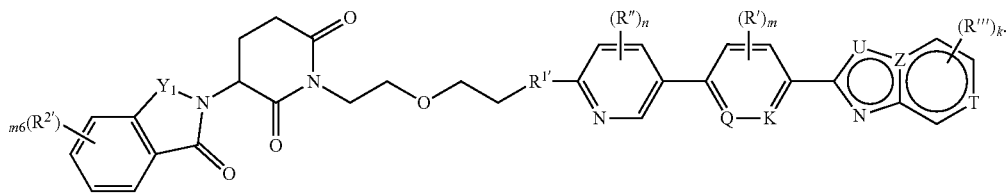

Formula 4

24. The compound of claim 23, wherein $R^{2'}$ is H, OH, $C_{1-3}$ alkyl, $C_{1-3}$ alkoxy, $C_{1-3}$ alkylamino or NH$_2$; and/or, m6 is 0, 1, 2 or 3; and/or, R''' is O, NH,

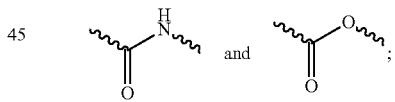

and/or, R' is H, halogen, OH, $C_{1-3}$ alkyl, $C_{1-3}$ haloalkyl or $C_{1-3}$ alkoxy; R" is H, halo, OH, NH$_2$, $C_{1-3}$ alkoxy, $C_{3-5}$ cycloalkyl, $C_{3-5}$ cycloalkylamino or $C_{1-3}$ alkylamino; and/or, R''' is H, OH, NH$_2$, $C_{1-3}$ alkyl, $C_{1-3}$ alkylamino, $C_{1-3}$ alkoxy or halogen.

25. The compound of claim 23, wherein the compound is of Formula 4-1;

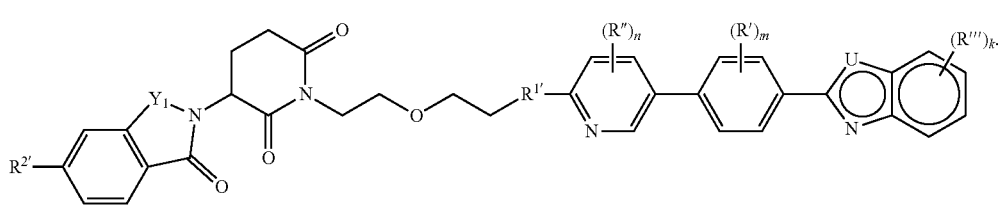

Formula 4-1

26. The compound of claim 15, wherein the compound is of Formula 16 or 17;

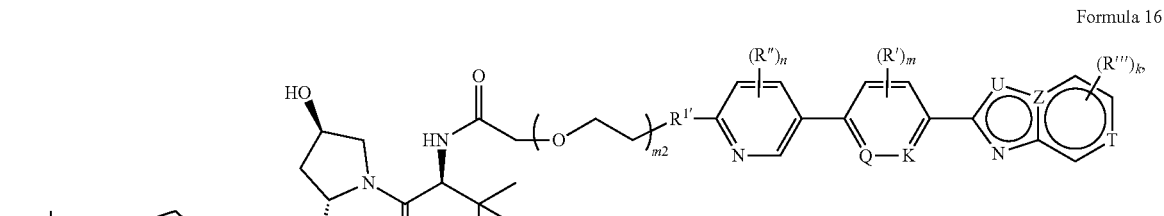

Formula 16

Formula 17

27. The compound of claim 26, wherein the compound is of Formula 16, and wherein Z is C, U is O or S and T is CH; or, Z is N, U is CH and T is CH; Z is C, T is N and U is CH.

28. The compound of claim 26, wherein the compound is of Formula 17, and wherein Z is C, U is O or S and T is CH; or, Z is N, U is CH and T is CH; Z is C, T is N and U is CH.

29. The compound of claim 1, wherein the compound is selected from a group consisting of:

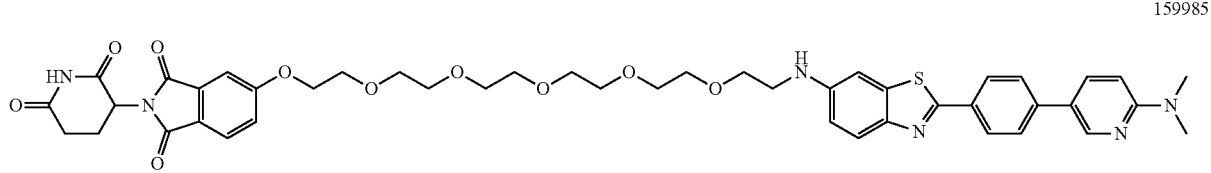

159985

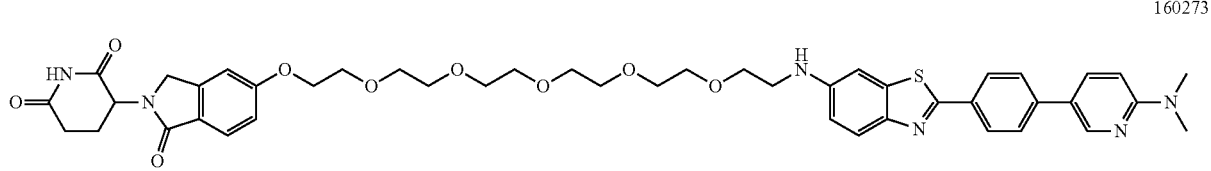

160273

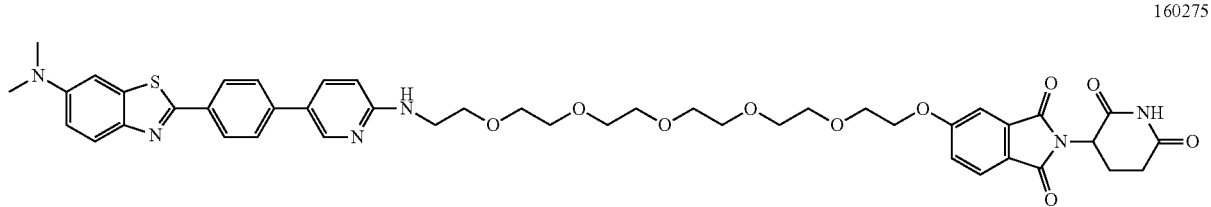

160275

-continued
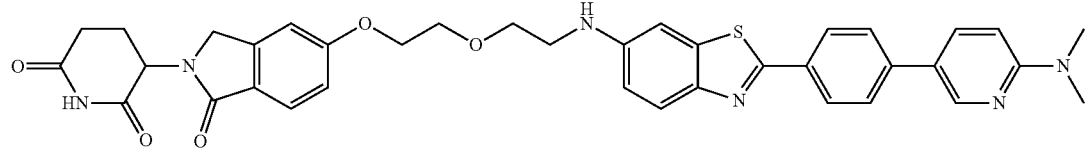 [SMILES: CN(C)c1ccc(-c2ccc(-c3nc4ccc(NCCOCCOc5ccc6c(c5)CN(C5CCC(=O)NC5=O)C6=O)cc4s3)cc2)cn1]
160313
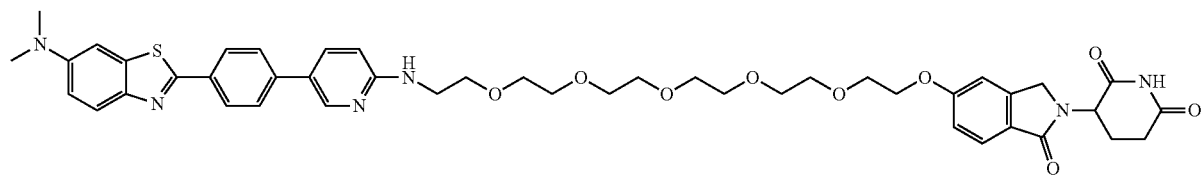
160383
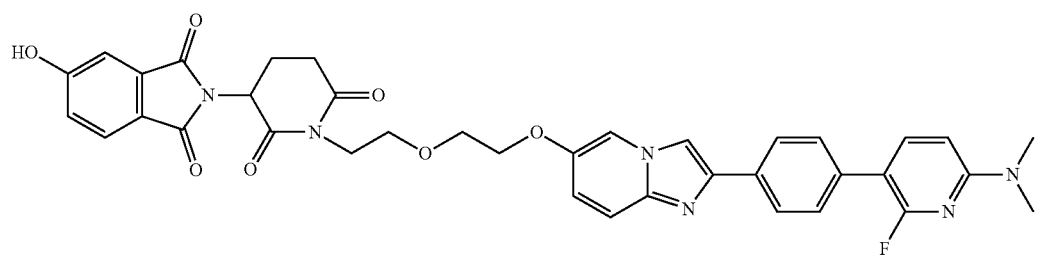 [SMILES: CN(C)c1ccc(-c2ccc(-c3cn4cc(OCCOCCN5C(=O)CCC(N6C(=O)c7ccc(O)cc7C6=O)C5=O)ccc4n3)cc2)c(F)n1]
170350
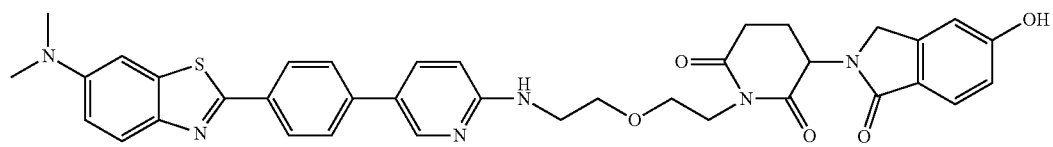
161177
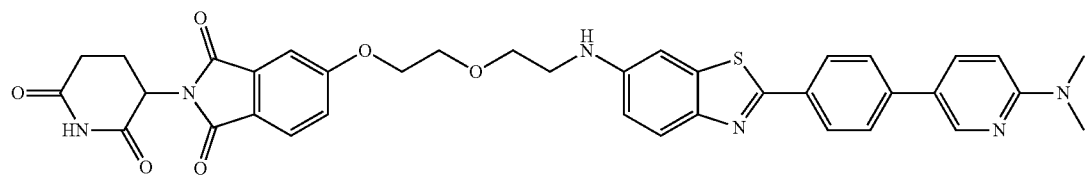
160219
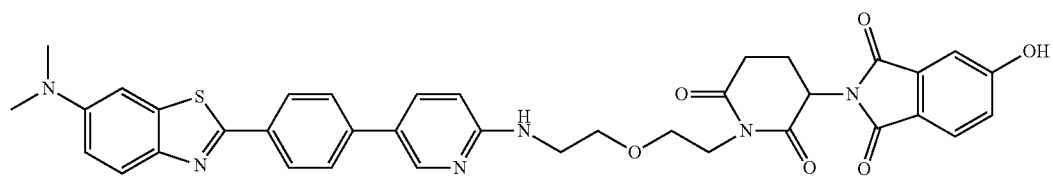
170351
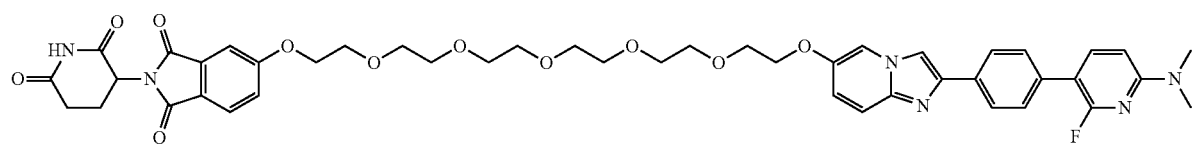
160744
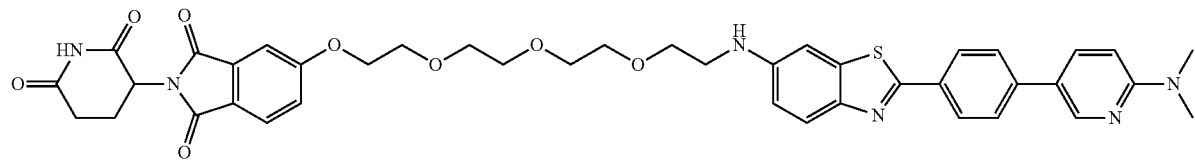
160939

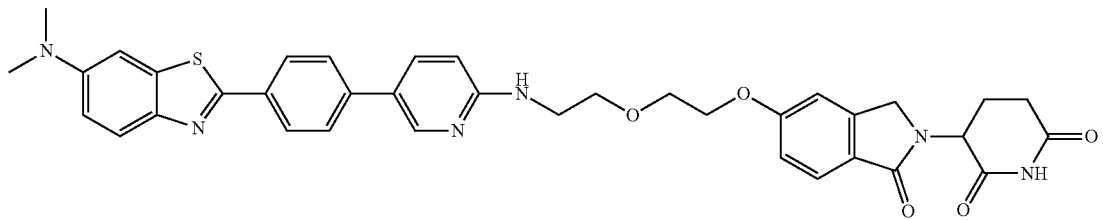 [SMILES: CN(C)c1ccc2nc(-c3ccc(-c4ccc(NCCOCCOc5ccc6c(c5)C(=O)N(C5CCC(=O)NC5=O)C6=O)nc4)cc3)sc2c1]
170352
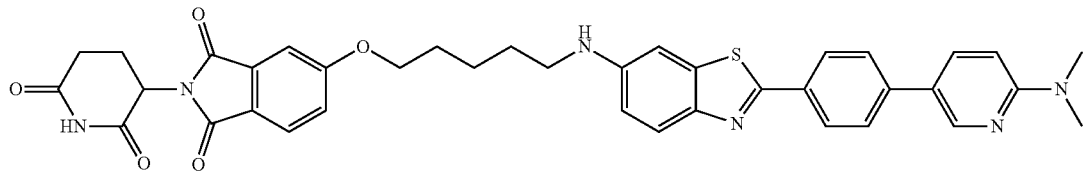
161103
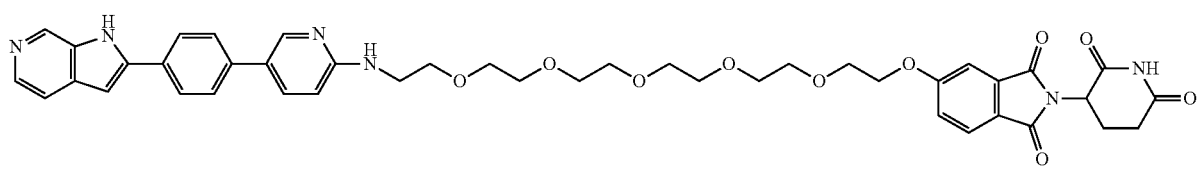
161104
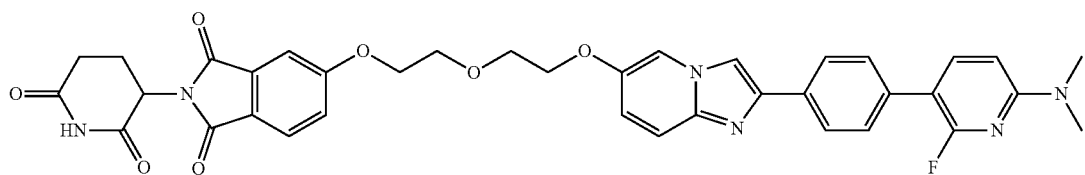
161111
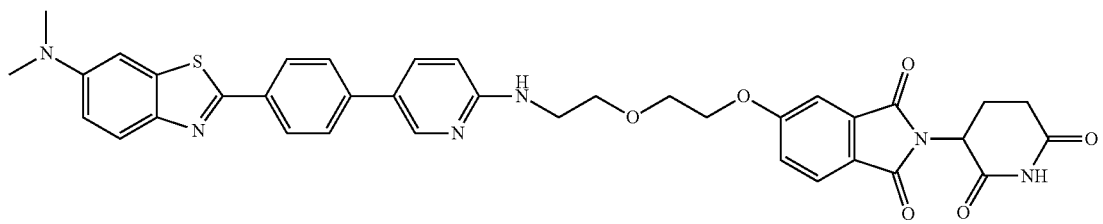
170353
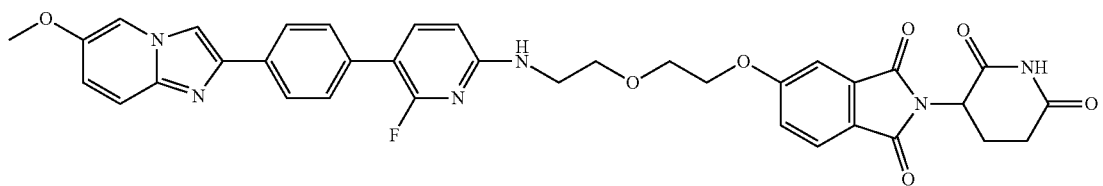
161215
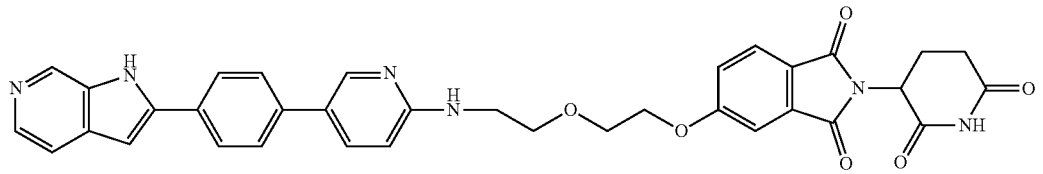
170354
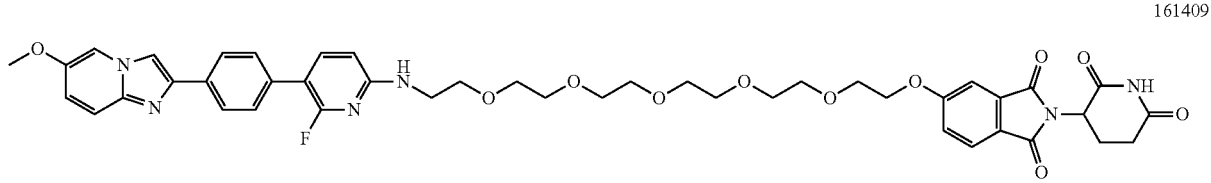
161409

170355
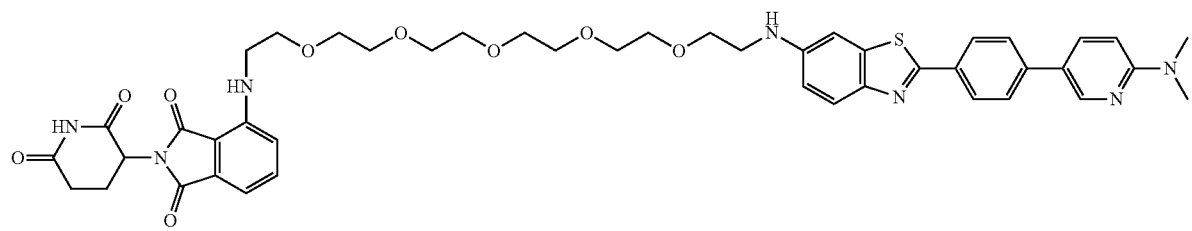 [SMILES: CN(C)c1ccc(-c2ccc(-c3nc4ccc(NCCOCCOCCOCCOCCOCCNc5cccc6c5C(=O)N(C5CCC(=O)NC5=O)C6=O)cc4s3)cc2)cn1]
170356
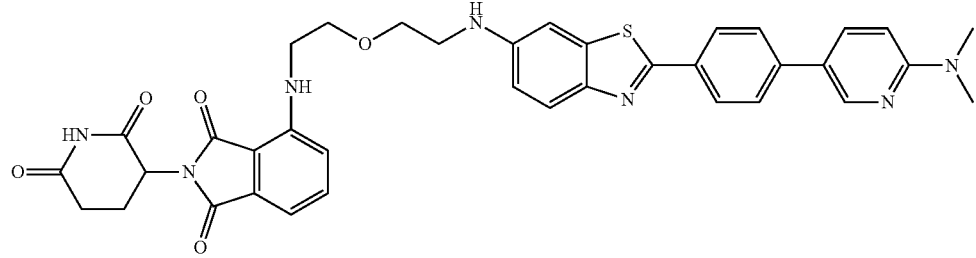
170357
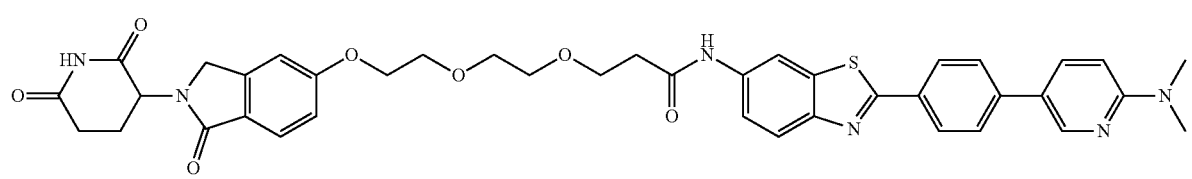
160624
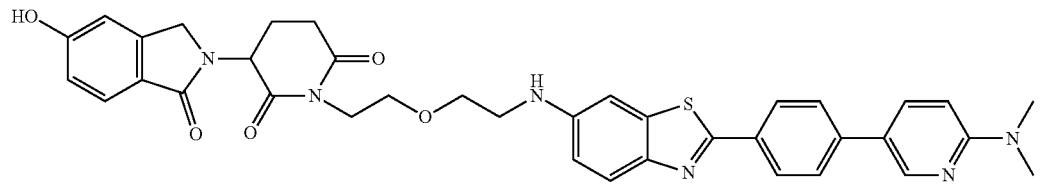
170358
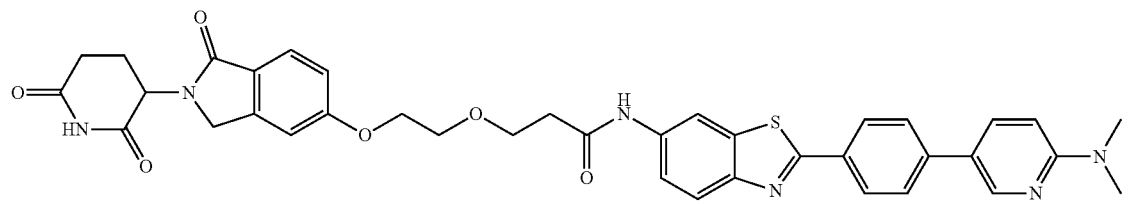
170359
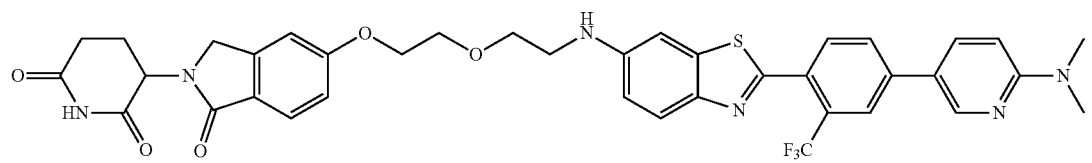
170450
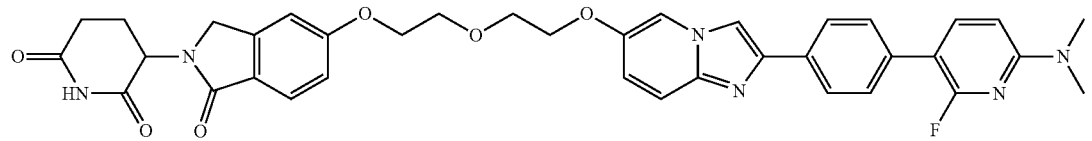 [SMILES: CN(C)c1ccc(-c2ccc(-c3cn4cc(OCCOCCOc5ccc6c(c5)CN(C5CCC(=O)NC5=O)C6=O)ccc4n3)cc2)c(F)n1]
170451
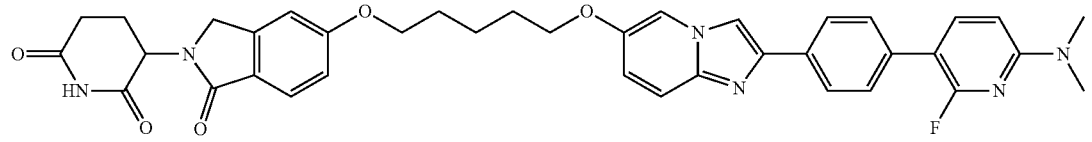 [SMILES: CN(C)c1ccc(-c2ccc(-c3cn4cc(OCCCCCOc5ccc6c(c5)CN(C5CCC(=O)NC5=O)C6=O)ccc4n3)cc2)c(F)n1]

-continued
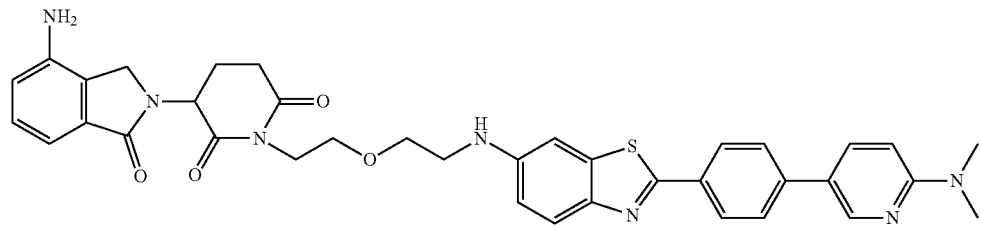
162641
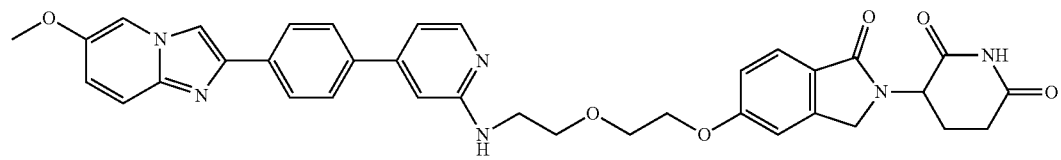
162640
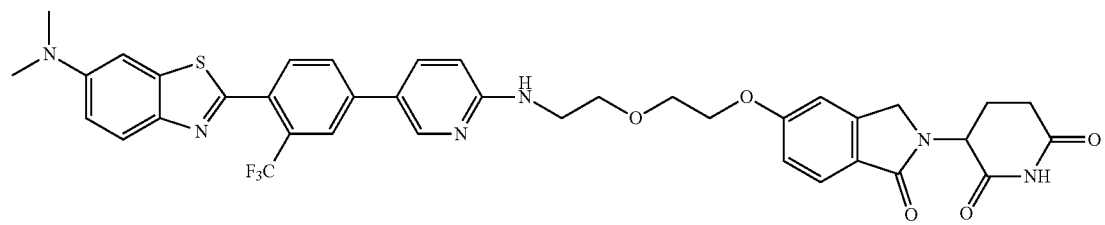 [SMILES: CN(C)c1ccc2nc(-c3ccc(-c4ccc(NCCOCCOc5ccc6c(c5)CN(C5CCC(=O)NC5=O)C6=O)nc4)cc3C(F)(F)F)sc2c1]
177031
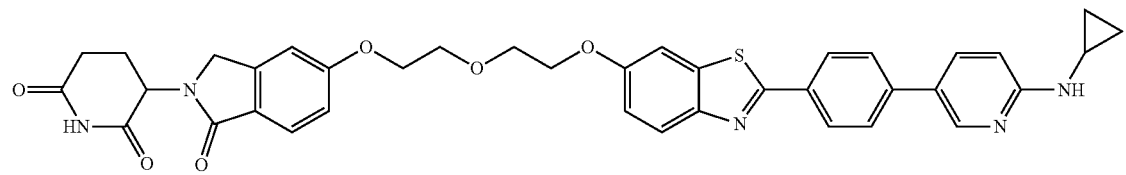 [SMILES: O=C1CCC(N2Cc3cc(OCCOCCOc4ccc5nc(-c6ccc(-c7ccc(NC8CC8)nc7)cc6)sc5c4)ccc3C2=O)C(=O)N1]
177032
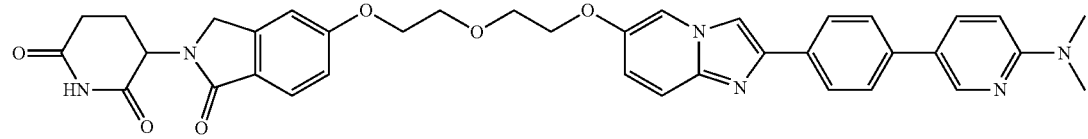
177033
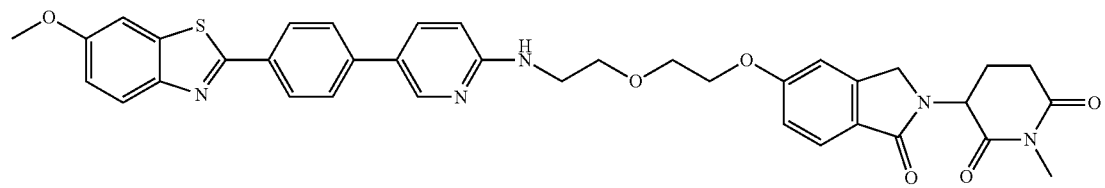 [SMILES: COc1ccc2nc(-c3ccc(-c4ccc(NCCOCCOc5ccc6c(c5)CN(C5CCC(=O)N(C)C5=O)C6=O)nc4)cc3)sc2c1]
177034
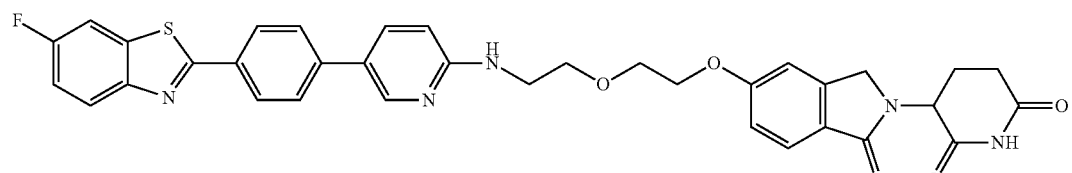
177035
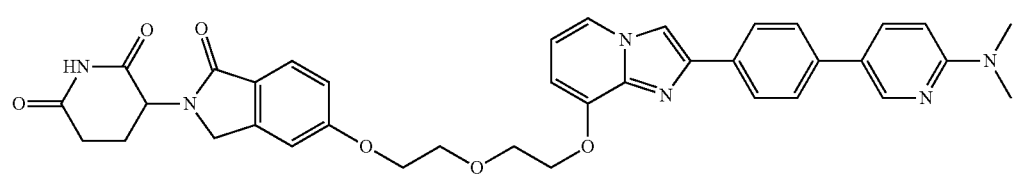 [SMILES: CN(C)c1ccc(-c2ccc(-c3cn4cccc(OCCOCCOc5ccc6c(c5)CN(C5CCC(=O)NC5=O)C6=O)c4n3)cc2)cn1]
162842

-continued
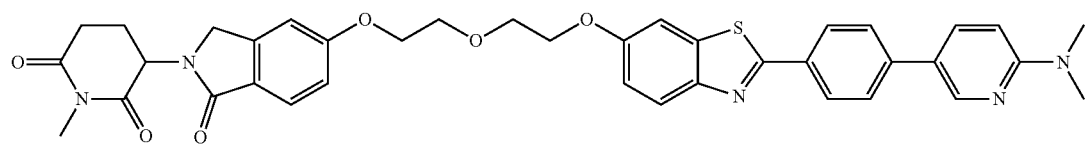
177036
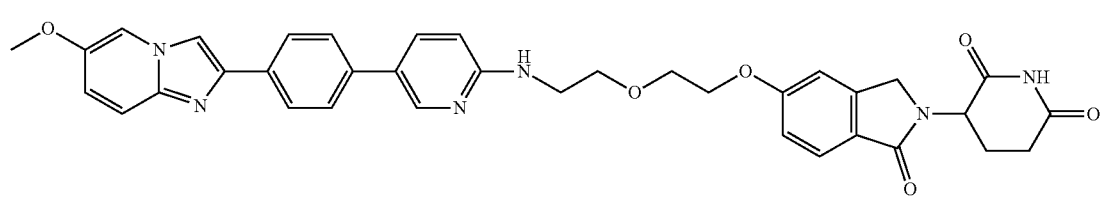 [SMILES: COc1ccc2nc(-c3ccc(-c4ccc(NCCOCCOc5ccc6c(c5)CN(C5CCC(=O)NC5=O)C6=O)nc4)cc3)cn2c1]
177037
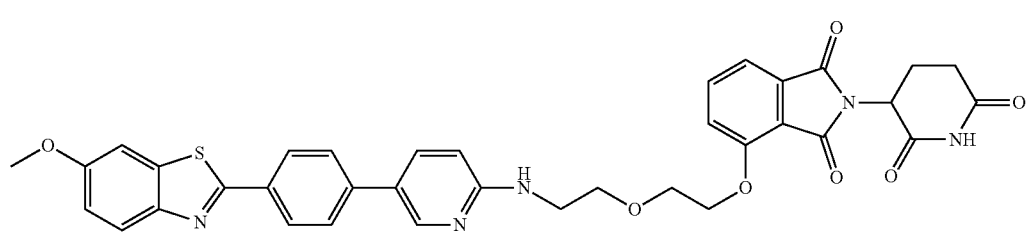 [SMILES: COc1ccc2nc(-c3ccc(-c4ccc(NCCOCCOc5cccc6c5C(=O)N(C5CCC(=O)NC5=O)C6=O)nc4)cc3)sc2c1]
177038
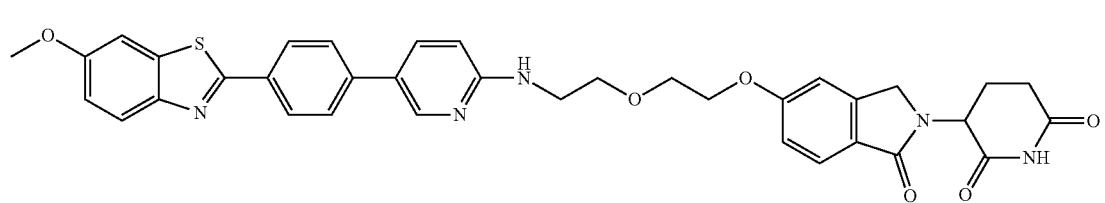 [SMILES: COc1ccc2nc(-c3ccc(-c4ccc(NCCOCCOc5ccc6c(c5)CN(C5CCC(=O)NC5=O)C6=O)nc4)cc3)sc2c1]
177039
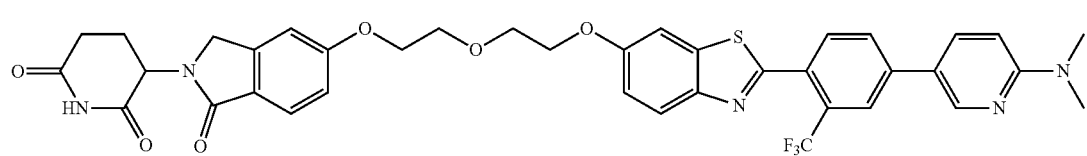 [SMILES: CN(C)c1ccc(-c2ccc(-c3nc4ccc(OCCOCCOc5ccc6c(c5)CN(C5CCC(=O)NC5=O)C6=O)cc4s3)c(C(F)(F)F)c2)cn1]
162903
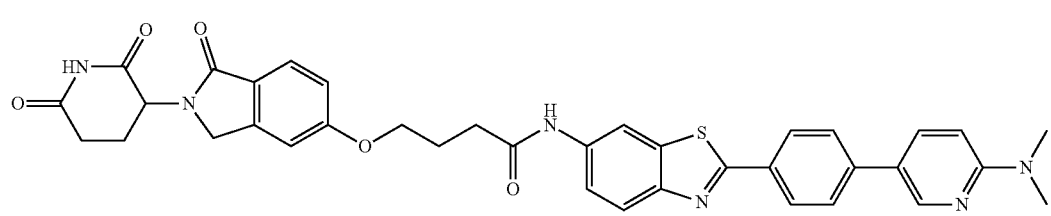 [SMILES: CN(C)c1ccc(-c2ccc(-c3nc4ccc(NC(=O)CCCOc5ccc6c(c5)CN(C5CCC(=O)NC5=O)C6=O)cc4s3)cc2)cn1]
170742
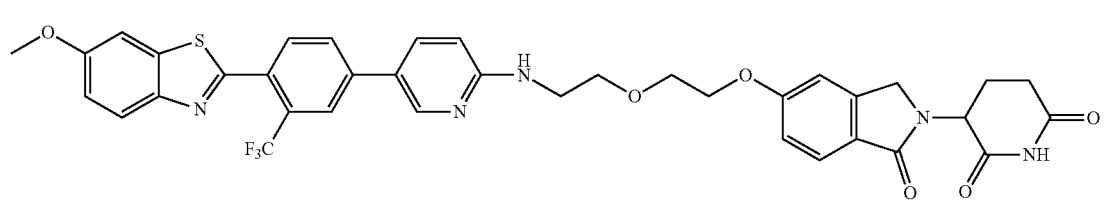
179143
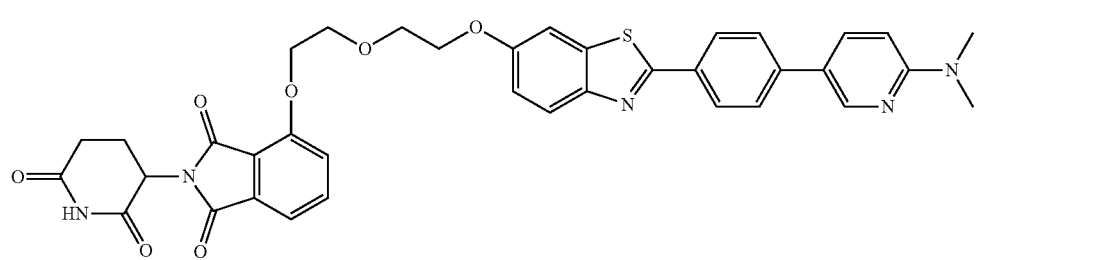
180944

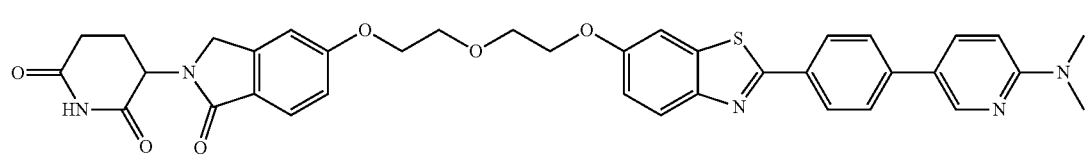 [SMILES: CN(C)c1ccc(-c2ccc(-c3nc4ccc(OCCOCCOc5ccc6c(c5)CN(C5CCC(=O)NC5=O)C6=O)cc4s3)cc2)cn1]
163123
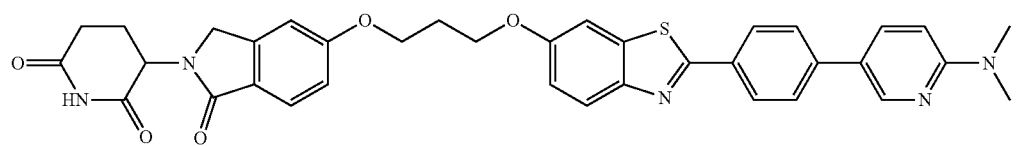
184605
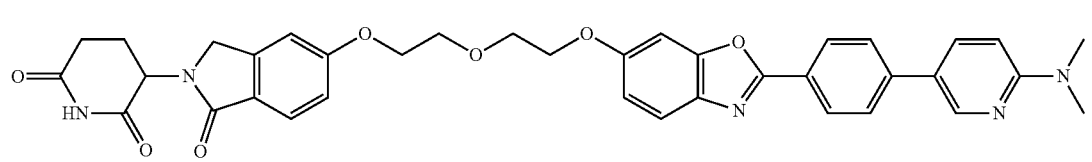 [SMILES: CN(C)c1ccc(-c2ccc(-c3nc4ccc(OCCOCCOc5ccc6c(c5)CN(C5CCC(=O)NC5=O)C6=O)cc4o3)cc2)cn1]
163365
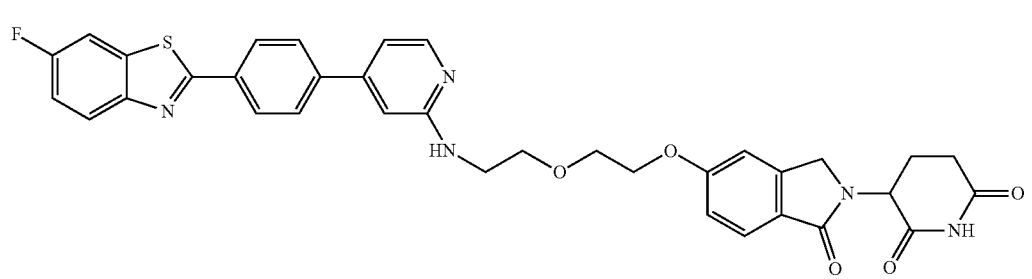 [SMILES: O=C1CCC(N2Cc3cc(OCCOCCNc4cc(-c5ccc(-c6nc7ccc(F)cc7s6)cc5)ccn4)ccc3C2=O)C(=O)N1]
180948
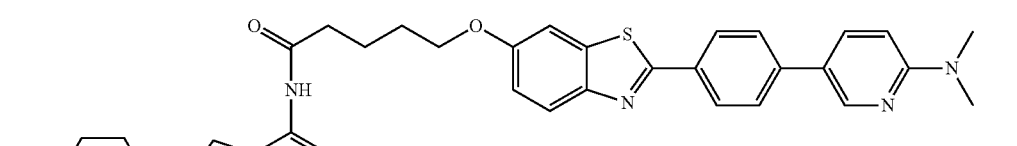
189149
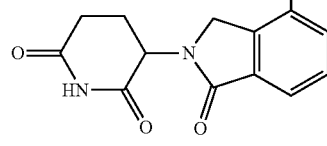
180950
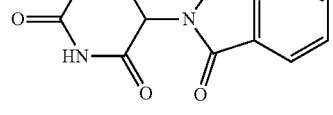
174251
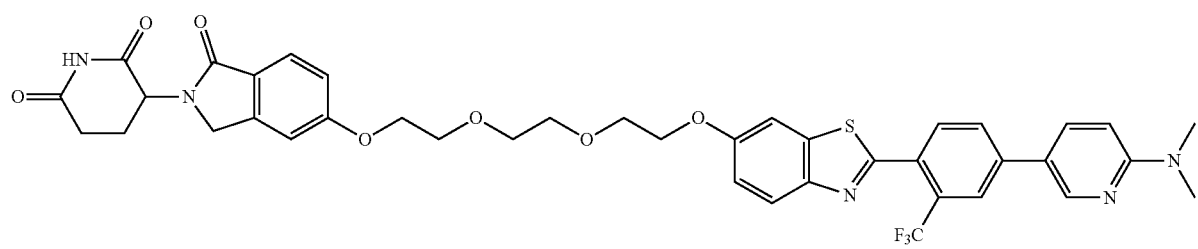

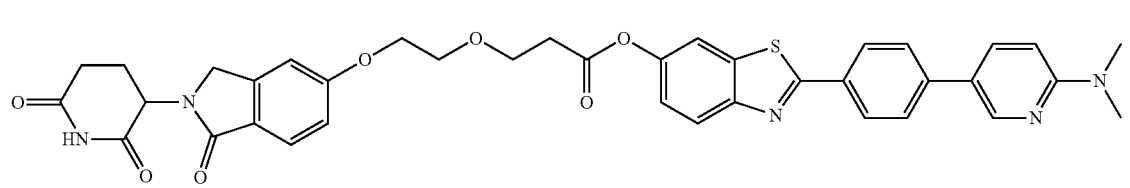 [SMILES: CN(C)c1ccc(-c2ccc(-c3nc4ccc(OC(=O)CCOCCOc5ccc6c(c5)CN(C5CCC(=O)NC5=O)C6=O)cc4s3)cc2)cn1]
175552
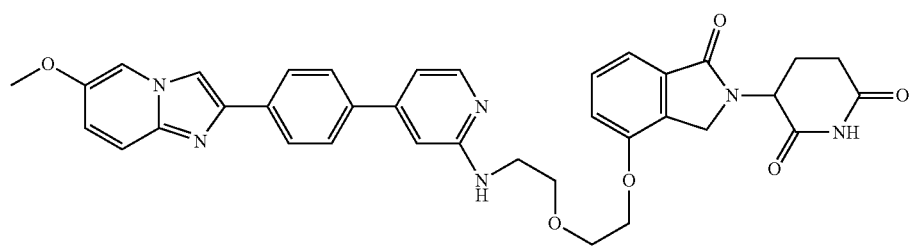 [SMILES: COc1ccc2nc(-c3ccc(-c4ccnc(NCCOCCOc5cccc6c5CN(C5CCC(=O)NC5=O)C6=O)c4)cc3)cn2c1]
190753
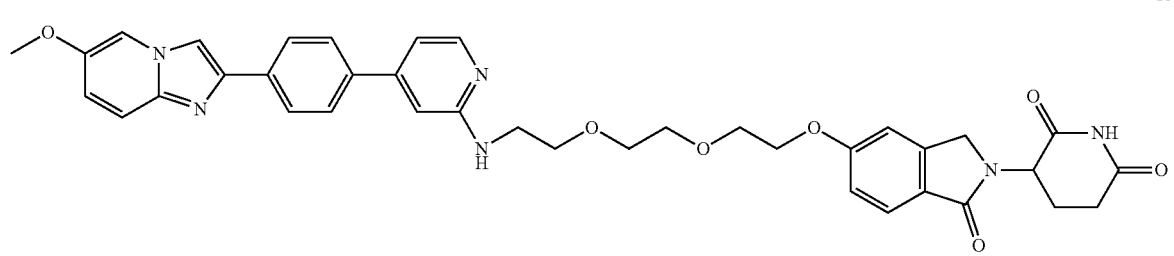
139854
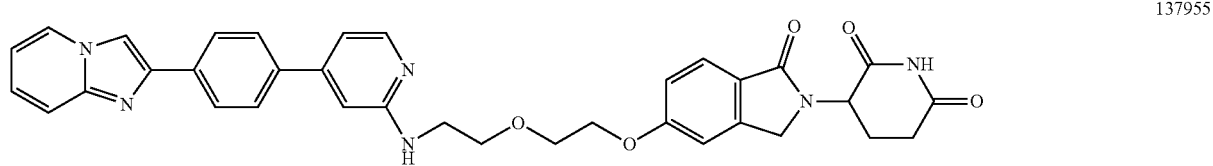
137955
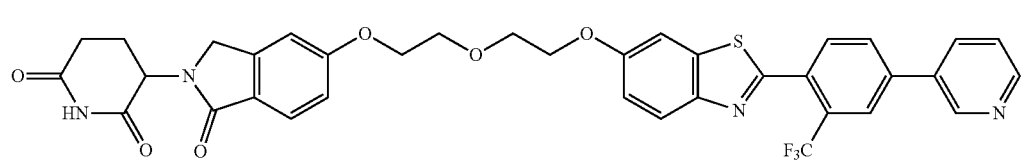 [SMILES: O=C1CCC(N2Cc3cc(OCCOCCOc4ccc5nc(-c6ccc(-c7cccnc7)cc6C(F)(F)F)sc5c4)ccc3C2=O)C(=O)N1]
186756
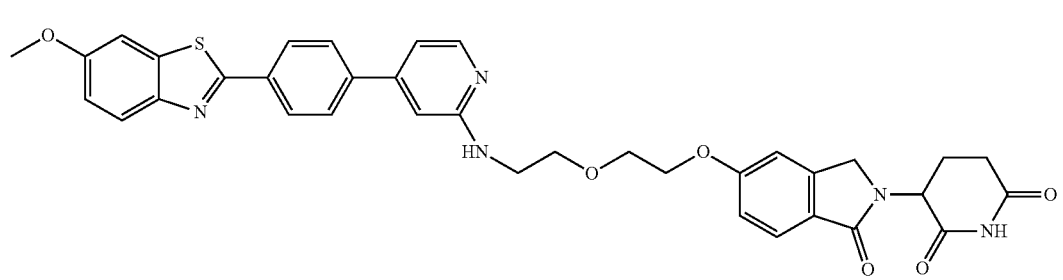 [SMILES: COc1ccc2nc(-c3ccc(-c4ccnc(NCCOCCOc5ccc6c(c5)CN(C5CCC(=O)NC5=O)C6=O)c4)cc3)sc2c1]
170257
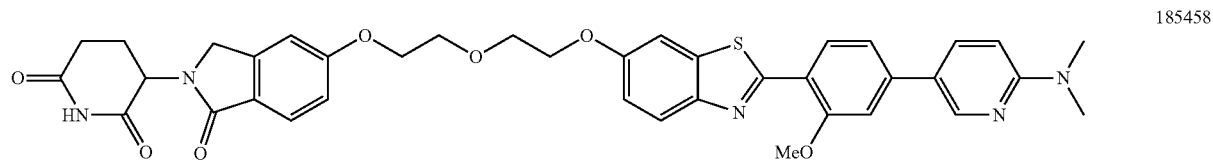
185458

-continued
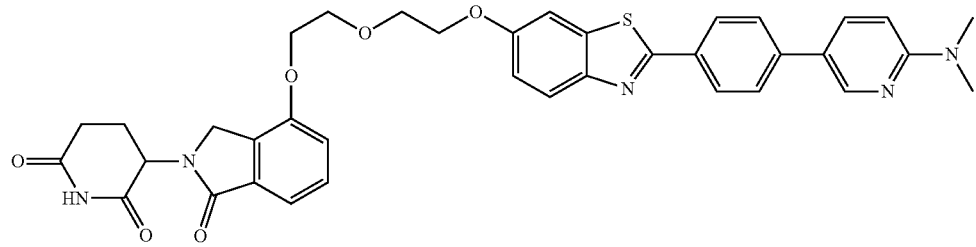 [SMILES: CN(C)c1ccc(-c2ccc(-c3nc4ccc(OCCOCCOc5cccc6c5CN(C5CCC(=O)NC5=O)C6=O)cc4s3)cc2)cn1]
132159
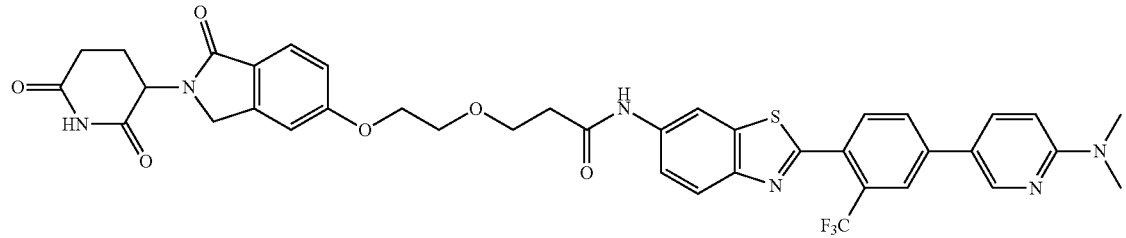
132560
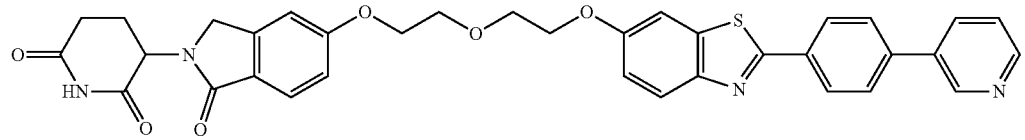
137361
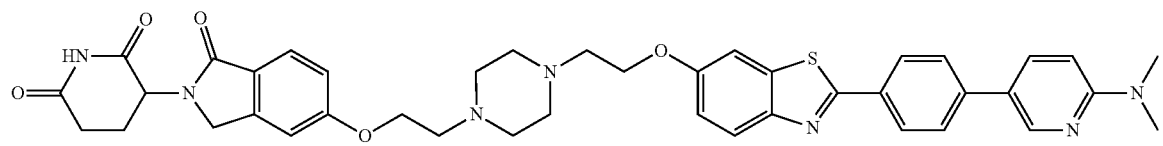 [SMILES: CN(C)c1ccc(-c2ccc(-c3nc4ccc(OCCN5CCN(CCOc6ccc7c(c6)CN(C6CCC(=O)NC6=O)C7=O)CC5)cc4s3)cc2)cn1]
180262
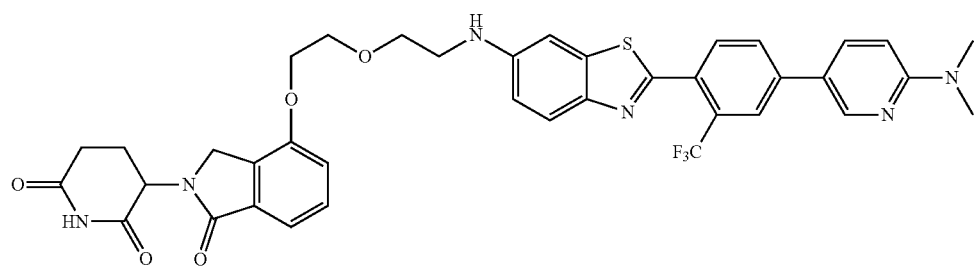
185563
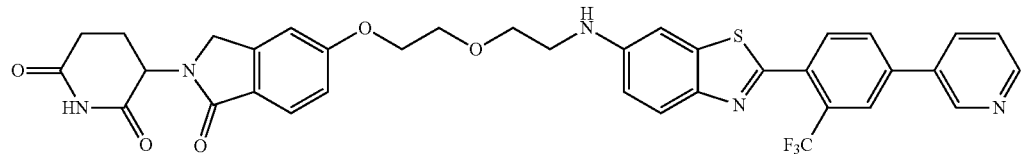 [SMILES: O=C1CCC(N2Cc3cc(OCCOCCNc4ccc5nc(-c6ccc(-c7cccnc7)cc6C(F)(F)F)sc5c4)ccc3C2=O)C(=O)N1]
181964
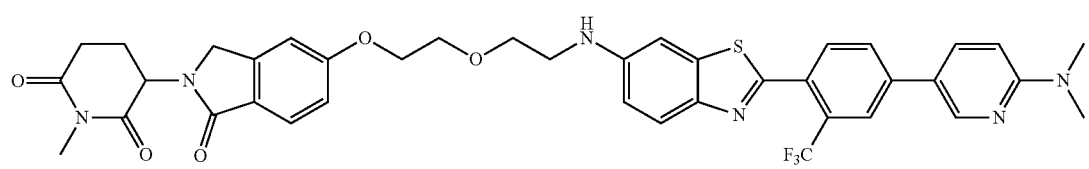 [SMILES: CN(C)c1ccc(-c2ccc(-c3nc4ccc(NCCCCCOc5ccc6c(c5)CN(C5CCC(=O)NC5=O)C6=O)cc4s3)c(C(F)(F)F)c2)cn1]
133065
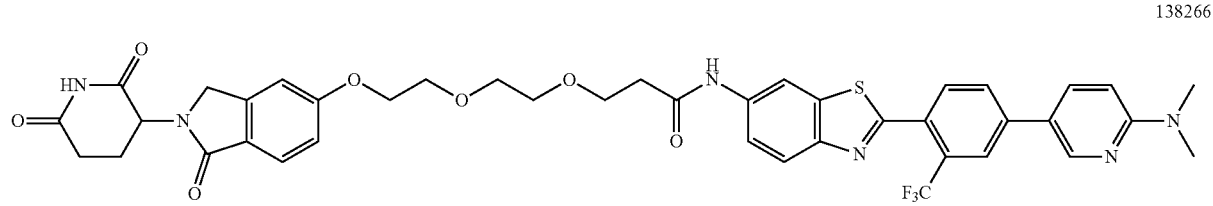
138266

-continued
136767
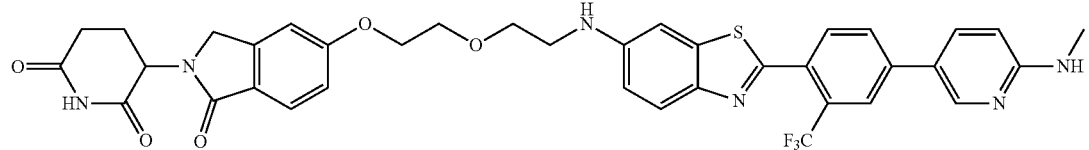
132168
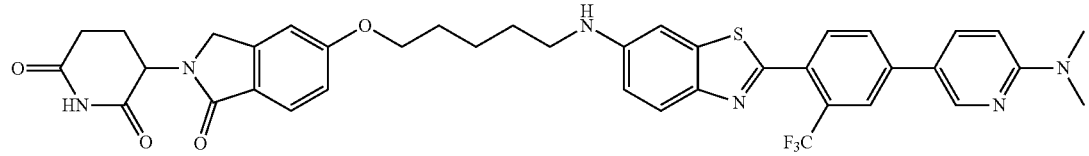
139269
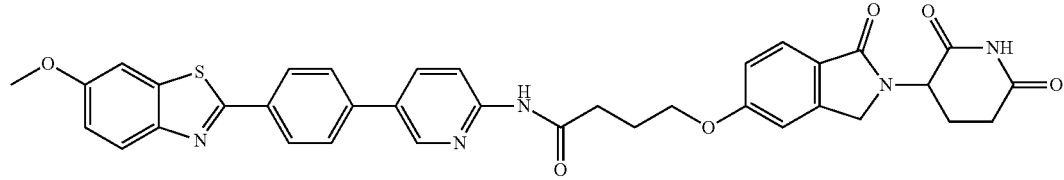
113070
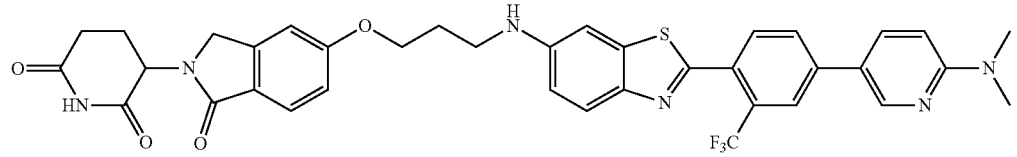
129071
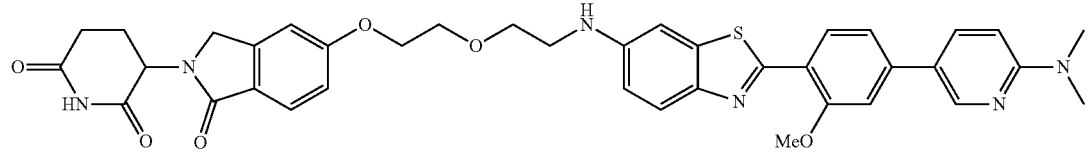 [SMILES: COc1cc(-c2ccc(N(C)C)nc2)ccc1-c1nc2ccc(NCCOCCOc3ccc4c(c3)CN(C3CCC(=O)NC3=O)C4=O)cc2s1]
112772
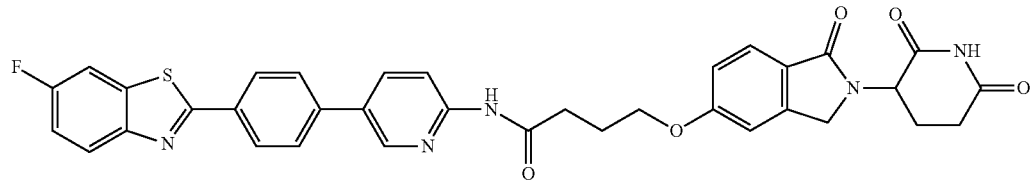 [SMILES: O=C1CCC(N2Cc3cc(OCCCC(=O)Nc4ccc(-c5ccc(-c6nc7ccc(F)cc7s6)cc5)cn4)ccc3C2=O)C(=O)N1]
127973
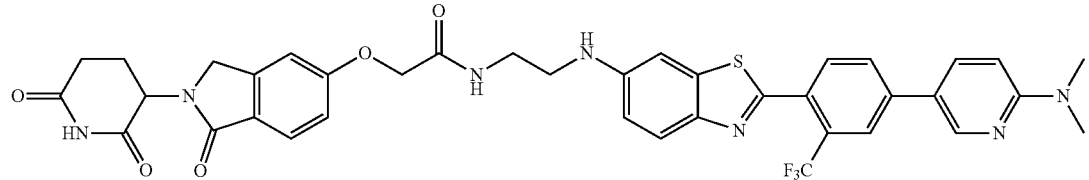 [SMILES: CN(C)c1ccc(-c2ccc(-c3nc4ccc(NCCNC(=O)COc5ccc6c(c5)CN(C5CCC(=O)NC5=O)C6=O)cc4s3)c(C(F)(F)F)c2)cn1]
123374
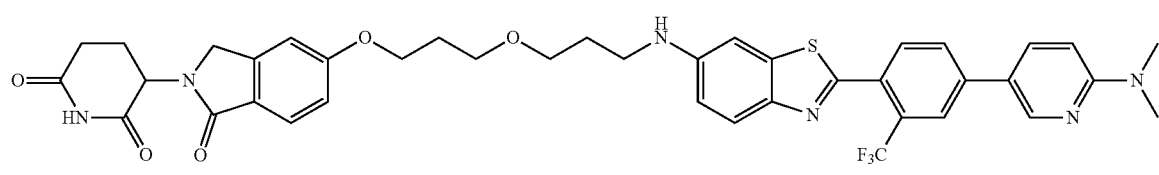 [SMILES: CN(C)c1ccc(-c2ccc(-c3nc4ccc(NCCCOCCCOc5ccc6c(c5)CN(C5CCC(=O)NC5=O)C6=O)cc4s3)c(C(F)(F)F)c2)cn1]
129975
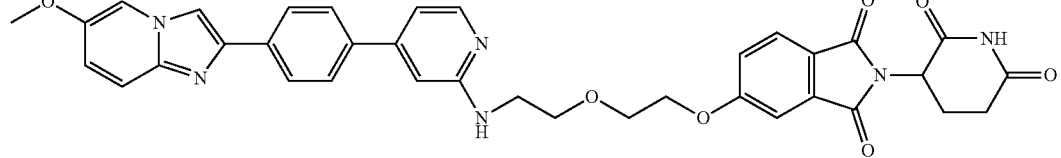

-continued
138876
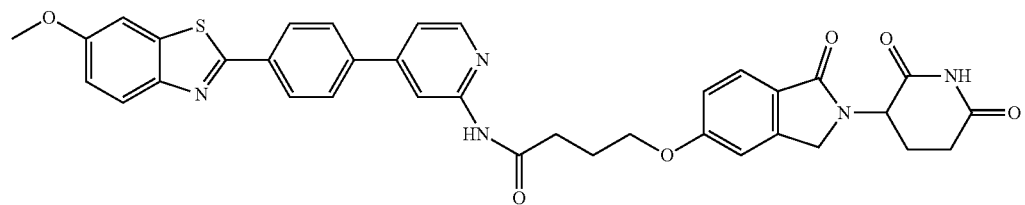 [SMILES: COc1ccc2nc(-c3ccc(-c4ccnc(NC(=O)CCCOc5ccc6c(c5)CN(C5CCC(=O)NC5=O)C6=O)c4)cc3)sc2c1]
130177
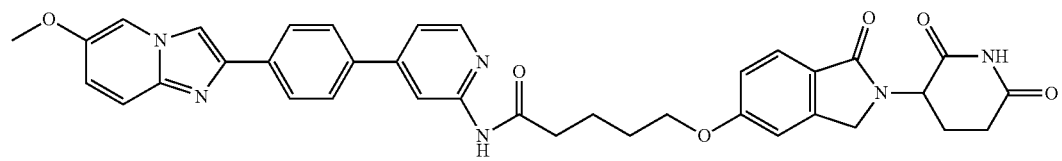 [SMILES: COc1ccc2nc(-c3ccc(-c4ccnc(NC(=O)CCCCOc5ccc6c(c5)CN(C5CCC(=O)NC5=O)C6=O)c4)cc3)cn2c1]
133678
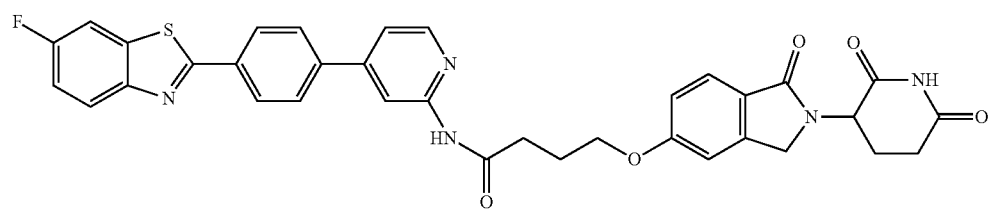
190279
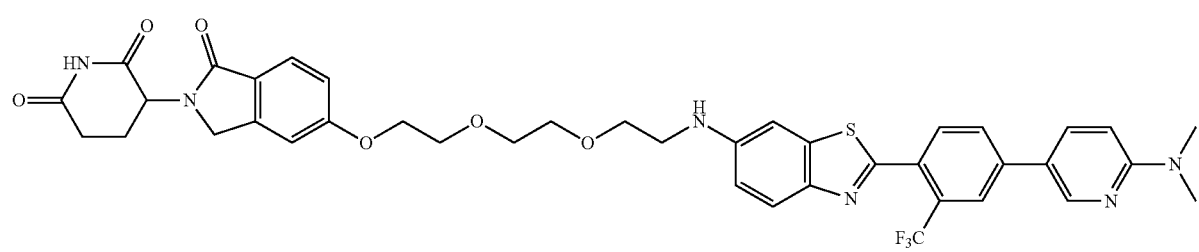
133380
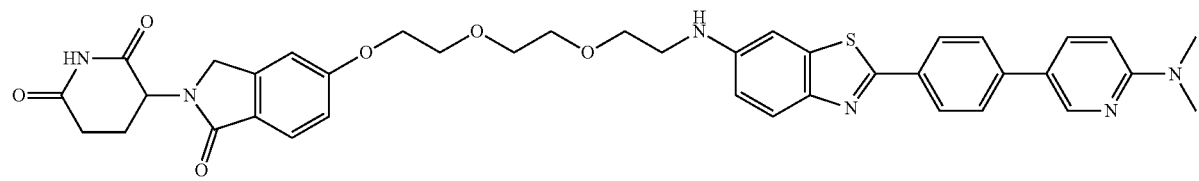
120581
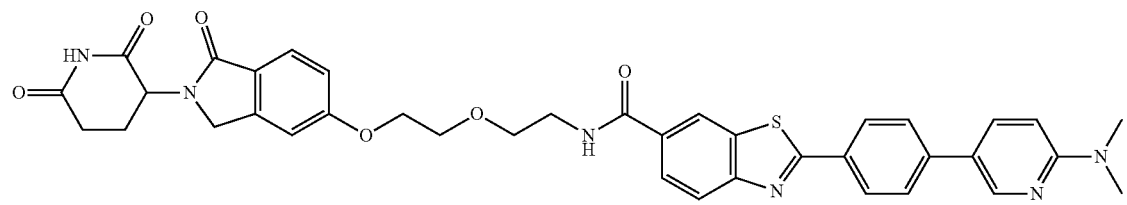 [SMILES: CN(C)c1ccc(-c2ccc(-c3nc4ccc(C(=O)NCCOCCOc5ccc6c(c5)CN(C5CCC(=O)NC5=O)C6=O)cc4s3)cc2)cn1]
161247
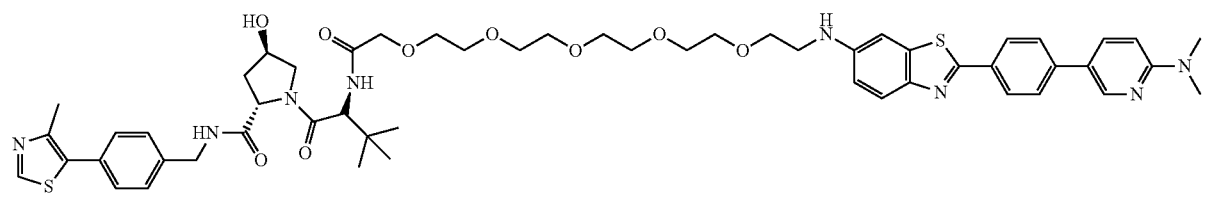

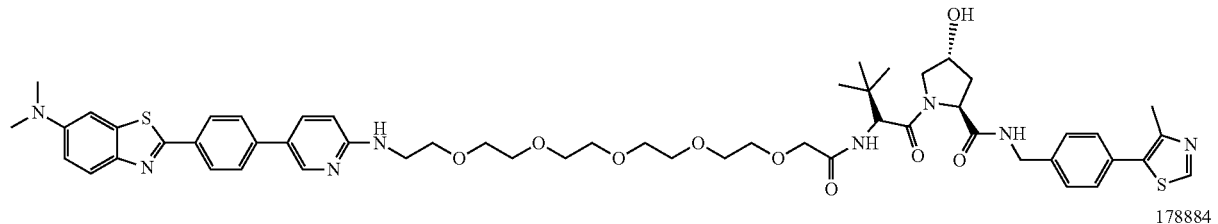
161598
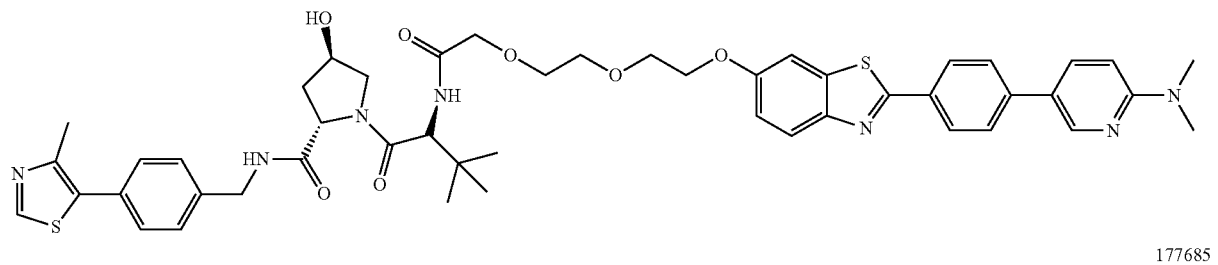
178884
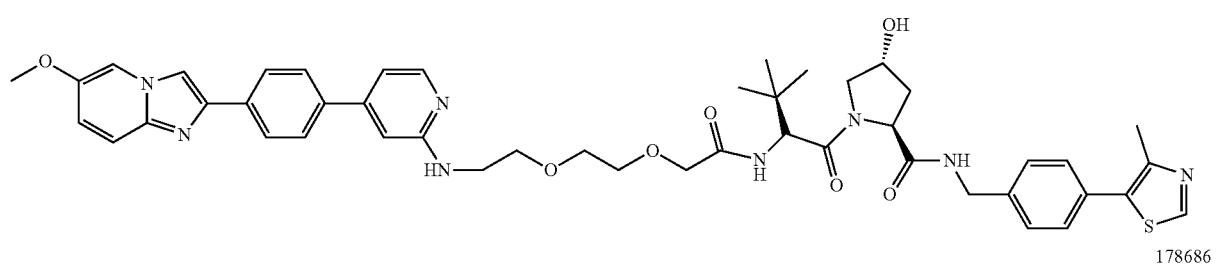
177685
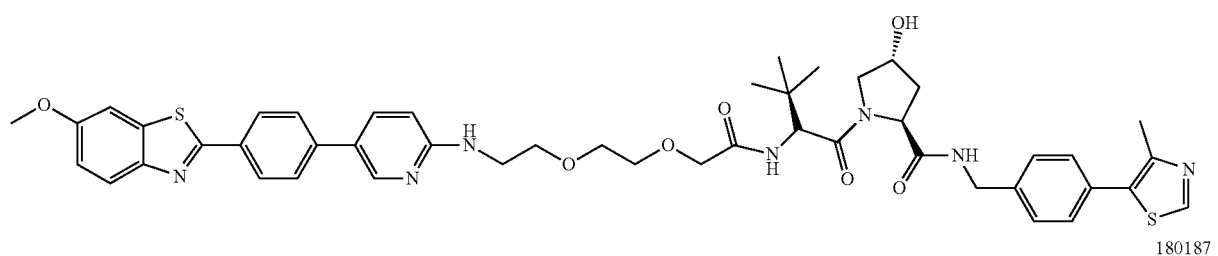
178686
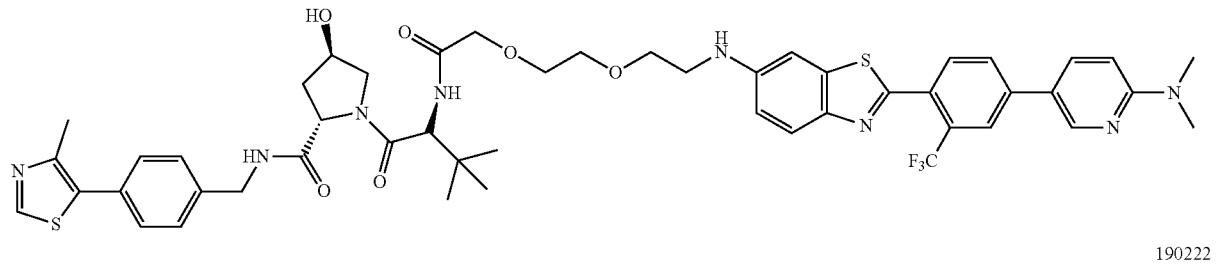
180187
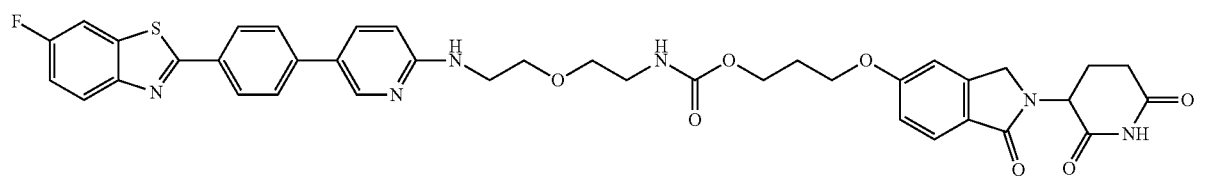 [SMILES: O=C1CCC(N2Cc3cc(OCCCOC(=O)NCCOCCNc4ccc(-c5ccc(-c6nc7ccc(F)cc7s6)cc5)cn4)ccc3C2=O)C(=O)N1]
190222
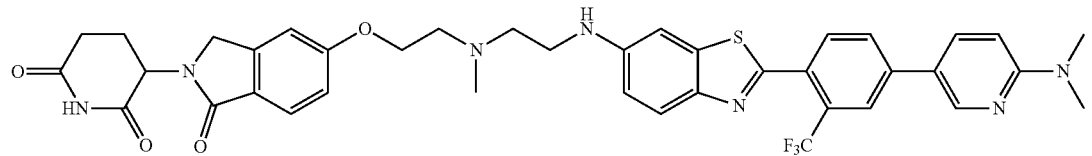
190083

129804
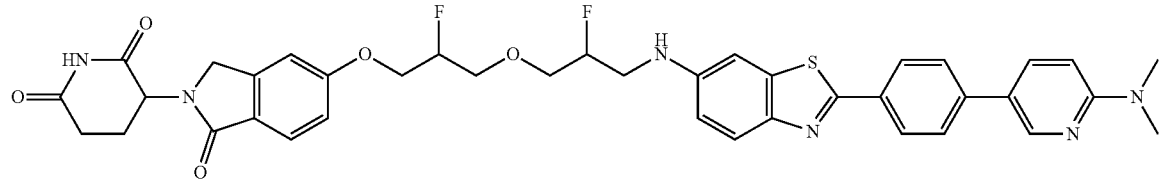
134555
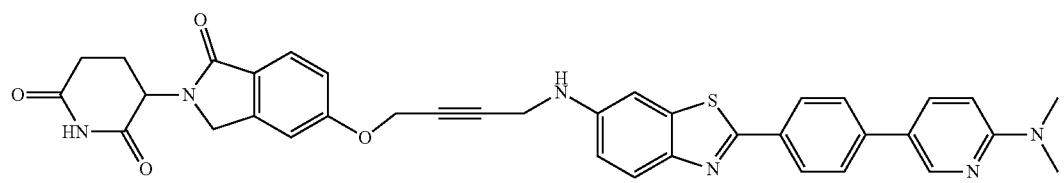
134666
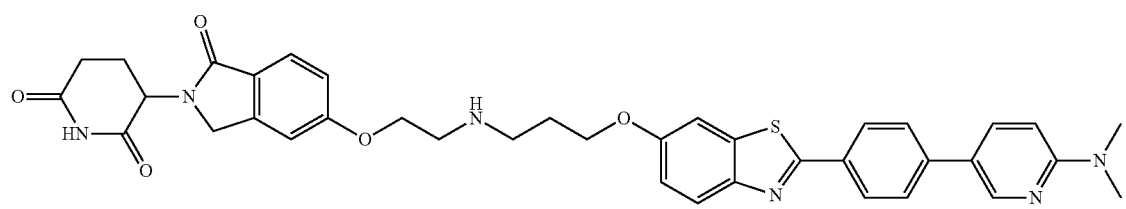
132777
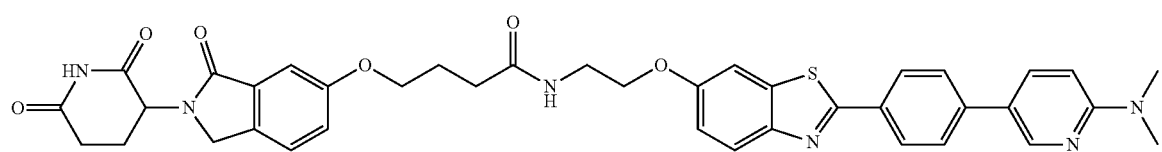 [SMILES: CN(C)c1ccc(-c2ccc(-c3nc4ccc(OCCNC(=O)CCCOc5ccc6c(c5)C(=O)N(C5CCC(=O)NC5=O)C6)cc4s3)cc2)cn1]
133298
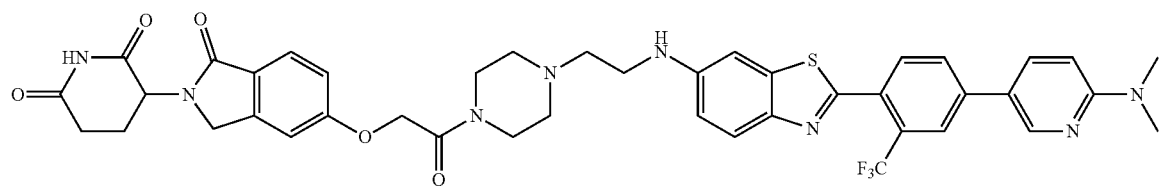 [SMILES: CN(C)c1ccc(-c2ccc(-c3nc4ccc(NCCN5CCN(C(=O)COc6ccc7c(c6)CN(C6CCC(=O)NC6=O)C7=O)CC5)cc4s3)c(C(F)(F)F)c2)cn1]
102291
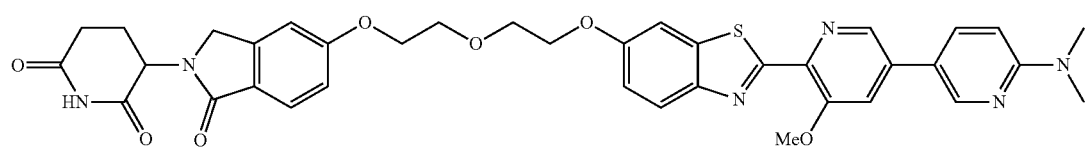
190892
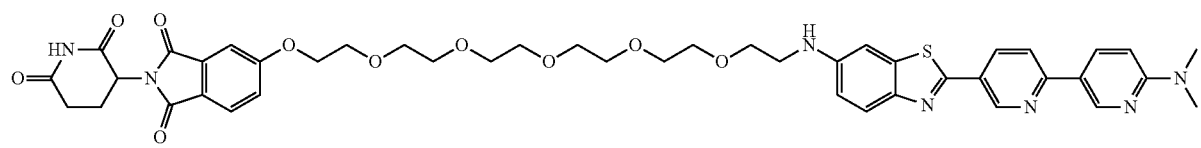
101193
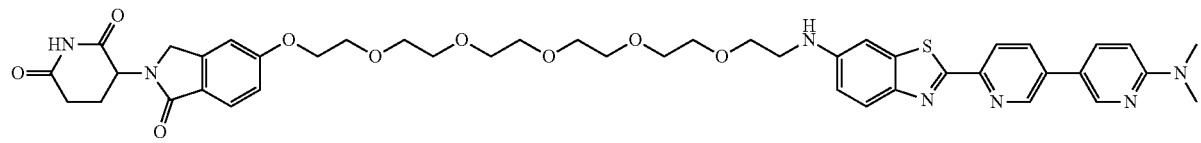

-continued
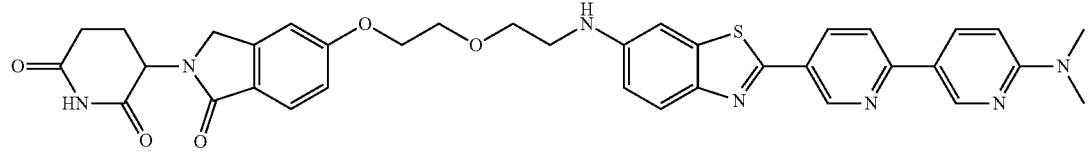
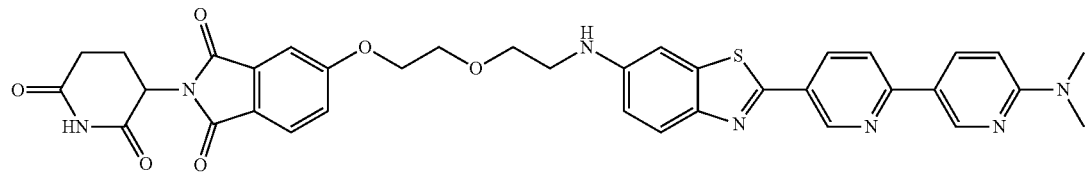
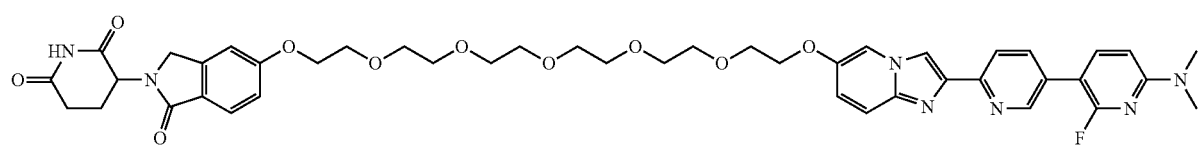
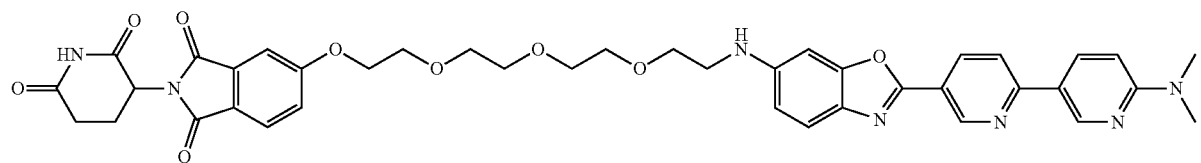
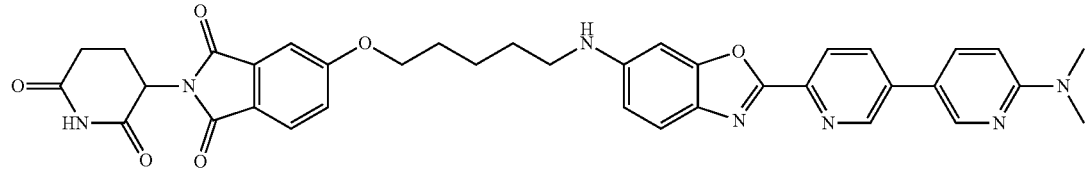
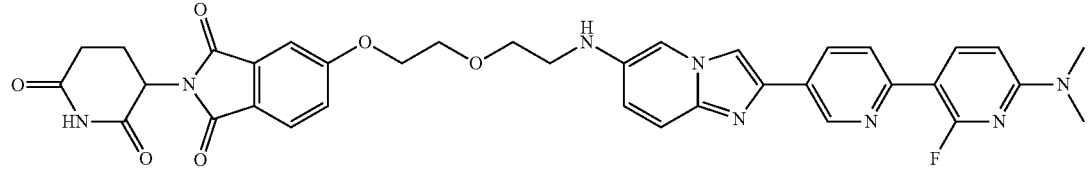
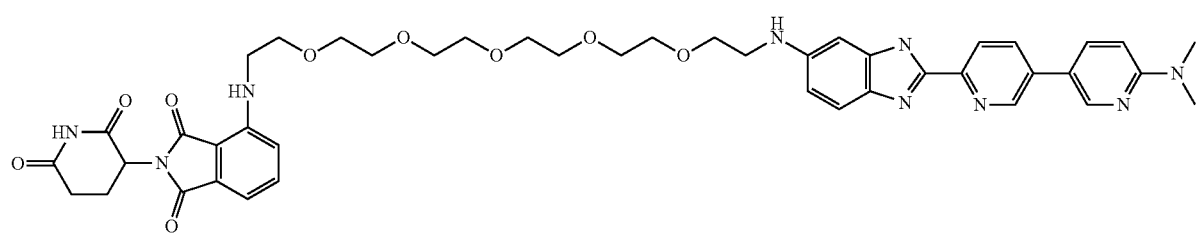
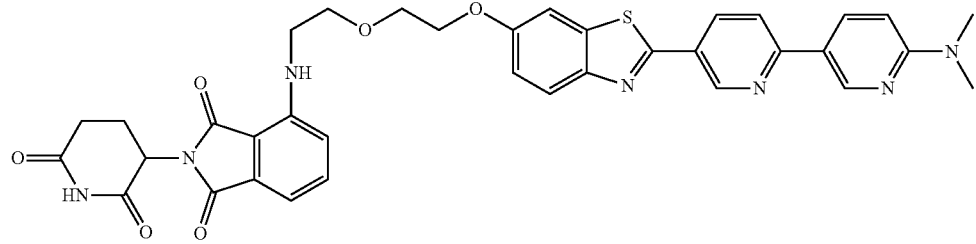 [SMILES: CN(C)c1ncc(-c2ccc(-c3nc4ccc(OCCOCCNc5cccc6c5C(=O)N(C5CCC(=O)NC5=O)C6=O)cc4s3)cn2)cn1]

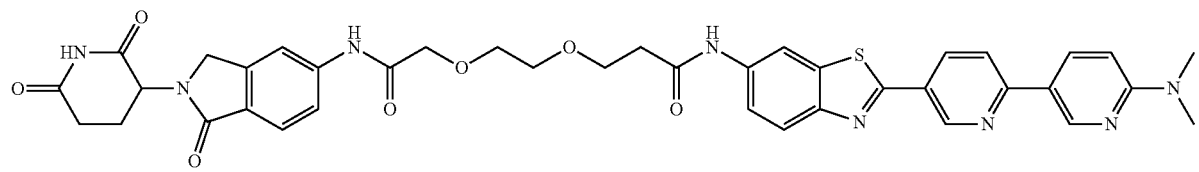
180196
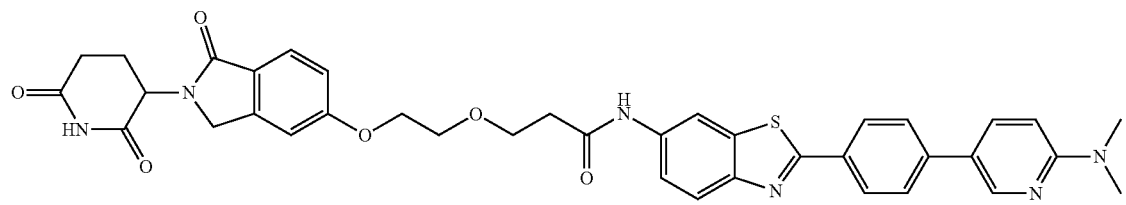 [SMILES: CN(C)c1ccc(-c2ccc(-c3nc4ccc(NC(=O)CCOCCOc5ccc6c(c5)CN(C5CCC(=O)NC5=O)C6=O)cc4s3)cc2)cn1]
180197
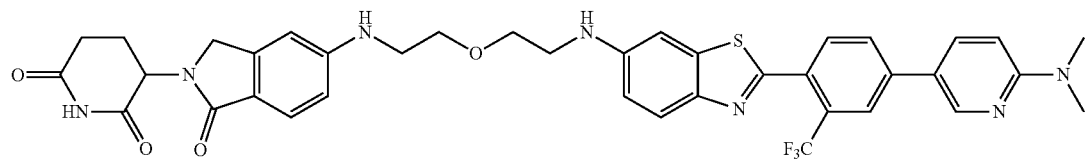
180198
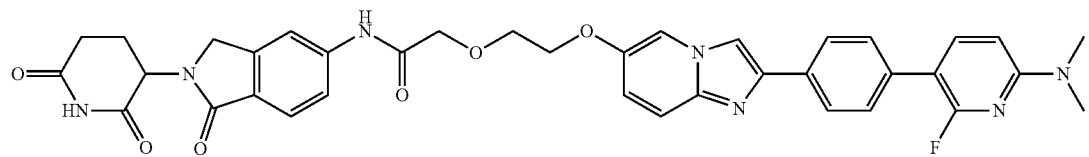 [SMILES: CN(C)c1ccc(-c2ccc(-c3cn4cc(OCCOCC(=O)Nc5ccc6c(c5)CN(C5CCC(=O)NC5=O)C6=O)ccc4n3)cc2)c(F)n1]
180199
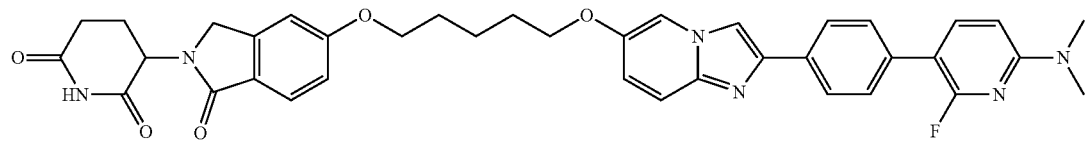
180215
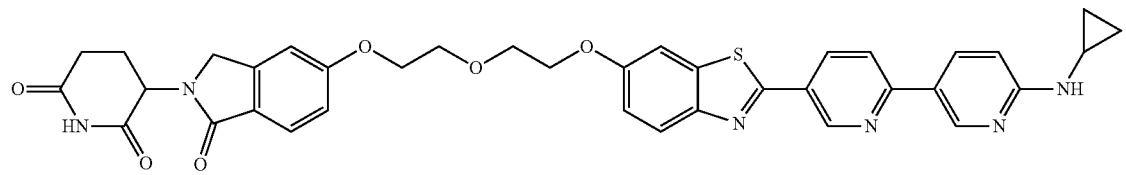
180216
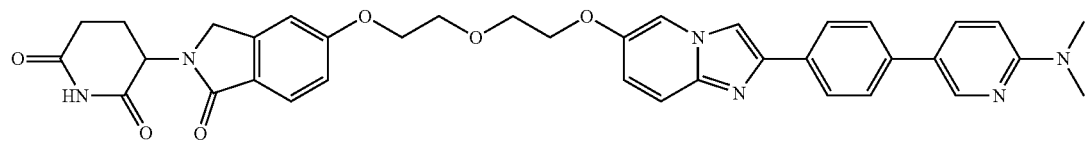
180217
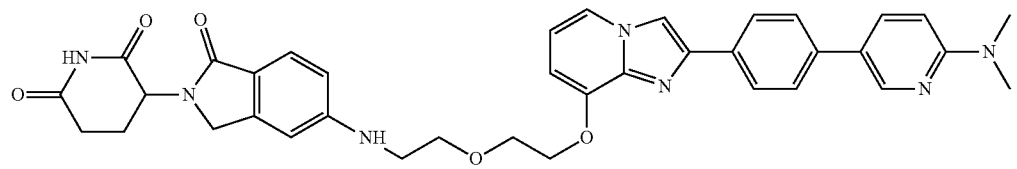 [SMILES: CN(C)c1ccc(-c2ccc(-c3cn4cccc(OCCOCCNc5ccc6c(c5)CN(C5CCC(=O)NC5=O)C6=O)c4n3)cc2)cn1]
180218
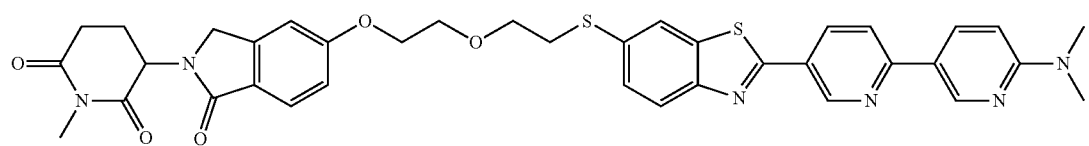 [SMILES: CN1C(=O)CCC(N2Cc3cc(OCCOCCSc4ccc5nc(-c6ccc(-c7ccc(N(C)C)nc7)nc6)sc5c4)ccc3C2=O)C1=O]
180219

-continued
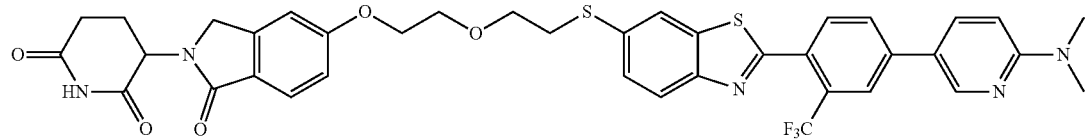
180310
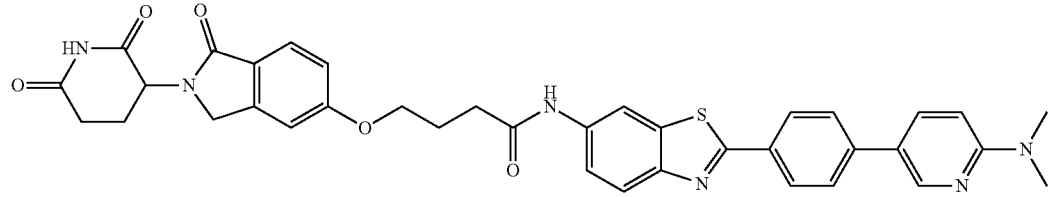 [SMILES: CN(C)c1ccc(-c2ccc(-c3nc4ccc(NC(=O)CCCOc5ccc6c(c5)CN(C5CCC(=O)NC5=O)C6=O)cc4s3)cc2)cn1]
180311
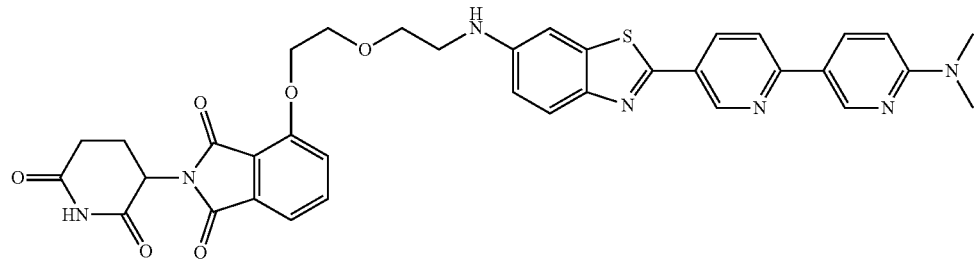
180312
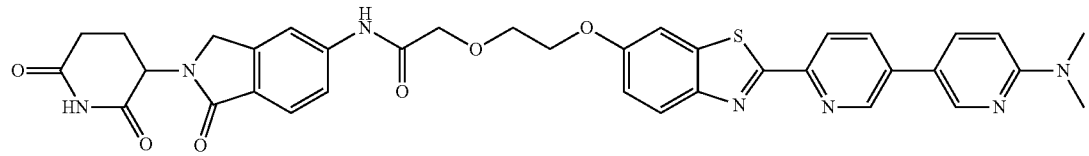 [SMILES: CN(C)c1ccc(-c2ccc(-c3nc4ccc(OCCOCC(=O)Nc5ccc6c(c5)CN(C5CCC(=O)NC5=O)C6=O)cc4s3)nc2)cn1]
180313
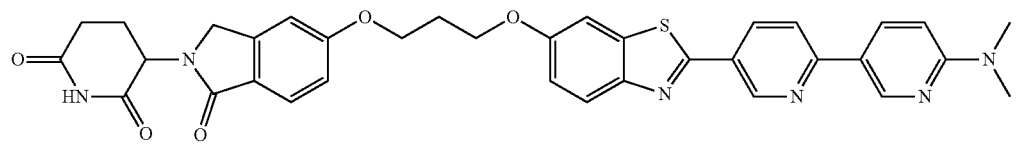 [SMILES: CN(C)c1ccc(-c2ccc(-c3nc4ccc(OCCCOc5ccc6c(c5)CN(C5CCC(=O)NC5=O)C6=O)cc4s3)cn2)cn1]
180314
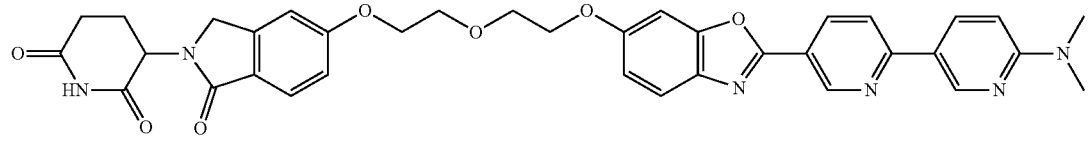
180315
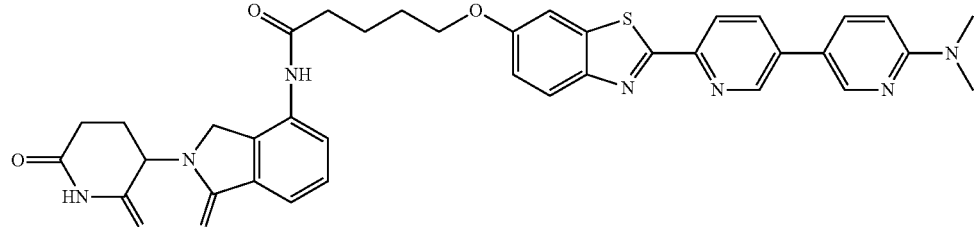
180316
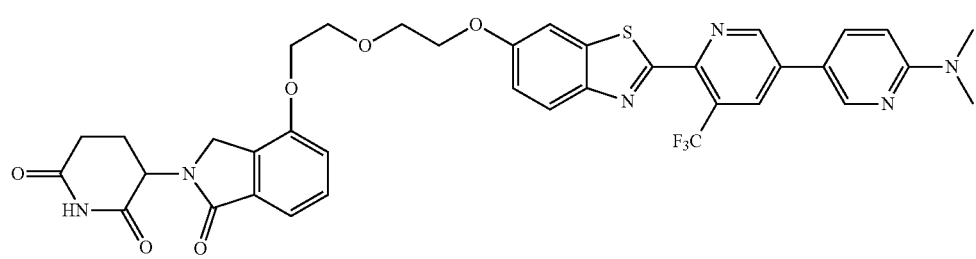 [SMILES: CN(C)c1ccc(-c2cnc(-c3nc4ccc(OCCOCCOc5cccc6c5CN(C5CCC(=O)NC5=O)C6=O)cc4s3)c(C(F)(F)F)c2)cn1]
180317

-continued
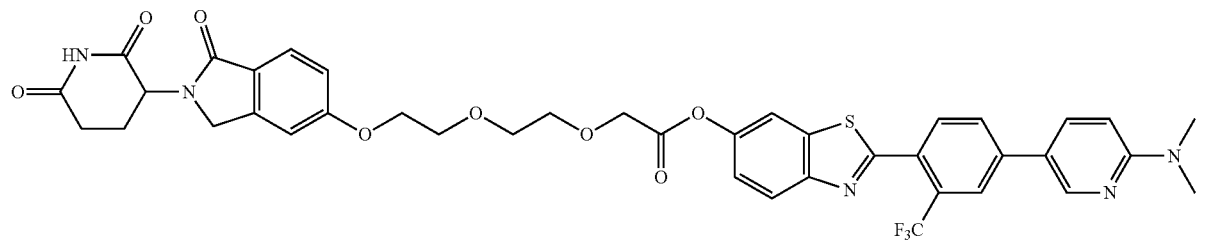 [SMILES: CN(C)c1ccc(-c2ccc(-c3nc4ccc(OC(=O)COCCOCCOc5ccc6c(c5)CN(C5CCC(=O)NC5=O)C6=O)cc4s3)c(C(F)(F)F)c2)cn1]
180318
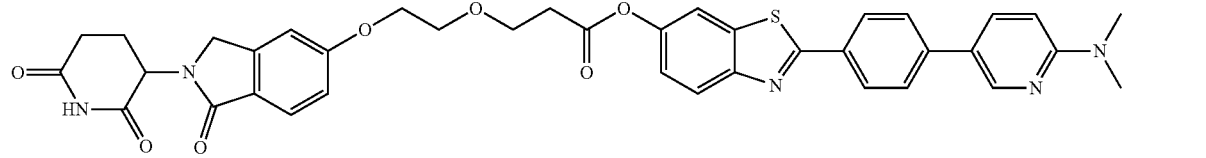 [SMILES: CN(C)c1ccc(-c2ccc(-c3nc4ccc(OC(=O)CCOCCOc5ccc6c(c5)CN(C5CCC(=O)NC5=O)C6=O)cc4s3)cc2)cn1]
120010
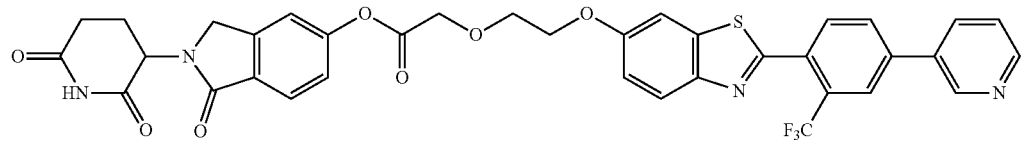
120011
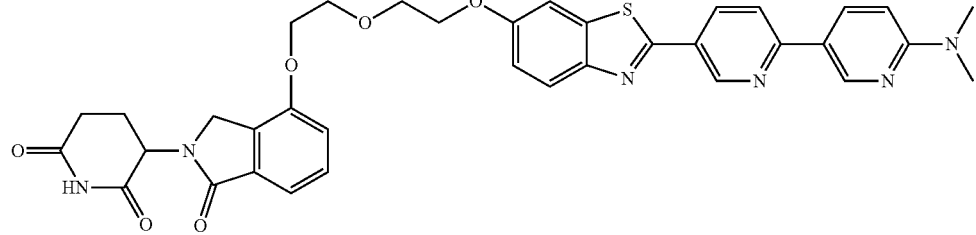
120012
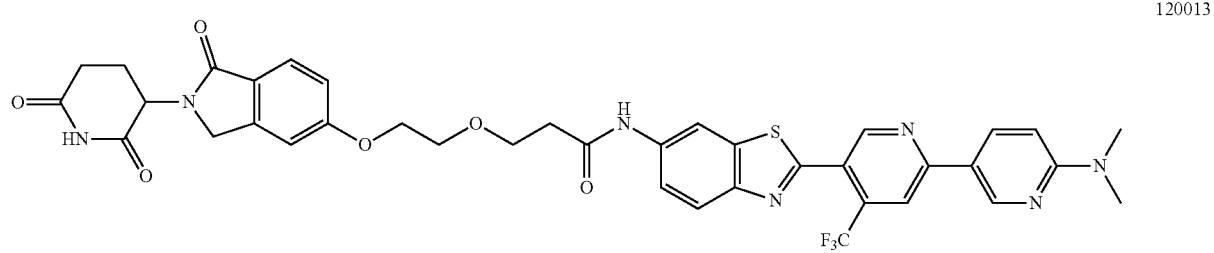
120013
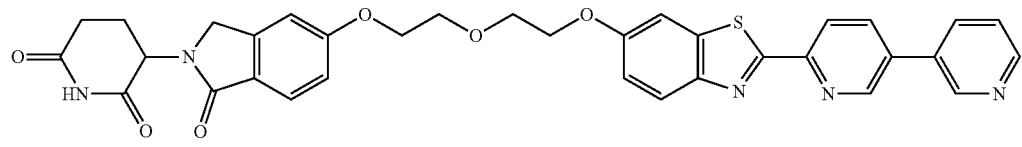
120014
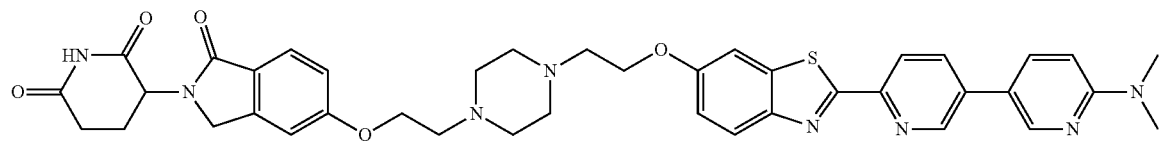
120015

-continued
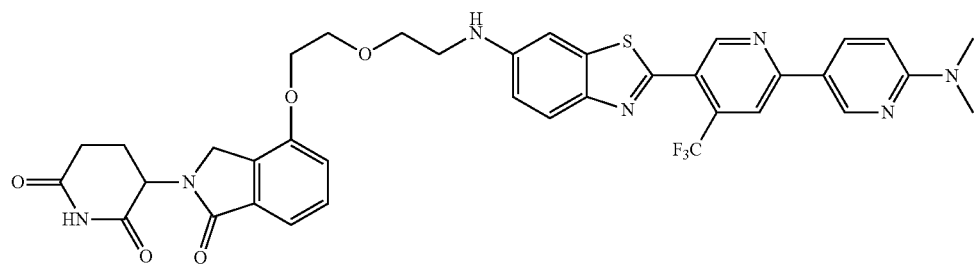
120016
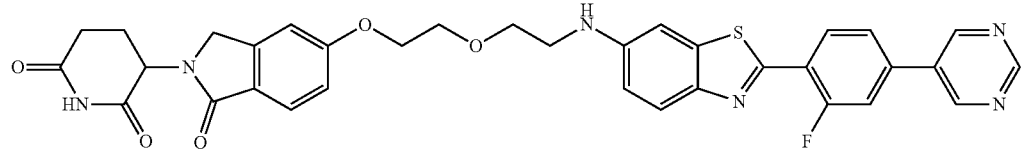 [SMILES: O=C1CCC(N2Cc3cc(OCCOCCNc4ccc5nc(-c6ccc(-c7cncnc7)cc6F)sc5c4)ccc3C2=O)C(=O)N1]
120017
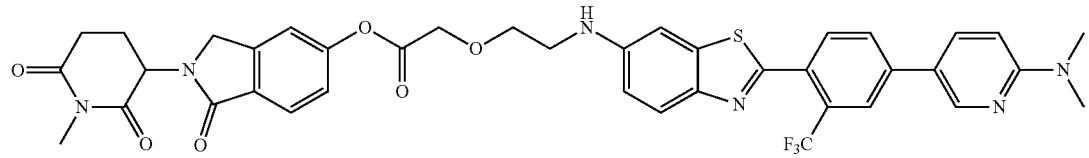
120018
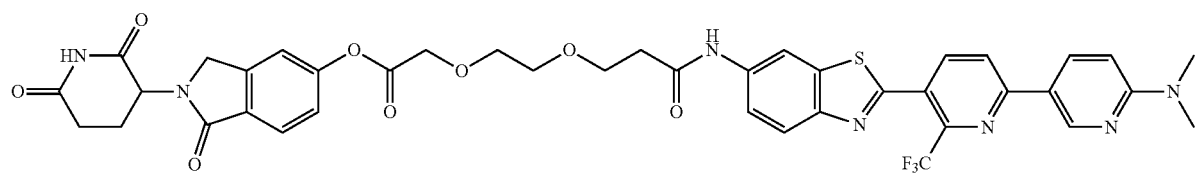
120019
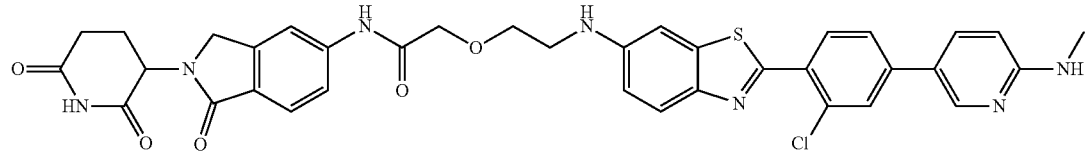
123013
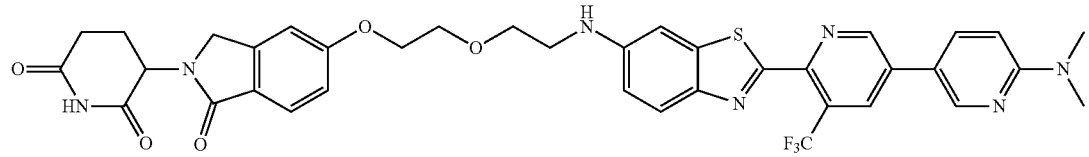
123014
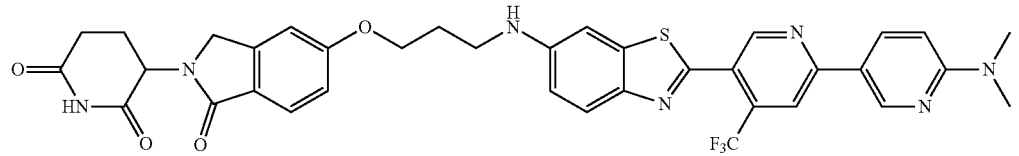 [SMILES: CN(C)c1ccc(-c2cc(C(F)(F)F)c(-c3nc4ccc(NCCCOc5ccc6c(c5)CN(C5CCC(=O)NC5=O)C6=O)cc4s3)cn2)cn1]
123015
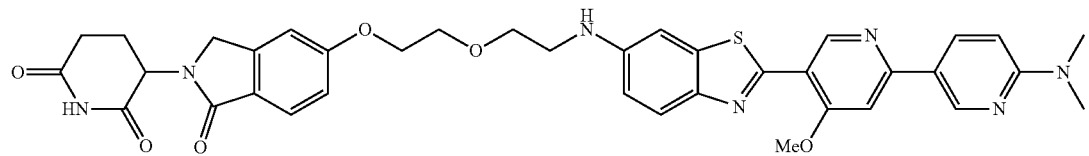
123016

-continued
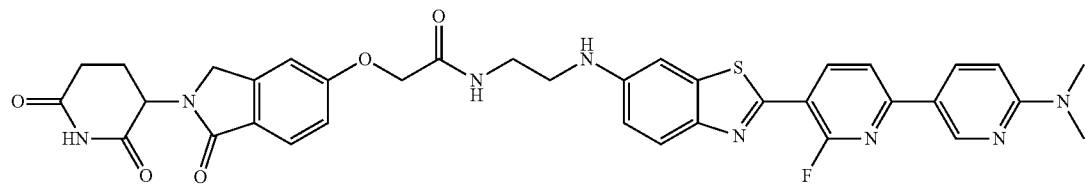 [SMILES: CN(C)c1ccc(-c2ccc(-c3nc4ccc(NCCNC(=O)COc5ccc6c(c5)CN(C5CCC(=O)NC5=O)C6=O)cc4s3)c(F)n2)cn1]
123017
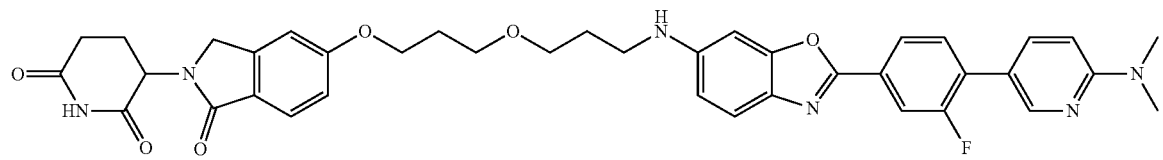 [SMILES: CN(C)c1ccc(-c2ccc(-c3nc4ccc(NCCCOCCCOc5ccc6c(c5)CN(C5CCC(=O)NC5=O)C6=O)cc4o3)cc2F)cn1]
123018
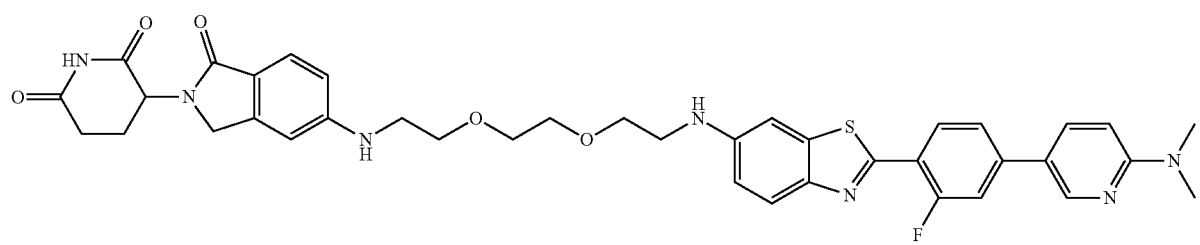 [SMILES: CN(C)c1ccc(-c2ccc(-c3nc4ccc(NCCOCCOCCNc5ccc6c(c5)CN(C5CCC(=O)NC5=O)C6=O)cc4s3)c(F)c2)cn1]
123019
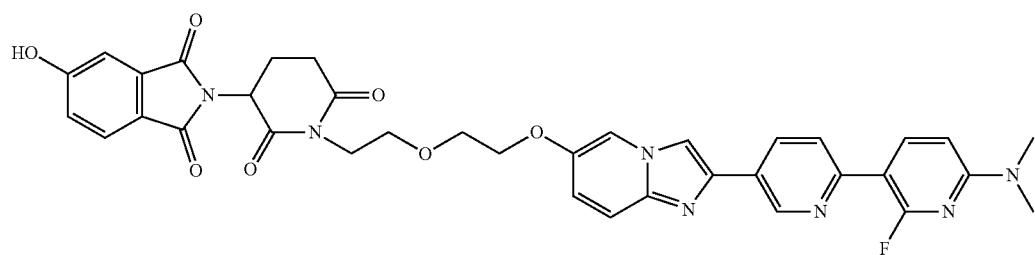
123413
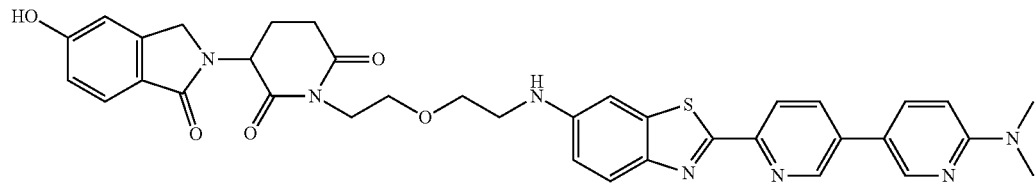 [SMILES: CN(C)c1ccc(-c2ccc(-c3nc4ccc(NCCOCCN5C(=O)CCC(N6Cc7cc(O)ccc7C6=O)C5=O)cc4s3)nc2)cn1]
123414
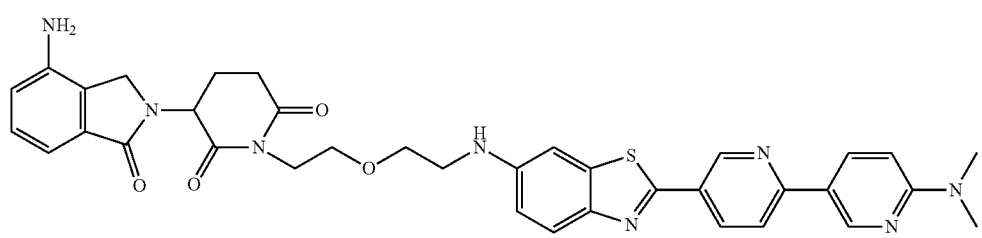 [SMILES: CN(C)c1ccc(-c2ccc(-c3nc4ccc(NCCOCCN5C(=O)CCC(N6Cc7c(N)cccc7C6=O)C5=O)cc4s3)cn2)cn1]
123415
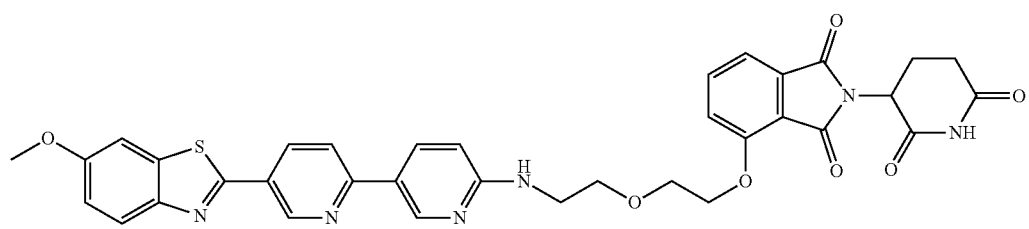
123416

123417
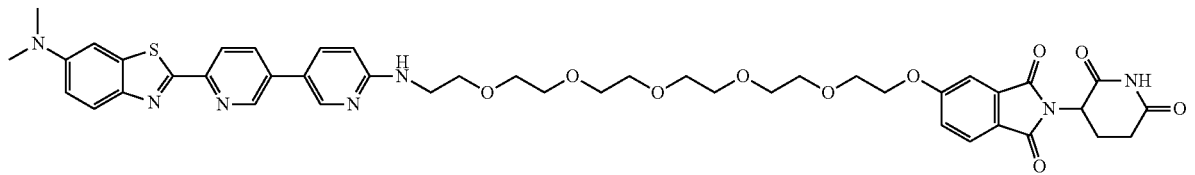 [SMILES: CN(C)c1ccc2nc(-c3ccc(-c4ccc(NCCOCCOCCOCCOCCOCCOc5ccc6c(c5)C(=O)N(C5CCC(=O)NC5=O)C6=O)nc4)cn3)sc2c1]
123418
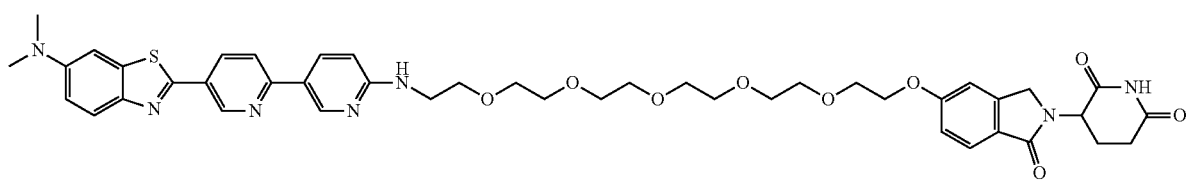 [SMILES: CN(C)c1ccc2nc(-c3ccc(-c4ccc(NCCOCCOCCOCCOCCOCCOc5ccc6c(c5)CN(C5CCC(=O)NC5=O)C6=O)nc4)nc3)sc2c1]
123419
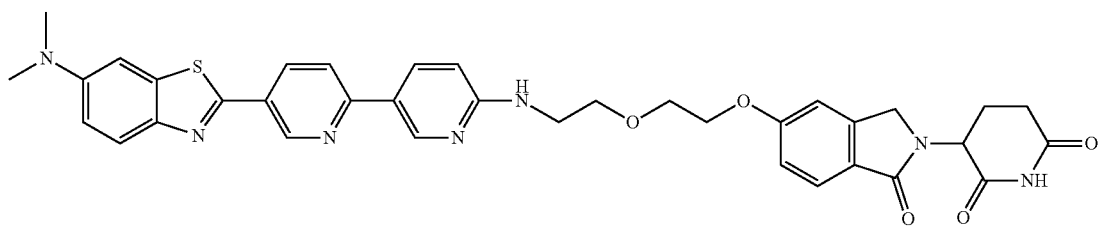 [SMILES: CN(C)c1ccc2nc(-c3ccc(-c4ccc(NCCOCCOc5ccc6c(c5)CN(C5CCC(=O)NC5=O)C6=O)nc4)nc3)sc2c1]
136171
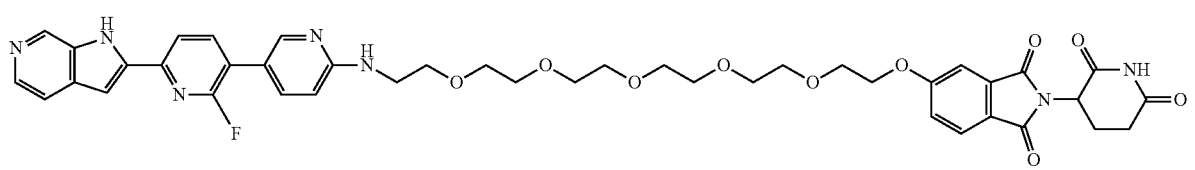
136172
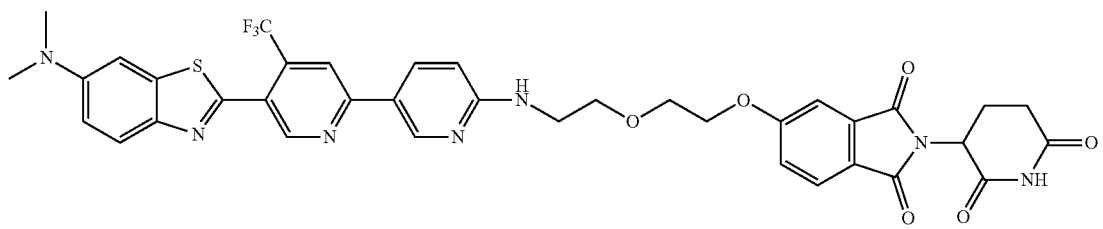 [SMILES: CN(C)c1ccc2nc(-c3cnc(-c4ccc(NCCOCCOc5ccc6c(c5)C(=O)N(C5CCC(=O)NC5=O)C6=O)nc4)cc3C(F)(F)F)sc2c1]
136173
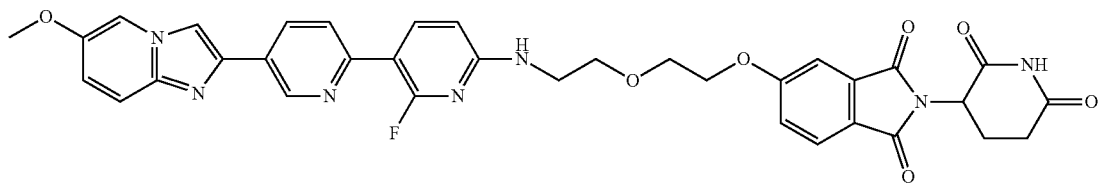
136174
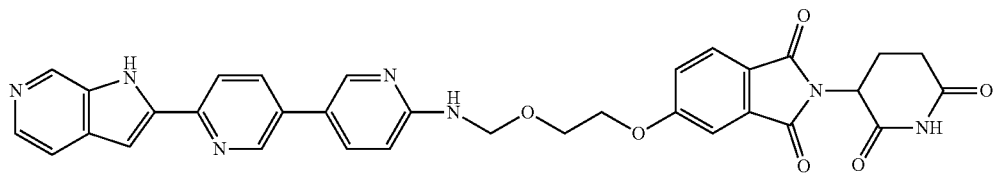
136175
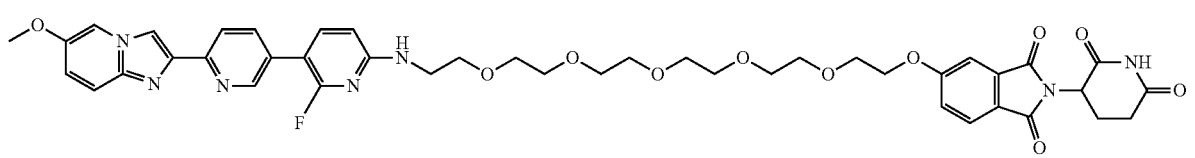

-continued
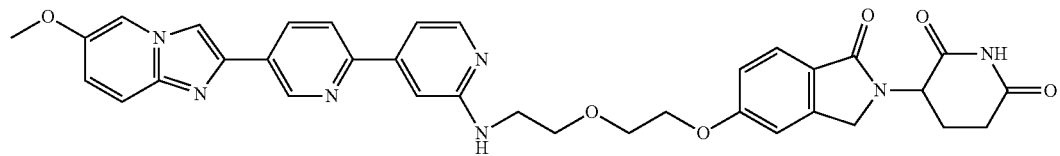
136176
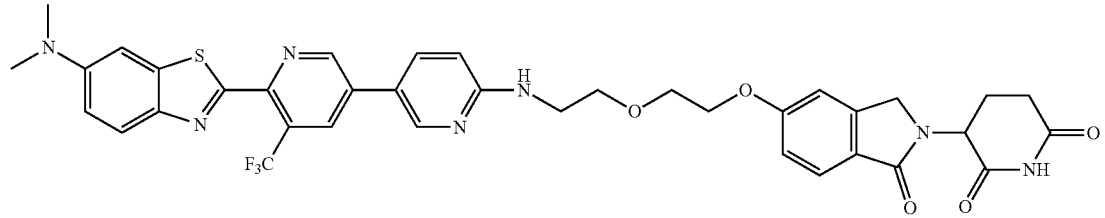 [SMILES: CN(C)c1ccc2nc(-c3ncc(-c4ccc(NCCOCCOc5ccc6c(c5)CN(C5CCC(=O)NC5=O)C6=O)nc4)cc3C(F)(F)F)sc2c1]
136177
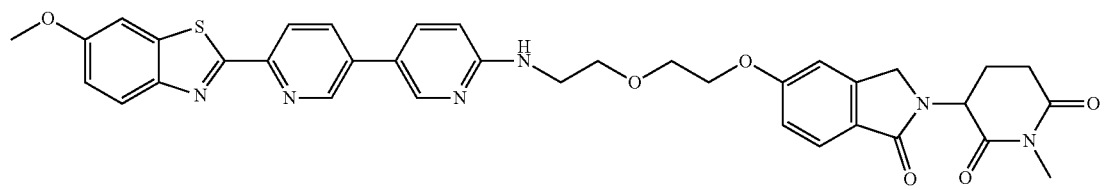
136178
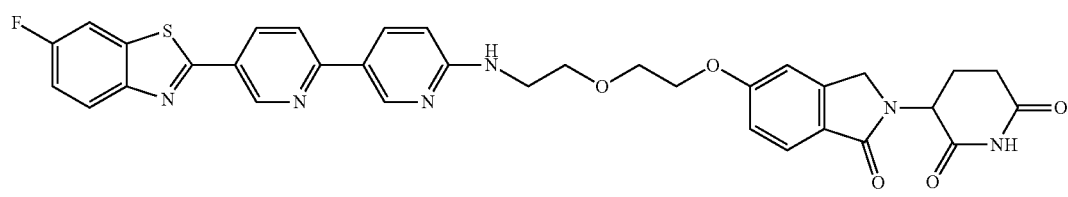 [SMILES: O=C1CCC(N2Cc3cc(OCCOCCNc4ccc(-c5ccc(-c6nc7ccc(F)cc7s6)cn5)cn4)ccc3C2=O)C(=O)N1]
136179
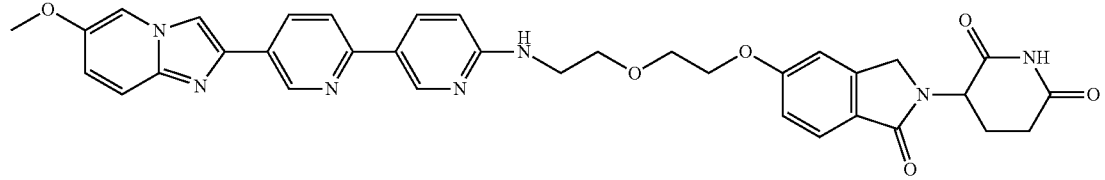
136571
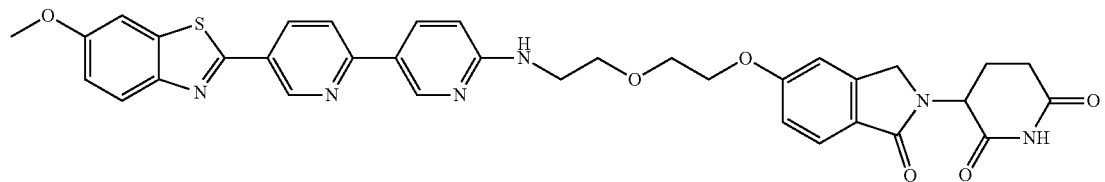 [SMILES: COc1ccc2nc(-c3ccc(-c4ccc(NCCOCCOc5ccc6c(c5)CN(C5CCC(=O)NC5=O)C6=O)nc4)nc3)sc2c1]
136572
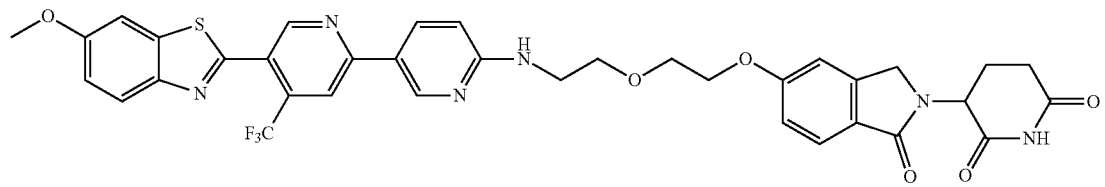 [SMILES: COc1ccc2nc(-c3cnc(-c4ccc(NCCOCCOc5ccc6c(c5)CN(C5CCC(=O)NC5=O)C6=O)nc4)cc3C(F)(F)F)sc2c1]
136573
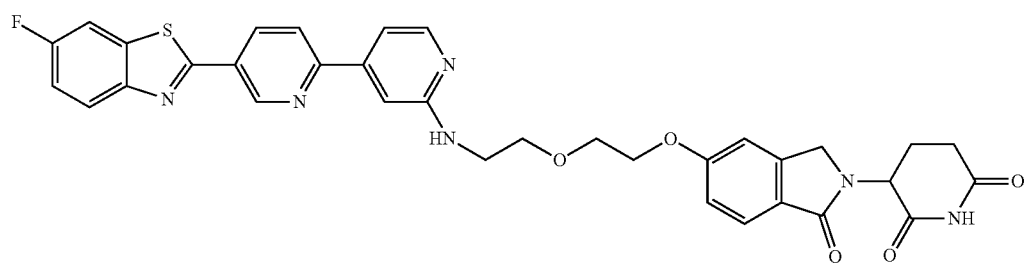
136574

-continued
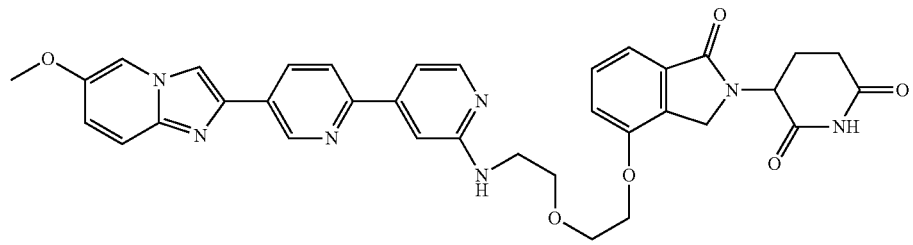
136575
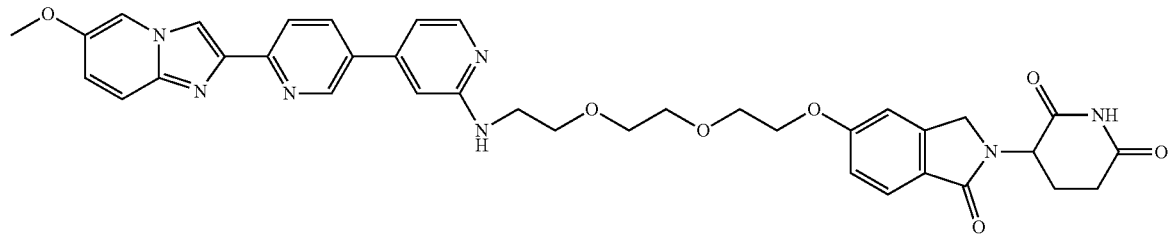 [SMILES: COc1ccc2nc(-c3ccc(-c4ccnc(NCCOCCOCCOc5ccc6c(c5)CN(C5CCC(=O)NC5=O)C6=O)c4)cn3)cn2c1]
136576
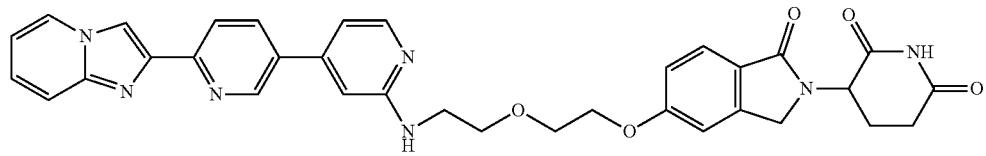 [SMILES: O=C1CCC(N2Cc3cc(OCCOCCNc4cc(-c5ccc(-c6cn7ccccc7n6)nc5)ccn4)ccc3C2=O)C(=O)N1]
136577
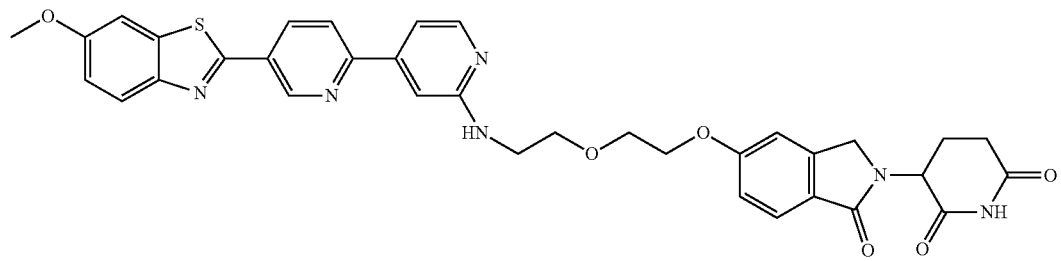 [SMILES: COc1ccc2nc(-c3ccc(-c4ccnc(NCCOCCOc5ccc6c(c5)CN(C5CCC(=O)NC5=O)C6=O)c4)nc3)sc2c1]
136578
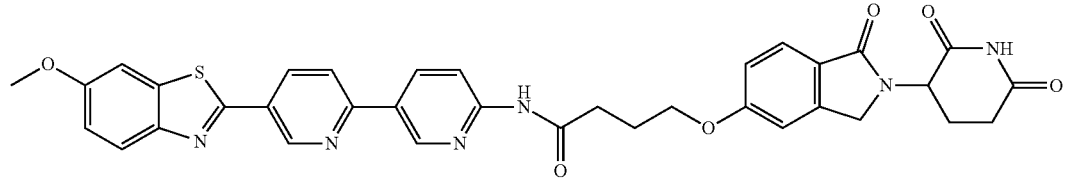 [SMILES: COc1ccc2nc(-c3ccc(-c4ccc(NC(=O)CCCOc5ccc6c(c5)CN(C5CCC(=O)NC5=O)C6=O)nc4)nc3)sc2c1]
136579
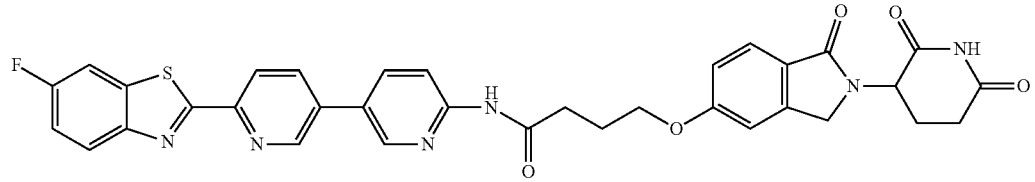
139571
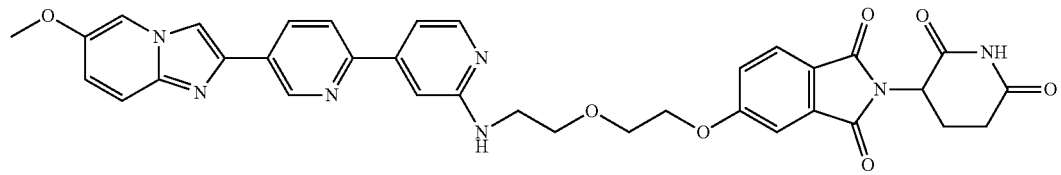
139572

-continued
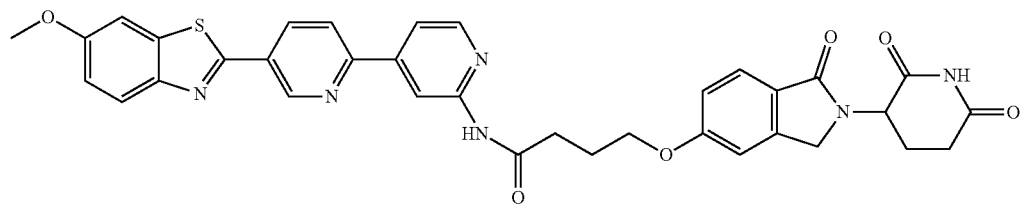 [SMILES: COc1ccc2nc(-c3ccc(-c4ccnc(NC(=O)CCCOc5ccc6c(c5)CN(C5CCC(=O)NC5=O)C6=O)c4)nc3)sc2c1]
139573
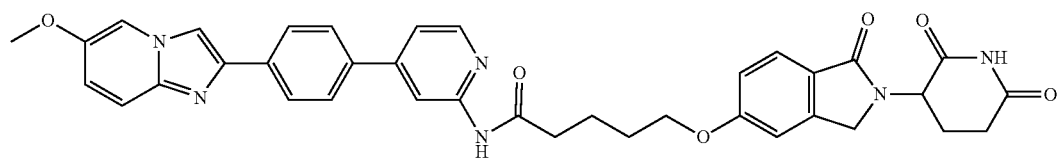
139574
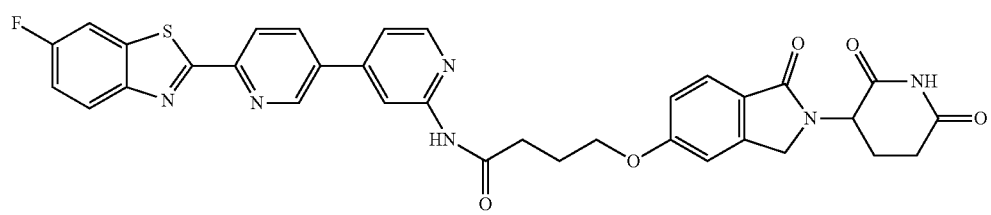 [SMILES: O=C1CCC(N2Cc3cc(OCCCC(=O)Nc4cc(-c5ccc(-c6nc7ccc(F)cc7s6)nc5)ccn4)ccc3C2=O)C(=O)N1]
139575
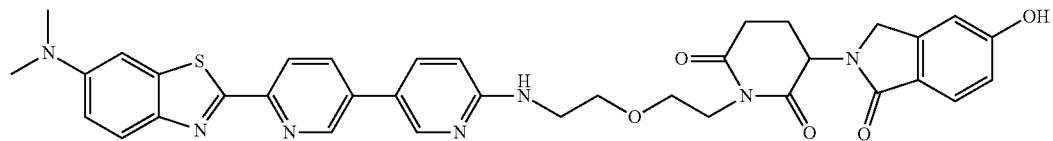 [SMILES: CN(C)c1ccc2nc(-c3ccc(-c4ccc(NCCOCCN5C(=O)CCC(N6Cc7cc(O)ccc7C6=O)C5=O)nc4)cn3)sc2c1]
139576
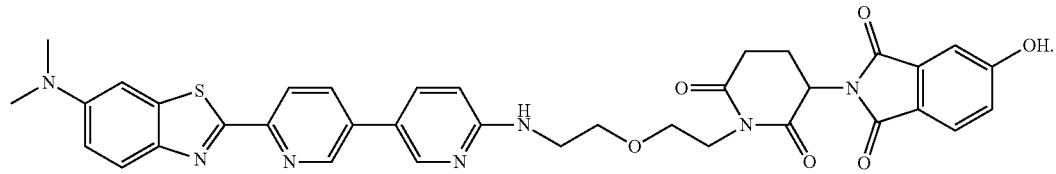
139577
30. A composition comprising the compound of claim 1, and a pharmaceutically acceptable excipient.
* * * * *